United States Patent
Perreault et al.

(10) Patent No.: US 10,239,917 B2
(45) Date of Patent: *Mar. 26, 2019

(54) METHOD FOR IDENTIFYING NOVEL MINOR HISTOCOMPATIBILITY ANTIGENS

(71) Applicant: UNIVERSITÉ DE MONTRÉAL, Montréal (CA)

(72) Inventors: Claude Perreault, Outremont (CA); Pierre Thibault, Ile-Bizzard (CA); Sébastien Lemieux, LaSalle (CA); Diana Paola Granados, Montréal (CA); Sriranganadane Dev, Montréal (CA); Mohamed Tariq Daouda, Montréal (CA); Olivier Caron-Lizotte, Longueuil (CA)

(73) Assignee: UNIVERSITÉ DE MONTRÉAL, Montréal (CA)

(*) Notice: Subject to any disclaimer, the term of this patent is extended or adjusted under 35 U.S.C. 154(b) by 0 days.

This patent is subject to a terminal disclaimer.

(21) Appl. No.: 15/299,387

(22) Filed: Oct. 20, 2016

(65) Prior Publication Data

US 2017/0044213 A1    Feb. 16, 2017

Related U.S. Application Data

(63) Continuation of application No. 14/421,310, filed as application No. PCT/CA2013/050580 on Jul. 25, 2013, now Pat. No. 9,500,651.

(60) Provisional application No. 61/683,361, filed on Aug. 15, 2012, provisional application No. 61/818,040, filed on May 1, 2013.

(51) Int. Cl.
| | |
|---|---|
| C07K 7/06 | (2006.01) |
| G06F 19/22 | (2011.01) |
| A61K 35/17 | (2015.01) |
| G01N 33/569 | (2006.01) |
| G06F 19/18 | (2011.01) |
| C12Q 1/6886 | (2018.01) |
| A61K 39/00 | (2006.01) |
| C07K 14/74 | (2006.01) |
| C12N 5/078 | (2010.01) |
| C12Q 1/6881 | (2018.01) |
| A61K 38/00 | (2006.01) |
| A61K 35/12 | (2015.01) |

(52) U.S. Cl.
CPC ............. *C07K 7/06* (2013.01); *A61K 35/17* (2013.01); *A61K 39/0011* (2013.01); *C07K 14/70539* (2013.01); *C12N 5/0634* (2013.01); *C12Q 1/6881* (2013.01); *C12Q 1/6886* (2013.01); *G01N 33/56977* (2013.01); *G06F 19/18* (2013.01); *G06F 19/22* (2013.01); *A61K 38/00* (2013.01); *A61K 2035/124* (2013.01); *A61K 2039/5158* (2013.01); *C12Q 2600/156* (2013.01); *G01N 2333/70539* (2013.01)

(58) Field of Classification Search
CPC ............ A61K 38/00; A61K 39/00; A61K 2039/5158; A61K 2039/585; C07K 2317/73; C07K 2317/34; C07K 14/70539; C07K 16/2815; C07K 16/2833; C12N 2502/1114; C12N 5/0638
See application file for complete search history.

(56) References Cited

FOREIGN PATENT DOCUMENTS

| WO | 2003/062401 A2 | 7/2003 |
|---|---|---|
| WO | 2010/116375 A1 | 10/2010 |

OTHER PUBLICATIONS

GenBank Database [Online] (Jul. 11, 2012) "RecName: Full= Protein RUBCNL-like," Accession No. Q9H714. National Center for Biotechnology Information. Accessible on the Internet at URL: https://www.ncbi.nlm.nih.gov/protein/Q9H714.3?report=girevhist. and https://www.ncbi.nlm.nih.gov/protein/Q9H714.3. [Last Accessed on Jun. 21, 2017], 7 pages.

Schuler et al. (2005) "SNEP: SNP-derived Epitope Prediction program for minor H antigens," Immunogenetics. 57:816-820.

SNEP—SNP-Derived Epitope Prediction Programme (Seach Performed on Jun. 19, 2017) Search Result: [Search Protein: CENPF, Choosen HLA subtype and peptide length: B0801_9] Search Tool Accessible on the Internet at URL: http://elchtools.de/SNEP.

SNEP—SNP-Derived Epitope Prediction Programme (Seach Performed on Jun. 19, 2017) Search Result: [Search Protein: ELF1, Choosen HLA subtype and peptide length: A0301_9] Search Tool Accessible on the Internet at URL: http://elchtools.de/SNEP.

SNEP—SNP-Derived Epitope Prediction Programme (Seach Performed on Jun. 19, 2017) Search Result: [Search Protein: FAM82B, Choosen HLA subtype and peptide length: A0301_10] Search Tool Accessible on the Internet at URL: http://elchtools.de/SNEP.

SNEP—SNP-Derived Epitope Prediction Programme (Seach Performed on Jun. 19, 2017) Search Result: [Search Protein: MTCH2, Choosen HLA subtype and peptide length: B0801_9] Search Tool Accessible on the Internet at URL: http://elchtools.de/SNEP.

(Continued)

*Primary Examiner* — Marcela M Cordero Garcia
*Assistant Examiner* — Jia-Hai Lee
(74) *Attorney, Agent, or Firm* — Lathrop Gage LLP; James H. Velema, Esq.

(57) ABSTRACT

A novel method for human minor histocompatibility antigen (MiHA) discovery, novel MiHAs identified using this method, as well as uses of the novel MiHAs, are described. One of the features of the novel method is the inclusion of personalized translated transcriptome and/or exome in the database used for peptide identification by mass spectroscopy (MS). Candidate MiHAs are identified by comparing the personalized transcriptome and/or exome to a reference genome and/or to the transcriptome and/or exome of an HLA-matched subject.

10 Claims, 11 Drawing Sheets

Specification includes a Sequence Listing.

(56) References Cited

OTHER PUBLICATIONS

SNEP—SNP-Derived Epitope Prediction Programme (Seach Performed on Jun. 19, 2017) Search Result: [Search Protein: ZWINT, Choosen HLA subtype and peptide length: B4402_10] Search Tool Accessible on the Internet at URL: http://elchtools.de/SNEP.
Yewdell et al. (2011) "DRiPs solidify: progress in understanding endogenous MHC class I antigen processing," Trends Immunol. 32:548-558.
Yu et al. (2008) "A precisely regulated gene expression cassette potently modulates metastasis and survival in multiple solid cancers," PLoS. Genet. 4:e1000129.
Extended European Search Report corresponding to European Patent Application No. 13829855.9, dated May 18, 2016.
International Search Report corresponding to International Patent Application No. PCT/CA2013/050580, dated Oct. 22, 2013.
Partial Supplementary European Search Report corresponding to European Patent Application No. 13829855.9, dated Jan. 27, 2016.
Meunier et al. (2009) "Two host factors regulate persistence of H7a-specific T cells injected in tumor bearing mice," PLoS One. 4:e4116.
Molldrem et al. (2005) "Graft-vs.-leukemia effects," In; Graft-vs.-Host Disease. Eds.: Ferrara et al. Marcel Dekker. New York, New York. pp. 155-194.
Mullally et al. (2007) "Beyond HLA: the significance of genomic variation for allogeneic hematopoietic stem cell transplantation," Blood. 109:1355-1362.
Murata et al. (2003) "A human minor histocompatibility antigen resulting from differential expression due to a gene deletion," J. Exp. Med. 197:1279-1289.
Neefjes et al. (2011) "Towards a systems understanding of MHC class I and MHC class II antigen presentation," Nat. Rev. Immunol. 11:823-836.
Nusbaum et al. (2006) "DNA sequence and analysis of human chromosome 8," Nature Letters. 439(19):331-335.
O'Brien et al. (2007) "CENP-F expression is associated with poor prognosis and chromosomal instability in patients with primary breast cancer," Int. J Cancer. 120:1434-1443.
Oishi et al. (2007) "RMD-1, a novel microtubule-associated protein, functions in chromosome segregation in Caenorhabditis elegans," J. Cell. Biol. 179:1149-1162.
O'Reilly et al. (2010) "Adoptive transfer of unselected or leukemia-reactive T-cells in the treatment of relapse following allogeneic hematopoietic cell transplantation," Semin. Immunol. 22:162-172.
Patrick et al. (Jan. 16, 2012) "Stress-induced NQO1 controls stability of C/EBPα against 20S proteasomal degradation to regulate p63 expression with implications in protection against chemical-induced skin cancer," Oncogene. 31(40):4362-4371.
Perreault et al. (2002) "Adoptive cancer immunotherapy: discovering the best targets," J. Mol. Med. 80:212-218.
Perreault et al. (1990) "Minor histocompatibility antigens," Blood. 76:1269-1280.
Perreault et al. (2010) "The origin and role of MHC class I-associated self-peptides," Prog. Mol. Biol. Transl. Sci. 92:41-60.
Popovic et al. (2011) "The only proposed T-cell epitope derived from the TEL-AML1 translocation is not naturally processed," Blood. 118:946-954.
Rezvani et al. (2008) "Characterizing and optimizing immune responses to leukaemia antigens after allogeneic stem cell transplantation," Best. Pract. Res. Clin. Haematol. 21:437-453.
Rijke et al. (2005) "A frameshift polymorphism in P2X5 elicits an allogeneic cytotoxic T lymphocyte response associated with remission of chronic myeloid leukemia," J. Clin. Lnvest. 115:3506-3516.
Roopenian e al. (2002) "The immunogenomics of minor histocompatibility antigens," Immunol. Rev. 190:86-94.
Rosenberg et al. (2004) "Cancer immunotherapy: moving beyond current vaccines," Nat. Med. 10:909-915.
Rosenberg et al. (2011) "Durable complete responses in heavily pretreated patients with metastatic melanoma using T cell transfer immunotherapy," Clin. Cancer Res. 17:4550-4557.
Schreiber et al. (2011) "Targeting mutations predictably," Blood. 118:830-831.
Sherry et al. (2001) "dbSNP: the NCBI database of genetic variation," Nucleic Acids Res. 29:308-311.
Shlomchik (2007) "Graft-versus-host disease," Nat. Rev. Immunol. 7:340-352.
Slager et al. (2006) "Identification of the angiogenic endothelial-cell growth factor-1/thymidine phosphorylase as a potential target for immunotherapy of cancer," Blood. 107:4954-4960.
Socie et al. (2009) "Acute graft-versus-host disease; from the bench to the bedside," Blood. 114:4327-4336.
Spaapen et al. (2008) "Targeting haematopoietic-specific minor histocompatibility antigens to distinguish graft-versus-tumour effects from graft-versus-host disease," Best Practice & Research Clinical Haematology. 21(3):543-557.
Spaapen et al. (2009) "Rapid identification of clinical relevant minor histocompatibility antigens via genome-wide zygosity-genotype correlation analysis," Clin. Cancer Res. 15:7137-7143.
Spaapen et al. (2008) "Toward targeting B cell cancers with CD4+ CTLs: identification of a CD19-encoded minor histocompatibility antigen using a novel genome-wide analysis," J. Exp. Med. 205:2863-2872.
Spierings et al. (2007) "Phenotype frequencies of autosomal minor histocompatibility antigens display significant differences among populations," PLoS. Genet. 3:e103.
Spierings et al. (2003) "The minor histocompatibility antigen HA-3 arises from differential proteasome-mediated cleavaue of the lymphoid blast crisis (Lbc) oncoprotein." Blood. 102:621-629.
Stumpf et al. (2009) "Identification of 4 new HLA-DR-restricted minor histocompatibility antigens as hematopoietic targets in anti-tumor immunity," Blood. 114:3684-3692.
Sykes et al. (2008) "Transplantation Immunology," In; Fundamental Immunology. Ed.: Paul. Lippincott Williams & Wilkins. Philadelphia, Pennsylvania. pp. 1426-1488.
Takahashi et al. (2008) "Regression of human kidney cancer following allogeneic stem cell transplantation is associated with recognition of an HERV-E antigen by T cells," J. Clin. Invest. 118:1099-1109.
Thomas (2005) "Foreword," In; Graft-vs.-Host Disease. Eds.: Ferrara et al. Marcel Dekker. New York, New York. pp. iii-iv.
Tosato et al. (2007) "Generation of Epstein-Barr Virus (EBV)-immortalized B cell lines," Curr. Protoc. Immunol. Chapter 7: Unit 7.22.
Tykodi et al. (2008) "C19orf48 Encodes a Minor Histocompatibility Antigen Recognized by CD8+ Cytotoxic T Cells from Renal Cell Carcinoma Patients," Clin. Cancer Res. 14(16):5260-5269.
Tykodi et al. (2004) "Allogeneic hematopoietic cell transplantation for metastatic renal cell carcinoma after nonmyeloablative conditioning: toxicity, clinical response, and immunological response to minor histocompatibility antigens," Clin. Cancer Res. 10:7799-7811.
Urbanucci et al. (Sep. 12, 2011) "Overexpression of androgen receptor enhances the binding of the receptor to the chromatin in prostate cancer," Oncogene. 31:2153-2163.
Van Bergen et al. (2010) "High-throughput characterization of 10 new minor histocompatibility antigens by whole genome association scanning," Cancer Res. 70:9073-9083.
Van Bergen et al. (2007) "Multiple myeloma—reactive T cells recognize an activation-induced minor histocompatibility antigen encoded by the ATP-dependent interferon-responsive (ADIR) gene," Blood. 109:4089-4096.
Vincent et al. (2011) "Next-generation leukemia immunotherapy," Blood. 118:2951-2959.
Vita et al. (2010) "The immune epitope database 2.0," Nucleic Acids Res. 38:D854-D862.
Vogelsang et al. (2003) "Pathogenesis and treatment of graft-versus-host disease after bone marrow transplant," Annu. Rev. Med. 54:29-52.

(56) References Cited

OTHER PUBLICATIONS

Wakai et al. (2011) "Prognostic significance of NQO1 expression in intrahepatic cholangiocarcinoma," Int. J Clin. Exp Pathol. 4:363-370.
Warren et al. (2006) "An antigen produced by splicing of noncontiguous peptides in the reverse order," Science. 313:1444-1447.
Warren et al. (2010) "Therapy of relapsed leukemia after allogeneic hematopoietic cell transplant with T cells specific for minor histocompatibility antigens," Blood. 115:3869-3878.
Xiang et al. (2010) "Identification of E74-like factor 1 (ELF1) as a transcriptional regulator of the Hox cofactor MEIS1," Exp. Hematol. 38(9):798-808.
Yang et al. (2007) "Allograft rejection mediated by memory T cells is resistant to regulation," Proc. Natl. Acad. Sci. USA. 104:19954-19959.
Yang et al. (2010) "Expression of Elf-1 and survivin in non-small cell lung cancer and their relationship to intratumoral microvessel density," Chin J. Cancer. 29:396-402.
Yang et al. (Sep. 2012) "NAD(P)H quinone oxidoreductase 1 (NQO1) genetic C609T polymorphism is associated with the risk of digestive tract cancer: a meta-analysis based on 21 case-control studies," Eur. J. Cancer Prev. 21(5):432-441.
Yewdell et al. (2003) "Making sense of mass destruction: quantitating MHC class I antigen presentation," Nature Rev. Immunol. 3:952-961.
Akatsuka et al. (2003) "Identification of a polymorphic gene, BCL2A1, encoding two novel hematopoietic lineage-specific minor histocompatibility antigens," J.Exp.Med. 197:1489-1500.
Andrews et al. (2008) "Oncogenic activation of the human Pygopus2 promoter by E74-like factor-1," Mol. Cancer Res. 6:259-266.
Barrett (2008) "Understanding and harnessing the graft-versus-leukaemia effect," Br. J. Haematol. 142:877-888.
Bencimon et al. (2005) "Prevalence of anticentromere F protein autoantibodies in 347 patients with non-Hodgkin's lymphoma," Ann. N. Y. Acad. Sci. 1050:319-326.
Bishop et al. (2004) "Allogeneic lymphocytes induce tumor regression of advanced metastatic breast cancer," J. Clin. Oncol. 22:3886-3892.
Bleakley et al. (2011) "Exploiting T cells specific for human minor histocompatibility antigens for therapy of leukemia," Immunol. Cell Biol. 89:396-407.
Bleakley et al. (2004) "Molecules and mechanisms of the graft-versus-leukaemia effect," Nat. Rev. Cancer. 4:371-380.
Brickner et al. (2001) "The immunogenicity of a new human minor histocompatibility antigen results from differential antigen processing," J. Exp. Med. 193:195-205.
Brickner et al. (2006) "The PANE1 gene encodes a novel human minor histocompatibility antigen that is selectively expressed in B-lymphoid cells and B-CLL," Blood. 107:3779-3786.
Brickner (2006) "Mechanisms of minor histocompatibility antigen immunogenicity: the role of infinitesimal versus structurally profound polymorphisms," Immunol. Res. 36:33-41.
Caron et al. (2011) "The MHC I immunopeptidome conveys to the cell surface an integrative view of cellular regulation," Mol. Syst. Biol. 7:533.
Chen et al. (2011) "Centromere protein F and survivin are associated with high risk and a poor prognosis in colorectal gastrointestinal stromal tumours," J. Clin. Pathol. 64:751-755.
Childs et al. (2004) "Nonmyeloablative allogeneic immunotherapy for solid tumors," Annu. Rev. Med. 55:459-475.
De La Guardia et al. (2001) "CENP-F gene amplification and overexpression in head and neck squamous cell carcinomas," Head Neck. 23:104-112.
De Verteuil et al. (2011) "Origin and plasticity of MHC I-associated self peptides," Autoimmun. Rev. 11(9):627-635.
De Verteuil et al. (2010) Deletion of immunoproteasome subunits imprints on the transcriptome and has a broad impact on peptides presented by major histocompatibility complex I molecules, Mol. Cell. Proteomics. 9:2034-2047.

Den Haan et al. (1998) "The minor histocompatibility antigen HA-1: a diallelic gene with a single amino acid polymorphism," Science. 279:1054-1057.
Den Haan et al. (1995) "Identification of a graft versus host disease-associated human minor histocompatibility antigen," Science. 268:1476-1480.
Ding et al. (Jan. 4, 2012) "Association of NQO1 rs1800566 polymorphism and the risk of colorectal cancer: a meta-analysis," Int. J Colorectal Dis. 27:885-892.
Dolstra et al. (1999) "A human minor histocompatibility antigen specific for B cell acute lymphoblastic leukemia," J. Exp. Med. 189:301-308.
Endo et al. (Oct. 24, 2011) "Terf/TRIM17 stimulates degradation of kinetochore protein ZWINT and regulates cell proliferation," J. Biochem. 151:139-144.
Feng et al. (2008) "Targeting minor histocompatibility antigens in graft versus tumor or graft versus leukemia responses," Trends Immunol. 29:624-632.
Ferrara et al. (2009) "Graft-versus-host disease," Lancet. 373:1550-1561.
Fontaine et al. (2001) "Adoptive transfer of T lymphocytes targeted to a single immunodominant minor histocompatibility antigen eradicates leukemia cells without causing graft-versus-host disease," Nat. Med. 7:789-794.
Fortier et al. (2008) "The MHC class I peptide repertoire is molded by the transcriptomem," J. Exp. Med. 205:595-610.
Granados et al. (Mar. 21, 2012) "MHC I-associated peptides preferentially derive from transcripts bearing miRNA recognition elements," Blood. 119(26):e181-191.
Greinix et al. (2011) "Diagnosis and staging of chronic graft-versus-host disease in the clinical practice," Biol. Blood Marrow Transplant. 17:167-175.
Griffioen et al. (2008) "Identification of phosphatidylinositol 4-kinase type II beta as HLA class II-restricted target in graft versus leukemia reactivity," Proc. Natl. Acad. Sci. USA. 105:3837-3842.
Grinberg et al. (2005) "Mitochondrial carrier homolog 2 is a target of tBID in cells signaled to die by tumor necrosis factor alpha," Mol. Cell Biol. 25:4579-4590.
Hanahan et al. (2011) "Hallmarks of cancer: the next generation," Cell. 144:646-674.
Ho et al. (Jun. 19, 2012) "Deregulation of rab and rab effector genes in bladder cancer," PLoS ONE. 7:e39469.
Hombrink et al. (2011) "High-throughput identification of potential minor histocompatibility antigens by MHC tetramer-based screening: feasibility and limitations," PLoS One. 6(8):e22523. pp. 1-12.
Horowitz et al. (1990) "Graft-versus-leukemia reactions after bone marrow transplantation," Blood. 75:555-562.
Huang et al. (Jun. 15, 2012) "An NQO1 substrate with potent antitumor activity that selectively kills by PARP1-induced programmed necrosis," 72(12):3038-47.
Inaba et al. (1999) "Primed T cells are more resistant to Fas-mediated activation-induced cell death than naive T cells," J. Immunol. 163:1315-1320.
Jamieson et al. (2011) "Two minor NQO1 and NQO2 alleles predict poor response of breast cancer patients to adjuvant doxorubicin and cyclophosphamide therapy," Pharmacogenet. Genomics. 21:808-819.
Kamei et al. (2009) "HapMap scanning of novel human minor histocompatibility antigens," Blood. 113:5041-5048.
Karosiene et al. (2011) "NetMHCcons: a consensus method for the major histocompatibility complex class I predictions," Immunogenetics. 64(3):177-186.
Katz et al. (Mar. 13, 2012) "Molecular basis of the interaction between proapoptotic truncated BID (tBID) protein and mitochondrial carrier homologue 2 (MTCH2) protein: key players in mitochondrial death pathway," J. Biol. Chem. 287:15016-15023.
Kawase et al. (2007) "Alternative splicing due to an intronic SNP in HMSD generates a novel minor histocompatibility antigen," Blood. 110:1055-1063.
Kawase et al. (2008) "Identification of human minor histocompatibility antigens based on genetic association with highly parallel genotyping of pooled DNA," Blood. 111:3286-3294.

(56) References Cited

OTHER PUBLICATIONS

Kessler et al. (2007) "Identification of T-cell epitopes for cancer immunotherapy," Leukemia. 21:1859-1874.

Kohrt et al. (Nov. 10, 2011) "Donor immunization with WT1 peptide augments antileukemic activity after MHC-matched bone marrow transplantation," Blood. 118(19):5319-5329.

Kolb et al. (1995) "Graft-versus-leukemia effect of donor lymphocyte transfusions in marrow grafted patients. European Group for Blood and Marrow Transplantation Working Party Chronic Leukemia," Blood. 86:2041-2050.

Kolb (2008) "Graft-versus-leukemia effects of transplantation and donor lymphocytes," Blood. 112:4371-4383.

Kolesar et al. (2011) "The NQO1*2/*2 polymorphism is associated with poor overall survival in patients following resection of stages II and IIIa non-small cell lung cancer," Oncol. Rep. 25:1765-1772.

Loveland et al. (1986) "The non-MHC transplantation antigens—neither weak nor minor," Immunol. Today. 7:223-229.

Mason (1998) "A very high level of crossreactivity is an essential feature of the T-cell receptor," Immunol. Today. 19:395-404.

Massague (2008) "TGFbeta in Cancer," Cell. 134:215-230.

Meunier et al. (2005) "T cells targeted against a single minor histocompatibility antigen can cure solid tumors," Nat. Med. 11:1222-1229.

Deluca et al. (2009) "High-throughput minor histocompatibility antigen prediction," Bioinformatics 25(18):2411-2417.

Halling-Brown et al. (2006) "SiPep: a system for the prediction of tissue-specific minor histocompatibility antigens," Int J Immunogenet. 33(4):289-95.

Jarmalavicius et al. (Aug. 6, 2012) "High immunogenicity of the human leukocyte antigen peptidomes of melanoma tumor cells," J Biol Chem. 287(40):33401-11.

Larsen (2010) "Bioinformatics in transplantation immunology," PhD Thesis. Center for Biological Sequence Analysis, Department of Systems Biology, Technical University of Denmark, Sep. 2010. (127 total pages).

Larsen et al. (2010) "Identification of CD8+ T Cell Epitopes in the West Nile Virus Polyprotein by Reverse-Immunology Using NetCTL," PLoS One 5(9):e12697. pp. 1-11.

Larsen et al. (2005) "An integrative approach to CTL epitope prediction: a combined algorithm integrating MHC class I binding, TAP transport efficiency, and proteasomal cleavage predictions," Eur J Immunol. 35(8):2295-303.

Lundegaard et al. (2012) "Predictions versus high-throughput experiments in T-cell epitope discovery: competition or synergy?" Expert Rev Vaccines. 11(1):43-54.

NetCTLpan server version 1.1 (search performed on Feb. 26, 2018) Search Results: [Search protein: C13orf18 G152R, chosen HLA allele: HLA-A*03:01, peptide lenght: 9 amino acids. Search tool available at URL: http://www.cbs.dtu.dk/services/NetCTLpan/.

Reche et al. (2005) "PEPVAC: a web server for multi-epitope vaccine development based on the prediction of supertypic MHC ligands," Nucleic Acids Research. 33(Web Server Issue):W138-W142.

Stranzl et al. (2010) "NetCTLpan: pan-specific MHC class I pathway epitope predictions," Immunogenetics. 6(6):357-68.

Tenzer et al. (2005) "Modeling the MHC class I pathway by combining predictions of proteasomal cleavage, TAP transport and MHC class I binding," Cell Mol Life Sci. 62(9):1025-37.

Examination Report corresponding to Japanese Patent Application No. 2015-526842, dated Mar. 12, 2018—provided with an English translation.

```
   1 gagaccagaa gcgggcgaat tgggcaccgg tggcggctgc gggcagtttg aattagactc
  61 tgggctccag cccgccgaag ccgcgccaga actgtactct ccgagaggtc gttttcccgt
 121 ccccgagagc aagtttattt acaaatgttg gagtaataaa gaaggcagaa caaaatgagc
 181 tgggcttttgg aagaatggaa agaagggctg cctacaagag ctcttcagaa aattcaagag
 241 cttgaaggac agcttgacaa actgaagaag gaaaagcagc aaaggcagtt tcagcttgac
 301 agtctcgagg ctgcgctgca gaagcaaaaa cagaaggttg aaaatgaaaa aaccgagggt
 361 acaaacctga aaagggagaa tcaaagattg atggaaatat gtgaaagtct ggagaaaact
 421 aagcagaaga tttctcatga acttcaagtc aaggagtcac aagtgaattt ccaggaagga
 481 caactgaatt caggcaaaaa acaaatagaa aaactggaac aggaacttaa aaggtgtaaa
 541 tctgagcttg aaagaagcca acaagctgcg cagtctgcag atgtctctct gaatccatgc
 601 aatacaccac aaaaaatttt tacaactcca ctaacaccaa gtcaatatta tagtggttcc
 661 aagtatgaag atctaaaaga aaaatataat aaagaggttg aagaacgaaa aagattagag
 721 gcagaggtta aagccttgca ggctaaaaaa gcaagccaga ctcttccaca agccaccatg
 781 aatcaccgcg acattgcccg gcatcaggct tcatcatctg tgttctcatg gcagcaagag
 841 aagacccaa gtcatctttc atctaattct caaagaactc caattaggag agatttctct
 901 gcatcttact tttctgggga acaagaggtg actccaagtc gatcaacttt gcaaataggg
 961 aaaagagatg ctaatagcag tttctttgac aattctagca gtcctcatct tttggatcaa
1021 ttaaaagcgc agaatcaaga gctaagaaac aagattaatg agttggaact acgcctgcaa
1081 ggacatgaaa aagaaatgaa aggccaagtg aataagtttc aagaactcca actccaactg
1141 gagaaagcaa aagtggaatt aattgaaaaa gagaaagttt tgaacaaatg tagggatgaa
1201 ctagtgagaa caacagcaca atacgaccag gcgtcaacca agtatactgc attggaacaa
1261 aaactgaaaa aattgacgga agatttgagt tgtcagcgac aaaatgcaga aagtgccaga
1321 tgttctctgg aacagaaaat taaggaaaaa gaaaaggagt tcaagaggaa gctctcccgt
1381 caacagcgtt ctttccaaac actggaccag gagtgcatcc agatgaaggc cagactcacc
1441 caggagttac agcaagccaa gaatatgcac aacgtcctgc aggctgaact ggataaactc
1501 acatcagtaa agcaacagct agaaaaacaat ttggaagagt ttaagcaaaa gttgtgcaga
1561 gctgaacagg cgttccaggc gagtcagatc aaggagaatg agctgaggag aagcatggag
1621 gaaatgaaga aggaaaacaa cctccttaag agtcactctg agcaaaaggc cagagaagtc
1681 tgccacctgg aggcagaact caagaacatc aaacagtgtt taaatcagag ccagaatttt
1741 gcagaagaaa tgaaagcgaa gaatacctct caggaaacca tgttaagaga tcttcaagaa
1801 aaaataaatc agcaagaaaa ctccttgact ttagaaaaac tgaagcttgc tgtggctgat
1861 ctggaaaagc agcgagattg ttctcaagac cttttgaaga aaagagaaca tcacattgaa
1921 caacttaatg ataagttaag caagacagag aaagagtcca aagccttgct gagtgcttta
1981 gagttaaaaa agaaagaata tgaagaattg aaagaagaga aaactctgtt ttcttgttgg
2041 aaaagtgaaa acgaaaaact tttaactcag atggaatcag aaaaggaaaa cttgcagagt
2101 aaaattaatc acttggaaac ttgtctgaag acacagcaaa taaaagtca tgaatacaac
2161 gagagagtaa gaacgctgga gatggacaga gaaaacctaa gtgtcgagat cagaaacctt
2221 cacaacgtgt tagacagtaa gtcagtggag gtagagaccc agaaactagc ttatatggag
2281 ctacagcaga aagctgagtt ctcagatcag aaacatcaga aggaaataga aaatatgtgt
2341 ttgaagactt ctcagcttac tgggcaagtt gaagatctag aacacaagct tcagttactg
2401 tcaaatgaaa taatggacaa agaccggtgt taccaagact tgcatgccga atatgagagc
2461 ctcagggatc tgctaaaatc caaagatgct tctctggtga caaatgaaga tcatcagaga
2521 agtctttttgg cttttgatca gcagcctgcc atgcatcatt cctttgcaaa tataattgga
2581 gaacaaggaa gcatgccttc agagaggagt gaatgtcgtt tagaagcaga ccaaagtccg
2641 aaaaattctg ccatcctaca aaatagagtt gattcacttg aattttcatt agagtctcaa
2701 aaacagatga actcagacct gcaaaagcag tgtgaagagt tggtgcaaat caaaggagaa
2761 atagaagaaa atctcatgaa agcagaacag atgcatcaaa gttttgtggc tgaaacaagt
2821 cagcgcatta gtaagttaca ggaagacact tctgctcacc agaatgttgt tgctgaaacc
2881 ttaagtgccc ttgagaacaa ggaaaaagag ctgcaacttt taaatgataa ggtagaaact
2941 gagcagcgag agattcaaga attaaaaaag agcaaccatc tacttgaaga ctctctaaag
3001 gagctacaac ttttatccga aaccctaagc ttggagaaga aagaaatgag ttccatcatt
3061 tctctaaata aagggaaat tgaagagctg acccaagaga atgggactct taaggaaatt
3121 aatgcatcct taaatcaaga gaagatgaac ttaatccaga aaagtgagag ttttgcaaac
3181 tatatagatg aaagggagaa aagcatttca gagttatctg atcagtacaa gcaagaaaaa
3241 cttattttac tacaaagatg tgaagaaacc ggaaatgcat atgaggatct tagtcaaaaa
3301 tacaaagcag cacaggaaaa gaattctaaa ttagaatgct tgctaaatga atgcactagt
3361 ctttgtgaaa ataggaaaaa tgagttggaa cagctaaagg aagcatttgc aaaggaacac
3421 caagaattct taacaaaatt agcatttgct gaagaaagaa atcagaatct gatgctagag
3481 ttggagacag tgcagcaagc tctgagatct gagatgacag ataaccaaaa caattctaag
```

FIG. 1A

```
3541 agcgaggctg gtggtttaaa gcaagaaatc atgactttaa aggaagaaca aaacaaaatg
3601 caaaaggaag ttaatgactt attacaagag aatgaacagc tgatgaaggt aatgaagact
3661 aaacatgaat gtcaaaatct agaatcagaa ccaattagga actctgtgaa agaaagagag
3721 agtgagagaa atcaatgtaa ttttaaacct cagatggatc ttgaagttaa agaaatttct
3781 ctagatagtt ataatgcgca gttggtgcaa ttagaagcta tgctaagaaa taaggaatta
3841 aaacttcagg aaagtgagaa ggagaaggag tgcctgcagc atgaattaca gacaattaga
3901 ggagatcttg aaaccagcaa tttgcaagac atgcagtcac aagaaattag tggccttaaa
3961 gactgtgaaa tagatgcgga agaaaagtat atttcagggc ctcatgagtt gtcaacaagt
4021 caaaacgaca atgcacacct tcagtgctct ctgcaaacaa caatgaacaa gctgaatgag
4081 ctagagaaaa tatgtgaaat actgcaggct gaaaagtatg aactcgtaac tgagctgaat
4141 gattcaaggt cagaatgtat cacagcaact aggaaaatgg cagaagaggt agggaaacta
4201 ctaaatgaag ttaaaatatt aaatgatgac agtggtcttc tccatggtga gttagtggaa
4261 gacataccag gaggtgaatt tggtgaacaa ccaaatgaac agcaccctgt gtctttggct
4321 ccattggacg agagtaattc ctacgagcac ttgacattgt cagacaaaga agttcaaatg
4381 cactttgccg aattgcaaga gaaattctta tctttacaaa gtgaacacaa aattttacat
4441 gatcagcact gtcagatgag ctctaaaatg tcagagctgc agacctatgt tgactcatta
4501 aaggccgaaa atttggtctt gtcaacgaat ctgagaaact ttcaaggtga cttggtgaag
4561 gagatgcagc tgggcttgga ggaggggctc gttccatccc tgtcatcctc ttgtgtgcct
4621 gacagctcta gtcttagcag tttgggagac tcctcctttt acagagctct tttagaacag
4681 acaggagata tgtctctttt gagtaattta gaaggggctg tttcagcaaa ccagtgcagt
4741 gtagatgaag tattttgcag cagtctgcag gaggagaatc tgaccaggaa agaaaccoct
4801 tcggccccga cgaagggtgt tgaagagctt gagtccctct gtgaggtgta ccggcagtcc
4861 ctcgagagc tagaagagaa aatgaaaagt caagggatta tgaaaaataa ggaaattcaa
4921 gagctcgagc agttattaag ttctgaaagg caagagcttg actgccttag gaagcagtat
4981 ttgtcagaaa atgaacagtg gcaacagaag ctgacaagcg tgactctgga gatggagtcc
5041 aagttggcgg cagaaaagaa acagacggaa caactgtcac ttgagctgga agtagcacga
5101 ctccagctac aaggtctgga cttaagttct cggtctttgc ttggcatcga cacagaagat
5161 gctattcaag gccgaaatga gagctgtgac atatcaaaag aacatacttc agaaactaca
5221 gaaagaacac caaagcatga tgttcatcag atttgtgata aagatgctca gcaggacctc
5281 aatctagaca ttgagaaaat aactgagact ggtgcagtga aacccacagg agagtgctct
5341 ggggaacagt ccccagatac caattatgag cctccagggg aagataaaac ccagggctct
5401 tcagaatgca tttctgaatt gtcatttctc ggtcctaatg ctttggtacc tatggatttc
5461 ctggggaatc aggaagatat ccataatctt caactgcggg taaaagagac atcaaatgag
5521 aatttgagat tacttcatgt gatagaggac cgtgacagaa aagttgaaag tttgctaaat
5581 gaaatgaaag aattagactc aaaactccat ttacaggagg tacaactaat gaccaaaatt
5641 gaagcatgca tagaattgga aaaaatagtt ggggaactta agaaagaaaa ctcagattta
5701 agtgaaaaat tggaatattt ttcttgtgat caccaggagt tactccagag agtagaaact
5761 tctgaaggcc tcaattctga tttagaaatg catgcagata aatcatcacg tgaagatatt
5821 ggagataatg tggccaaggt gaatgacagc tggaaggga gatttcttga tgtggaaaat
5881 gagctgagta ggatcagatc ggagaaagct agcattgagc atgaagccct ctacctggag
5941 gctgacttag aggtagttca aacagagaag ctatgtttag aaaaagacaa tgaaaataag
6001 cagaaggtta ttgtctgcct tgaagaagaa ctctcagtgg tcacaagtga gagaaaccag
6061 cttcgtggag aattagatac tatgtcaaaa aaaaccacgg cactggatca gttgtctgaa
6121 aaaatgaagg agaaaacaca agagcttgag tctcatcaaa gtgagtgtct ccattgcatt
6181 caggtggcag aggcagaggt gaaggaaaag acggaactcc ttcagacttt gtcctctgat
6241 gtgagtgagc tgttaaaaga caaaactcat ctccaggaaa agctgcagag tttggaaaag
6301 gactcacagg cactgtcttt gacaaaatgt gagctggaaa accaaattgc acaactgaat
6361 aaagagaaag aatttgcttgt caaggaatct gaaagcctgc aggccagact gagtgaatca
6421 gattatgaaa agctgaatgt ctccaaggcc ttggaggccg cactggtgga gaaaggtgag
6481 ttcgcattga ggctgagctc aacacaggag gaagtgcatc agctgagaag aggcatcgag
6541 aaactgagag ttcgcattga ggccgatgaa agaagcagc tgcacatcgc agagaaactg
6601 aaagaacgcg agcgggagaa tgattcactt aaggataaag ttgagaacct tgaaagggaa
6661 ttgcagatgt cagaagaaaa ccaggagcta gtgattcttg atgccgagaa ttccaaagca
6721 gaagtagaga ctctaaaaac acaaatagaa gagatggcca gaagcctgaa agtttttgaa
6781 ttagaccttg tcacgttaag gtctgaaaga gaaaatctga caaaacaaat acaagaaaaa
6841 caggtcagt tgtcagaact agacaagtta ctctcttcat ttaaaagtct gttagaagaa
6901 aaggagcaag cagagataca gatcaaagaa gaatctaaaa ctgcagtgga gatgcttcag
6961 aatcagttaa aggagctaaa tgaggcagta gcagccttgt gtggtgacca agaaattatg
```

FIG. 1B

```
7021 aaggccacag aacagagtct agacccacca atagaggaag agcatcagct gagaaatagc
7081 attgaaaagc tgagagcccg cctagaagct gatgaaaaga agcagctctg tgtcttacaa
7141 caactgaagg aaagtgagca tcatgcagat ttacttaagg gtagagtgga gaaccttgaa
7201 agagagctag agatagccag gacaaaccaa gagcatgcag ctcttgaggc agagaattcc
7261 aaaggagagg tagagaccct aaaagcaaaa atagaaggga tgacccaaag tctgagaggt
7321 ctggaattag atgttgttac tataaggtca gaaaaagaaa atctgacaaa tgaattacaa
7381 aaagagcaag agcgaatatc tgaattagaa ataataaatt catcatttga aaatattttg
7441 caagaaaaag agcaagagaa agtacagatg aaagaaaaat caagcactgc catggagatg
7501 cttcaaacac aattaaaaga gctcaatgag agagtggcag ccctgcataa tgaccaagaa
7561 gcctgtaagg ccaaagagca gaatcttagt agtcaagtag agtgtcttga acttgagaag
7621 gctcagttgc tacaaggcct tgatgaggcc aaaaataatt atattgtttt gcaatcttca
7681 gtgaatggcc tcattcaaga agtagaagat ggcaagcaga aactggagaa gaaggatgaa
7741 gaaatcagta gactgaaaaa tcaaattcaa gaccaagagc agcttgtctc taaactgtcc
7801 caggtggaag gagagcacca actttggaag gagcaaaact tagaactgag aaatctgaca
7861 gtggaattgg agcagaagat ccaagtgcta caatccaaaa atgcctcttt gcaggacaca
7921 ttagaagtgc tgcagagttc ttacaagaat ctagagaatg agcttgaatt gacaaaaatg
7981 gacaaaatgt cctttgttga aaaagtaaac aaaatgactg caaaggaaac tgagctgcag
8041 agggaaatgc atgagatggc acagaaaaca gcagagctgc aagaagaact cagtggagag
8101 aaaaataggc tagctggaga gttgcagtta ctgttggaag aaataaagag cagcaaagat
8161 caattgaagg agctcacact agaaaatagt gaattgaaga agagcctaga ttgcatgcac
8221 aaagaccagg tggaaaagga agggaaagtg agagaggaaa tagctgaata tcagctacgg
8281 cttcatgaag ctgaaaagaa acaccaggct ttgcttttgg acacaaacaa acagtatgaa
8341 gtagaaatcc agacataccg agagaaattg acttctaaag aagaatgtct cagttcacag
8401 aagctggaga tagacctttt aaagtctagt aaagaagagc tcaataattc attgaaagct
8461 actactcaga ttttggaaga attgaagaaa accaagatgg acaatctaaa atatgtaaat
8521 cagttgaaga aggaaaatga acgtgcccag gggaaaatga agttgttgat caaatcctgt
8581 aaacagctgg aagaggaaaa ggagatactg cagaaagaac tctctcaact tcaagctgca
8641 caggagaagc agaaaacagg tactgttatg gataccaagg tcgatgaatt aacaactgag
8701 atcaaagaac tgaaagaaac tcttgaagaa aaaccaagg aggcagatga atacttggat
8761 aagtactgtt ccttgcttat aagccatgaa aagttagaga aagctaaaga gatgttagag
8821 acacaagtgg cccatctgtg ttcacagcaa tctaaacaag attcccgagg gtctccttg
8881 ctaggtccag ttgttccagg accatctcca atcccttctg ttactgaaaa gaggttatca
8941 tctggccaaa ataaagcttc aggcaagagg caaagatcca gtggaatatg ggagaatggt
9001 agaggaccaa cacctgctac cccagagagc ttttctaaaa aaagcaagaa agcagtcatg
9061 agtggtattc accctgcaga agacacggaa ggtactgagt ttgagccaga gggacttcca
9121 gaagttgtaa agaaagggtt tgctgacatc ccgacaggaa agactagccc atatatcctg
9181 cgaagaacaa ccatggcaac tcggaccagc ccccgcctgg ctgcacagaa gttagcgcta
9241 tccccactga gtctcggcaa agaaaatctt gcagagtcct ccaaaccaac agctggtggc
9301 agcagatcac aaaaggtcaa agttgctcag cggagcccag tagattcagg caccatcctc
9361 cgagaaccca ccacgaaatc cgtcccagtc aataatcttc ctgagagaag tccgactgac
9421 agcccagag agggcctgag ggtcaagcga ggccgacttg tccccagccc caaagctgga
9481 ctggagtcca acggcagtga gaactgtaag gtccagtgaa ggcactttgt gtgtcagtac
9541 ccctgggagg tgccagtcat tgaatagata aggctgtgcc tacaggactt ctctttagtc
9601 agggcatgct ttattagtga ggagaaaaca attccttaga agtcttaaat atattgtact
9661 ctttagatct cccatgtgta ggtattgaaa agtttggaa gcactgatca cctgttagca
9721 ttgccattcc tctactgcaa tgtaaatagt ataaagctat gtatataaag ctttttggta
9781 atatgttaca attaaaatga caagcactat atcacaatct ctgtttgtat gtgggttta
9841 cactaaaaaa atgcaaaaca cattttattc ttctaattaa cagctcctag gaaaatgtag
9901 acttttgctt tatgatattc tatctgtagt atgaggcatg gaatagtttt gtatcgggaa
9961 tttctcagag ctgagtaaaa tgaaggaaaa gcatgttatg tgttttttaag gaaaatgtgc
10021 acacatatac atgtaggagt gtttatcttt ctcttacaat ctgttttaga catctttgct
10081 tatgaaacct gtacatatgt gtgtgtgggt atgtgtttat ttccagtgag ggctgcaggc
10141 ttcctagagg tgtgctatac catgcgtctg tcgttgtgct ttttctgtt tttagaccaa
10201 tttttttacag ttctttggta agcattgtcg tatctggtga tggattaaca tatagccttt
10261 gttttctaat aaaatagtcg ccttcgtttt ctgtaaaaaa aaaaaaaaa aaaaaa
```

FIG. 1C

```
   1 mswaleewke glptralqki qeleqqldkl kkekqqrqfq ldsleaalqk qkqkvenekt
  61 egtnlkrenq rlmeicesle ktkqkishel qvkesqvnfq egqlnsgkkq iekleqelkr
 121 ckselersqq aaqsadvsln pcntpqkift tpltpsqyys gskyedlkek ynkeveerkr
 181 leaevkalqa kkasqtlpqa tmnhrdiarh qasssvfswq qektpshlss nsqrtpirrd
 241 fsasyfsgeq evtpsrstlq igkrdanssf fdnsssphll dqlkaqnqel rnkinelelr
 301 lqghekemkg qvnkfqelql qlekakveli ekekvlnkcr delvrttaqy dqastkytal
 361 eqklkklted lscqrqnaes arcsleqkik ekekefqeel srqqrsfqtl dqeciqmkar
 421 ltqelqqakn mhnvlqaeld kltsvkqqle nnleefkqkl craeqafqas qikenelrrs
 481 meemkkennl lkshseqkar evchleaelk nikqclnqsq nfaeemkakn tsqetmlrdl
 541 qekinqqens ltleklklav adlekqrdcs qdllkkrehh ieqlndklsk tekeskalls
 601 alelkkkeye elkeektlfs cwksenekll tqmesekenl qskinhletc lktqqikshe
 661 ynervrtlem drenlsveir nlhnvldsks vevetqklay melqqkaefs dqkhqkeien
 721 mclktsqltg qvedlehklq llsneimdkd rcyqdlhaey eslrdllksk daslvtnedh
 781 qrsllafdqq pamhhsfani iqeqqsmpse rsecrleadq spknsailqn rvdslefsle
 841 sqkqmnsdlq kqceelvqik geieenlmka eqmhqsfvae tsqrisklqe dtsahqnvva
 901 etlsalenke kelqllndkv eteqaeiqel kksnhlleds lkelqllset lslekkemss
 961 iislnkreie eltqengtlk einaslnqek mnliqksesf anyidereks iselsdqykq
1021 eklillqrce etgnayedls qkykaaqekn skleclinec tslcenrkne leqlkeafak
1081 ehqefltkla faeernqnlm leletvqqal rsemtdnqnn skseagglkq eimtlkeeqn
1141 kmqkevndli qeneqlmkvm ktkhecqnle sepirnsvke resernqcnf kpqmdlevke
1201 isldsynaql vqleamlrnk elklqeseke keclqhelqt irgdletsnl qdmqsqeisg
1261 lkdceidaee kyisgphels tsqndnahlq cslqttmnkl nelekiceil qaekyelvte
1321 lndsrsecit atrkmaeevg kllnevkiln ddsgllhgel vedipggefg eqpneqhpvs
1381 lapldesnsy ehltlsdkev qmhfaelqek flslqsehki lhdqhcqmss kmselqtyvd
1441 slkaenlvls tnlrnfqgdl vkemqlglee glvpslsssc vpdsssissl gdssfyrall
1501 eqtgdmslls nlegavsanq csvdevfcss lqeenltrke tpsapakgve eleslcevyr
1561 qslekleekm esqgimknke iqeleqllss erqeldclrk qylseneqwq qkltsvtlem
1621 esklaaekkq teqlslelev arlqlqgldl ssrsllgidt edaiqgrnes cdiskehtse
1681 ttertpkhdv hqicdkdaqq dlnldiekit etgavkptge csgeqspdtn yeppgedktq
1741 gsseciseIs fsgpnalvpm dflgnqedih nlqlrvkets nenlrllhvi edrdrkvesl
1801 lnemkeldsk lhlqevqlmt kieacielek ivgelkkens dlsekleyfs cdhqellqrv
1861 etseglnsdl emhadkssre digdnvakvn dswkerfldv enelsrirse kasiehealy
1921 leadlevvqt eklclekdne nkqkvivcle eelsvvtser nqlrgeldtm skkttaldql
1981 sekmkektqe leshqseclh ciqvaeaevk ektellqtls sdvsellkdk thlqeklqsl
2041 ekdsqalslt kcelenqiaq lnkekellvk eseslqarls esdyeklnvs kaleaalvek
2101 gefalrlsst qeevhqlrrg ieklrvriea dekkqlhiae klkererend slkdkvenle
2161 relqmseenq elvildaens kaevetlktq ieemarslkv feldlvtlrs ekenltkqiq
2221 ekqgqlseld kllssfksll eekeqaeiqi keesktavem lqnqlkelne avaalcgdqe
2281 imkateqsld ppieeehqlr nsieklrarl eadekkqlcv lqqlkesehh adllkgrven
2341 lereleiart nqehaaleae nskgevetlk akiegmtqsl rgleldvvti rsekenltne
2401 lqkeqerise leiinssfen ilqekeqekv qmkeksstam emlqtqlkel nervaalhnd
2461 qeackakeqn lssqveclel ekaqllqgld eaknnyivlq ssvngliqev edgkqklekk
2521 deeisrlknq iqdqeqlvsk lsqvegehql wkeqnlelrn ltveleqkiq vlqsknaslq
2581 dtlevlqssy knlenelelt kmdkmsfvek vnkmtakete lqremhemaq ktaelqeels
2641 geknrlagel qllleeikss kdqlkeltle nselkksldc mhkdqvekeg kvreeiaeyq
2701 lrlheaekkh qallldtnkq yeveiqtyre kltskeecls sqkleidllk sskeelnnsl
2761 kattqileel kktkmdnlky vnqlkkener aqgkmkllik sckqleeeke ilqkelsqlq
2821 aaqekqktgt vmdtkvdelt teikelketl eektkeadey ldkycsllis heklekakem
2881 letqvahlcs qqskqdsrgs pllgpvvpgp spipsvtekr lssgqnkasg krqrssgiwe
2941 ngrgptpatp esfskkskka vmsgihpaed tegtefepeg lpevvkkgfa diptgktspy
3001 ilrrttmatr tsprlaaqkl alsplslgke nlaesskpta ggsrsqkvkv aqrspvdsgt
3061 ilrepttksv pvnnlpersp tdspreglrv krgrlvpspk aglesngsen ckvq
```

FIG. 1D

```
   1 gattgtggga aggcagctga actcggcgcc tggaaagatg gaggcagcgg agacagaggc
  61 ggaagctgca gccctagagg tcctggctga ggtggcaggc atcttggaac ctgtaggcct
 121 gcaggaggag gcagaactgc cagccaagat cctggttgag tttgtggtgg actctcagaa
 181 gaaagacaag ctgctctgca gccagcttca ggtagcggat ttcctgcaga acatcctggc
 241 tcaggaggac actgctaagg gtctcgaccc cttggcttct gaagacacga gccgacagaa
 301 ggcaattgca gctaaggaac aatggaaaga gctgaaggcc acctacaggg agcacgtaga
 361 ggccatcaaa attggcctca ccaaggccct gactcagatg gaggaagccc agaggaaacg
 421 gacacaactc cgggaagcct tgagcagct ccaggccaag aaacaaatgg ccatggagaa
 481 acgcagagca gtccagaacc agtggcagct acaacaggag aagcatctgc agcatctggc
 541 ggaggtttct gcagaggtga gggagcgtaa gacagggact cagcaggagc ttgacagggt
 601 gtttcagaaa cttggaaacc tgaagcagca ggcagaacag gagcgggaca agctgcagag
 661 gtatcagacc ttcctccagc ttctgtatac cctgcagggt aagctgttgt tccctgaggc
 721 tgaggctgag gcagagaatc ttccagatga taaaccccag cagccgactc gaccccagga
 781 gcagagtaca ggagacacca tggggagaga ccctggtgtg tccttcaagg ctgttggtct
 841 acaacctgct ggagatgtaa atttgccatg acttcctgga ggacagcagc atggagaaag
 901 atcctagaaa aggcctctga cttccctcac ctcccaacca tcattacagg aaagactgtg
 961 aactcctgag ttcagcttga tttctgacta catcccagca agctctggca tctgtggatt
1021 aaaatccctg gatctctctc agttgtgtat ttgttcatct tcatatgctg gcaggaacaa
1081 ctattaatac agatactcag aagccaataa catgacagga gctgggactg gtttgaacac
1141 agggtgtgca gatggggagg gggtactggc cttgggcctc ctatgatgca gacatggtga
1201 atttaattca aggaggagga gaatgttttta ggcaggtggt tatatgtggg aagataattt
1261 tattcatgga tccaaatgtt tgttgagtcc tttcttgtg ctaaggttct tgcggtgaac
1321 cagaattata acagtgagct catctgactg ttttaggatg tacagcctag tgttaacatt
1381 cttggtatct ttttgtgcct tatctaaaac atttctcgat cactggtttc agatgttcat
1441 ttattatatt cttttcaaag attcagagat tggcttttgt catccactat tgtatgtttt
1501 gtttcattga cctctagtga taccttgatc tttcccactt tctgttttcg gattggagaa
1561 gatgtacctt ttttgtcaac tcttactttt atcagatgat caactcacgt atttggatct
1621 ttatttgttt tctcaaataa atatttaagg ttatacattt aaaaaaaaaa aaaaaaaaa
1681 aaaaaaa
```

FIG. 2A

```
   1 meaaeteaea aalevlaeva gilepvglqe eaelpakilv efvvdsqkkd kllcsqlqva
  61 dflqnilaqe dtakgldpla sedtsrqkai aakeqwkelk atyrehveai kigltkaltq
 121 meeaqrkrtq lreafeqlqa kkqmamekrr avqnqwqlqq ekhlqhlaev saevrrerktg
 181 tq**qeld<u>r</u>vfq kl**gnlkqqae qerdklqryq tflqllytlq gkllfpeaea eaenlpddkp
 241 qqptrpqeqs tgdtmgrdpg vsfkavglqp agdvnlp
```

FIG. 2B

```
   1 gagcgcctgc cgtttctcgg ggcgggacgg gggggcgggg actgggcgga gaggcgcgtg
  61 ctgctgcgtg cgtgcgcgcg cgccgcgggc gggccagtga aaccggcggc cctggcacgt
 121 gacctaggac cggctcaccg ggtcgcttgg tggctccgtc tgtctgtccg tccgcccgcg
 181 ggtgccatca tggcggacgc ggccagtcag gtgctcctgg gctccggtct caccatcctg
 241 tccagccgc tcatgtacgt gaaagtgctc atccaggtgg gatatgagcc tcttcctcca
 301 acaataggac gaaatatttt tgggcggcaa gtgtgtcagc ttcctggtct ctttagttat
 361 gctcagcaca ttgccagtat cgatgggagg cgcgggttgt tcacaggctt aactccaaga
 421 ctgtgttcgg gagtccttgg aactgtggtc catggtaaag ttttacagca ttaccaggag
 481 agtgacaagg gtgaggagtt aggacctgga aatgtacaga aagaagtctc atcttccttt
 541 gaccacgtta tcaaggagac aactcgagag atgatcgctc gttctgctgc taccctcatc
 601 acacatccct tccatgtgat cactctgaga tctatgtac agttcattgg cagagaatcc
 661 aagtactgtg gactttgtga ttccataata accatctatc gggaagaggg cattctagga
 721 tttttcgcgg gtcttgttcc tcgccttcta ggtgacatcc tttctttgtg gctgtgtaac
 781 tcactggcct acctcgtcaa tacctatgca ctggacagtg gggtttctac catgaatgaa
 841 atgaagagtt attctcaagc tgtcacagga ttttttgcga gtatgttgac ctatcccttt
 901 gtgcttgtct ccaatcttat ggctgtcaac aactgtggtc ttgctggtgg atgccctcct
 961 tactcccaa tatatacgtc ttggatagac tgttggtgca tgctacaaaa agaggggaat
1021 atgagccgag gaaatagctt attttccgg aaggtccccct ttgggaagac ttattgttgt
1081 gacctgaaaa tgttaatttg aagatgtggg gcagggacag tgacatttct gtagtcccag
1141 atgcacagaa ttatgggaga gaatgttgat ttctatacag tgtggcgcgc ttttttaata
1201 atcatttaat cttgggaaaa ttcaggtgtt tggtgtctgc cttttttgtt cttttttcca
1261 gcacaacata acttaccact gatactcccc ctttagttat tctgaattag gatatttttg
1321 ctccaaattc ttatttact taaccagaag ggaaaaaaag ttgtattttc ctgaagctac
1381 aggcacttg tcatgtgatt tttgagtctc aatttaaggc tttgtaaaat gaagagtaga
1441 attccaagaa aaatgagaaa taattttgta aaacttaaca aaatcactaa attaaactat
1501 atgggaggtt atgaattact ttttcttggg tagaccctaa aatgtcagta gcatgcacca
1561 gaatctgact cccattatgc ttctaagcac atttcattga ccttgtctct catacttcaa
1621 gaaaaggaca gtacattgct acattaccct agaaagtctg tgtgaggatc tgcccccttca
1681 gtctgttatt gcaaagtaat aaaatgtcac ctacagggag cctctgagcc tactctagtt
1741 caagaggcta cctgaaaaaa aataaataag ataaagggtc agcaacaaca aagaaaaaga
1801 caattacaga aaataagcaa gatttggaaa ggaagtataa tggcacttt ttcctcaaag
1861 gaagttcttg ttttcacata aaatatgaaa agcagatcct gcaggagtaa ccccccttctt
1921 taagagccaa gtatttgcca gtgcttaaat tacaccatac agttctaatt atatataatc
1981 ttttgttctt cagttttttg ttttgtttcc ttttttgttat tgttgccgaa ggtgagtagt
2041 tttgcatttc tgatgacagc cttggaaagt atatttgtaa ctccatgtct ggtaatgcca
2101 acccaagtcg acatgggtct taggacactg accacctcac atgccatacc ctcagttaag
2161 catgttaaca tttataggag gaaaaaatc actttgggag aaaataaaat tcaactcaag
2221 cataaagctt ctgttactc aggccttcta aaaagcaggt taaatgctc taaaatgaga
2281 aagcctgtgg tttcacttat ttatataact cactggagca ttgccaaatg agtaagcact
2341 taattcgctg cttctgagac ttctctgtca aaacagcccc actgataata ttagacagaa
2401 cgagaatgca ggggtctctt ccctcccctg gggtttagga agctcatgag gagctcggct
2461 taaaatgtct ttgatgtctc ttccttttgc tcaaaaagta atgtcaattt tatatactat
2521 ttcaatatta ctatctgcat ttgttttaat ataaaaatgt ttgctgccta ccttttttctc
2581 ccaaaaaatc tttaagtaaa gatgatctgg gaaaatgtgc catgttta
```

FIG. 3A

```
  1 madaasqvll gsgltilsqp lmyvkvliqv gyeplpptig rnifgrqvcq lpglfsyaqh
 61 iasidgrrgl ftgltprlcs gvlgtvvhgk vlqhyqesdk geelgpgnvq kevsssfdhv
121 ikettremia rsaatlithp fhvitlrsmv qfigreskyc glcdsiitiy reegilgffa
181 glvprllgdi lslwlcnsla ylvntyalds gvstmnemks ysqavtgffa smltypfvlv
241 snlmavnncg laggcppysp iytswidcwc mlqkegnmsr gnslffrkvp fgktyccdlk
301 mli
```

FIG. 3B

```
   1 agaaacactt ggtttcatgt atgactcata agctgaagca cagacaccac ttccccaatc
  61 tacaggagcc attttaacag ctaaaacttg tcggattgct ttttattttc aagctcaaaa
 121 gacgatagag aaagaatact tgaaggccaa gaagcttgag agaagaaaaa tttcagaaaa
 181 attgtctcaa tttgactaga atatcaatga accaggaaaa ctgaagcacc ttccctaaag
 241 aaaacttggg tatacaatta ctccacagac agagctgagg gttttttacc caaatcagtc
 301 actggatttt gctgcctgat acgtgaatct tcttggaatt tttctcatgt ggatctaagg
 361 ggaatgcttt attatggctg ctgttgtcca acagaacgac ctagtatttg aatttgctag
 421 taacgtcatg gaggatgaac gacagcttgg tgatccagct attttcctg ccgtaattgt
 481 ggaacatgtt cctggtgctg atattctcaa tagttatgcc ggtctagcct gtgtggaaga
 541 gcccaatgac atgattactg agagttcact ggatgttgct gaagaagaaa tcatagacga
 601 tgatgatgat gacatcaccc ttacagttga agcttcttgt catgacgggg atgaaacaat
 661 tgaaactatt gaggctgctg aggcactcct caatatggat tcccctggcc ctatgctgga
 721 tgaaaaacga ataaataata atatatttag ttcacctgaa gatgacatgg ttgttgcccc
 781 agtcacccat gtgtccgtca cattagatgg gattcctgaa gtgatggaaa cacagcaggt
 841 gcaagaaaaa tatgcagact caccgggagc ctcatcacca gaacagccta agaggaaaaa
 901 aggaagaaaa actaaaccac cacgaccaga ttccccagcc actacgccaa atatatctgt
 961 gaagaagaaa aacaaagatg gaaagggaaa cacaatttat ctttgggagt ttttactggc
1021 actgctccag gacaaggcta cttgtcctaa atacatcaag tggacccagc gagagaaagg
1081 catttttaaa ttggtggatt ctaaagcagt gtccaggttg tgggggaagc acaaaaacaa
1141 acctgatatg aattatgaga ccatggaag agcactcagg tactattacc aaaggggtat
1201 tctggcaaaa gtggaaggtc agcgcttggt gtatcagttt aaagaaatgc caaaagatct
1261 tatatatata aatgatgagg atccaagttc cagcatagag tcttcagatc catcgctatc
1321 ttcatcagcc acttcaaata ggaatcaaac cagccggtcg agagtatctt caagtccagg
1381 ggtaaaagga ggagccacta cagttctaaa accagggaat tctaaagctg caaaacccaa
1441 agatcctgtg gaagttgcac aaccatcaga agttttgagg acagtgcagc ccacgcagtc
1501 tccatatcct acccagctct tccggactgt tcatgtagta cagccagtac aggctgtccc
1561 agagggagaa gcagctagaa ccagtaccat gcaggatgaa acattaaatt cttccgttca
1621 gagtattagg actatacagg ctccaaccca agttccagtg gttgtgtctc ctaggaatca
1681 gcagttgcat acagtaacac tccaaacagt gccactcaca acagttatag ccagcacaga
1741 tccatcagca ggtactggat ctcagaagtt tattttacaa gccattccat catcacagcc
1801 catgacagta ctgaaagaaa atgtcatgct gcagtcacaa aaggcgggct ctcctccttc
1861 aattgtcttg ggccctgccc aggttcagca ggtccttact agcaatgttc agaccatttg
1921 caatggaacc gtcagtgtgg cttcctctcc atccttcagt gctactgcac ctgtggtgac
1981 cttttctcct cgcagttcac agctggttgc tcacccacct ggcactgtaa tcacttcagt
2041 tatcaaaact caagaaacaa aaactcttac acaggaagta gagaaaaagg aatctgaaga
2101 tcatttgaaa gagaacactg agaaaacgga gcagcagcca cagccttatg tgatggtagt
2161 gtccagttcc aatggattta cttctccaggt agctatgaaa caaaacgaac tgctggaacc
2221 caactctttt tagttaatat accaaagctt atgaataatt gtttgttaat tgaacatttt
2281 caattatatg cagactgact gattctaaga taaattctaa ggaggtttct aattttgtaa
2341 ttgttaaaaa tagagttaat tttgactttg ttagatgagg gaggaaaact caactgtttc
2401 tctttgttat ctaaatgttt cagaattcaa tcgtgaagga acaggcattt tacactatga
2461 agacattctt ttgagatttt tatttcagtt gctatatcat aagcattttt aaagtttctt
2521 ttctaatttt acattgtatt agatttctg attcttttgt aaatacagaa cttaaataga
2581 aggcaacagg aaatttatat aggaactatt ttcattccac ttgtgtaagt taagtcttga
2641 ctctttcaaa tgcaaaaaac ctattttatg ctttgttaaa attatggtgt cacttagatt
2701 gactttagtt gactgcacta tataatatag aactatgaat atgtagaata acatgaaaaa
2761 ttggaggtgc tggtggtatg gctgaccctg tttcagaagc aggatagtat aaaagcatca
2821 gcctaagaat ggcactccca ctaactagct atgtaatctt gacctctttg ggctttagtt
2881 cctctcataa aaggaagaga tgtattggat tagactagat gatcaccact ttctcttcta
2941 gttctaatt ttttaattct aatacctata ttttcaagtt atgtcaatta atcattatc
3001 aggttatttc ctaatgtaag aatagctaaa atgttgcaga gaataagtg acccaacaaa
3061 atttattcat ctgttatggg taagatctgc cataaattct tcctaaataa tttgtttact
3121 aactctttag gccactgtgc tttgcggtcc attagtaaac ttgtgttgct aagtgctaaa
3181 cagaatactg ctattttgag agagtcaaga ctctttctta agggccaaga aagcaacttg
3241 agccttgggc taatctggct gagtagtcag ttataaaagc ataattgctt tatattttgg
3301 atcatttttt actggggggcg gacttggggg gggttgcata caaagataac atatatatcc
3361 aactttctga aatgaaatgt tttagatta cttttcaac tgtaaataat gtacatttaa
3421 tgtcacaaga aaaaaatgtc ttctgcaaat tttctagtat aacagaaatt tttgtagatg
3481 aaaaaaatca ttatgtttag aggtctaatg ctatgttttc atattacaga gtgaatttgt
```

FIG. 4A

```
3541 atttaaacaa aaatttaaat tttggaatcc tctaaacatt tttgtatctt taattggttt
3601 attattaaat aaatcatata aaaattctca gtgtctgttt tcaggcaaaa gtttcttaaa
3661 gaataagtgt gcagagaata ttactagaac atcagcatta cttaatgttt ataaataaat
3721 ttcattagtc agaattgcaa aaaaaaaaaa aaaaaaaaa
```

FIG. 4B

```
  1 maavvqqndl vfefasnvme derqlgdpai fpavivehvp gadilnsyag lacveepndm
 61 itessldvae eeiidddddd itltveasch dgdetietie aaeallnmds pgpmldekri
121 nnnifssped dmvvapvthv svtldgipev metqqvqeky adspgasspe qpkrkkgrkt
181 kpprpdspat tpnisvkkkn kdgkgntiyl wefllallqd katcpkyikw tqrekgifkl
241 vdskavsrlw gkhknkpdmn yetmgralry yyqrgilakv egqrlvyqfk empkdliyin
301 dedpsssies sdpslsssat snrnqtsrsr vssspgvkgg attvlkpgns kaakpkdpve
361 vaqpsevlrt vqptqspypt qlfrtvhvvq pvqavpegea artstmqdet lnssvqsirt
421 iqaptqvpvv vsprnqqlht vtlqtvpltt viastdpsag tgsqkfilqa ipssqpmtvl
481 kenvmlqsqk agsppsivlg paqvqqvlts nvqticngtv svasspsfsa tapvvtfspr
541 ssqlvahppg tvitsviktq etktltqeve kkesedhlke ntekteqqpq pyvmvvsssn
601 gftsqvamkq nellepnsf
```

FIG. 4C

```
   1 ccgcccttgt aggctgtcca cctcaaacgg gccggacagg atatataaga gagaatgcac
  61 cgtgcactac acacgcgact cccacaaggt tgcagccgga gccgcccagc tcaccgagag
 121 cctagttccg gccagggtcg ccccggcaac cacgagccca gccaatcagc gccccggact
 181 gcaccagagc catggtcggc agaagagcac tgatcgtact ggctcactca gagaggacgt
 241 ccttcaacta tgccatgaag gaggctgctg cagcggcttt gaagaagaaa ggatgggagg
 301 tggtggagtc ggacctctat gccatgaact tcaatcccat catttccaga aaggacatca
 361 caggtaaaact gaaggaccct gcgaacttc agtatcctgc cgagtctgtt ctggcttata
 421 aagaaggcca tctgagccca gatattgtgg ctgaacaaaa gaagctggaa gccgcagacc
 481 ttgtgatatt ccagttcccc ctgcagtggt ttggagtccc tgccattctg aaaggctggt
 541 ttgagcgagt gttcatagga gagtttgctt acacttacgc tgccatgtat gacaaaggac
 601 ccttccggag taagaaggca gtgctttcca tcaccactgg tggcagtggc tccatgtact
 661 ctctgcaagg gatccacggg gacatgaatg tcattctctg gccaattcag agtggcattc
 721 tgcattcttg tggcttccaa gtcttagaac ctcaactgac atatagcatt gggcacactc
 781 cagcagacgc ccgaattcaa atcctggaag gatggaagaa acgcctggag aatatttggg
 841 atgagacacc actgtatttt gctccaagca gcctctttga cctaaacttc caggcaggat
 901 tcttaatgaa aaaagaggta caggatgagg agaaaaacaa gaaatttggc ctttctgtgg
 961 gccatcactt gggcaagtcc atcccaactg acaaccagat caaagctaga aaatgagatt
1021 ccttagcctg gatttccttc taacatgtta tcaaatctgg gtatctttcc aggcttccct
1081 gacttgcttt agtttttaag atttgtgttt ttctttttcc acaaggaata aatgagaggg
1141 aatcgactgt attcgtgcat ttttggatca tttttaactg attcttatga ttactatcat
1201 ggcatataac caaaatccga ctgggctcaa gaggccactt agggaaagat gtagaaagat
1261 gctagaaaaa tgttctttaa aggcatctac acaatttaat tcctctttttt agggctaaag
1321 ttttagggta cagtttggct aggtatcatt caactctcca atgttctatt aatcacctct
1381 ctgtagttta tggcagaagg gaattgctca gagaaggaaa agactgaatc tacctgccct
1441 aagggactta acttgtttgg tagttagcca tctaatgctt gtttatgata ttcttgctt
1501 tcaattacaa agcagttact aatatgccta gcacaagtac cactcttggt cagcttttgt
1561 tgtttatata cagtacacag ataccttgaa aggaagagct aataaatctc ttctttgctg
1621 cagtcatcta cttttttttt aattaaaaaa aattttttt tgaagcagtc ttgctctgtt
1681 acccaggctg gagtgcagtg gtgtgatctc ggctcactgc aacctctgcc tcccaggttc
1741 cagcaattct cctgcctcag cctccctagt agctgggatg acaggcgcct gccatcatgc
1801 ctgactaatt tttgtatttt tagtagagac ggcgtttcac catgttggcc aggctggtct
```

FIG. 5A

```
1861 caaactcctg acctcaggtg atccgcctac ctcagcctcc caaagtgctg ggattacagg
1921 cgtgatccac cacacctggc ccttgcaatc ttctacttta aggtttgcag agataaacca
1981 ataaatccac accgtacatc tgcaatatga attcaagaaa ggaaatagta ccttcaatac
2041 ttaaaaatag tcttccacaa aaaatacttt atttctgatc tatacaaatt ttcagaaggt
2101 tattttcttt atcattgcta aactgatgac ttactatggg atgggtcca gtcccatgac
2161 cttggggtac aattgtaaac ctagagtttt atcaactttg gtgaacagtt ttggcataat
2221 agtcaatttc tacttctgga agtcatctca ttccactgtt ggtattatat aattcaagga
2281 gaatatgata aaacactgcc ctcttgtggt gcattgaaag aagagatgag aaatgatgaa
2341 aaggttgcct gaaaaatggg agacagcctc ttacttgcca agaaaatgaa gggattggac
2401 cgagctggaa aacctccttt accagatgct gactggcact ggtggttttt gctctcgaca
2461 gtatccacaa tagctgacgg ctgggtgttt cagtttgaaa atattttgtt gccttcatct
2521 tcactgcaat tttgtgtaaa tttctcaaag atctgaatta aataaataaa attcatttct
2581 acagacccac aaaaaaaaaa a
```

FIG. 5B

```
  1 mvgrralivl ahsertsfny amkeaaaaal kkkgwevves dlyamnfnpi isrkditgkl
 61 kdpanfqypa esvlaykegh lspdivaeqk kleaadlvif qfplqwfgvp ailkgwferv
121 figefaytya amydkgpfrs kkavlsittg gsgsmyslqg ihgdmnvilw piqsgilhfc
181 gfqvlepqlt ysightpada riqilegwkk rleniwdetp lyfapsslfd lnfqagflmk
241 kevqdeeknk kfglsvghhl gksiptdnqi kark
```

FIG. 5C

```
   1 ggatttctag gaggaccggc agaggcgcgc ataggtgcgt ggtgctgggc ccgggcgccg
  61 cggcaccggt gtaggagcgc gcatctccag agtttcttcc atctgggcga cgtctcggtg
 121 cctgcgcgg gaacgcgct ttgcttccct gaggagcttc tagagagcta cggtggcccc
 181 cgtgtgggag gcggggggcg tggcggcgtc ggggcgtcgc tgtccctcc tcggtagctc
 241 tcctccctcc cctttctgct gttaccggga gcgcggtggc cacggaacgc tgcccggagc
 301 cgcgcgaggg aggacccgac gcgcggcgtt tacccagcgc agcgttccac cgctcgggtt
 361 tggctggata aaataaaaaa tggggatatt gacctcctgt cactactgca tgactttga
 421 tggtttccaa tcattacttt ctcctctgtg tcaatctgcc tcttcgagaa attcatactc
 481 ctgaatagct ctccagaccc ccagctggcc atgtggtgag ttcagggccc aaatcaagta
 541 gtaccagcaa tcagggaact cctatctgtt ttgaatggat tcacaccagc cacaagcctg
 601 gaaagatggt gtcacaatct acagtcaggc aggattctcc tgtggagccc tgggaaggga
 661 tcagcgatca ctctggcatt attgatggtt cgcccagact cctgaacact gaccatcctc
 721 cttgccaatt agacatcagg ctcatgaggc acaaagctgt ctggattaac ccccaggatg
 781 tgcagcaaca gccgcaggac ttgcaatctc aggtgccagc agcagggaac agtgggaccc
 841 attttgtgac agatgctgcc tctccctcag gcccttcacc ttcgtgcctc ggggactccc
 901 tggcagagac aacgttgtct gaggatacca cagactccgt tggcagcgct tctccccatg
 961 gctcgagtga aaagagtagc agcttctctc tgtcctcaac agaggtacac atggtccgcc
1021 caggatactc tcatcgggtg tctctgccca caagccctgg gattttgcc acctccccat
1081 atcctgagac tgacagtgct ttttttgagc cttcccatct gacatctgct gctgatgaag
1141 gtgctgttca agtcagtaga gaaccatttt cttcgaattc cttctcacca gaggtatttg
1201 tgctgcctgt tgatgtagaa aaggaaaatg cccactttta tgttgcagat atgattatat
1261 cagcaatgga gaaaatgaag tgtaacattc tgagtcaaca gcagacagag agctggagta
1321 aagaagtcag tgggttactt gggagtgatc agcctgactc tgaaatgact tttgatacca
1381 acataaagca agagtctggg tcttctactt cttcatacag tggctatgaa ggttgtgctg
1441 tgttacaggt cagcccagtg actgaaacac gtacttacca tgatgtgaaa gagatttgca
1501 aatgcgatgt tgatgaattt gttatttag agcttggaga ttttaatgat atcacagaaa
1561 cctgtagctg ttcctgcagc tcctctaaga gtgtcactta tgagccagac ttcaattctg
1621 cagaactatt agccaaagag ctgtaccgcg tgttccagaa gtgctggata ctgtcagtag
1681 ttaattctca gctggcaggt tccctgagtg cagctggctc gatagtcgta aatgaagagt
1741 gtgtccgaaa agactttgaa tccagtatga atgtagtaca ggaaattaaa tttaagtcta
```

FIG. 6A

```
1801 ggatcagagg gactgaagac tgggctcctc ctagatttca aatcatattt aatattcatc
1861 caccactcaa gagggacctt gtggtggcag cccagaattt tttctgtgcc ggctgtggaa
1921 ctccagtaga gcctaagttt gtgaagcggc tccggtactg cgaataccta gggaagtatt
1981 tctgtgactg ctgccactca tatgcagagt cgtgcatccc tgcccgaatc ctgatgatgt
2041 gggacttcaa gaagtactac gtcagcaatt tctccaaaca gctgctcgac agcatatggc
2101 accagcccat tttcaatttg ctgagcatcg gccaaagcct gtatgcgaaa gccaaggagc
2161 tggacagagt gaaggaaatt caggagcagc tcttccatat caagaagctg ttgaagacct
2221 gtaggtttgc taacagtgca ttaaaggagt tcgagcaggt gccgggacac ttgactgatg
2281 agctccacct gttctccctt gaggacctgg tcaggatcaa gaaagggctg ctggcaccct
2341 tactcaagga cattctgaaa gcttcccttg cacatgtggc tggctgtgag ctgtgtcaag
2401 gaaagggctt tatttgtgaa ttttgccaga atacgactgt catcttccca tttcagacag
2461 caacatgtag aagatgttca gcgtgcaggg cttgctttca caaacagtgc ttccagtcct
2521 ccgagtgccc ccggtgtgcg aggatcacag cgaggagaaa acttctggaa agtgtggcct
2581 ctgcagcaac atgatgcccc tgagtactgt gaaaaagact gttcaacatg ccttatgata
2641 acaccgattt gtgtctatta ttggtgacat tgttttagat attgggtatt gtatattaag
2701 gaaaaagatg gtctatattc tctttattgc atatacttaa tgtttcaaaa gaatgcagat
2761 tctgtgttta agcacagggc tgatagttgt ggttttgttt acaaatgttc tgttttggct
2821 gctattggtt tttttaaagag gtttttttata cttttgtatt tgaatagtta tgtttcactg
2881 atgctgagcc agtttgtatg tgtgtgcata tatgtgaact gtaactgaca agatgaatta
2941 ctcagtttct ctttctctaa agcttgtttg atgaaactgg ttggtccttt cagtgaacaa
3001 aaatatgacc ccaaatctgt ttgctctggc ttttatttct tcaggaagca gacttccact
3061 taaatgccat tttgtgattg tgtcaatcat acacatttta tttacttcag agtttgaata
3121 gagagtacac atttcttctg cagatttatt tcatgatgag tttgagttgc ttagcagggc
3181 gtgtgggtcc cgttgaagtg cagtttgaag caactgcttc tagatggcac tctttcaggt
3241 ggcacaaatt gaacctgtat ttgtcatctc tgttccacac actgcaatgt caagggatgc
3301 agaagtgagt agaattccat ccctgccctt gaggatccttg ctttaacaga tgtaaaactg
3361 aacataaggt atttgcagat ttaaacgaac tgggggaaat aatgaacagt gtgattctag
3421 taataacatt aaaatcatag acattgacta ataaggttaa atgaatcaca aaacctttat
3481 gaatttcttt tttctaatag ttcttatatg ttttcctgaa acatgtgagc ctattctttt
3541 ttcttctact ttctatatac tttctcccac ttgagaaagg ggccttgagg ctgggtccct
3601 tcatggtata cctttagact gaacggtttg caacctaggg cttgggcatt acattccctg
3661 ggattcacat gccctaacta aacctacctt gattttctca gacagcacag gcaggcaata
3721 aagcgtcaca gattgtcccc taacccccatc cagccatgtg tatgagtgtg ttttattcaa
3781 tgggatagta ctgagcacat gaaagaaatg aatgacttct gtcaatctct tttcattcag
3841 tcttctcatt ctgtcaattg ttttctcatc cgcagtgcct ctgccagaac tgtgctcaca
3901 tccattattt aagccagatc ttttctaagt attatagaag tgtagaggca catagaataa
3961 ataaaaccag acttcaaaaa aaaaaaaaaa aaa
```

FIG. 6B

```
  1 mvsqstvrqd spvepwegis dhsgiidgsp rllntdhppc qldirlmrhk avwinpqdvq
 61 qqpqdlqsqv paagnsgthf vtdaaspsgp spsclgdsla ettlsedttd svgsasphgs
121 seksssfsls stevhmvrpg yshrvslpts pgilatspyp etdsaffeps hltsaadega
181 vqvsrrtiss nsfspevfvl pvdvekenah fyvadmiisa mekmkcnils qqqteswske
241 vsgllgsdqp dsemtfdtni kqesgsstss ysgyegcavl qvspvtetrt yhdvkeickc
301 dvdefvilel gdfnditetc scscsssksv tyepdfnsae llakelyrvf qkcwilsvvn
361 sqlagslsaa gsivvneecv rkdfessmnv vqeikfksri rgtedwappr fqiifnihpp
421 lkrdlvvaaq nffcagcgtp vepkfvkrlr yceylgkyfc dcchsyaesc iparilmmwd
481 fkkyyvsnfs kqlldsiwhq pifnllsigq slyakakeld rvkeiqeqlf hikkllktcr
541 fansalkefe qvpghltdel hlfsledlvr ikkgllapll kdilkaslah vagcelcqgk
601 gficefcqnt tvifpfqtat crrcsacrac fhkqcfqsse cprcaritar rkllesvasa
661 at
```

FIG. 6C

```
   1 aaaccatggg ggcggaagag gtgctgggca ggaggcggaa gaggtgctgt gcaggaggcg
  61 ggcgggcgcg gttctttccg gaaggattga atctccttta gccccgcccg cctccgtagc
 121 tgcctgaagt agtgcagggt cagcccgcaa gttgcaggtc atggcgctgg ctgctcgact
 181 gtggcgcctt ctgcctttcc gacgtggagc cgccccgggg tctcgtctcc ctgcggggac
 241 ttcgggcagc cgcgggcatt gcggcccctg tcgattccgc ggcttcgagg taatgggaaa
 301 cccaggaact ttcaaaagag gccttttact ctcagctttg tcgtatttgg gttttgaaac
 361 ttaccaggtt atctctcagg ctgctgtggt tcatgccaca gccaaagttg aagaaatact
 421 tgaacaagca gactacctgt atgaaagcgg agaaacagaa aaactttatc agttgctaac
 481 ccaatacaag gaaagtgaag atgcagagtt actgtggcgt ttggcacggg catcacgtga
 541 tgtagctcag cttagcagaa cctcagaaga ggagaaaaag ctattggtgt atgaagccct
 601 agagtatgca aaaagagcac tagaaaaaaa tgaatcaagt tttgcatctc ataagtggta
 661 tgcaatctgc cttagtgatg ttggagatta tgaaggcatc aaggctaaaa ttgcaaatgc
 721 atatatcatc aaggagcatt ttgagaaagc aattgaactg aaccctaaag atgctacttc
 781 aattcacctt atgggtattt ggtgctatac atttgccgaa atgccttggt atcaaagaag
 841 aattgctaaa atgctgtttg caactcctcc tagttccacc tatgagaagg ccttaggcta
 901 ctttcacagg gcagaacaag tggatccaaa cttctacagc aaaaacttac ttcttttagg
 961 aaagacatac ttgaaactac acaacaaaaa gcttgctgct ttctggctaa tgaaagccaa
1021 ggactatcca gcacacacag aggaggataa acagatacag acagaagctg ctcagttgct
1081 tacaagtttc agtgagaaga attgagaact tttcagagaa gatttatgaa atagctaata
1141 aacattgcct ttttcttttaa ttctaaactt aatatatgaa ctataactgt tctacggctt
1201 tttaaatgtt gtgaccattt aaccgtgtaa atataaaata ttctaggctt cttcacaaat
1261 aataggtaa aataaataat cgccataaga gtggtagaaa taaatctcca tggctcaggc
1321 aaagagatta ttttgcatcc tggataccag caatgcaaaa tggtatgaga tttctaagga
1381 ttgatcacat tgggatggga gatcaagcaa agaaatattt gtagaggagg ggaaatggat
1441 ctataggga tatacagggg gatggatttt caaattggat tgattctaag ttgaaatctt
1501 gaagagaagg tgtggtgaca gtggttagga tgttgtgggt tcctgacata agtagttaa
1561 atgatatatc ttggagctaa cctgtgtaag taagaacta agtaaggaga tgactaaaaa
1621 tggagtagtt tcctttttta tttttttgag acagagtctc actttgtttc ccaggctggt
1681 gtgcagtggc acaatctcgg cccactgcag cctccgcctc ccgggttcaa gtgattctcc
1741 tgccttagcc tcctgagtgg ctggattac agggttgtac caccacactc ggctaacttt
1801 tgtattttg gtagagatgg ggttttgcca tgttggctag gctggtctca aactcctggc
1861 ctcaagtgat ctgcccgcct tggcctccca aattgctggg attacaggcg tgagccaccg
1921 cacctggcca gtttacttta aatgtggtgt agtctcatgg taaactgaat ttgtcatcag
1981 atgcaaagtt ctattcccta atggaatgga aggaacacaa aacttaagag tgaaatggaa
2041 tactaagatg ttttttaaata ggcaggacta tgctactcac ttgaggctgg agtgccacca
2101 ctgcaaaatc tttttaagtt ttgtaaaaag gagcatcttg aatccactta gataaagaca
2161 gactgtgtgt gtaggtggat ttttcccaaa ggatttggga attgtaatgt tacaatgaac
2221 tgtatggata tgtttgtcat gtacattttc aaacaaaaag gaaaactgaa agtagtgatc
2281 tttgtatacc catctcttag attcagtgat tttgctatat aggttgtgta tcccttatct
2341 gaaatacttg ggactagtag aagcatcttg gatttgggat gttttttccaa attttggaat
2401 acctgcatac acacaataag atatcttgga gatgggaccc aagtttaaac acaaattcac
2461 ttgtttcata tataccttat gcacatagct tgaaggtaac tttatataac attattttta
2521 ataatttgt gcattgagac caagtttgca taccttgaac catcagaaag caaaggtgtc
2581 attatctcag ccactcatgt gggtaatttg tggttggttg atgtcaccat cattcctgac
2641 tgaatgtata tgctaccaat aagcagttat tttcttatac ttattcatgc ataagtactt
2701 aacagtaaaa aatatgacat aactcgcaca ggaacaagga tggcaaaaaa aaaaatatga
2761 cacaccactg atacagtgaa aaaataatgt ggtcagggta gctaggcaac agtagcatca
2821 ccagaaacct gtatcagctg ttaaacggca acaacaatgg caggctttca gtttcccact
2881 taatgatgct gtattttaaa aggttattgt atactgtaat tttattttg taggtgaaga
2941 gaaacagaag cagctgaagg gccaggaagt gggtcttttct agggatgtgg cattctgctg
3001 gatggctttt taaaatgggt tttttccttt agggagaccg aataaactgt gttgtgcacc
3061 tgca
```

FIG. 7A

```
  1 malaarlwrl lpfrrgaapg srlpagtsgs rghcgpcrfr gfevmgnpgt fkrglllsal
 61 sylgfetyqv isqaavvhat akveeileqa dylyesgete klyqlltqyk esedaellwr
121 larasrdvaq lsrtseeekk llvyealeya kralekness fashkwyaic lsdvgdyegi
181 kakianayii kehfekaiel npkdatsihl mgiwcytfae mpwyqrriak mlfatppsst
241 yekalgyfhr aeqvdpnfys knlllllgkty lklhnkklaa fwlmkakdyp ahteedkqiq
301 teaaqlltsf sekn
```

FIG. 7B

METHOD FOR IDENTIFYING NOVEL MINOR HISTOCOMPATIBILITY ANTIGENS

CROSS-REFERENCE TO RELATED APPLICATIONS

This application is a continuation of U.S. patent application Ser. No. 14/421,310, filed Feb. 12, 2015, which is a 35 U.S.C. § 371 national phase application of PCT/CA2013/050580, filed Jul. 25, 2013, which claims the benefit of U.S. provisional application Ser. No. 61/683,361, filed on Aug. 15, 2012, and of U.S. provisional application Ser. No. 61/818,040, filed on May 1, 2013, which are incorporated herein by reference in their entirety.

TECHNICAL FIELD

The present invention generally relates to histocompatibility antigens, and more specifically to minor histocompatibility antigens (MiHAs), identification and use thereof.

SEQUENCE LISTING

Pursuant to 37 C.F.R. 1.821(c), a sequence listing is submitted herewith as an ASCII complaint text file named "585721 GGT-009USCON Sequence Listing-TXT.txt", created on Feb. 12, 2015 and having a size of ~147 kilobytes. The content of the aforementioned file is hereby incorporated by reference in its entirety.

BACKGROUND ART

Histocompatibility antigens are a group of cell membrane alloantigens that are recognized by T lymphocytes and thereby initiate graft rejection or graft-versus-host disease (GVHD) following transplantation (1). In the early days of immunogenetics, the identification of major histocompatibility complex (MHC) antigens was based on their strong immunogenicity in skin transplant experiments between congenic-resistant strains of mice. Other less potent antigens were called minor histocompatibility antigens (MiHA). It soon became obvious that a distinction between major and minor antigens based solely on their immunogenicity was imprecise, as some MHC antigens are weak immunogens while some MiHA appear "neither weak nor minor" (2;3) It is now known that MHC antigens (also referred to as HLA antigens) are transmembrane glycoproteins encoded by closely linked polymorphic loci located on chromosome 6 in humans. Their primary role is to bind endogenous and exogenous peptides that are scrutinized by T cells. MHC (or HLA) molecules present thousands of peptides at the surface of human cells (4;5). These MHC-associated peptides (MAPs) are referred to as the immunopeptidome and they originate from proteasomal processing and further processing of endogenous proteins (6-8). The immunopeptidome of identical twins (also referred to as syngeneic subjects) is identical. By contrast, MAPs present on cells from HLA-identical non-syngeneic subjects are classified into two categories: i) invariant MAPs which are present in all subjects with a given HLA type, and ii) MiHAs which are MAPs present in some but absent in other subjects (9). When T cells are transplanted into an MHC-identical host, they react promptly and specifically to what they see as non-self: host-specific MiHAs. MiHAs are essentially genetic polymorphisms that are immunogenic for T cells. MiHAs are a consequence of any form of accumulated genetic variation that translates to differential MAP display (3;9-13).

Two main strategies can be used for cancer immunotherapy: vaccination and adoptive T-cell immunotherapy (ATCI). The term "ATCI" refers to transfusion of T lymphocytes that may come from different types of donors: the patient (autologous), a genetically-identical twin (syngeneic), or a non-identical donor (allogeneic). To date, ATCI has yielded much higher cancer remission and cure rates than vaccines, and the most widely used form of cancer ATCI is allogeneic hematopoietic cell transplantation (AHCT) (17-22). The graft-versus-tumor (GVT) effect induced by allogeneic AHCT is due mainly to T-cell responses against host MiHAs: GVT is abrogated if the donor is an identical twin (no MiHA differences with the recipient) or if the graft is T-cell depleted (20;23). More than 200,000 individuals treated for hematological malignancies owe their life to the MiHA-dependent GVT effect which represents the most striking evidence of the ability of the human immune system to eradicate neoplasias (18;24-28). Though the allogeneic GVT effect is being used essentially to treat patients with hematologic malignancies, preliminary evidence suggests that it may be also effective for the treatment of solid tumors (29-33). Nonetheless, the considerable potential of MiHA-targeted cancer immunotherapy has not been properly exploited in medicine. In current medical practice, MiHA-based ATCI is limited to "conventional" AHCT, that is, injection of hematopoietic cells from an allogeneic HLA-matched donor. Such unselective injection of allogeneic lymphocytes is a very rudimentary form of MiHA-targeted therapy. First, it lacks specificity and is therefore highly toxic: unselected allogeneic T cells react against a multitude of host MiHAs and thereby induce GVHD in 60% of recipients. GVHD is always incapacitating and frequently lethal (34-38). Second, conventional AHCT induces only an attenuated form of GVT reaction because donor T cells are not being primed (pre-activated) against specific MiHAs expressed on cancer cells prior to injection into the patient. While primed T cells are resistant to tolerance induction, nave T cells can be tolerized by tumor cells (39-42).

It has been demonstrated in mice models of AHCT that, by replacing unselected donor lymphocytes with CD8 T cells primed against a single MiHA, it was possible to cure leukemia and solid tumors without causing GVHD or any untoward effect (33;43;44). Success depends on two main points: selection of an immunodominant (highly immunogenic) MiHA expressed on neoplastic cells, and priming of donor CD8 T cells against the target MiHA prior to AHCT. A recent article (20) describes why MiHA-targeted ATCI is so effective and how translation of this approach in the clinic could have a significant impact on cancer immunotherapy. Implementation of MiHA-targeted ATCI in humans has been limited mainly by the paucity of molecularly defined human MiHAs. Thus, only 33% of patients with leukemia would be eligible for MiHA-based ATCI (15).

Human MiHAs have been discovered using reductionist T-cell based methods. Starting with cytotoxic T lymphocytes (CTLs) from an individual reactive against cells of another HLA-identical subject, investigators have tried and identified MiHAs recognized by these T cells. Different methods have used to do so. First, CTLs were tested on MiHA-negative cells coated with MAPs eluted from MiHA-positive cells. The MAP eluates were fractionated and ultimately the MiHA recognized by CTLs was sequenced by mass spectrometry (MS) (48-53). Second, CTLs were used to screen MiHA-negative cells transfected with cDNA libraries to identify MiHA-coding transcripts (16;54-59). Finally, CTLs have been tested on lymphoblastoid cell lines from many subjects and linkage analyses were performed (based for instance on whole genome association scans or HapMap resources) on lines recognized or not by CTLs (60-67).

The various methods used to discover MiHAs present significant caveats. Firstly, they are not really suitable for high-throughput MiHA discovery: MiHA discovery is made one by one and depends on the availability of a CTL line. Secondly, only MiHAs that have been eluted from living cells and identified by MS can be considered to be validated (direct identification). In the other cases (indirect identification), uncertainty remains as to the exact structure of MiHAs naturally presented at the cell surface (an important criterion for MiHA-targeted immunotherapy). The ambiguity stems mainly from two factors: i) T cells are eminently cross-reactive and can recognize more than one peptide (68); ii) bioinformatic tools used for identification of MAPs in general and MiHAs in particular do not have sufficient reliability to replace direct proteomic identification (69-71).

Thus, there is a need for novel approaches for the identification of MiHAs.

The present description refers to a number of documents, the content of which is herein incorporated by reference in their entirety.

SUMMARY OF THE INVENTION

In a first aspect, the present invention provides a method of identifying a minor histocompatibility antigen (MiHA) candidate, the method comprising: (a) isolating and sequencing MHC-associated peptides (MAPs) in a first cell sample from a first subject; (b) performing a whole transcriptome and/or exome sequencing on a second cell sample obtained from said first subject; (c) comparing the sequenced whole transcriptome and/or exome to a reference genome to identify single nucleotide variations (SNVs) between the transcriptome and/or exome of said first subject and the reference genome; (d) in silico translating the sequences containing the identified SNVs to identify peptide sequences comprising at least one non-synonymous mutation caused by said SNVs; (e) comparing the sequences of the MAPs isolated in (a) with the peptide sequences identified in (d); and (f) identifying a MiHA candidate based on said comparison.

In another aspect, the present invention provides a method of identifying a minor histocompatibility antigen (MiHA) candidate, the method comprising: (a) isolating and sequencing MHC-associated peptides (MAPs) in a first cell sample from a first and second subjects, wherein said first and second subjects are human leukocyte antigen (HLA)-matched; (b) performing a whole transcriptome and/or exome sequencing on a second cell sample obtained from said first and second subjects; (c) comparing the sequenced whole transcriptomes and/or exomes to identify single nucleotide variations (SNVs) between the transcriptomes and/or exomes of said first and second subjects; (d) in silico translating the sequences containing the identified SNVs to identify peptide sequences comprising at least one non-synonymous mutation caused by said SNVs; (e) comparing the sequences of the MAPs isolated in (a) with the peptide sequences identified in (d); and (f) identifying a MiHA candidate based on said comparison.

In an embodiment, the above-mentioned MiHA candidate is a MAP whose sequence comprises at least one mutation relative to the corresponding sequence translated from the reference genome.

In an embodiment, the above-mentioned MiHA candidate is a MAP present in the first cell sample from said first subject but absent from the first cell sample from said second subject.

In an embodiment, the above-mentioned reference genome is the Genome Reference Consortium Human Build 37 (GRCh37).

In an embodiment, the above-mentioned first and/or second cell sample is a peripheral blood cell sample. In a further embodiment, the above-mentioned peripheral blood cell sample an immortalized peripheral blood cell sample. In a further embodiment, the above-mentioned immortalized peripheral blood cell sample is an Epstein-Barr virus (EBV)-transformed B lymphoblastoid cell line.

In an embodiment, the above-mentioned isolating MAPs comprises (i) releasing said MAPs from said cell sample by mild acid treatment; and (ii) subjecting the released MAPs to chromatography.

In an embodiment, the above-mentioned method further comprises filtering the released peptides with a size exclusion column prior to said chromatography. In a further embodiment, the above-mentioned size exclusion column has a cut-off of about 3000 Da. In an embodiment, the above-mentioned chromatography is cation exchange chromatography.

In an embodiment, the above-mentioned peptide sequences of (d) have a length of 12 amino acids or less. In a further embodiment, the above-mentioned peptide sequences of (d) have a length of 8 to 11 amino acids.

In an embodiment, the above-mentioned comparing comprises subjecting the MAPs isolated in (a) to mass spectrometry and comparing the MS spectra obtained with the peptide sequences identified in (d).

In an embodiment, the above-mentioned method further comprises determining the binding of the MiHA candidate identified in (f) to a major histocompatibility complex (MHC) class I molecule.

In another aspect, the present invention provides a peptide of 50 amino acids or less comprising the sequence (I)

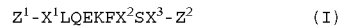

$$Z^1-X^1LQEKFX^2SX^3-Z^2 \quad (I)$$

wherein $Z^1$ is an amino terminal modifying group or is absent; $X^1$ is a sequence of 1 to 43 amino acids or is absent; $X^2$ is L or S; $X^3$ is a sequence of 1 to 43 amino acids or is absent; and $Z^2$ is a carboxy terminal modifying group or is absent. In an embodiment, $X^1$ is an acidic amino acid, in a further embodiment glutamic acid (E). In an embodiment, $X^3$ is an amino acid, in a further embodiment a hydrophobic amino acid, more particularly leucine (L). In an embodiment, $X^2$ is L. In another embodiment, $X^2$ is S. In an embodiment, the peptide comprises the sequence ELQEKFLSL (SEQ ID NO: 15), in a further embodiment the peptide is ELQEKFLSL (SEQ ID NO: 15). In another embodiment, the peptide comprises the sequence ELQEKFSSL (SEQ ID NO: 16), in a further embodiment the peptide is ELQEKFSSL (SEQ ID NO: 16).

In another aspect, the present invention provides a method of treating cancer, said method comprising administering to a subject in need thereof an effective amount of CD8 T lymphocytes recognizing a MHC class I molecule of the HLA-B*0801 allele loaded with the above-mentioned peptide (I). In an embodiment, the above-mentioned method further comprises determining whether said subject expresses a CENPF nucleic acid comprising a T or a C at a position corresponding to nucleotide 4409 in the nucleic acid sequence of human CENPF (FIGS. 1A to 1D, NCBI Reference Sequence: NM_016343.3), and/or a CENPF polypeptide comprising a leucine or serine residue at a position corresponding to residue 1412 in the protein sequence of human CENPF (FIG. 1E, NCBI Reference Sequence: NP_057427.3), wherein (a) if said subject expresses a CENPF nucleic acid comprising a T at a position corresponding to nucleotide 4409 in the nucleic acid sequence of human CENPF and/or a CENPF polypeptide comprising a leucine residue at a position corresponding to residue 1412 in the protein sequence of human CENPF, $X^2$ is L in said peptide; (b) if said subject expresses a CENPF nucleic acid comprising a C at a position corresponding to nucleotide 4409 in the nucleic acid sequence of human CENPF and/or a CENPF polypeptide comprising a serine residue at a position corresponding to residue 1412 in the protein sequence of human CENPF, $X^2$ is S in said peptide.

In an embodiment, the above-mentioned determining comprises sequencing a CENPF nucleic acid. In an embodiment, the above-mentioned CD8 T lymphocytes are in vitro expanded CD8 T lymphocytes.

In an embodiment, the above-mentioned method further comprises: (i) if said subject is the subject of (a), culturing CD8 T lymphocytes from a second subject comprising a C at a position corresponding to nucleotide 4409 in the nucleic acid sequence of human CENPF and/or a CENPF polypeptide comprising a serine residue at a position corresponding to residue 1412 in the protein sequence of human CENPF in the presence of cells expressing a MHC class I molecule of the HLA-B*0801 allele loaded with the above-mentioned peptide (I), wherein $X^2$ is L in said peptide, under conditions suitable for CD8 T lymphocyte expansion; or (ii) if said subject is the subject of (b), culturing CD8 T lymphocytes from a second subject comprising a T at a position corresponding to nucleotide 4409 in the nucleic acid sequence of human CENPF and/or a CENPF polypeptide comprising a leucine residue at a position corresponding to residue 1412 in the protein sequence of human CENPF in the presence of cells expressing a MHC class I molecule of the HLA-B*0801 allele loaded with the above-mentioned peptide (I), wherein $X^2$ is S in said peptide, under conditions suitable for CD8 T lymphocyte expansion.

In an embodiment, the above-mentioned subject is an allogeneic stem cell transplantation (ASCT) recipient.

In another aspect, the present invention provides a method of expanding CD8 T lymphocytes for adoptive T-cell immunotherapy, said method comprising: (a) determining whether a candidate donor expresses a CENPF nucleic acid comprising a T or a C at a position corresponding to nucleotide 4409 in the nucleic acid sequence of human CENPF (FIGS. 1A to 1D, NCBI Reference Sequence: NM_016343.3), and/or a CENPF polypeptide comprising a leucine or serine residue at a position corresponding to residue 1412 in the protein sequence of human CENPF (FIG. 1E, NCBI Reference Sequence: NP_057427.3) and (b)(i) if said candidate donor expresses a CENPF nucleic acid comprising a T at a position corresponding to nucleotide 4409 in the nucleic acid sequence of human CENPF and/or a CENPF polypeptide comprising a leucine residue at a position corresponding to residue 1412 in the protein sequence of human CENPF, culturing CD8 T lymphocytes from said candidate donor in the presence of cells expressing a MHC class I molecule of the HLA-B*0801 allele loaded with the above-mentioned peptide (I), wherein $X^2$ is S in said peptide, under conditions suitable for CD8 T lymphocyte expansion; or (b)(ii) if said candidate donor expresses a CENPF nucleic acid comprising a C at a position corresponding to nucleotide 4409 in the nucleic acid sequence of human CENPF and/or a CENPF polypeptide comprising a serine residue at a position corresponding to residue 1412 in the protein sequence of human CENPF, culturing CD8 T lymphocytes from said candidate donor in the presence of cells expressing a MHC class I molecule of the HLA-B*0801 allele loaded with the above-mentioned peptide (I), wherein $X^2$ is L in said peptide, under conditions suitable for CD8 T lymphocyte expansion.

In another aspect, the present invention provides a peptide of 50 amino acids or less comprising the sequence (II)

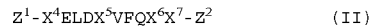

$$Z^1-X^4ELDX^5VFQX^6X^7-Z^2 \qquad (II)$$

wherein $Z^1$ is an amino terminal modifying group or is absent; $X^4$ is a sequence of 1 to 43 amino acids or is absent; $X^5$ is G or R; $X^6$ is an amino acid or is absent; $X^7$ is a sequence of 1 to 43 amino acids or is absent; and $Z^2$ is a carboxy terminal modifying group or is absent.

In an embodiment, $X^4$ is glutamine (Q). In an embodiment, $X^6$ is an amino acid, in a further embodiment a basic amino acid, more particularly lysine (K). In an embodiment, $X^7$ is an amino acid, in a further embodiment leucine (L). In an embodiment, $X^5$ is G. In another embodiment, $X^5$ is R. In an embodiment, the peptide comprises the sequence QELDGVFQKL (SEQ ID NO:17). In a further embodiment, the peptide is QELDGVFQKL (SEQ ID NO:17). In another embodiment, the peptide comprises the sequence QELDRVFQKL (SEQ ID NO:18). In a further embodiment, the peptide is QELDRVFQKL (SEQ ID NO:18).

In another aspect, the present invention provides a method of treating cancer, said method comprising administering to a subject in need thereof an effective amount of CD8 T lymphocytes recognizing a MHC class I molecule of the HLA-B*4403 allele loaded with the above-mentioned peptide (II).

In an embodiment, the above-mentioned method further comprises determining whether said subject expresses a ZWINT nucleic acid comprising an A or a G at a position corresponding to nucleotide 596 in the nucleic acid sequence of human ZWINT (FIG. 2A, NCBI Reference Sequence: NM_007057.3), and/or a ZWINT polypeptide comprising a arginine or glycine residue at a position corresponding to residue 187 in the protein sequence of human ZWINT (FIG. 2B, NCBI Reference Sequence: NP_008988.2), wherein (a) if said subject expresses a ZWINT nucleic acid comprising an A at a position corresponding to nucleotide 596 in the nucleic acid sequence of human ZWINT and/or a ZWINT polypeptide comprising an arginine residue at a position corresponding to residue 187 in the protein sequence of human ZWINT, $X^5$ is R in said peptide; (b) if said subject expresses a ZWINT nucleic acid comprising a G at a position corresponding to nucleotide 596 in the nucleic acid sequence of human ZWINT and/or a ZWINT polypeptide comprising a glycine residue at a position corresponding to residue 187 in the protein sequence of human ZWINT, $X^5$ is G in said peptide.

In an embodiment, the above-mentioned determining comprises sequencing a human ZWINT nucleic acid. In an embodiment, the above-mentioned CD8 T lymphocytes are in vitro expanded CD8 T lymphocytes.

In an embodiment, the above-mentioned method further comprises: (i) if said subject is the subject of (a), culturing CD8 T lymphocytes from a second subject comprising a G at a position corresponding to nucleotide 596 in the nucleic acid sequence of human ZWINT and/or a ZWINT polypeptide comprising a glycine residue at a position corresponding to residue 187 in the protein sequence of human ZWINT in the presence of cells expressing a MHC class I molecule of the HLA-B*4403 allele loaded with the above-mentioned peptide (II), wherein $X^5$ is R in said peptide, under conditions suitable for CD8 T lymphocyte expansion; or (ii) if said subject is the subject of (b), culturing CD8 T lymphocytes from a second subject comprising an A at a position corresponding to nucleotide 596 in the nucleic acid sequence of human ZWINT and/or a ZWINT polypeptide comprising an arginine residue at a position corresponding to residue 187 in the protein sequence of human ZWINT in the presence of cells expressing a MHC class I molecule of the HLA-B*4403 allele loaded with the above-mentioned peptide (II), wherein $X^5$ is G in said peptide, under conditions suitable for CD8 T lymphocyte expansion. In an embodiment, the above-mentioned subject is an allogeneic stem cell transplantation (ASCT) recipient.

In another aspect, the present invention provides a method of expanding CD8 T lymphocytes for adoptive T-cell immunotherapy, said method comprising: (a) determining whether a candidate donor expresses a ZWINT nucleic acid comprising an A or a G at a position corresponding to nucleotide 596 in the nucleic acid sequence of human ZWINT (FIG. 2A, NCBI Reference Sequence: NM_007057.3), and/or a ZWINT polypeptide comprising a arginine or glycine residue at a position corresponding to residue 187 in the protein sequence of human ZWINT (FIG. 2B, NCBI Reference Sequence: NP_008988.2) and (b)(i) if said candidate donor expresses a ZWINT nucleic acid comprising an A at a position corresponding to nucleotide 596 in the nucleic acid sequence of human ZWINT and/or a ZWINT polypeptide comprising an arginine residue at a position corresponding to residue 187 in the protein sequence of human ZWINT, culturing CD8 T lymphocytes from said candidate donor in the presence of cells expressing a MHC class I molecule of the HLA-B*4403 allele loaded with the above-mentioned peptide (II), wherein $X^5$ is G in said peptide, under conditions suitable for CD8 T lymphocyte expansion; or (b)(ii) if said candidate donor expresses a ZWINT nucleic acid comprising a G at a position corresponding to nucleotide 596 in the nucleic acid sequence of human ZWINT and/or a ZWINT polypeptide comprising a glycine residue at a position corresponding to residue 187 in the protein sequence of human ZWINT, culturing CD8 T lymphocytes from said candidate donor in the presence of cells expressing a MHC class I molecule of the HLA-B*4403 allele loaded with the above-mentioned peptide (II), wherein $X^5$ is R in said peptide, under conditions suitable for CD8 T lymphocyte expansion.

In another aspect, the present invention provides a peptide of 50 amino acids or less comprising the sequence (III)

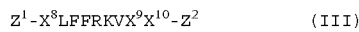

wherein $Z^1$ is an amino terminal modifying group or is absent; $X^8$ is a sequence of 1 to 43 amino acids or is absent; $X^9$ is P or A; $X^{10}$ is a sequence of 1 to 43 amino acids or is absent; and $Z^2$ is a carboxy terminal modifying group or is absent. In an embodiment, $X^8$ is serine (S). In an embodiment, $X^{10}$ is an amino acid, in a further embodiment an aromatic amino acid, more particularly phenylalanine (F). In an embodiment, $X^9$ is P. In another embodiment, $X^9$ is A. In an embodiment, the peptide comprises the sequence SLFFRKVPF (SEQ ID NO:19). In a further embodiment, the peptide is SLFFRKVPF (SEQ ID NO:19). In another embodiment, the peptide comprises the sequence SLFFRKVAF (SEQ ID NO:20). In a further embodiment, the peptide is SLFFRKVAF (SEQ ID NO:20).

In another aspect, the present invention provides a method of treating cancer, said method comprising administering to a subject in need thereof an effective amount of CD8 T lymphocytes recognizing a MHC class I molecule of the HLA-B*0801 allele loaded with the above-mentioned peptide.

In an embodiment, the above-mentioned method further comprises determining whether said subject expresses a MTCH2 nucleic acid comprising a C or a G at a position corresponding to nucleotide 1057 in the nucleic acid sequence of human MTCH2 (FIG. 3A, NCBI Reference Sequence: NM_014342.3), and/or a MTCH2 polypeptide comprising a proline or alanine residue at a position corresponding to residue 290 in the protein sequence of human MTCH2 (FIG. 3B, NCBI Reference Sequence: NP_055157.1), wherein (a) if said subject expresses a MTCH2 nucleic acid comprising a C at a position corresponding to nucleotide 1057 in the nucleic acid sequence of human MTCH2 and/or a MTCH2 polypeptide comprising a proline residue at a position corresponding to residue 290 in the protein sequence of human MTCH2, $X^9$ is P in said peptide; (b) if said subject expresses a MTCH2 nucleic acid comprising a G at a position corresponding to nucleotide 1057 in the nucleic acid sequence of human MTCH2 and/or a MTCH2 polypeptide comprising an alanine residue at a position corresponding to residue 290 in the protein sequence of human MTCH2, $X^5$ is A in said peptide.

In an embodiment, the above-mentioned determining comprises sequencing a human MTCH2 nucleic acid. In an embodiment, the above-mentioned CD8 T lymphocytes are in vitro expanded CD8 T lymphocytes.

In an embodiment, the above-mentioned method further comprises: (i) if said subject is the subject of (a), culturing CD8 T lymphocytes from a second subject comprising a G at a position corresponding to nucleotide 1057 in the nucleic acid sequence of human MTCH2 and/or a MTCH2 polypeptide comprising an alanine residue at a position corresponding to residue 290 in the protein sequence of human MTCH2 in the presence of cells expressing a MHC class I molecule of the HLA-B*0801 allele loaded with the above-mentioned peptide (III), wherein $X^9$ is P in said peptide, under conditions suitable for CD8 T lymphocyte expansion; or (ii) if said subject is the subject of (b), culturing CD8 T lymphocytes from a second subject comprising a C at a position corresponding to nucleotide 1057 in the nucleic acid sequence of human MTCH2 and/or a MTCH2 polypeptide comprising a proline residue at a position corresponding to residue 290 in the protein sequence of human MTCH2 in the presence of cells expressing a MHC class I molecule of the HLA-B*0801 allele loaded with the above-mentioned peptide (III), wherein $X^9$ is A in said peptide, under conditions suitable for CD8 T lymphocyte expansion.

In an embodiment, the above-mentioned subject is an allogeneic stem cell transplantation (ASCT) recipient.

In another aspect, the present invention provides a method of expanding CD8 T lymphocytes for adoptive T-cell immunotherapy, said method comprising: (a) determining whether a candidate donor expresses a MTCH2 nucleic acid comprising a C or a G at a position corresponding to nucleotide 1057 in the nucleic acid sequence of human MTCH2 (FIG. 3A, NCBI Reference Sequence: NM_014342.3), and/or a MTCH2 polypeptide comprising a proline or alanine residue at a position corresponding to residue 290 in the protein sequence of human MTCH2 (FIG. 3B, NCBI Reference Sequence: NP_055157.1) and (b)(i) if said candidate donor expresses a MTCH2 nucleic acid comprising a C at a position corresponding to nucleotide 1057 in the nucleic acid sequence of human MTCH2 and/or a MTCH2 polypeptide comprising a proline residue at a position corresponding to residue 290 in the protein sequence of human MTCH2, culturing CD8 T lymphocytes from said candidate donor in the presence of cells expressing a MHC class I molecule of the HLA-B*0801 allele loaded with the above-mentioned peptide (III), wherein $X^9$ is A in said peptide, under conditions suitable for CD8 T lymphocyte expansion; or (b)(ii) if said candidate donor expresses a MTCH2 nucleic acid comprising a G at a position corresponding to nucleotide 1057 in the nucleic acid sequence of human MTCH2 and/or a MTCH2 polypeptide comprising an alanine residue at a position corresponding to residue 290 in the protein sequence of human MTCH2, culturing CD8 T lymphocytes from said candidate donor in the presence of cells expressing a MHC class I molecule of the HLA-B*0801 allele loaded with the above-mentioned peptide (III), wherein $X^9$ is P in said peptide, under conditions suitable for CD8 T lymphocyte expansion.

In another aspect, the present invention provides a peptide of 50 amino acids or less comprising the sequence (IV)

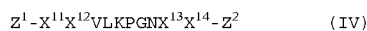

$$Z^1-X^{11}X^{12}VLKPGNX^{13}X^{14}-Z^2 \quad (IV)$$

wherein $Z^1$ is an amino terminal modifying group or is absent; $X^{11}$ is a sequence of 1 to 43 amino acids or is absent; $X^{12}$ is S or T; $X^{13}$ is an amino acid or is absent; $X^{14}$ is a sequence of 1 to 43 amino acids or is absent; and $Z^2$ is a carboxy terminal modifying group or is absent. In an embodiment, $X^{11}$ is absent. In an embodiment, the above-mentioned $X^{13}$ is an amino acid, in a further embodiment serine (S). In an embodiment, $X^{14}$ is an amino acid, in a further embodiment a basic amino acid, more particularly lysine (K). In an embodiment, $X^{12}$ is S. In another embodiment, $X^{12}$ is T. In an embodiment, the above-mentioned peptide comprises the sequence SVLKPGNSK (SEQ ID NO:21). In a further embodiment, the peptide is SVLKPGNSK (SEQ ID NO:21). In another embodiment, the above-mentioned peptide comprises the sequence TVLKPGNSK (SEQ ID NO:22). In a further embodiment, the peptide is TVLKPGNSK (SEQ ID NO:22).

In another aspect, the present invention provides a method of treating cancer, said method comprising administering to a subject in need thereof an effective amount of CD8 T lymphocytes recognizing a MHC class I molecule of the HLA-A*0301 allele loaded with the above-mentioned peptide (IV).

In an embodiment, the above-mentioned method further comprises determining whether said subject expresses an ELF1 nucleic acid comprising an A or T at a position corresponding to nucleotide 1400 in the nucleic acid sequence of human ELF1 (FIGS. 4A and 4B, NCBI Reference Sequence: NM_172373.3) and/or an ELF1 polypeptide having a threonine or a serine at a position corresponding to residue 343 in the ELF1 protein sequence (FIG. 4C, NCBI Reference Sequence: NP_758961.1), wherein (a) if said subject expresses an ELF1 nucleic acid comprising an A at a position corresponding to nucleotide 1400 in the nucleic acid sequence of human ELF1 and/or an ELF1 polypeptide comprising a threonine residue at a position corresponding to residue 343 in the protein sequence of human ELF1, $X^{12}$ is T in said peptide; (b) if said subject expresses an ELF1 nucleic acid comprising a T at a position corresponding to nucleotide 1400 in the nucleic acid sequence of human ELF1 and/or an ELF1 polypeptide comprising a serine residue at a position corresponding to residue 343 in the protein sequence of human ELF1, $X^{12}$ is S in said peptide.

In an embodiment, the above-mentioned determining comprises sequencing a human ELF1 nucleic acid. In an embodiment, the above-mentioned CD8 T lymphocytes are in vitro expanded CD8 T lymphocytes.

In an embodiment, the above-mentioned method further comprises: (i) if said subject is the subject of (a), culturing CD8 T lymphocytes from a second subject comprising a T at a position corresponding to nucleotide 1400 in the nucleic acid sequence of human ELF1 and/or an ELF1 polypeptide comprising a serine residue at a position corresponding to residue 343 in the protein sequence of human ELF1 in the presence of cells expressing a MHC class I molecule of the HLA-A*0301 allele loaded with the peptide, wherein $X^{12}$ is T in said peptide, under conditions suitable for CD8 T lymphocyte expansion; or (ii) if said subject is the subject of (b), culturing CD8 T lymphocytes from a second subject comprising an A at a position corresponding to nucleotide 1400 in the nucleic acid sequence of human ELF1 and/or an ELF1 polypeptide comprising a threonine residue at a position corresponding to residue 343 in the protein sequence of human ELF1 in the presence of cells expressing a MHC class I molecule of the HLA-A*0301 allele loaded with the peptide, wherein $X^{12}$ is S in said peptide, under conditions suitable for CD8 T lymphocyte expansion.

In an embodiment, the above-mentioned subject is an allogeneic stem cell transplantation (ASCT) recipient.

In another aspect, the present invention provides a method of expanding CD8 T lymphocytes for adoptive T-cell immunotherapy, said method comprising: (a) determining whether a candidate donor expresses an ELF1 nucleic acid comprising an A or T at a position corresponding to nucleotide 1400 in the nucleic acid sequence of human ELF1 (FIGS. 4A and 4B, NCBI Reference Sequence: NM_172373.3) and/or an ELF1 polypeptide having a threonine or a serine at a position corresponding to residue 343 in the ELF1 protein sequence (FIG. 4C, NCBI Reference Sequence: NP_758961.1) and (b)(i) if said candidate donor expresses an ELF1 nucleic acid comprising an A at a position corresponding to nucleotide 1400 in the nucleic acid sequence of human ELF1 and/or an ELF1 polypeptide having a threonine at a position corresponding to residue 343 in the ELF1 protein sequence, culturing CD8 T lymphocytes from said candidate donor in the presence of cells expressing a MHC class I molecule of the HLA-A*0301 allele loaded with the above-mentioned peptide (IV), wherein $X^{12}$ is S in said peptide, under conditions suitable for CD8 T lymphocyte expansion; or (b)(ii) if said candidate donor expresses an ELF1 nucleic acid comprising a T at a position corresponding to nucleotide 1400 in the nucleic acid sequence of human ELF1 and/or an ELF1 polypeptide having a serine at a position corresponding to residue 343 in the ELF1 protein sequence, culturing CD8 T lymphocytes from said candidate donor in the presence of cells expressing a MHC class I molecule of the HLA-A*0301 allele loaded with the above-mentioned peptide (IV), wherein $X^{12}$ is T in said peptide, under conditions suitable for CD8 T lymphocyte expansion.

In another aspect, the present invention provides a peptide of 50 amino acids or less comprising the sequence V

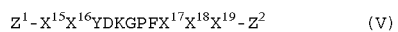

$$Z^1-X^{15}X^{16}YDKGPFX^{17}X^{18}X^{19}-Z^2 \quad (V)$$

wherein $Z^1$ is an amino terminal modifying group or is absent; $X^{15}$ is a sequence of 1 to 43 amino acids or is absent;

$X^{16}$ is an amino acid or is absent; $X^{17}$ is R or W; $X^{18}$ is an amino acid or is absent; $X^{19}$ is a sequence of 1 to 43 amino acids or is absent; $Z^2$ is a carboxy terminal modifying group or is absent. In an embodiment, the above-mentioned $X^{16}$ is an amino acid, in a further embodiment a methionine (M). In an embodiment, $X^{15}$ is an amino acid, in a further embodiment an alanine (A). In an embodiment, $X^{18}$ is an amino acid, in a further embodiment a serine (S). In an embodiment, $X^{19}$ is an amino acid, in a further embodiment a basic amino acid, more particularly lysine (K). In an embodiment, $X^{17}$ is R. In another embodiment, $X^{17}$ is W. In an embodiment, the above-mentioned peptide comprises the sequence AMYDKGPFRSK (SEQ ID NO:23). In an embodiment, the above-mentioned peptide is AMYDKGP-FRSK (SEQ ID NO:23). In another embodiment, the above-mentioned peptide comprises the sequence AMYDKGPF-WSK (SEQ ID NO:24). In an embodiment, the above-mentioned peptide is AMYDKGPFWSK (SEQ ID NO:24).

In another aspect, the present invention provides a method of treating cancer, said method comprising administering to a subject in need thereof an effective amount of CD8 T lymphocytes recognizing a MHC class I molecule of the HLA-A*0301 allele loaded with the above-mentioned peptide (V).

In an embodiment, the above-mentioned method further comprises determining whether said subject expresses an NQO1 nucleic acid comprising an C or T at a position corresponding to nucleotide 615 in the nucleic acid sequence of human NQO1 (FIG. 5A, NCBI Reference Sequence: NM_000903.2) and/or an NQO1 polypeptide having an arginine or a tryptophan at a position corresponding to residue 139 in the NQO1 protein sequence (FIG. 5B, NCBI Reference Sequence: NP_000894.1), wherein (a) if said subject expresses a NQO1 nucleic acid comprising an C at a position corresponding to nucleotide 615 in the nucleic acid sequence of human NQO1 and/or a NQO1 polypeptide comprising an arginine residue at a position corresponding to residue 139 in the protein sequence of human NQO1, $X^{17}$ is R in said peptide; (b) if said subject expresses an NQO1 nucleic acid comprising a T at a position corresponding to nucleotide 615 in the nucleic acid sequence of human NQO1 and/or a NQO1 polypeptide comprising a tryptophan residue at a position corresponding to residue 139 in the protein sequence of human NQO1, $X^{17}$ is W in said peptide.

In an embodiment, the above-mentioned determining comprises sequencing a human NQO1 nucleic acid. In an embodiment, the above-mentioned CD8 T lymphocytes are in vitro expanded CD8 T lymphocytes.

In an embodiment, the above-mentioned method further comprises: (i) if said subject is the subject of (a), culturing CD8 T lymphocytes from a second subject comprising a T at a position corresponding to nucleotide 615 in the nucleic acid sequence of human NQO1 and/or a NQO1 polypeptide comprising a tryptophan residue at a position corresponding to residue 139 in the protein sequence of human NQO1 in the presence of cells expressing a MHC class I molecule of the HLA-A*0301 allele loaded with the above-mentioned peptide (V), wherein $X^{17}$ is R in said peptide, under conditions suitable for CD8 T lymphocyte expansion; or (ii) if said subject is the subject of (b), culturing CD8 T lymphocytes from a second subject comprising a C at a position corresponding to nucleotide 615 in the nucleic acid sequence of human NQO1 and/or a NQO1 polypeptide comprising an arginine residue at a position corresponding to residue 139 in the protein sequence of human NQO1 in the presence of cells expressing a MHC class I molecule of the HLA-A*0301 allele loaded with the above-mentioned peptide (V), wherein $X^{17}$ is W in said peptide, under conditions suitable for CD8 T lymphocyte expansion.

In an embodiment, the above-mentioned subject is an allogeneic stem cell transplantation (ASCT) recipient.

In another aspect, the present invention provides a method of expanding CD8 T lymphocytes for adoptive T-cell immunotherapy, said method comprising: (a) determining whether said subject expresses an NQO1 nucleic acid comprising an C or T at a position corresponding to nucleotide 615 in the nucleic acid sequence of human NQO1 (FIG. 5A, NCBI Reference Sequence: NM_000903.2) and/or an NQO1 polypeptide having an arginine or a tryptophan at a position corresponding to residue 139 in the NQO1 protein sequence (FIG. 5B, NCBI Reference Sequence: NP_000894.1) and (b)(i) if said candidate donor expresses a NQO1 nucleic acid comprising an C at a position corresponding to nucleotide 615 in the nucleic acid sequence of human NQO1 and/or a NQO1 polypeptide comprising an arginine residue at a position corresponding to residue 139 in the protein sequence of human NQO1, culturing CD8 T lymphocytes from said candidate donor in the presence of cells expressing a MHC class I molecule of the HLA-A*0301 allele loaded with the above-mentioned peptide (V), wherein $X^{17}$ is W in said peptide, under conditions suitable for CD8 T lymphocyte expansion; or (b)(ii) if said candidate donor expresses a NQO1 nucleic acid comprising a T at a position corresponding to nucleotide 615 in the nucleic acid sequence of human NQO1 and/or a NQO1 polypeptide comprising a tryptophan residue at a position corresponding to residue 139 in the protein sequence of human NQO1, culturing CD8 T lymphocytes from said candidate donor in the presence of cells expressing a MHC class I molecule of the HLA-A*0301 allele loaded with the above-mentioned peptide (V), wherein $X^{17}$ is R in said peptide, under conditions suitable for CD8 T lymphocyte expansion.

In another aspect, the present invention provides a peptide of 50 amino acids or less comprising the sequence VI $$Z^1-X^{20}X^{21}X^{22}SLPTSPX^{23}X^{24}-Z^2 \qquad (VI)$$

wherein $Z^1$ is an amino terminal modifying group or is absent; $X^{20}$ is a sequence of 1 to 43 amino acids or is absent; $X^{21}$ is an amino acid or is absent; $X^{22}$ is an amino acid or is absent; $X^{23}$ is G or R; $X^{24}$ is a sequence of 1 to 43 amino acids or is absent; $Z^2$ is a carboxy terminal modifying group or is absent. In an embodiment, the peptide has a length of 8 to 12 amino acids. In an embodiment, $X^{22}$ is an amino acid, in a further embodiment valine (V). In an embodiment, $X^{21}$ is an amino acid, in a further embodiment arginine (R). In an embodiment, $X^{23}$ is glycine (G), in another embodiment $X^{23}$ is arginine (R). In an embodiment, the above-mentioned peptide comprises the sequence RVSLPTSPG (SEQ ID NO:25). In an embodiment, the above-mentioned peptide is RVSLPTSPG (SEQ ID NO:25). In another embodiment, the above-mentioned peptide comprises the sequence RVS-LPTSPR (SEQ ID NO:26). In an embodiment, the above-mentioned peptide is RVSLPTSPR (SEQ ID NO:26).

In another aspect, the present invention provides a method of treating cancer, said method comprising administering to a subject in need thereof an effective amount of CD8 T lymphocytes recognizing a MHC class I molecule of the HLA-A*0301 allele loaded with the above-mentioned peptide of sequence VI.

In an embodiment, the above-mentioned method further comprising determining whether said subject expresses a KIAA0226L nucleic acid comprising a G or A at a position corresponding to nucleotide 1059 in the nucleic acid sequence of human KIAA0226L (FIGS. 6A and 6B, NCBI Reference Sequence: NM_025113.2) and/or an KIAA0226L polypeptide having a glycine or an arginine at a position corresponding to residue 152 in the KIAA0226L protein sequence (FIG. 6C, NCBI Reference Sequence: NP_079389.2), wherein (a) if said subject expresses a KIAA0226L nucleic acid comprising a G at a position corresponding to nucleotide 1059 in the nucleic acid sequence of human KIAA0226L and/or a KIAA0226L polypeptide comprising a glycine residue at a position corresponding to residue 152 in the protein sequence of human KIAA0226L, $X^{23}$ is G in said peptide of sequence VI; (b) if said subject expresses a KIAA0226L nucleic acid comprising an A at a position corresponding to nucleotide 1059 in the nucleic acid sequence of human a KIAA0226L and/or a KIAA0226L polypeptide comprising an arginine residue at a position corresponding to residue 152 in the protein sequence of human KIAA0226L, $X^{23}$ is R in said peptide of sequence VI.

In another embodiment, the determining comprises sequencing a human KIAA0226L nucleic acid. In an embodiment, the above-mentioned CD8 T lymphocytes are in vitro expanded CD8 T lymphocytes.

In an embodiment, the above-mentioned method further comprises: (i) if said subject is the subject of (a) above, culturing CD8 T lymphocytes from a second subject comprising an A at a position corresponding to nucleotide to nucleotide 1059 in the nucleic acid sequence of human KIAA0226L and/or a KIAA0226L polypeptide comprising an arginine residue at a position corresponding to residue 152 in the protein sequence of human KIAA0226L in the presence of cells expressing a MHC class I molecule of the HLA-A*0301 allele loaded with the peptide of sequence VI, wherein $X^{23}$ is G in said peptide, under conditions suitable for CD8 T lymphocyte expansion; or (ii) if said subject is the subject of (b) above, culturing CD8 T lymphocytes from a second subject comprising a G at a position corresponding to nucleotide 1059 in the nucleic acid sequence of human KIAA0226L and/or a KIAA0226L polypeptide comprising a glycine residue at a position corresponding to residue 152 in the protein sequence of human KIAA0226L in the presence of cells expressing a MHC class I molecule of the HLA-A*0301 allele loaded with the peptide of sequence VI, wherein $X^{23}$ is R in said peptide, under conditions suitable for CD8 T lymphocyte expansion.

In an embodiment, the above-mentioned subject is an allogeneic stem cell transplantation (ASCT) recipient.

In another aspect, the present invention provides a method of expanding CD8 T lymphocytes for adoptive T-cell immunotherapy, said method comprising: (a) determining whether a candidate donor expresses a KIAA0226L nucleic acid comprising a G or A at a position corresponding to nucleotide 1059 in the nucleic acid sequence of human KIAA0226L (FIGS. 6A and 6B, NCBI Reference Sequence: NM_025113.2) and/or an KIAA0226L polypeptide having a glycine or an arginine at a position corresponding to residue 152 in the KIAA0226L protein sequence (FIG. 6C, NCBI Reference Sequence: NP_079389.2) and (b)(i) if said candidate donor expresses a KIAA0226L nucleic acid comprising G at a position corresponding to nucleotide 1059 in the nucleic acid sequence of human KIAA0226L and/or a KIAA0226L polypeptide comprising a glycine residue at a position corresponding to residue 152 in the protein sequence of human KIAA0226L, culturing CD8 T lymphocytes from said candidate donor in the presence of cells expressing a MHC class I molecule of the HLA-A*0301 allele loaded with the peptide of sequence VI, wherein $X^{23}$ is R in said peptide, under conditions suitable for CD8 T lymphocyte expansion; or (b)(ii) if said subject expresses a KIAA0226L nucleic acid comprising an A at a position corresponding to nucleotide 1059 in the nucleic acid sequence of human a KIAA0226L and/or a KIAA0226L polypeptide comprising an arginine residue at a position corresponding to residue 152 in the protein sequence of human KIAA0226L, culturing CD8 T lymphocytes from said candidate donor in the presence of cells expressing a MHC class I molecule of the HLA-A*0301 allele loaded with the peptide of sequence VI, wherein $X^{23}$ is G in said peptide, under conditions suitable for CD8 T lymphocyte expansion.

In another aspect, the present invention provides a peptide of 50 amino acids or less comprising the sequence VII $$Z^1-X^{25}X^{26}X^{27}GNPGTFX^{28}X^{29}-Z^2 \qquad (VII)$$

wherein $Z^1$ is an amino terminal modifying group or is absent; $X^{25}$ is a sequence of 1 to 43 amino acids or is absent; $X^{26}$ is an amino acid or is absent; $X^{27}$ is an amino acid or is absent; $X^{28}$ is K or N; $X^{29}$ is a sequence of 1 to 43 amino acids or is absent; $Z^2$ is a carboxy terminal modifying group or is absent. In an embodiment, the peptide has a length of 8 to 12 amino acids. In an embodiment, $X^{27}$ is an amino acid, more specifically methionine (M). In an embodiment, $X^{26}$ is an amino acid, more specifically valine (V). In an embodiment, $X^{28}$ is K. In another embodiment, $X^{28}$ is N. In an embodiment, the peptide comprises the sequence VMGNPGTFK (SEQ ID NO: 27). In a further embodiment, the peptide is VMGNPGTFK (SEQ ID NO: 27). In another embodiment, the peptide comprises the sequence VMGNPGTFN (SEQ ID NO: 28). In an embodiment, the peptide is VMGNPGTFN (SEQ ID NO: 28).

In another aspect, the present invention provides a method of treating cancer, said method comprising administering to a subject in need thereof an effective amount of CD8 T lymphocytes recognizing a MHC class I molecule of the HLA-A*0301 allele loaded with the above-mentioned peptide of sequence VII.

In an embodiment, the above-mentioned method further comprises determining whether said subject expresses an RMDN1 nucleic acid comprising an A or C at a position corresponding to nucleotide 316 in the nucleic acid sequence of human RMDN1 (FIG. 7A, NCBI Reference Sequence: NM_016033.2) and/or an RMDN1 polypeptide having a lysine or an asparagine at a position corresponding to residue 52 in the RMDN1 protein sequence (FIG. 7B, NCBI Reference Sequence: NP_057117.2), wherein (a) if said subject expresses an RMDN1 nucleic acid comprising an A at a position corresponding to nucleotide 316 in the nucleic acid sequence of human RMDN1 and/or an RMDN1 polypeptide comprising a lysine residue at a position corresponding to residue 52 in the protein sequence of human RMDN1, $X^{28}$ is K in said peptide of sequence VII; (b) if said subject expresses an RMDN1 nucleic acid comprising a C at a position corresponding to nucleotide 316 in the nucleic acid sequence of human RMDN1 and/or a RMDN1 polypeptide comprising an asparagine residue at a position corresponding to residue 52 in the protein sequence of human RMDN1, $X^{28}$ is N in said peptide of sequence VII.

In another embodiment, the determining comprises sequencing a human RMDN1 nucleic acid. In an embodiment, the above-mentioned CD8 T lymphocytes are in vitro expanded CD8 T lymphocytes.

In an embodiment, the above-mentioned method further comprises: (i) if said subject is the subject of (a), culturing CD8 T lymphocytes from a second subject comprising a C at a position corresponding to nucleotide 316 in the nucleic acid sequence of human RMDN1 and/or a RMDN1 polypeptide comprising an asparagine residue at a position corresponding to residue 52 in the protein sequence of human RMDN1 in the presence of cells expressing a MHC class I molecule of the HLA-A*0301 allele loaded with the peptide of sequence VII, wherein $X^{28}$ is K in said peptide, under conditions suitable for CD8 T lymphocyte expansion; or (ii) if said subject is the subject of (b) above, culturing CD8 T lymphocytes from a second subject comprising an A at a position corresponding to nucleotide 316 in the nucleic acid sequence of human RMDN1 and/or a RMDN1 polypeptide comprising a lysine residue at a position corresponding to residue 52 in the protein sequence of human RMDN1 in the presence of cells expressing a MHC class I molecule of the HLA-A*0301 allele loaded with the peptide of sequence VII, wherein $X^{28}$ is N in said peptide, under conditions suitable for CD8 T lymphocyte expansion.

In an embodiment, the above-mentioned subject is an allogeneic stem cell transplantation (ASCT) recipient.

In another aspect, the present invention provides a method of expanding CD8 T lymphocytes for adoptive T-cell immunotherapy, said method comprising: (a) determining whether a candidate donor expresses an RMDN1 nucleic acid comprising an A or C at a position corresponding to nucleotide 316 in the nucleic acid sequence of human RMDN1 (FIG. 7A, NCBI Reference Sequence: NM_016033.2) and/or an RMDN1 polypeptide having a lysine or an asparagine at a position corresponding to residue 52 in the RMDN1 protein sequence (FIG. 7B, NCBI Reference Sequence: NP_057117.2) and (b)(i) if said subject expresses an RMDN1 nucleic acid comprising an A at a position corresponding to nucleotide 316 in the nucleic acid sequence of human RMDN1 and/or an RMDN1 polypeptide comprising a lysine residue at a position corresponding to residue 52 in the protein sequence of human RMDN1, culturing CD8 T lymphocytes from said candidate donor in the presence of cells expressing a MHC class I molecule of the HLA-A*0301 allele loaded with the peptide of sequence VII, wherein $X^{28}$ is N in said peptide, under conditions suitable for CD8 T lymphocyte expansion; or (b)(ii) if said subject expresses an RMDN1 nucleic acid comprising a C at a position corresponding to nucleotide 316 in the nucleic acid sequence of human RMDN1 and/or a RMDN1 polypeptide comprising an asparagine residue at a position corresponding to residue 52 in the protein sequence of human RMDN1, culturing CD8 T lymphocytes from said candidate donor in the presence of cells expressing a MHC class I molecule of the HLA-A*0301 allele loaded with the peptide of sequence VII, wherein $X^{28}$ is R in said peptide, under conditions suitable for CD8 T lymphocyte expansion.

In an embodiment, $Z^1$ is absent in the above-mentioned peptide (I)-(VII). In an embodiment, $Z^2$ is absent in the above-mentioned peptide (I)-(VII).

In another aspect, the present invention provides a MiHA identified by the above-mentioned method. In an embodiment, the MiHA is a peptide of sequences (I)-(VII) as defined herein.

In another aspect, the present invention provides a nucleic acid encoding the above-mentioned peptide (I)-(VII).

In another aspect, the present invention provides an isolated major histocompatibility complex (MHC) class I molecule loaded with the peptide (I)-(VII). In another aspect, the present invention provides an isolated cell expressing at its surface a MHC class I molecule loaded with the above-mentioned peptide (I)-(VII).

In an embodiment, the major histocompatibility complex (MHC) class I molecule is of the HLA-A*0301, HLA-B*0801 or HLA-B*4403 allele. In a further embodiment, the major histocompatibility complex (MHC) class I molecule is of the HLA-A*0301 allele. In another embodiment, the major histocompatibility complex (MHC) class I molecule is of the HLA-B*0801 allele. In another embodiment, the major histocompatibility complex (MHC) class I molecule is of the HLA-B*4403 allele.

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the appended drawings:

FIGS. 1A to C show the nucleotide sequence of human centromer protein F, 350/400 kDa (mitosin) (CENPF) cDNA (SEQ ID NO:1). The coding region is in italics;

FIG. 1D shows the amino acid sequence of human CENPF polypeptide (SEQ ID NO:2);

FIG. 2A shows the nucleotide sequence of human ZW10 interactor (ZWINT) cDNA (SEQ ID NO:3). The coding region is in italics;

FIG. 2B shows the amino acid sequence of human ZWINT polypeptide (SEQ ID NO:4);

FIG. 3A shows the nucleotide sequence of human mitochondrial carrier homolog 2 (MTCH2) cDNA (SEQ ID NO:5). The coding region is in italics;

FIG. 3B shows the amino acid sequence of human MTCH2 polypeptide (SEQ ID NO:6);

FIGS. 4A and 4B show the nucleotide sequence of human ELF1 [E74-like factor 1 (ets domain transcription factor)] cDNA (SEQ ID NO:7). The coding region is in italics;

FIG. 4C shows the amino acid sequence of human ELF1 polypeptide (SEQ ID NO:8);

FIGS. 5A and 5B show the nucleotide sequence of human NQO1 [NAD(P)H dehydrogenase, quinone 1] cDNA (SEQ ID NO:9). The coding region is in italics;

FIG. 5C shows the amino acid sequence of human NQO1 polypeptide (SEQ ID NO:10);

FIGS. 6A and 6B show the nucleotide sequence of human KIAA0226L cDNA (SEQ ID NO:11). The coding region is in italics;

FIG. 6C shows the amino acid sequence of human KIAA0226L polypeptide (SEQ ID NO:12);

FIG. 7A shows the nucleotide sequence of human RMDN1 cDNA (SEQ ID NO:13). The coding region is in italics; and FIG. 7B shows the amino acid sequence of human RMDN1 polypeptide (SEQ ID NO:14).

DISCLOSURE OF INVENTION

Terms and symbols of genetics, molecular biology, biochemistry and nucleic acid used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like. All terms are to be understood with their typical meanings established in the relevant art.

The articles "a" and "an" are used herein to refer to one or to more than one (i.e. to at least one) of the grammatical object of the article. By way of example, "an element" means one element or more than one element. Throughout this specification, unless the context requires otherwise, the words "comprise," "comprises" and "comprising" will be understood to imply the inclusion of a stated step or element or group of steps or elements but not the exclusion of any other step or element or group of steps or elements.

Described herein is a novel method for human MiHA discovery, novel MiHAs identified using this method, as well as uses of the novel MiHAs. One of the features of the method is the inclusion of personalized translated transcriptome and/or exome in the database used for peptide identification by mass spectroscopy (MS). Candidate MiHAs are identified by comparing the personalized transcriptome and/or exome to a reference genome and/or to the transcriptome and/or exome of an HLA-matched subject (e.g., an HLA-identical sibling).

Accordingly, in a first aspect, the present invention provides a method of identifying a minor histocompatibility antigen (MiHA) candidate, the method comprising: (a) isolating and determining the sequence of MHC-associated peptides (MAPs) in a first cell sample from a first subject; (b) performing a whole transcriptome and/or exome sequencing on a second cell sample obtained from said first subject; (c) comparing the sequenced whole transcriptome and/or exome to a reference genome to identify single nucleotide variations (SNVs) between the transcriptome and/or exome of said first subject and the reference genome; (d) in silico translating the sequences containing the identified SNVs to identify peptide sequences comprising at least one non-synonymous mutation caused by said SNVs; (e) comparing the sequences of the MAPs isolated in (a) with the peptide sequences identified in (d); and (f) identifying a MiHA candidate based on said comparison.

In an embodiment, the MiHA candidate is a MAP whose sequence comprises at least one mutation relative to the corresponding sequence translated from the reference genome.

In another aspect, the present invention provides a method of identifying a minor histocompatibility antigen (MiHA) candidate, the method comprising: (a) isolating MHC-associated peptides (MAPs) in a first cell sample from a first and second subjects, wherein said first and second subjects are human leukocyte antigen (HLA)-matched; (b) performing a whole transcriptome and/or exome sequencing on a second cell sample obtained from said first and second subjects; (c) comparing the sequenced whole transcriptomes and/or exomes to identify single nucleotide variations (SNVs) between the transcriptomes and/or exomes of said first and second subjects; (d) in silico translating the sequences containing the identified SNVs to identify peptide sequences comprising at least one non-synonymous mutation caused by said SNVs; (e) comparing the sequences of the MAPs isolated in (a) with the peptide sequences identified in (d); and (f) identifying a MiHA candidate based on said comparison. In an embodiment, the MiHA candidate is a MAP present in the first cell sample from said first subject but absent from the first cell sample from said second subject.

The term "reference genome" as used herein refers to the human genome assemblies reported in the literature, and includes for example the Genome Reference Consortium Human Build 37 (GRCh37, Genome Reference Consortium; The International Human Genome Sequencing Consortium. Nature. 2004; 431:931-945), Hs_Celera_WGSA (Celera Genomics; Istrail S. et al., *Proc Natl Acad Sci USA*. 2004 Feb. 17; 101(7):1916-21). Epub 2004 Feb. 9), HuRef and HuRefPrime (J. Craig Venter Institute; Levy S, et al. *PLoS Biology*. 2007; 5:2113-2144), YH1 and BGIAF (Beijing Genomics Institute; Li R, et al. *Genome Research*. 2010; 20: 265-272), as well as HsapALLPATHS1 (Broad Institute). In an embodiment, the reference genome is GRCh37.

In various embodiments, the above-noted first sample may be from any source that contains cells expressing MHC class I molecules, including a tissue or body fluid from the subject, such as blood, serum, immune cells (e.g., lymphocytes), blood cells (e.g., PBMCs or a subset thereof), tissues, or a cell line derived from primary cells. In an embodiment, the first sample is a blood cell sample, for example a PBMC sample, or a cell line derived from blood cells such as PBMCs (e.g., an immortalized cell line). Methods for generating a cell line from primary cells, or for immortalizing primary cells, are known in the art and include, for example, immortalization of primary cells by recombinant expression of human telomerase reverse transcriptase (TERT) (Barsov E V, *Curr Protoc Immunol*. 2011 November; Chapter 7: Unit 7.21B), immortalization by recombinant expression of viral genes such as Simian virus 40 (SV40) T antigen, adenovirus E1A and E1B, human papillomavirus (HPV) E6 and E7 and Epstein-Barr Virus (EBV), as well as inactivation of tumor suppression genes such as p53 or Rb. Methods for immortalization of B lymphocytes by EBV are disclosed in Tosato G and Cohen J I. *Curr Protoc Immunol*. 2007 February; Chapter 7: Unit 7.22. Products/reagents for immortalizing mammalian cells are commercially available, for example from ATCC™. In an embodiment, the first sample is an immortalized cell line derived from primary cells obtained from the subject, in a further embodiment an immortalized B cell line, such as an EBV-transformed B lymphoblastoid cell line (B-LCL).

Methods for isolating MHC-associated peptides (MAPs) from a cell sample are well known in the art. The most commonly used technique is mild acid elution (MAE) of MHC-associated peptides from living cells, as described in Fortier et al. (*J. Exp. Med*. 205(3): 595-610, 2008). Another technique is immunoprecipitation or affinity purification of peptide-MHC class I complexes followed by peptide elution (see, e.g., Gebreselassie et al., *Hum Immunol*. 2006 November; 67(11): 894-906). Two high-throughput strategies based on the latter approach have been implemented. The first is based on transfection of cell lines with expression vectors coding soluble secreted MHCs (lacking a functional transmembrane domain) and elution of peptides associated with secreted MHCs (Barnea et al., *Eur J Immunol*. 2002 January; 32(1):213-22; and Hickman H D et al., *J Immunol*. 2004 Mar. 1; 172(5):2944-52). The second approach hinges on chemical or metabolic labeling to provide quantitative profiles of MHC-associated peptides (Weinzierl A O et al., *Mol Cell Proteomics*. 2007 January; 6(1):102-13. Epub 2006 Oct. 29; Lemmel C et al., *Nat Biotechnol*. 2004 April; 22(4):450-4. Epub 2004 Mar. 7; Milner E, *Mol Cell Proteomics*. 2006 February; 5(2):357-65. Epub 2005 Nov. 4).

Eluted MAPs may be subjected to any purification/enrichment steps, including size exclusion chromatography or ultrafiltration (using a filter with a cut-off of about 5000 Da, for example about 3000 Da), and/or ion exchange chromatography (e.g., cation exchange chromatography), prior to further analysis. The sequence of the eluted MAPs may be determined using any method known in the art for sequencing peptides/proteins, such as mass spectroscopy (as described below) and the Edman degradation reaction.

In various embodiments, the above-noted second sample may be from any source that contains genomic DNA, RNA, and/or proteins, for example a tissue or body fluid from the subject, such as blood, serum, immune cells (e.g., lymphocytes), blood cells (e.g., PBMCs), tissues, or a cell line derived from primary cells (as described above). In an embodiment, the second sample is an immortalized cell line derived from primary cells obtained from the subject, in a further embodiment an immortalized B cell line, such as an EBV-transformed B lymphoblastoid cell line (B-LCL). The cell sample may be subjected to commonly used isolation and/or purification techniques for enrichment in nucleic acids (genomic DNA, mRNA) and/or proteins.

In an embodiment, transcriptome libraries are generated/constructed from the RNA obtained from the sample. Transcriptome library construction may include one or more of the following steps: poly-A mRNA enrichment/purification; RNA fragmentation and priming for cDNA synthesis; reverse transcription (RT) (using random primers); second round of RT to generate a double-stranded cDNA, cDNA purification; end repair of fragmented cDNA, adenylation of the 3' ends, ligation of adaptors and enrichment of DNA fragments containing adapter molecules. Kits suitable for transcriptome library construction are commercially available, for example from Life Technologies (Ambion® RNA-Seq Library Construction Kit), Applied Biosystems (AB Library Builder™ Whole Transcriptome Core Kit), Qiagen (Quantilect™ Whole Transcriptome Kit) and Sigma-Aldrich (TransPlex® Complete Whole Transcriptome Amplification Kit)

In an embodiment, genomic libraries are generated/constructed from the genomic DNA obtained from the sample. Genomic library construction may include one or more of the following steps: DNA shearing, DNA end repair, 3' ends adenylation, ligation of adaptors, purification of ligation products and amplification (e.g., PCR) to enrich DNA fragments that have adapter molecules. Kits suitable for genomic library construction are commercially available, for example from Illumina (TruSeq™ DNA Sample Preparation Kit (v2) (Cat. No. FC-930-1021), Life Technologies (SOLiD® Fragment Library Construction Kit and New England BioLabs (NEBNext® DNA Library Preparation).

In another embodiment, the genomic (DNA-Seq) libraries are subjected to an enrichment step to sequence only the coding portion (exome) of the human genome. Kits suitable for exome enrichment are commercially available, for example from Illumina (TruSeq™ exome enrichment kit, FC-930-1012), Life Technologies (TargetSeq™ Exome and Custom Enrichment System, A14060-A14063), FlexGen (FleXome whole exome enrichment kit v2), Roche NimbleGen (SeqCap EZ Human Exome Library v2.0) and Agilent Technologies (SureSelect All Exon kits)

Methods to perform whole transcriptome or exome sequencing (RNA-Seq) are known in the art (see, for example, Wang et al., Nature Reviews Genetics 10, 57-63, January 2009; Genome Biology 2011, 12(9), Exome sequencing special issue). Various platforms for performing whole transcriptome/exome sequencing exist, such as the Illumina Genome Analyzer platform, the Applied Biosystems (ABI) Solid™ Sequencing platform or Life Science's 454 Sequencing platform (Roche).

The identification of single nucleotide variations (SNVs) or single nucleotide polymorphisms (SNPs) between two or more sequences, for example between (i) the transcriptome and/or exome of a subject and a reference genome and/or (ii) the transcriptomes and/or exomes of two different subjects, may be performed using any sequence comparison/SNP identification methods or tools, including the SNP calling program Casava™ from Illumina, SNPdetector (Zhang et al., PLoS Comput Biol. 2005 October; 1(5): e53), the SNP & Variation Suite from Golden Helix, the Genome-wide human SNP arrays from Affymetrix, the SAMtools mpileup from MassGenomics, etc.

The in silico translation of nucleic acid sequences to protein sequences may be performed using any suitable softwares or tools, including the ExPASy Translate tool, Vector NTI™ (Life Technologies), pyGeno (Granados et al., 2012), Virtual Ribosome (CBS, University of Denmark), etc. The in silico translation of transcriptomes and/or exomes permits the identification of peptide sequences comprising at least one non-synonymous mutation caused by the SNVs. In an embodiment, all possible amino acid (aa) sequence variants of 15 amino acids or less (in embodiments, 14, 13, 12, 11 amino acids or less) comprising at least one non-synonymous mutation are computed, listed and used in the comparing step (e). Thus, for each non-synonymous mutation caused by the SNVs, a window of 90 bp (84, 78, 72 or 66 bp) around each one of the polymorphic positions is computed to obtain the list of every possible amino acid (aa) sequence variant defined by these 90 bp (84, 78, 72 or 66 bp) (30, 28, 26, 24 or 22 aa) windows. In this way, a list of most possible aa sequences of at most 15 aa (in embodiments, 14, 13, 12, 11 aa) affected by non-synonymous polymorphisms may be obtained. For the identification of MHC class II-associated MAPs (which may be longer, up to about 30 amino acids), all possible amino acid (aa) sequence variants of for example 30 amino acids or less (in embodiments, 25, 20, 19, 18, 17, 16, 15, 14, 13, 12 amino acids or less) comprising at least one non-synonymous mutation are computed, listed and used in the comparing step (e). Thus, for each non-synonymous mutation caused by the SNVs, a window of 180 bp around each one of the polymorphic positions is computed to obtain the list of every possible amino acid (aa) sequence variant defined by these 180 bp (60 aa) windows. In this way, a list of most possible aa sequences of at most 30 aa affected by non-synonymous polymorphisms may be obtained.

In an embodiment, all possible amino acid (aa) sequence variants of 12 or 11 amino acids or less comprising at least one non-synonymous mutation are computed, listed and used in the comparing step (e). Thus, for each non-synonymous mutation caused by the SNVs, a window of 72 or 66 bp around each one of the polymorphic positions is computed to obtain the list of every possible amino acid (aa) sequence variant defined by these 72 or 66 bp (24 or 22 aa) windows. In this way, a list of most possible aa sequences of at most 12 or 11 aa affected by non-synonymous polymorphisms was obtained.

In embodiment, the above-noted peptide sequences have a length of about 7 to about 15 amino acids (e.g., 7, 8, 9, 10, 11, 12, 13, 14 or 15), in a further embodiment of about 8 or 9 to about 11 or 12 amino acids (e.g., 8, 9, 10, 11 or 12).

In an embodiment, the comparison of the sequences of the MAPs isolated from the first sample with the peptide sequences derived from the transcriptome and/or exome identified above (i.e. comprising at least one non-synonymous mutation caused by the SNVs) comprises subjecting the isolated MAPs to mass spectrometry and comparing the MS spectra obtained with the peptide sequences derived from the transcriptome and/or exome. In an embodiment, the mass spectrometry is liquid chromatography-mass spectrometry (LC-MS), in a further embodiment LC-MS coupled to peptide mass fingerprinting (LC-MS/MS).

In an embodiment, the method further comprises determining the binding of the MiHA candidate identified to a MHC class I molecule. The binding may be a predicted binding affinity ($IC_{50}$) of peptides to the allelic products, which may be obtained using tools such as the NetMHCcons software version 1.0 (http://www.cbs.dtu.dk/services/NetMHCcons/) (Karosiene et al., 2011). An overview of the various available MHC class I peptide binding tools is provided in Peters B et al., *PLoS Comput Biol* 2006, 2(6):e65; Trost et al., *Immunome Res* 2007, 3(1):5; Lin et al., *BMC Immunology* 2008, 9:8)

In an embodiment, peptides with a predicted $IC_{50}$ below 50 nM are considered as strong binders and peptides with an $IC_{50}$ between about 50 and about 500 nM are considered as weak binders.

The binding of the MiHA candidate identified to a MHC class I molecule may be determined using other known methods, for example the T2 Peptide Binding Assay. T2 cell lines are deficient in TAP but still express low amounts of MHC class I on the surface of the cells. The T2 binding assay is based upon the ability of peptides to stabilize the MHC class I complex on the surface of the T2 cell line. T2 cells are incubated with a specific peptide (e.g., a candidate MiHA), stabilized MHC class I complexes are detected using a pan-HLA class I antibody, an analysis is carried out (by flow cytometry, for example) and binding is assessed in relation to a non-binding negative control. The presence of stabilized peptide/MHC class I complexes at the surface is indicative that the peptide (e.g., candidate MiHA) binds to MHC class I molecules.

The binding of a peptide of interest (e.g., candidate MiHA) to MHC may also be assessed based on its ability to inhibit the binding of a radiolabeled probe peptide to MHC molecules. MHC molecules are solubilized with detergents and purified by affinity chromatography. They are then incubated for 2 days at room temperature with the inhibitor peptide (e.g., candidate MiHA) and an excess of a radiolabeled probe peptide, in the presence of a cocktail of protease inhibitors. At the end of the incubation period, MHC-peptide complexes are separated from unbound radiolabeled peptide by size-exclusion gel-filtration chromatography, and the percent bound radioactivity is determined. The binding affinity of a particular peptide for an MHC molecule may be determined by co-incubation of various doses of unlabeled competitor peptide with the MHC molecules and labeled probe peptide. The concentration of unlabeled peptide required to inhibit the binding of the labeled peptide by 50% (IC50) can be determined by plotting dose versus % inhibition (see, e.g., *Current Protocols in Immunology* (1998) 18.3.1-18.3.19, John Wiley & Sons, Inc.).

The binding of the MiHA candidate identified to a MHC class I molecule may be determined using an epitope discovery system, such as the ProImmune REVEAL & ProVE® epitope discovery system.

In another aspect, the present invention provides a peptide (e.g., an isolated or synthetic peptide) of 50 amino acids or less comprising the sequence (I) to (VII) described herein.

In another aspect, the present invention provides a peptide (e.g., an isolated or synthetic peptide) of 50 amino acids or less comprising the sequence (I):

wherein Z1 is an amino terminal modifying group or is absent; X1 is a sequence of 1 to 43 amino acids or is absent; X2 is L or S; X3 is a sequence of 1 to 43 amino acids or is absent; and Z2 is a carboxy terminal modifying group or is absent.

In another aspect, the present invention provides a peptide (e.g., an isolated or synthetic peptide) of 50 amino acids or less comprising the sequence (II):

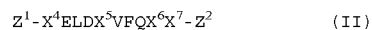

wherein $Z^1$ is an amino terminal modifying group or is absent; $X^4$ is a sequence of 1 to 43 amino acids or is absent; $X^5$ is G or R; $X^6$ is an amino acid or is absent; $X^7$ is a sequence of 1 to 43 amino acids or is absent; and $Z^2$ is a carboxy terminal modifying group or is absent.

In another aspect, the present invention provides a peptide (e.g., an isolated or synthetic peptide) of 50 amino acids or less comprising the sequence (III):

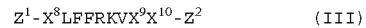

wherein $Z^1$ is an amino terminal modifying group or is absent; $X^8$ is a sequence of 1 to 43 amino acids or is absent; $X^9$ is P or A; $X^{10}$ is a sequence of 1 to 43 amino acids or is absent; and $Z^2$ is a carboxy terminal modifying group or is absent.

In another aspect, the present invention provides a peptide (e.g., an isolated or synthetic peptide) of 50 amino acids or less comprising the sequence (IV):

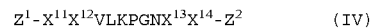

wherein $Z^1$ is an amino terminal modifying group or is absent; $X^{11}$ is a sequence of 1 to 43 amino acids or is absent; $X^{12}$ is S or T; $X^{13}$ is an amino acid or is absent; $X^{14}$ is a sequence of 1 to 43 amino acids or is absent; and $Z^2$ is a carboxy terminal modifying group or is absent.

In another aspect, the present invention provides a peptide (e.g., an isolated or synthetic peptide) of 50 amino acids or less comprising the sequence (V):

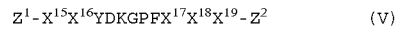

wherein $Z^1$ is an amino terminal modifying group or is absent; $X^{15}$ is a sequence of 1 to 43 amino acids or is absent; $X^{16}$ is an amino acid or is absent; $X^{17}$ is R or W; $X^{18}$ is an amino acid or is absent; $X^{19}$ is a sequence of 1 to 43 amino acids or is absent; $Z^2$ is a carboxy terminal modifying group or is absent.

In another aspect, the present invention provides a peptide (e.g., an isolated or synthetic peptide) of 50 amino acids or less comprising the sequence (VI):

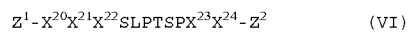

wherein $Z^1$ is an amino terminal modifying group or is absent; $X^{20}$ is a sequence of 1 to 43 amino acids or is absent; $X^{21}$ is an amino acid or is absent; $X^{22}$ is an amino acid or is absent; $X^{23}$ is G or R; $X^{24}$ is a sequence of 1 to 43 amino acids or is absent; $Z^2$ is a carboxy terminal modifying group or is absent.

In another aspect, the present invention provides a peptide (e.g., an isolated or synthetic peptide) of 50 amino acids or less comprising the sequence (VII):

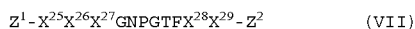

$$Z^1-X^{25}X^{26}X^{27}GNPGTFX^{28}X^{29}-Z^2 \qquad (VII)$$

wherein $Z^1$ is an amino terminal modifying group or is absent; $X^{25}$ is a sequence of 1 to 43 amino acids or is absent; $X^{26}$ is an amino acid or is absent; $X^{27}$ is an amino acid or is absent; $X^{28}$ is K or N; $X^{29}$ is a sequence of 1 to 43 amino acids or is absent; $Z^2$ is a carboxy terminal modifying group or is absent.

In another aspect, the present invention provides a peptide of 50 amino acids or less comprising any one of the sequences (I) to (VII) as defined herein.

In general, peptides presented in the context of HLA class I vary in length from about 7 to about 15 amino acid residues, and a longer peptide (e.g., of 50 amino acids or less) can be enzymatically processed to a peptide of such length. In embodiments, the peptide is 45, 40, 35, 30, 25, 20 or 15 amino acids or less. A peptide comprising the above-noted sequence/motif provided by the invention typically is at least 7 amino acids in length but preferably at least 8 or 9 amino acids. The upper length of a peptide provided by the invention is no more than 15 amino acids, but preferably no more than about 13, 12 or 11 amino acids in length. In embodiments, the above-mentioned peptide is about 8 to 12 amino acids long (e.g., 8, 9, 10, 11 or 12 amino acids long), small enough for a direct fit in an HLA class I molecule, but it may also be larger, between 12 to about 20, 25, 30, 35, 40, 45 or 50 amino acids and presented by HLA molecules only after cellular uptake and intracellular processing by the proteasome and transport before presentation in the groove of an MHC molecule.

The term "amino acid" as used herein includes both L- and D-isomers of the naturally occurring amino acids as well as other amino acids (e.g., naturally-occurring amino acids, non-naturally-occurring amino acids, amino acids which are not encoded by nucleic acid sequences, etc.) used in peptide chemistry to prepare synthetic analogs of peptides. Examples of naturally occurring amino acids are glycine, alanine, valine, leucine, isoleucine, serine, threonine, etc.

Other amino acids include for example non-genetically encoded forms of amino acids, as well as a conservative substitution of an L-amino acid. Naturally-occurring non-genetically encoded amino acids include, for example, beta-alanine, 3-amino-propionic acid, 2,3-diaminopropionic acid, alpha-aminoisobutyric acid (Aib), 4-amino-butyric acid, N-methylglycine (sarcosine), hydroxyproline, ornithine (e.g., L-ornithine), citrulline, t-butylalanine, t-butylglycine, N-methylisoleucine, phenylglycine, cyclohexylalanine, norleucine (Nle), norvaline, 2-naphthylalanine, pyridylalanine, 3-benzothienyl alanine, 4-chlorophenylalanine, 2-fluorophenylalanine, 3-fluorophenylalanine, 4-fluorophenylalanine, penicillamine, 1,2,3,4-tetrahydro-isoquinoline-3-carboxylix acid, beta-2-thienylalanine, methionine sulfoxide, L-homoarginine (Hoarg), N-acetyl lysine, 2-amino butyric acid, 2-amino butyric acid, 2,4,-diaminobutyric acid (D- or L-), p-aminophenylalanine, N-methylvaline, homocysteine, homoserine (HoSer), cysteic acid, epsilon-amino hexanoic acid, delta-amino valeric acid, or 2,3-diaminobutyric acid (D- or L-), etc. These amino acids are well known in the art of biochemistry/peptide chemistry.

In embodiments, the peptides of the present invention include peptides with altered sequences containing substitutions of functionally equivalent amino acid residues, relative to the above-mentioned sequences. For example, one or more amino acid residues within the sequence can be substituted by another amino acid of a similar polarity (having similar physico-chemical properties) which acts as a functional equivalent, resulting in a silent alteration. Substitution for an amino acid within the sequence may be selected from other members of the class to which the amino acid belongs. For example, positively charged (basic) amino acids include arginine, lysine and histidine (as well as homoarginine and ornithine). Nonpolar (hydrophobic) amino acids include leucine, isoleucine, alanine, phenylalanine, valine, proline, tryptophan and methionine. Uncharged polar amino acids include serine, threonine, cysteine, tyrosine, asparagine and glutamine. Negatively charged (acidic) amino acids include glutamic acid and aspartic acid. The amino acid glycine may be included in either the nonpolar amino acid family or the uncharged (neutral) polar amino acid family. Substitutions made within a family of amino acids are generally understood to be conservative substitutions.

The above-mentioned peptide may comprise all L-amino acids, all D-amino acids or a mixture of L- and D-amino acids. In an embodiment, the above-mentioned peptide comprises all L-amino acids.

The peptide may also be N- and/or C-terminally capped or modified to prevent degradation, increase stability or uptake. In an embodiment, the amino terminal residue (i.e., the free amino group at the N-terminal end) of the peptide is modified (e.g., for protection against degradation), for example by covalent attachment of a moiety/chemical group ($Z^1$). $Z^1$ may be a straight chained or branched alkyl group of one to eight carbons, or an acyl group (R—CO—), wherein R is a hydrophobic moiety (e.g., acetyl, propionyl, butanyl, iso-propionyl, or iso-butanyl), or an aroyl group (Ar—CO—), wherein Ar is an aryl group. In an embodiment, the acyl group is a $C_1$-$C_{16}$ or $C_3$-$C_{16}$ acyl group (linear or branched, saturated or unsaturated), in a further embodiment, a saturated $C_1$-$C_6$ acyl group (linear or branched) or an unsaturated $C_3$-$C_6$ acyl group (linear or branched), for example an acetyl group ($CH_3$—CO—, Ac). In an embodiment, $Z^1$ is absent.

The carboxy terminal residue (i.e., the free carboxy group at the C-terminal end of the peptide) of the peptide may be modified (e.g., for protection against degradation), for example by amidation (replacement of the OH group by a $NH_2$ group), thus in such a case $Z^2$ is a $NH_2$ group. In an embodiment, $Z^2$ may be an hydroxamate group, a nitrile group, an amide (primary, secondary or tertiary) group, an aliphatic amine of one to ten carbons such as methyl amine, iso-butylamine, iso-valerylamine or cyclohexylamine, an aromatic or arylalkyl amine such as aniline, napthylamine, benzylamine, cinnamylamine, or phenylethylamine, an alcohol or $CH_2OH$. In an embodiment, $Z^2$ is absent.

In an embodiment, the peptide comprises the sequence ELQEKFLSL (SEQ ID NO:15), in a further embodiment the peptide is ELQEKFLSL (SEQ ID NO:15). In another embodiment, the peptide comprises the sequence ELQEKFSSL (SEQ ID NO:16), in a further embodiment the peptide is ELQEKFSSL (SEQ ID NO:16).

In an embodiment, the peptide comprises the sequence QELDGVFQKL (SEQ ID NO:17). In a further embodiment, the peptide is QELDGVFQKL (SEQ ID NO:17). In another embodiment, the peptide comprises the sequence QELDRVFQKL (SEQ ID NO:18). In a further embodiment, the peptide is QELDRVFQKL (SEQ ID NO:18).

In an embodiment, the peptide comprises the sequence SLFFRKVPF (SEQ ID NO:19). In a further embodiment, the peptide is SLFFRKVPF (SEQ ID NO:19). In another embodiment, the peptide comprises the sequence SLFFRKVAF (SEQ ID NO:20). In a further embodiment, the peptide is SLFFRKVAF (SEQ ID NO:20).

In an embodiment, the above-mentioned peptide comprises the sequence SVLKPGNSK (SEQ ID NO:21). In a further embodiment, the peptide is SVLKPGNSK (SEQ ID NO:21). In another embodiment, the above-mentioned peptide comprises the sequence TVLKPGNSK (SEQ ID NO:22). In a further embodiment, the peptide is TVLKPGNSK (SEQ ID NO:22).

In an embodiment, the above-mentioned peptide comprises the sequence AMYDKGPFRSK (SEQ ID NO:23). In an embodiment, the above-mentioned peptide is AMYDKGPFRSK (SEQ ID NO:23). In another embodiment, the above-mentioned peptide comprises the sequence AMYDKGPFVVSK (SEQ ID NO:24). In an embodiment, the above-mentioned peptide is AMYDKGPFVVSK (SEQ ID NO:24).

In an embodiment, the above-mentioned peptide comprises the sequence RVSLPTSPG (SEQ ID NO:25). In an embodiment, the above-mentioned peptide is RVSLPTSPG (SEQ ID NO:25). In another embodiment, the above-mentioned peptide comprises the sequence RVSLPTSPR (SEQ ID NO:26). In an embodiment, the above-mentioned peptide is RVSLPTSPR (SEQ ID NO:26).

In an embodiment, the above-mentioned peptide comprises the sequence VMGNPGTFK (SEQ ID NO:27). In an embodiment, the above-mentioned peptide is VMGNPGTFK (SEQ ID NO:27). In another embodiment, the above-mentioned peptide comprises the sequence VMGNPGTFN (SEQ ID NO:28). In an embodiment, the above-mentioned peptide is VMGNPGTFN (SEQ ID NO:28).

The peptides of the invention may be produced by expression in a host cell comprising a nucleic acid encoding the peptides (recombinant expression) or by chemical synthesis (e.g., solid-phase peptide synthesis). Peptides can be readily synthesized by manual and/or automated solid phase procedures well known in the art. Suitable syntheses can be performed for example by utilizing "T-boc" or "Fmoc" procedures. Techniques and procedures for solid phase synthesis are described in for example Solid Phase Peptide Synthesis: A Practical Approach, by E. Atherton and R. C. Sheppard, published by IRL, Oxford University Press, 1989. Alternatively, the peptides may be prepared by way of segment condensation, as described, for example, in Liu et al., *Tetrahedron Lett.* 37: 933-936, 1996; Baca et al., *J. Am. Chem. Soc.* 117: 1881-1887, 1995; Tam et al., *Int. J. Peptide Protein Res.* 45: 209-216, 1995; Schnolzer and Kent, *Science* 256: 221-225, 1992; Liu and Tam, *J. Am. Chem. Soc.* 116: 4149-4153, 1994; Liu and Tam, *Proc. Natl. Acad. Sci. USA* 91: 6584-6588, 1994; and Yamashiro and Li, *Int. J. Peptide Protein Res.* 31: 322-334, 1988). Other methods useful for synthesizing the peptides are described in Nakagawa et al., *J. Am. Chem. Soc.* 107: 7087-7092, 1985.

Peptides comprising naturally occurring amino acids encoded by the genetic code may also be prepared using recombinant DNA technology using standard methods.

Accordingly, in another aspect, the invention further provides a nucleic acid (isolated) encoding the above-mentioned peptides of sequences I-VII. In an embodiment, the nucleic acid does not encode the full-length CENPF, ZWINT, MTCH2, ELF1, NQO1, KIAA0226L or RMDN1 polypeptide. In an embodiment, the nucleic acid has a length of 150 nucleotides or less, in further embodiments 135, 120, 105, 90, 75, 60, 45, 42 or 39 nucleotides or less. In other embodiments, the nucleic acid comprises from about 21 nucleotides to about 45 nucleotides, from about 24 to about 36 nucleotides, for example 24, 27, 30, 33 or 36 nucleotides.

"Isolated", as used herein, refers to a peptide or nucleic molecule separated from other components that are present in the natural source of the macromolecule (other nucleic acids, proteins, lipids, sugars, etc.). "Synthetic", as used herein, refers to a peptide or nucleic molecule that is not isolated from its natural sources, e.g., which is produced through recombinant technology or using chemical synthesis.

In an embodiment, the above-mentioned peptide is substantially pure. A compound is "substantially pure" when it is separated from the components that naturally accompany it. Typically, a compound is substantially pure when it is at least 60%, more generally 75%, 80% or 85%, preferably over 90% and more preferably over 95%, by weight, of the total material in a sample. Thus, for example, a polypeptide that is chemically synthesized or produced by recombinant technology will generally be substantially free from its naturally associated components. A nucleic acid molecule is substantially pure when it is not immediately contiguous with (i.e., covalently linked to) the coding sequences with which it is normally contiguous in the naturally occurring genome of the organism from which the nucleic acid is derived. A substantially pure compound can be obtained, for example, by extraction from a natural source; by expression of a recombinant nucleic acid molecule encoding a peptide compound; or by chemical synthesis. Purity can be measured using any appropriate method such as column chromatography, gel electrophoresis, HPLC, etc.

The nucleic acid may be in a vector, such as a cloning vector or an expression vector, that may be transfected into a host cell. Alternatively, the nucleic acid may be incorporated into the genome of the host cell. In either event, the host cell expresses the nucleic acid, and in turn the encoded peptide. The invention also provides a vector or plasmid comprising the above-mentioned nucleic acid. The vector or plasmid contains the necessary elements for the transcription and translation of the inserted coding sequence, and may contain other components such as resistance genes, cloning sites, etc. Methods that are well known to those skilled in the art may be used to construct expression vectors containing sequences encoding peptides or polypeptides and appropriate transcriptional and translational control/regulatory elements operably linked thereto. These methods include in vitro recombinant DNA techniques, synthetic techniques, and in vivo genetic recombination. Such techniques are described in Sambrook. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

"Operably linked" refers to a juxtaposition of components, particularly nucleotide sequences, such that the normal function of the components can be performed. Thus, a coding sequence that is operably linked to regulatory sequences refers to a configuration of nucleotide sequences wherein the coding sequences can be expressed under the regulatory control, that is, transcriptional and/or translational control, of the regulatory sequences. "Regulatory/control region" or "regulatory/control sequence", as used herein, refers to the non-coding nucleotide sequences that are involved in the regulation of the expression of a coding nucleic acid. Thus the term regulatory region includes promoter sequences, regulatory protein binding sites, upstream activator sequences, and the like.

In another aspect, the present invention provides an MHC class I molecule loaded with the above-mentioned peptide.

In an embodiment, the MHC molecule is a HLA-B8 molecule, in a further embodiment a HLA-B*0801 molecule. In an embodiment, the peptide is non-covalently bound to the MHC class I molecule (i.e., the peptide is loaded into the peptide binding groove/pocket but is not covalently attached to the MHC class I molecule). In another embodiment, the peptide is covalently attached/bound to the MHC class I molecule. In such a construct, the peptide and the MHC class I molecule are produced as a fusion protein, typically with a short (e.g., 5 to 20 residues, preferably about 10) flexible linker or spacer (e.g., a polyglycine linker). In another aspect, the invention provides a nucleic acid encoding a peptide-MHC class I fusion protein. In an embodiment, the MHC class I molecule-peptide complex is multimerized. Accordingly, in another aspect, the present invention provides a multimer of MHC class I molecule loaded (covalently or not) with the above-mentioned peptide. A great number of strategies have been developed for the production of MHC multimers, including MHC dimers, tetramers, pentamers, octamers, etc. (reviewed in Bakker and Schumacher, *Current Opinion in Immunology* 2005, 17:428-433). MHC multimers are useful, for example, for the detection and purification of antigen-specific T cells.

In yet another aspect, the present invention provides a cell (e.g., a host cell), in an embodiment an isolated cell, comprising the above-mentioned nucleic acid or vector. In another aspect, the present invention provides a cell expressing at its cell surface an MHC molecule (e.g., a HLA-B8 molecule, such as a HLA-B*0801 molecule, and/or an HLA-A3 molecule, such as a HLA-A*0301 molecule and/or an HLA-B44 allele such as HLA-B*4403) loaded with the above-mentioned peptide. In an embodiment, the host cell is a primary cell, a cell line or an immortalized cell. In another embodiment, the cell is an antigen-presenting cell (APC).

Nucleic acids and vectors can be introduced into cells via conventional transformation or transfection techniques. The terms "transformation" and "transfection" refer to techniques for introducing foreign nucleic acid into a host cell, including calcium phosphate or calcium chloride co-precipitation, DEAE-dextran-mediated transfection, lipofection, electroporation, microinjection and viral-mediated transfection. Suitable methods for transforming or transfecting host cells can for example be found in Sambrook et al. (supra), and other laboratory manuals. Methods for introducing nucleic acids into mammalian cells in vivo are also known, and may be used to deliver the vector DNA of the invention to a subject for gene therapy.

In another embodiment, the present invention provides T cell receptor (TCR) molecules capable of interacting with the above-mentioned MHC molecule/peptide (MiHA) complex, and nucleic acid molecules encoding such TCR molecules. A TCR according to the present invention will preferably be capable of specifically interacting with an MiHA of the present invention loaded on an MHC molecule, preferably at the surface of a living cell in vitro or in vivo. T cell receptors and in particular nucleic acids encoding TCR's according to the invention may for instance be applied to transfer a TCR from one T cell to another T cell and generate new T cell clones capable of specifically recognizing the MiHA. By this TCR cloning method, T cell clones may be provided that essentially are of the genetic make-up of an allogeneic donor, for instance a donor of lymphocytes. The method to provide T cell clones capable of recognizing an MiHA according to the invention may be generated for and can be specifically targeted to tumor cells expressing the MiHA in a graft recipient, preferably an ASCT and/or donor lymphocyte infusion (DLI) recipient subject. Hence the invention provides CD8 T lymphocytes encoding and expressing a T cell receptor capable of interacting with the above-mentioned peptide/MHC molecule complex. Said T lymphocyte may be a recombinant or a naturally selected T lymphocyte. CD8 T lymphocytes of the invention may also be used for or in the methods and pharmaceutical compositions (see below). This specification thus provides at least two methods for producing CD8 T lymphocytes of the invention, comprising the step of bringing undifferentiated lymphocytes into contact with a peptide/MHC molecule complex (typically expressed at the surface of cells, such as APCs) under conditions conducive of triggering an immune response, which may be done in vitro or in vivo for instance in a patient receiving a graft. Alternatively, it may be carried out in vitro by cloning a gene encoding the TCR specific for interacting with a peptide/MHC molecule complex, which may be obtained from a cell obtained from the previous method or from a subject exhibiting an immune response against peptide/MHC molecule complex, into a host cell and/or a host lymphocyte obtained from a graft recipient or graft donor, and optionally differentiate to cytotoxic T lymphocytes (CTLs).

The potential impact of MiHA-based cancer immunotherapy is significant. For hematologic cancers (e.g., leukemia), the use of anti-MiHA T cells may replace conventional AHCT because it may provide superior anti-leukemic activity without causing GVHD. As a corollary it may benefit to many patients with hematologic malignancy who cannot be treated by conventional AHCT because their risk/reward (GVHD/GVT) ratio is too high. Finally, since studies in mice have shown that MiHA-based immunotherapy may be effective for treatment of solid tumors, MiHA-based cancer immunotherapy may be used to MiHA-targeted therapy of non-hematologic cancers, such as solid cancers.

High-avidity T cell responses capable of eradicating tumors can be generated in an allogeneic setting. In hematological malignancies, allogeneic HLA-matched hematopoietic stem cell transplantation (ASCT) provides a platform for allogeneic immunotherapy due to the induction of T cell-mediated graft-versus-tumor (GVT) immune responses. Immunotherapy in an allogeneic setting enables induction of effective T cell responses due to the fact that T cells of donor origin are not selected for low reactivity against self-antigens of the recipient. Therefore, high-affinity T cells against tumor- or recipient-specific antigens can be found in the T cell inoculum administered to the patient during or after ASCT. The main targets of the tumor-reactive T cell responses are polymorphic proteins for which donor and recipient are disparate, namely MiHAs. The MiHA peptide sequences identified herein may be used for the production of synthetic peptides to be used i) for in vitro priming and expansion of MiHA-specific T cells to be injected into transplant (AHCT) recipients and/or ii) as vaccines to boost the graft-vs.-tumor effect (GVTE) in recipients of MiHA-specific T cells, subsequent to the transplantation.

In another aspect, the present invention provides the use of the above-mentioned peptide of sequences (I) to (VII) in the immunotherapy of cancer.

Accordingly, in another aspect, the present invention provides a method of treating cancer, said method comprising administering to a subject in need thereof an effective amount of CD8 T lymphocytes recognizing a MHC class I molecule loaded with the above-mentioned peptide.

In another aspect, the present invention provides the use of CD8 T lymphocytes recognizing a MHC class I molecule loaded with the above-mentioned peptide for treating cancer in a subject. In another aspect, the present invention provides the use of CD8 T lymphocytes recognizing a MHC class I molecule loaded with the above-mentioned peptide for the preparation/manufacture of a medicament for treating cancer in a subject. In an embodiment, the subject is a transplant (e.g., AHCT) recipient.

In an embodiment, the above-mentioned method or use further comprises determining whether said subject expresses a CENPF nucleic acid comprising a T or a C at a position corresponding to nucleotide 4409 in the nucleic acid sequence of human CENPF (FIGS. 1A to 1C, NCBI Reference Sequence: NM_016343.3), and/or a CENPF polypeptide comprising a leucine or serine residue at a position corresponding to residue 1412 in the protein sequence of human CENPF (FIG. 1D, NCBI Reference Sequence: NP_057427.3), wherein (a) if said subject expresses a CENPF nucleic acid comprising a T at a position corresponding to nucleotide 4409 in the nucleic acid sequence of human CENPF and/or a CENPF polypeptide comprising a leucine residue at a position corresponding to residue 1412 in the protein sequence of human CENPF, $X^2$ is L in the peptide; (b) if said subject expresses a CENPF nucleic acid comprising a C at a position corresponding to nucleotide 4409 in the nucleic acid sequence of human CENPF and/or a CENPF polypeptide comprising a serine residue at a position corresponding to residue 1412 in the protein sequence of human CENPF, $X^2$ is S in the peptide.

In an embodiment, the above-mentioned method or use further comprises determining whether said subject expresses a ZWINT nucleic acid comprising an A or a G at a position corresponding to nucleotide 596 in the nucleic acid sequence of human ZWINT (FIG. 2A, NCBI Reference Sequence: NM_007057.3), and/or a ZWINT polypeptide comprising a arginine or glycine residue at a position corresponding to residue 187 in the protein sequence of human ZWINT (FIG. 2B, NCBI Reference Sequence: NP_008988.2), wherein (a) if said subject expresses a ZWINT nucleic acid comprising an A at a position corresponding to nucleotide 596 in the nucleic acid sequence of human ZWINT and/or a ZWINT polypeptide comprising an arginine residue at a position corresponding to residue 187 in the protein sequence of human ZWINT, $X^5$ is R in said peptide; (b) if said subject expresses a ZWINT nucleic acid comprising a G at a position corresponding to nucleotide 596 in the nucleic acid sequence of human ZWINT and/or a ZWINT polypeptide comprising a glycine residue at a position corresponding to residue 187 in the protein sequence of human ZWINT, $X^5$ is G in said peptide.

In an embodiment, the above-mentioned method further comprises determining whether said subject expresses a MTCH2 nucleic acid comprising a C or a G at a position corresponding to nucleotide 1057 in the nucleic acid sequence of human MTCH2 (FIG. 3A, NCBI Reference Sequence: NM_014342.3), and/or a MTCH2 polypeptide comprising a proline or alanine residue at a position corresponding to residue 290 in the protein sequence of human MTCH2 (FIG. 3B, NCBI Reference Sequence: NP_055157.1), wherein (a) if said subject expresses a MTCH2 nucleic acid comprising a C at a position corresponding to nucleotide 1057 in the nucleic acid sequence of human MTCH2 and/or a MTCH2 polypeptide comprising a proline residue at a position corresponding to residue 290 in the protein sequence of human MTCH2, $X^9$ is P in said peptide; (b) if said subject expresses a MTCH2 nucleic acid comprising a G at a position corresponding to nucleotide 1057 in the nucleic acid sequence of human MTCH2 and/or a MTCH2 polypeptide comprising an alanine residue at a position corresponding to residue 290 in the protein sequence of human MTCH2, $X^5$ is A in said peptide.

In an embodiment, the above-mentioned method further comprises determining whether said subject expresses an ELF1 nucleic acid comprising an A or T at a position corresponding to nucleotide 1400 in the nucleic acid sequence of human ELF1 (FIGS. 4A and 4B, NCBI Reference Sequence: NM_172373.3) and/or an ELF1 polypeptide having a threonine or a serine at a position corresponding to residue 343 in the ELF1 protein sequence (FIG. 4C, NCBI Reference Sequence: NP_758961.1), wherein (a) if said subject expresses an ELF1 nucleic acid comprising an A at a position corresponding to nucleotide 1400 in the nucleic acid sequence of human ELF1 and/or an ELF1 polypeptide comprising a threonine residue at a position corresponding to residue 343 in the protein sequence of human ELF1, $X^{12}$ is T in said peptide; (b) if said subject expresses an ELF1 nucleic acid comprising a T at a position corresponding to nucleotide 1400 in the nucleic acid sequence of human ELF1 and/or an ELF1 polypeptide comprising a serine residue at a position corresponding to residue 343 in the protein sequence of human ELF1, $X^{12}$ is S in said peptide.

In an embodiment, the above-mentioned method further comprises determining whether said subject expresses an NQO1 nucleic acid comprising an C or T at a position corresponding to nucleotide 615 in the nucleic acid sequence of human NQO1 (FIG. 5A, NCBI Reference Sequence: NM_000903.2) and/or an NQO1 polypeptide having an arginine or a tryptophan at a position corresponding to residue 139 in the NQO1 protein sequence (FIG. 5B, NCBI Reference Sequence: NP_000894.1), wherein (a) if said subject expresses a NQO1 nucleic acid comprising an C at a position corresponding to nucleotide 615 in the nucleic acid sequence of human NQO1 and/or a NQO1 polypeptide comprising an arginine residue at a position corresponding to residue 139 in the protein sequence of human NQO1, $X^{17}$ is R in said peptide; (b) if said subject expresses an NQO1 nucleic acid comprising a T at a position corresponding to nucleotide 615 in the nucleic acid sequence of human NQO1 and/or a NQO1 polypeptide comprising a tryptophan residue at a position corresponding to residue 139 in the protein sequence of human NQO1, $X^{17}$ is W in said peptide.

In an embodiment, the above-mentioned method further comprises determining whether said subject expresses a KIAA0226L nucleic acid comprising a G or A at a position corresponding to nucleotide 1059 in the nucleic acid sequence of human KIAA0226L (FIGS. 6A and 6B, NCBI Reference Sequence: NM_025113.2) and/or an KIAA0226L polypeptide having a glycine or an arginine at a position corresponding to residue 152 in the KIAA0226L protein sequence (FIG. 6C, NCBI Reference Sequence: NP_079389.2), wherein (a) if said subject expresses a KIAA0226L nucleic acid comprising a G at a position corresponding to nucleotide 1059 in the nucleic acid sequence of human KIAA0226L and/or a KIAA0226L polypeptide comprising a glycine residue at a position corresponding to residue 152 in the protein sequence of human KIAA0226L, $X^{23}$ is G in said peptide; (b) if said subject expresses a KIAA0226L nucleic acid comprising an A at a position corresponding to nucleotide 1059 in the nucleic acid sequence of human a KIAA0226L and/or a KIAA0226L polypeptide comprising an arginine residue at a position corresponding to residue 152 in the protein sequence of human KIAA0226L, $X^{23}$ is R in said peptide.

In an embodiment, the above-mentioned method further comprises determining whether said subject expresses an RMDN1 nucleic acid comprising an A or C at a position corresponding to nucleotide 316 in the nucleic acid sequence of human RMDN1 (FIG. 7A, NCBI Reference Sequence: NM_016033.2) and/or an RMDN1 polypeptide having a lysine or an asparagine at a position corresponding to residue 52 in the RMDN1 protein sequence (FIG. 7B, NCBI Reference Sequence: NP_057117.2), wherein (a) if said subject expresses an RMDN1 nucleic acid comprising an A at a position corresponding to nucleotide 316 in the nucleic acid sequence of human RMDN1 and/or an RMDN1 polypeptide comprising a lysine residue at a position corresponding to residue 52 in the protein sequence of human RMDN1, $X^{28}$ is K in said peptide; (b) if said subject expresses an RMDN1 nucleic acid comprising a C at a position corresponding to nucleotide 316 in the nucleic acid sequence of human RMDN1 and/or a RMDN1 polypeptide comprising an asparagine residue at a position corresponding to residue 52 in the protein sequence of human RMDN1, $X^{28}$ is N in said peptide.

The above-noted polymorphism (nucleotide variation) in the nucleic acid and/or protein of interest (e.g., CENPF, ZWINT, MTCH2, ELF1, NQO1, KIAA0226L or RMDN1) may be detected by a number of methods which are known in the art. Examples of suitable methods for detecting alterations at the nucleic acid level include sequencing of the nucleic acid sequence of the nucleic acid of interest (e.g., CENPF, ZWINT, MTCH2, ELF1, NQO1, KIAA0226L or RMDN1); hybridization of a nucleic acid probe capable of specifically hybridizing to a nucleic acid of interest (e.g., CENPF, ZWINT, MTCH2, ELF1, NQO1, KIAA0226L or RMDN1) comprising the polymorphism (the first allele) and not to (or to a lesser extent to) a corresponding nucleic acid that do not comprise the polymorphism (the second allele) (under comparable hybridization conditions, such as stringent hybridization conditions), or vice-versa; restriction fragment length polymorphism analysis (RFLP); Amplified fragment length polymorphism PCR (AFLP-PCR); amplification of a nucleic acid fragment using a primer specific for one of the allele, wherein the primer produces an amplified product if the allele is present and does not produce the same amplified product when the other allele is used as a template for amplification (e.g., allele-specific PCR). Other methods include in situ hybridization analyses and single-stranded conformational polymorphism analyses. Further, nucleic acids of interest (e.g., CENPF, ZWINT, MTCH2, ELF1, NQO1, KIAA0226L or RMDN1 nucleic acids) may be amplified using known methods (e.g., polymerase chain reaction [PCR]) prior to or in conjunction with the detection methods noted herein. The design of various primers for such amplification is known in the ad. The nucleic acid (mRNA) may also be reverse transcribed into cDNA prior to analysis.

Examples of suitable methods for detecting alterations/polymorphisms at the polypeptide level include sequencing of the polypeptide of interest (e.g., CENPF, ZWINT, MTCH2, ELF1, NQO1, KIAA0226L or RMDN1); digestion of the polypeptide followed by mass spectrometry or HPLC analysis of the peptide fragments, wherein the alteration/polymorphism of the polypeptide of interest (e.g., CENPF, ZWINT, MTCH2, ELF1, NQO1, KIAA0226L or RMDN1) results in an altered mass spectrometry or HPLC spectrum as compared to the native polypeptide of interest (e.g., CENPF, ZWINT, MTCH2, ELF1, NQO1, KIAA0226L or RMDN1); and immunodetection using an immunological reagent (e.g., an antibody, a ligand) which exhibits altered immunoreactivity with a polypeptide comprising the alteration (first allele) relative to a corresponding native polypeptide not comprising the alteration (second allele), for example by targeting an epitope comprising the amino acid change. Immunodetection can measure the amount of binding between a polypeptide molecule and an anti-protein antibody by the use of enzymatic, chromodynamic, radioactive, magnetic, or luminescent labels which are attached to either the anti-protein antibody or a secondary antibody which binds the anti-protein antibody. In addition, other high affinity ligands may be used. Immunoassays which can be used include e.g. ELISAs, Western blots, and other techniques known to those of ordinary skill in the art (see Harlow and Lane, Antibodies: A Laboratory Manual, Cold Spring Harbor Laboratory Press, Cold Spring Harbor, N.Y., 1999 and Edwards R, Immunodiagnostics: A Practical Approach, Oxford University Press, Oxford; England, 1999).

All these detection techniques may also be employed in the format of microarrays, protein-arrays, antibody microarrays, tissue microarrays, electronic biochip or protein-chip based technologies (see Schena M., Microarray Biochip Technology, Eaton Publishing, Natick, Mass., 2000).

Further, nucleic acids of interest (e.g., CENPF, ZWINT, MTCH2, ELF1, NQO1, KIAA0226L or RMDN1 nucleic acids) may be amplified using known methods (e.g., polymerase chain reaction [PCR]) prior to or in conjunction with the detection methods noted herein. The design of various primers for such amplification is known in the art.

In an embodiment, the above determining comprises sequencing in a biological sample from a subject a region of a nucleic acid corresponding to the region encompassing (i) nucleotide 4409 of a human CENPF nucleic acid (SEQ ID NO:1), (ii) nucleotide 596 in the nucleic acid of a human ZWINT nucleic acid (SEQ ID NO:3), (iii) nucleotide 1057 in the nucleic acid of a human MTCH2 nucleic acid (SEQ ID NO:5), (iv) nucleotide 1400 in the nucleic acid of a human ELF1 nucleic acid (SEQ ID NO:7), (v) nucleotide 615 in the nucleic acid of a human NQO1 nucleic acid (SEQ ID NO:9), (vi) nucleotide 1059 in the nucleic acid of a human KIAA0226L nucleic acid (SEQ ID NO:11) and/or (vii) nucleotide 316 in the nucleic acid of a human RMDN1 nucleic acid (SEQ ID NO:13).

In an embodiment, the above-mentioned CD8 T lymphocytes are in vitro expanded CD8 T lymphocytes. Expanded CD8 T lymphocytes may be obtained by culturing primary CD8 T lymphocytes (from a donor) under conditions permitting the proliferation and/or differentiation of the CD8 T lymphocytes. Such conditions typically include contacting the CD8 T lymphocytes with cells, such as APCs, expressing at their surface peptide/MHC complexes, in the presence of growth factors and/or cytokines such as IL-2, IL-7 and/or IL-15 (see, e.g., Montes et al., Clin *Exp Immunol*. 2005 November; 142(2):292-302). Such expanded CD8 T lymphocytes are then administered to the recipient, for example through intravenous infusion.

In an embodiment, the subject is an allogeneic stem cell transplantation (ASCT) or donor lymphocyte infusion (DLI) recipient.

In another aspect, the present invention provides a method of expanding CD8 T lymphocytes for adoptive T-cell immunotherapy, said method comprising (a) determining whether a candidate donor expresses a CENPF nucleic acid comprising a T or a C at a position corresponding to nucleotide 4409 in the nucleic acid sequence of human CENPF (FIGS. 1A to 1D, NCBI Reference Sequence: NM_016343.3), and/or a CENPF polypeptide comprising a leucine or serine residue at a position corresponding to residue 1412 in the protein sequence of human CENPF (FIG. 1E, NCBI Reference Sequence: NP_057427.3) and (b)(i) if said candidate donor expresses a CENPF nucleic acid comprising a T at a position corresponding to nucleotide 4409 in the nucleic acid sequence of human CENPF and/or a CENPF polypeptide comprising a leucine residue at a position corresponding to residue 1412 in the protein sequence of human CENPF, culturing CD8 T lymphocytes from said candidate donor in the presence of cells expressing a MHC class I molecule of the HLA-B*0801 allele loaded with the above-mentioned peptide, wherein $X^2$ is S in said peptide, under conditions suitable for CD8 T lymphocyte expansion; or (b)(ii) if said candidate donor expresses a CENPF nucleic acid comprising a C at a position corresponding to nucleotide 4409 in the nucleic acid sequence of human CENPF and/or a CENPF polypeptide comprising a serine residue at a position corresponding to residue 1412 in the protein sequence of human CENPF, culturing CD8 T lymphocytes from said candidate donor in the presence of cells expressing a MHC class I molecule of the HLA-B*0801 allele loaded with the above-mentioned peptide, wherein $X^2$ is L in said peptide, under conditions suitable for CD8 T lymphocyte expansion.

In another aspect, the present invention provides a method of expanding CD8 T lymphocytes for adoptive T-cell immunotherapy, said method comprising: (a) determining whether a candidate donor expresses a ZWINT nucleic acid comprising an A or a G at a position corresponding to nucleotide 596 in the nucleic acid sequence of human ZWINT (FIG. 2A, NCBI Reference Sequence: NM_007057.3), and/or a ZWINT polypeptide comprising a arginine or glycine residue at a position corresponding to residue 187 in the protein sequence of human ZWINT (FIG. 2B, NCBI Reference Sequence: NP_008988.2) and (b)(i) if said candidate donor expresses a ZWINT nucleic acid comprising an A at a position corresponding to nucleotide 596 in the nucleic acid sequence of human ZWINT and/or a ZWINT polypeptide comprising an arginine residue at a position corresponding to residue 187 in the protein sequence of human ZWINT, culturing CD8 T lymphocytes from said candidate donor in the presence of cells expressing a MHC class I molecule of the HLA-B*4403 allele loaded with the above-mentioned peptide (II), wherein $X^5$ is G in said peptide, under conditions suitable for CD8 T lymphocyte expansion; or (b)(ii) if said candidate donor expresses a ZWINT nucleic acid comprising a G at a position corresponding to nucleotide 596 in the nucleic acid sequence of human ZWINT and/or a ZWINT polypeptide comprising a glycine residue at a position corresponding to residue 187 in the protein sequence of human ZWINT, culturing CD8 T lymphocytes from said candidate donor in the presence of cells expressing a MHC class I molecule of the HLA-B*4403 allele loaded with the above-mentioned peptide (II), wherein $X^5$ is R in said peptide, under conditions suitable for CD8 T lymphocyte expansion.

In another aspect, the present invention provides a method of expanding CD8 T lymphocytes for adoptive T-cell immunotherapy, said method comprising: (a) determining whether a candidate donor expresses a MTCH2 nucleic acid comprising a C or a G at a position corresponding to nucleotide 1057 in the nucleic acid sequence of human MTCH2 (FIG. 3A, NCBI Reference Sequence: NM_014342.3), and/or a MTCH2 polypeptide comprising a proline or alanine residue at a position corresponding to residue 290 in the protein sequence of human MTCH2 (FIG. 3B, NCBI Reference Sequence: NP_055157.1) and (b)(i) if said candidate donor expresses a MTCH2 nucleic acid comprising a C at a position corresponding to nucleotide 1057 in the nucleic acid sequence of human MTCH2 and/or a MTCH2 polypeptide comprising a proline residue at a position corresponding to residue 290 in the protein sequence of human MTCH2, culturing CD8 T lymphocytes from said candidate donor in the presence of cells expressing a MHC class I molecule of the HLA-B0801 allele loaded with the peptide, wherein $X^9$ is A in said peptide, under conditions suitable for CD8 T lymphocyte expansion; or (b)(ii) if said candidate donor expresses a MTCH2 nucleic acid comprising a G at a position corresponding to nucleotide 1057 in the nucleic acid sequence of human MTCH2 and/or a MTCH2 polypeptide comprising an alanine residue at a position corresponding to residue 290 in the protein sequence of human MTCH2, culturing CD8 T lymphocytes from said candidate donor in the presence of cells expressing a MHC class I molecule of the HLA-B*0801 allele loaded with the peptide, wherein $X^9$ is P in said peptide, under conditions suitable for CD8 T lymphocyte expansion.

In another aspect, the present invention provides a method of expanding CD8 T lymphocytes for adoptive T-cell immunotherapy, said method comprising: (a) determining whether a candidate donor expresses an ELF1 nucleic acid comprising an A or T at a position corresponding to nucleotide 1400 in the nucleic acid sequence of human ELF1 (FIGS. 4A and 4B, NCBI Reference Sequence: NM_172373.3) and/or an ELF1 polypeptide having a threonine or a serine at a position corresponding to residue 343 in the ELF1 protein sequence (FIG. 4C, NCBI Reference Sequence: NP_758961.1) and (b)(i) if said candidate donor expresses an ELF1 nucleic acid comprising an A at a position corresponding to nucleotide 1400 in the nucleic acid sequence of human ELF1 and/or an ELF1 polypeptide having a threonine at a position corresponding to residue 343 in the ELF1 protein sequence, culturing CD8 T lymphocytes from said candidate donor in the presence of cells expressing a MHC class I molecule of the HLA-A*0301 allele loaded with the above-mentioned peptide (IV), wherein $X^{12}$ is S in said peptide, under conditions suitable for CD8 T lymphocyte expansion; or (b)(ii) if said candidate donor expresses an ELF1 nucleic acid comprising a T at a position corresponding to nucleotide 1400 in the nucleic acid sequence of human ELF1 and/or an ELF1 polypeptide having a serine at a position corresponding to residue 343 in the ELF1 protein sequence, culturing CD8 T lymphocytes from said candidate donor in the presence of cells expressing a MHC class I molecule of the HLA-A*0301 allele loaded with the above-mentioned peptide (IV), wherein $X^{12}$ is T in said peptide, under conditions suitable for CD8 T lymphocyte expansion.

In another aspect, the present invention provides a method of expanding CD8 T lymphocytes for adoptive T-cell immunotherapy, said method comprising: (a) determining whether said subject expresses an NQO1 nucleic acid comprising a C or T at a position corresponding to nucleotide 615 in the nucleic acid sequence of human NQO1 (FIG. 5A, NCBI Reference Sequence: NM_000903.2) and/or an NQO1 polypeptide having an arginine or a tryptophan at a position corresponding to residue 139 in the NQO1 protein sequence (FIG. 5B, NCBI Reference Sequence: NP_000894.1) and (b)(i) if said candidate donor expresses a NQO1 nucleic acid comprising a C at a position corresponding to nucleotide 615 in the nucleic acid sequence of human NQO1 and/or a NQO1 polypeptide comprising an arginine residue at a position corresponding to residue 139 in the protein sequence of human NQO1, culturing CD8 T lymphocytes from said candidate donor in the presence of cells expressing a MHC class I molecule of the HLA-A*0301 allele loaded with the above-mentioned peptide (V), wherein $X^{17}$ is W in said peptide, under conditions suitable for CD8 T lymphocyte expansion; or (b)(ii) if said candidate donor expresses a NQO1 nucleic acid comprising a T at a position corresponding to nucleotide 615 in the nucleic acid sequence of human NQO1 and/or a NQO1 polypeptide comprising a tryptophan residue at a position corresponding to residue 139 in the protein sequence of human NQO1, culturing CD8 T lymphocytes from said candidate donor in the presence of cells expressing a MHC class I molecule of the HLA-A*0301 allele loaded with the above-mentioned peptide (V), wherein $X^{17}$ is R in said peptide, under conditions suitable for CD8 T lymphocyte expansion.

In another aspect, the present invention provides a method of expanding CD8 T lymphocytes for adoptive T-cell immunotherapy, said method comprising: (a) determining whether said subject expresses a KIAA0226L nucleic acid comprising a G or A at a position corresponding to nucleotide 1059 in the nucleic acid sequence of human KIAA0226L (FIGS. 6A and 6B, NCBI Reference Sequence: NM_025113.2) and/or a KIAA0226L polypeptide having a glycine or an arginine at a position corresponding to residue 152 in the KIAA0226L protein sequence (FIG. 6C, NCBI Reference Sequence: NP_079389.2) and (b)(i) if said candidate donor expresses a KIAA0226L nucleic acid comprising a G at a position corresponding to nucleotide 1059 in the nucleic acid sequence of human KIAA0226L and/or a KIAA0226L polypeptide comprising a glycine residue at a position corresponding to residue 152 in the protein sequence of human KIAA0226L, culturing CD8 T lymphocytes from said candidate donor in the presence of cells expressing a MHC class I molecule of the HLA-A*0301 allele loaded with the above-mentioned peptide (VI), wherein $X^{23}$ is R in said peptide, under conditions suitable for CD8 T lymphocyte expansion; or (b)(ii) if said candidate donor expresses a KIAA0226L nucleic acid comprising an A at a position corresponding to nucleotide 1059 in the nucleic acid sequence of human KIAA0226L and/or a KIAA0226L polypeptide comprising an arginine residue at a position corresponding to residue 152 in the protein sequence of human KIAA0226L, culturing CD8 T lymphocytes from said candidate donor in the presence of cells expressing a MHC class I molecule of the HLA-A*0301 allele loaded with the above-mentioned peptide (VI), wherein $X^{23}$ is G in said peptide, under conditions suitable for CD8 T lymphocyte expansion.

In another aspect, the present invention provides a method of expanding CD8 T lymphocytes for adoptive T-cell immunotherapy, said method comprising: (a) determining whether said subject expresses an RMDN1 nucleic acid comprising an A or C at a position corresponding to nucleotide 316 in the nucleic acid sequence of human RMDN1 (FIG. 7A, NCBI Reference Sequence: NM_016033.2) and/or an RMDN1 polypeptide having a lysine or an asparagine at a position corresponding to residue 52 in the RMDN1 protein sequence (FIG. 7B, NCBI Reference Sequence: NP_057117.2) and (b)(i) if said candidate donor expresses a RMDN1 nucleic acid comprising a A at a position corresponding to nucleotide 316 in the nucleic acid sequence of human RMDN1 and/or a RMDN1 polypeptide comprising a lysine residue at a position corresponding to residue 52 in the protein sequence of human RMDN1, culturing CD8 T lymphocytes from said candidate donor in the presence of cells expressing a MHC class I molecule of the HLA-A*0301 allele loaded with the above-mentioned peptide (VII), wherein $X^{28}$ is N in said peptide, under conditions suitable for CD8 T lymphocyte expansion; or (b)(ii) if said candidate donor expresses a RMDN1 nucleic acid comprising a C at a position corresponding to nucleotide 316 in the nucleic acid sequence of human RMDN1 and/or a RMDN1 polypeptide comprising an arginine residue at a position corresponding to residue 52 in the protein sequence of human RMDN1, culturing CD8 T lymphocytes from said candidate donor in the presence of cells expressing a MHC class I molecule of the HLA-A*0301 allele loaded with the above-mentioned peptide (VII), wherein $X^{28}$ is K in said peptide, under conditions suitable for CD8 T lymphocyte expansion.

In an embodiment, the above-mentioned cancer comprises tumor cells expressing CENPF, ZWINT, MTCH2, ELF1, NQO1, KIAA0226L and/or RMDN1.

In an embodiment, the above-mentioned cancer comprises tumor cells expressing CENPF, and is a hematopoietic cancer, such as leukemia, lymphoma, or myeloma, or a solid tumor such as head and neck squamous cell carcinomas, breast cancer, non-Hodgkin's lymphoma or gastrointestinal cancer.

In another embodiment, the above-mentioned cancer comprises tumor cells expressing ZWINT, and is a breast, prostate or bladder cancer.

In another embodiment, the above-mentioned cancer comprises tumor cells expressing MTCH2, and is a solid tumor/cancer, in a further embodiment lung, thyroid, liver, esophagus, colon or breast cancer, or osteosarcoma.

In another embodiment, the above-mentioned cancer comprises tumor cells expressing ELF1, and is leukemia, lung cancer (e.g., non-small cell lung cancer), breast cancer or ovarian cancer.

In another embodiment, the above-mentioned cancer comprises tumor cells expressing NQO1, and is lung cancer (e.g., non-small cell lung cancer), skin cancer, breast cancer, liver cancer (e.g., intrahepatic cholangiocarcinoma) digestive tract cancer such as colorectal cancer, or pancreatic cancer.

In another embodiment, the above-mentioned cancer comprises tumor cells expressing KIAA0226L, and is a lymphoma (e.g., Burkitt's lymphoma), skin cancer, breast cancer, liver cancer (e.g., intrahepatic cholangiocarcinoma) digestive tract cancer such as colorectal cancer, or pancreatic cancer.

Although the present invention has been described hereinabove by way of specific embodiments thereof, it can be modified, without departing from the spirit and nature of the subject invention as defined in the appended claims. In the claims, the word "comprising" is used as an open-ended term, substantially equivalent to the phrase "including, but not limited to". The singular forms "a", "an" and the include corresponding plural references unless the context clearly dictates otherwise.

MODE(S) FOR CARRYING OUT THE
INVENTION

The present invention is illustrated in further details by the following non-limiting examples.

Example 1: Materials and Methods

Cell Culture.
Peripheral blood mononuclear cells (PBMCs) were isolated from blood samples of 2 HLA-identical siblings. Epstein-Barr virus (EBV)-transformed B lymphoblastoid cell lines (B-LCLs) were derived from PBMCs with Ficoll-Paque™ Plus (Amersham) as described (Tosato and Cohen, 2007). Established B-LCLs were maintained in RPMI 1640 medium supplemented with 10% fetal bovine serum, 25 mM of HEPES, 2 mM L-glutamine and penicillin-streptomycin (all from Invitrogen).

HLA Typing.

High-resolution HLA genotyping was performed at the Maisonneuve-Rosemont Hospital. The HLA genotype of our subjects was HLA-A*0301/2902, HLA-B*0801/*4403, HLA-C*0701/*1601 and HLA-DRB1*0301/*0701.

RNA Extraction.

Total RNA was isolated from 5 million B-LCLs using RNeasy™ mini kit including DNase I treatment (Qiagen) according to the manufacturer's instructions. Total RNA was quantified using the NanoDrop™ 2000 (Thermo Scientific) and RNA quality was assessed with the 2100 Bioanalyzer™ (Agilent Technologies).

Preparation of Transcriptome Libraries.

Transcriptome libraries were generated from 1 µg of total RNA using the TruSeq™ RNA Sample Prep Kit (v2) (RS-930-1021, Illumina) following the manufacturer's protocol. Briefly, poly-A mRNA was purified using poly-T oligo-attached magnetic beads using two rounds of purification. During the second elution of the poly-A RNA, the RNA was fragmented and primed for cDNA synthesis. Reverse transcription (RT) of the first strand was done using random primers and SuperScript™ II (InvitroGene). A second round of RT was also done to generate a double-stranded cDNA, which was then purified using Agencourt AMpure™ XP PCR purification system (Beckman Coulter). End repair of fragmented cDNA, adenylation of the 3' ends and ligation of adaptors were done following the manufacturer's protocol. Enrichment of DNA fragments containing adapter molecules on both ends was done using 15 cycles of PCR amplification and the Illumina™ PCR mix and primers cocktail.

DNA Extraction.

Genomic DNA was extracted from 5 million B-LCLs using the PureLink™ Genomic DNA Mini Kit (Invitrogen) according to the manufacturer's instructions. DNA was quantified and quality-assessed using the NanoDrop™ 2000 (Thermo Scientific).

Preparation of Genomic DNA Libraries and Exome Enrichment.

Genomic libraries were constructed from 1 µg of genomic DNA using the TruSeq™ DNA Sample Preparation Kit (v2) (FC-930-1021, Illumina) following the manufacturer's protocol. This included the following steps: DNA shearing using a Covaris™ S2 instrument, DNA end repair, 3' ends adenylation, ligation of adaptors, purification of ligation products and PCR amplification to enrich DNA fragments that have adapter molecules.

DNA-Seq libraries were subjected to an enrichment step to sequence only the coding portion (exome) of the human genome. 500 ng of DNA-Seq libraries were used for hybrid selection-based exome enrichment with the TruSeq™ exome enrichment kit (FC-930-1012, Illumina) according to the manufacturer's instructions.

Whole Transcriptome Sequencing (RNA-Seq) and Exome Sequencing.

Paired-end (2×100 bp) sequencing was performed using the Illumina HiSeq2000™ machine running TruSeq™ v3 chemistry. Cluster density was targeted at around 600-800 k clusters/mm$^2$. Two RNA-Seq or four exomes libraries were sequenced per lane (8 lanes per slide). Detail of the Illumina sequencing technologies can be found at http://www.illumina.com/applications/detail/sequencinq/dna_sequencing.ilmn. Briefly, DNA or RNA libraries are incorporated into a fluidic flow cell design with 8 individual lanes. The flow cell surface is populated with capture oligonucleotide anchors, which hybridize the appropriately modified DNA segments of a sequencing library. By a process called "bridge amplification," captured DNA templates are amplified in the flow cell by "arching" over and hybridizing to an adjacent anchor oligonucleotide primer. The sequencing reaction is performed by hybridizing a primer complementary to the adapter sequence and then cyclically adding DNA polymerase and a mixture of 4 differently colored fluorescent reversible dye terminators to the captured DNA in the flow cell. By using this approach, unmodified DNA fragments and unincorporated nucleotides are washed away, while captured DNA fragments are extended one nucleotide at a time. After each nucleotide-coupling cycle takes place, the flow cell is scanned, and digital images are acquired to record the locations of fluorescently labeled nucleotide incorporations. Following imaging, the fluorescent dye and the terminal 3 blocker are chemically removed from the DNA before the next nucleotide coupling cycle.

Read Mapping.

Sequence data were mapped to the human reference genome (hg19) using the Ilumina Casava™ 1.8.1 and the Eland™ v2 mapping softwares. First, the *.bcl files were converted into compressed FASTQ files, following by demultiplexing of separate multiplexed sequence runs by index. Then, single reads were aligned to the human reference genome using the multiseed and gapped alignment method. Multiseed alignment works by aligning the first seed of 32 bases and consecutive seeds separately. Gapped alignment extends each candidate alignment to the full length of the read and allows for gaps up to 10 bases. The following criteria were applied: i) a read has to have at least one seed that matches with at most 2 mismatches, and for that seed no gaps are allowed and ii) for the whole read any number of gaps were allowed, as long as they correct at least five mismatches downstream. For each candidate alignment a probability score was calculated. This score is based on the sequencing base quality values and the positions of the mismatches. The alignment score of a read, which is expressed on the Phred scale, was computed from the probability scores of the candidate alignments. The best alignment for a given read corresponded to the candidate alignment with the highest probability score and it was picked if the alignment score exceeded a threshold. Reads that mapped at 2 or more locations (multireads) were not included in further analyses. An additional alignment was done against splice junctions and contaminants (mitochondrial and ribosomal RNA).

Identification of Single Nucleotide Variations.

The first step of the process consists of retrieving the list of all single nucleotide variations (SNV) observed between the reference genome (GRCh37.p2, NCBI) and the sequenced transcriptome of each of our subjects. This was done by using the SNP calling program Casava™ v1.8.2 from Ilumina (http://support.illumina.com/sequencing/sequencing_software/casava.ilmn). Casava calculates and retrieves statistics about every observed SNV including its position, the reference base, the raw counts for each base, the most probable genotype (max_gt) and the probability of the most probable genotype (Qmax_gt). Among the SNVs called by Casava™ only those that had a high confidence (Qmax_gt value>20) were considered. SNVs with Qmax_gt value below this threshold were assigned with the reference base instead. This strategy was used to identify SNVs at the transcript level between each of our subjects and the reference genome.

In Silico Translated Transcriptome.

The sequences containing the identified SNVs of each individual were further processed. For each sequence, all transcripts reported in Ensembl (http://useast.ensembl.org/info/data/ftp/index.html Flicek et al., Ensembl 2012, *Nucleic Acids Research* 2012 40 Database issue: D84-D90) were retrieved and in silico translated each of them into proteins using our in-house software pyGeno (Granados et al., 2012). The in silico translated transcriptomes included cases in which more than one non-synonymous allele was found for a given position. Supposing that a polymorphic position could affect 11mers or smaller peptides upstream or downstream, a window of 66 bp around each one of these polymorphic positions was considered and computed every possible amino acid (aa) sequence variant defined by these 66 bp (or 22 aa) windows. In this way, a list of most possible aa sequences of at most 11 aa affected by non-synonymous polymorphisms was obtained. The number of aa sequences affected by one non-synonymous polymorphism was limited to 10240 to limit the size of the file. All translated sequences were compiled into a single FASTA file that was used as a database for the identification of MHC class I-associated peptides (see "MS/MS sequencing and peptide clustering" section).

Mass Spectrometry and Peptide Sequencing.

Three biological replicates of $4 \times 10^8$ exponentially growing B-LCLs were prepared from each subject. MHC class I-associated peptides were released by mild acid treatment, pretreated by desalting with an HLB cartridge, filtered with a 3000 Da cut-off column and separated by cation exchange chromatography (SCX) using an off-line 1100 series binary LC system (Agilent Technologies) as previously described (Fortier et al., 2008). Peptides were loaded at 8 uL/min on a homemade strong cation exchange (SCX) column (0.3 mm internal diameter×50 mm length) packed with SCX bulk material (Polysulfoethyl A™, PolyLC). Peptides were separated into five fractions using a linear gradient of 0-25% B in 25 min (solvent A: 5 mM ammonium formate, 15% acetonitrile, ACN, pH 3.0; solvent B: 2 M ammonium formate, 15% ACN, pH 3.0) and brought to dryness using a Speedvac.

MHC class I-associated peptide fractions were resuspended in 2% aqueous ACN (0.2% formic acid) and analyzed by LC-MS/MS using an Eksigent™ LC system coupled to a LTQ-Orbitrap™ mass spectrometer (Thermo Electron) (Fortier et al., 2008; de Verteuil et al., 2010; Caron et al., 2011). Peptides were separated in a custom $C_{18}$ reversed phase column (150 μm i.d.×100 mm, Jupiter Proteo™ 4 μm, Phenomenex) at a flow rate of 600 nL/min using a linear gradient of 3-60% aqueous ACN (0.2% formic acid) in 69 mins. Full mass spectra were acquired with the Orbitrap™ analyzer operated at a resolving power of 60 000 (at m/z 400) and collision-activated dissociation tandem mass spectra were acquired in data-dependent mode with the linear ion trap analyzer. Mass calibration used an internal lock mass (protonated $(Si(CH_3)_2O))_6$; m/z 445.120029) and mass accuracy of peptide measurements was within 5 ppm.

MS/MS Sequencing and Peptide Clustering.

Mass spectra were analyzed using Xcalibur™ software and peak lists were generated using Mascot™ distiller version 2.1.1 (Matrix Science, http://www.matrix-science.com). Database searches were performed against a non-redundant human Uniprot database (containing 110,361 sequences, released on 28 Jul. 2011) (version 101 of the UniProt Gene Ontology Annotation available from the European Bioinformatics Institute (EBI), an academic research institute located on the Wellcome Trust Genome Campus in Hinxton near Cambridge (UK), part of the European Molecular Biology Laboratory; http://www.ebi.ac.uk/Information/. Magrane et al., Database Vol. 2011, Article ID bar009; The UniProt Consortium, *Nucleic Acids Res.* 2011 January; 39(Database issue): D214-D219) and databases specific for each individual (see "in silico translated transcriptome" section) using Mascot (version 2.3, Matrix Science). A Mascot search against a concatenated target/decoy database consisting of combined forward and reverse versions of the Ensembl human reference genome database and of each subject-specific database. Non-redundant peptide sequences with a cutoff score threshold above 15 were selected. The tolerances for precursor and fragment mass values were set to 0.02 and 0.05 Dalton, respectively. Searches were performed without enzyme specificity and a variable modification for oxidation (Met) and deamidation (Asn, Gln). Raw data files were converted to peptide maps comprising m/z values, charge state, retention time and intensity for all detected ions above a threshold of 8000 counts using in-house software (Proteoprofile) (Fortier et al., 2008; de Verteuil et al., 2010; Caron et al., 2011). Peptide maps were aligned together and peptide ions of each map (including non-sequenced ions) were aggregated to their corresponding Mascot identification, creating a peptide abundance profile. When multiple Mascot identifications were associated to the same ions, only the one with the highest score was kept. The intensity counts were then summed for identical peptide sequences resulting in a non-redundant abundance profile of identified peptide sequences.

Selection of MiHA Candidates and Identification of Proteins Source of MiHAs.

Peptides were filtered by their length and those peptides with the canonical MHC I-associated peptide length (typically 8-11 mers) were kept. Peptides were considered to be undetected/not expressed if they were absent in 3 replicates per subject, and detected/expressed if they were identified in at least 2 replicates per subject. The predicted binding affinity ($IC_{50}$) of peptides to the allelic products was obtained using NetMHCcons version 1.0 (http://www.cbs.dtu.dk/services/NetMHCcons/) (Karosiene et al., 2011) and was used to classify MHC I peptides. Peptides with an $IC_{50}$ below 50 nM were considered as strong binders and peptides with an $IC_{50}$ between 50 and 500 nM were considered as weak binders.

MiHA peptides were selected according to the following criteria:
i) Presence of a non-synonymous SNV between the 2 subjects in the peptide-coding region leading to the exclusive surface expression of the corresponding peptide(s) in one of the 2 subjects. These constitute MiHA differences between the subjects.
ii) Presence of a reported non-synonymous SNP in the peptide-coding region of the subjects leading to surface expression of the corresponding peptide(s). These constitute MiHA differences between the subjects and other individuals harboring the alternate allele for the reported SNP.

The RNA (cDNA) and DNA sequences encoding MiHAs candidates were manually inspected using the Integrative Genomics Viewer v2.0 (The Broad Institute). The UCSC Repeat Masker track was included to discard candidates that corresponded to repetitive regions. A dbSNP (build 135) track was also used to identify those SNVs in the MiHA-encoding region that corresponded to reported SNPs. MiHA candidates were further inspected for mass accuracy and MS/MS spectra were validated manually using the Xcalibur™ software (Thermo Xcalibur 2.2 SP1.48 version).

Example 2: Novel High-Throughput Method for Discovery of Human MiHAs

Since MiHAs are i) peptides ii) whose presence depends on genetic polymorphisms, it was reasoned that high-throughput MiHA discovery would involve a combination of MS and personalized whole transcriptome and/or exome sequencing. Genomic data alone are insufficient for MiHA discovery because even if a genetic polymorphism is identified in a gene, i) only 0.1% of expressed peptides are presented as MAPs at the cell surface and ii) the effect of polymorphisms in trans cannot be predicted (5;6). In MS analyses, peptides are identified through database search with softwares such as Mascot. These databases contain the translated genome of reference and do not include genetic polymorphisms. Since MiHAs are the result of genetic polymorphisms, they cannot be discovered by standard MS alone.

A novel method for human MiHA discovery was developed. One of the key elements of the method is the inclusion of personalized translated transcriptome in the database used for peptide identification by MS.

PBMCs were isolated from blood samples of 2 HLA-identical siblings who are HLA-A*0301/2902, HLA-B*0801/*4403, HLA-C*0701/*1601. Epstein-Barr virus (EBV)-transformed B lymphoblastoid cell lines (B-LCLs) were derived from PBMCs with Ficoll-Paque™ Plus. Three biological replicates of 4×10$^8$ exponentially growing B-LCLs were prepared from each subject. MAPs were released by mild acid treatment and separated by cation exchange chromatography MAP fractions were analyzed by LC-MS/MS.

On each subject, a whole-exome and transcriptome sequencing was performed, and variants were identified. Based on the list of variants for each subject and human transcript annotations, a complete repertoire of subject-specific protein sequences was produced by translating annotated transcripts. While whole-exome sequencing provided a comprehensive identification of polymorphisms in coding regions, RNA-seq provided a most useful complementary dataset since i) it can highlight differences in transcript levels between two subjects (due for instance to polymorphisms in promoter regions), and ii) it covers unannotated genes or pseudogenes not covered by the exome capture protocol. The latter genes can be a source of MAPs and may have a significant contribution to the MiHA landscape. The translated exome-transcriptome were then used as a personalized Mascot protein sequence database, helping to retrieve MAPs overlapping variant locations and most importantly documenting differences in the MAP repertoire of HLA-identical siblings: a MAP present in only one of two HLA-identical siblings is an MiHA.

Example 3: Novel MiHAs Identified

Allelic MiHAs comprising the amino acid sequence ELQEKFLSL vs. ELQEKFSSL have been identified. These MiHAs are presented at the cell surface by the MHC class I allele HLA-B*0801. These peptides are not listed in the Immune Epitope Database (Vita et al., 2010) which includes a repertoire of all well characterized peptides presented by MHC molecules (HLA in humans). These MiHAs derive from a single nucleotide polymorphism in the centromer protein F, 350/400 kDa (mitosin) (CENPF) gene. This single nucleotide polymorphism is listed as rs3795517 in the dbSNP database (Sherry et al., 2001) (http://www.ncbi.nlm.nih.gov/projects/SNP/). Two alleles are found at this locus; one codes for a CENPF protein containing the ELQEKFLSL sequence, and the other codes for a CENPF protein with the ELQEKFSSL sequence. The single nucleotide polymorphism corresponds to a T to C substitution at a position corresponding to nucleotide 4409 in the nucleic acid sequence of human CENPF (FIGS. 1A to 1D, NCBI Reference Sequence: NM_016343.3), leading to a leucine to serine substitution at a position corresponding to residue 1412 in the CENPF protein sequence (FIG. 1E, NCBI Reference Sequence: NP_057427.3). CENPF is a transient kinetochore protein that plays multiple roles in cell division. CENPF expression increases in the G2 phase but it is rapidly proteolyzed at the end of mitosis. Overexpression of CENPF has been found in various hematopoietic cancers and solid tumors including head and neck squamous cell carcinomas (de la Guardia et al., 2001), breast cancer (O'Brien et al., 2007), non-Hodgkin's lymphoma (Bencimon et al., 2005) and gastrointestinal cancer (Chen et al., 2011). Also, according to the EMBL-EBI Gene Expression Atlas (Kapushesky et al., Nucl. Acids Res. (2012) (D1): D1077-D1081), overexpression of CENPF was detected in sarcomas (leiomyosarcomas), glioblastomas, lung adenocarcinomas, colorectal cancers/colon carcinomas, prostate cancer, bladder cancers, lymphomas (peripheral T-cell lymphomas) and leukemias (acute lymphocytic leukemias, T acute lymphoblastic leukemias). Accordingly, in an embodiment, the peptide of the sequence (I) described herein may be used in the immunotherapy of one or more of these cancers.

The amino acid sequence of another pair of MiHAs identified herein is QELDGVFQKL vs. QELDRVFQKL. These MiHAs are presented at the cell surface by HLA-B*4403 molecules. These peptides are not listed in the Immune Epitope Database (Vita et al., 2010). These MiHAs derive from a single nucleotide polymorphism in the ZWINT (ZW10 interactor) gene. This single nucleotide polymorphism is listed as rs2241666 in the dbSNP database (Sherry et al., 2001). Two alleles are found at this locus; one codes for a ZWINT protein containing the QELDGVFQKL sequence, and the other codes for a ZWINT protein with the QELDRVFQKL. sequence. The single nucleotide polymorphism corresponds to an A to G substitution at a position corresponding to nucleotide 596 in the nucleic acid sequence of human ZWINT (FIG. 2A, NCBI Reference Sequence: NM_007057.3), leading to an arginine to glycine substitution at a position corresponding to residue 187 in the ZWINT protein sequence (FIG. 2B, NCBI Reference Sequence: NP_008988.2). ZWINT is a known component of the kinetochore complex that is required for the mitotic spindle checkpoint. Overexpression of ZWINT has been observed in several types of cancer (notably breast, prostate and bladder) and correlates with an increased proliferation of cancer cells (Endo et al., 2012; Ho et al., 2012; Urbanucci et al., 2012). Also, according to the EMBL-EBI Gene Expression Atlas (Kapushesky et al., Nucl. Acids Res. (2012) 40 (D1): D1077-D1081), overexpression of ZWINT was detected in lung cancer (adenocarcinoma), head and neck squamous cell carcinoma, colorectal/colon cancer, renal carcinomas as well as lymphomas (mucosa-associated lymphoid tissue lymphomas, peripheral T-cell lymphomas). Accordingly, in an embodiment, the peptide of the sequence (II) described herein may be used in the immunotherapy of one or more of these cancers.

The amino acid sequence of a third pair of MiHAs identified herein is SLFFRKVPF vs. SLFFRKVAF. These MiHAs are presented at the cell surface by HLA-B*0801 molecules. These peptides are not listed in the Immune Epitope Database (Vita et al., 2010). These MiHAs derive from a single nucleotide polymorphism in the MTCH2 (mitochondrial carrier homologue 2) gene. This single nucleotide polymorphism is listed as rs1064608 in the dbSNP database (Sherry et al., 2001). Two alleles are found at this locus; one codes for a MTCH2 protein containing the SLFFRKVAF sequence, and the other codes for a MTCH2 protein with the SLFFRKVPF sequence. The single nucleotide polymorphism corresponds to a C to G substitution at a position corresponding to nucleotide 1057 in the nucleic acid sequence of human MTCH2 (FIG. 3A, NCBI Reference Sequence: NM_014342.3), leading to a proline to alanine substitution at a position corresponding to residue 290 in the MTCH2 protein sequence (FIG. 3B, NCBI Reference Sequence: NP_055157.1). MTCH2 interact with proapoptotic truncated BID and thereby regulate apoptosis, and is upregulated/involved in several types of cancer, notably solid tumors (lung, thyroid, liver, esophagus, colon, breast) and osteosarcoma (Yu et al., 2008, Grinberg et al., 2005; Katz et al., 2012). Also, according to the EMBL-EBI Gene Expression Atlas (Kapushesky et al., Nucl. Acids Res. (2012) 40 (D1): D1077-D1081), overexpression of MTCH2 was detected in lymphomas, leukemias and myelomas. Accordingly, in an embodiment, the peptide of the sequence (III) described herein may be used in the immunotherapy of one or more of these cancers.

The amino acid sequence of a fourth pair of MiHAs identified herein is SVLKPGNSK vs. TVLKPGNSK. These MiHAs are presented at the cell surface by HLA-A*0301 molecules. These peptides are not listed in the Immune Epitope Database (Vita et al., 2010). These MiHAs derive from a single nucleotide polymorphism in the ELF1 [E74-like factor 1 (ets domain transcription factor)] gene. This single nucleotide polymorphism is listed as rs1056820 in the dbSNP database (Sherry et al., 2001). Two alleles are found at this locus; one codes for an ELF1 protein containing the SVLKPGNSK sequence, and the other codes for an ELF1 protein with the TVLKPGNSK sequence. The single nucleotide polymorphism corresponds to an A to T substitution at a position corresponding to nucleotide 1400 in the nucleic acid sequence of human ELF1 (FIGS. 4A and 4B, NCBI Reference Sequence: NM_172373.3), leading to a threonine to serine substitution at a position corresponding to residue 343 in the ELF1 protein sequence (FIG. 4C, NCBI Reference Sequence: NP_758961.1). ELF1 is a transcriptional factor that is involved in the transcriptional activation of oncogenic pathways in cancer cells, such as leukemias, non-small cell lung cancer, breast and ovarian cancer (Andrews et al., 2008; Xiang et al., 2010; Yang et al., 2010). Also, according to the EMBL-EBI Gene Expression Atlas (Kapushesky et al., Nucl. Acids Res. (2012) 40 (D1): D1077-D1081), overexpression of ELF1 was detected in sarcomas (e.g., osteosarcomas), glioblastomas, pancreatic cancer and leukemias (acute myeloid leukemia), lymphomas (Burkitt's lymphomas). Accordingly, in an embodiment, the peptide of the sequence (IV) described herein may be used in the immunotherapy of one or more of these cancers.

The amino acid sequence of another pair of MiHAs is AMYDKGPFRSK vs. AMYDKGPFWSK. These MiHAs are presented at the cell surface by HLA-A*0301. These peptides are not listed in the Immune Epitope Database (Vita et al., 2010). These MiHAs derive from a single nucleotide polymorphism in the NQO1 [NAD(P)H dehydrogenase, quinone 1] gene. This single nucleotide polymorphism is listed as r51131341 in the dbSNP database (Sherry et al., 2001). Two alleles are found at this locus; one codes for an NQO1 protein containing the AMYDKGPFRSK sequence, and the other codes for an NQO1 protein with the AMYDKGPFWSK sequence. The single nucleotide polymorphism corresponds to a C to T substitution at a position corresponding to nucleotide 615 in the nucleic acid sequence of human NQO1 (FIG. 5A, NCBI Reference Sequence: NM_000903.2), leading to an arginine to tryptophan substitution at a position corresponding to residue 139 in the NQO1 protein sequence (FIG. 5B, NCBI Reference Sequence: NP_000894.1). NQO1 is a cytosolic enzyme that catalyzes the reduction of various quinones using flavin adenine dinucleotide (FAD) as a cofactor. This protein's enzymatic activity prevents the one electron reduction of quinones that results in the production of radical species. Mutations in this NQO1 have been associated with susceptibility to various forms of cancer and altered expression of this NQO1 protein has been seen in many tumors, including non-small cell lung cancer, skin cancer (e.g., melanomas), breast cancer, liver cancer (e.g., intrahepatic cholangiocarcinoma) and digestive tract cancer such as colorectal cancer (Kolesar et al., 2011; Wakai et al., 2011; Jamieson et al., 2011; Ding et al., 2012; Yang et al., 2012; Patrick and Jaiswal, 2012). An NQO1 Substrate was recently shown to possess potent antitumor activity against a wide spectrum of cancer cells, such as pancreatic and lung cancer cells (Huang et al., 2012). Also, according to the EMBL-EBI Gene Expression Atlas (Kapushesky et al., Nucl. Acids Res. (2012) 40 (D1): D1077-D1081), overexpression of NQO1 was detected in lymphomas (Hodgkin's lymphomas, anaplastic large cell lymphoma) and brain cancers (glioblastomas, subependymal giant cell astrocytomas). Accordingly, in an embodiment, the peptide of the sequence (V) described herein may be used in the immunotherapy of one or more of these cancers.

The amino acid sequence of another pair of MiHAs is RVSLPTSPG vs. RVSLPTSPR. These MiHAs are presented at the cell surface by HLA-A*0301. These peptides are not listed in the Immune Epitope Database (Vita et al., 2010) which includes a repertoire of all well characterized peptides presented by MHC molecules (HLA in humans).

These MiHAs derive from a single nucleotide polymorphism in the KIAA0226-like gene (also known as C13orf18). This single nucleotide polymorphism is listed as rs1408184 in the dbSNP database (Sherry et al., 2001). Two alleles are found at this locus; one codes for an KIAA0226L protein containing the RVSLPTSPG sequence, and the other codes for an KIAA0226L protein with the RVSLPTSPR sequence. The single nucleotide polymorphism corresponds to a G to A substitution at a position corresponding to nucleotide 1059 in the nucleic acid sequence of human KIAA0226L (FIG. 6A, NCBI Reference Sequence: NM_025113.2), leading to a glycine to arginine substitution at a position corresponding to residue 152 in the KIAA0226L protein sequence (FIG. 6B, NCBI Reference Sequence: NP_079389.2). The function of KIAA0226L is largely unknown, and according to the BioGPS database, KIAA0226L is upregulated in B lymphocytes and Burkitt's lymphoma cells. Also, according to the EMBL-EBI Gene Expression Atlas (Kapushesky et al., Nucl. Acids Res. (2012) 40 (D1): D1077-D1081), overexpression of KIAA0226L was detected in colon cancer (carcinoma), glioblastoma, and anaplastic large cell lymphoma (Chowdary D et al., J Mol Diagn. 2006 February; 8(1):31-9; Ancona N et al., BMC Bioinformatics. 2006 Aug. 19; 7:387; Freije W A et al., Cancer Res. 2004 Sep. 15; 64(18):6503-10; Sun et al., Cancer Cell. 2006 April; 9(4):287-300; Piccaluga et al., J Clin Invest. 2007 March; 117(3):823-34. Epub 2007 Feb. 15). Accordingly, in an embodiment, the peptide of the sequence (VI) described herein may be used in the immunotherapy of one or more of these cancers.

The amino acid sequence of another pair of MiHAs is VMGNPGTFK vs. VMGNPGTFN. These MiHAs are presented at the cell surface by HLA-A*0301. These peptides are not listed in the Immune Epitope Database (Vita et al., 2010) which includes a repertoire of all well characterized peptides presented by MHC molecules (HLA in humans).

These MiHAs derive from a single nucleotide polymorphism in the RMDN1 (regulator of microtubule dynamics 1) gene (also known as FAM82B). This single nucleotide polymorphism is listed as rs6980476 in the dbSNP database (Sherry et al., 2001). Two alleles are found at this locus; one codes for an RMDN1 protein containing the VMGNPGTFK sequence, and the other codes for an RMDN1 protein with the VMGNPGTFN sequence. The single nucleotide polymorphism corresponds to an A to C substitution at a position corresponding to nucleotide 316 in the nucleic acid sequence of human RMDN1 (FIG. 7A, NCBI Reference Sequence: NM_016033.2), leading to a lysine to asparagine substitution at a position corresponding to residue 52 in the RMDN1 protein sequence (FIG. 7B, NCBI Reference Sequence: NP_057117.2). RMDN1 is a microtubule-associated protein that plays a role in chromosome segregation in *Caenorhabditis elegans* (Oishi et al., *J Cell Biol.* 179, 1149-1162, 2007). According to the BioGPS database, RMDN1 is upregulated in B lymphoblasts and Burkitt's lymphoma cells. Also, according to the EMBL-EBI Gene Expression Atlas (Kapushesky et al., *Nucl. Acids Res.* (2012) 40 (D1): D1077-D1081), overexpression of RMDN1 was detected in leiomyosarcoma (Perot et al., *Cancer Res.* 2009 Mar. 15; 69(6):2269-78; Chibon et al., *Nat Med.* 2010 July; 16(7): 781-7), breast cancer/carcinoma such as invasive ductal carcinoma (Chen et al., *Breast Cancer Res Treat.* 2010 January; 119(2):335-46; Cheng et al., *Cancer Res.* 2008 Mar. 15; 68(6):1786-96), and brain cancers such as glioblastomas and astrocytomas (subependymal giant cell astrocytomas (Sun et al., *Cancer Cell.* 2006 April; 9(4):287-300; Tyburczy et al., *Am J Pathol.* 2010 April; 176(4):1878-90). Accordingly, in an embodiment, the peptide of the sequence (VII) described herein may be used in the immunotherapy of one or more of these cancers.

Although the present invention has been described hereinabove by way of specific embodiments thereof, it can be modified, without departing from the spirit and nature of the subject invention as defined in the appended claims. In the claims, the word "comprising" is used as an open-ended term, substantially equivalent to the phrase "including, but not limited to". The singular forms "a", "an" and "the" include corresponding plural references unless the context clearly dictates otherwise.

REFERENCES

1. Sykes, M., K. Woods, and D. H. Sachs. 2008. Transplantation Immunology. In Fundamental Immunology. W. E. Paul, editor. Lippincott Williams & Wilkins, Philadelphia. 1426-1488.
2. Loveland, B. and E. Simpson. 1986. The non-MHC transplantation antigens—neither weak nor minor. Immunol. Today 7:223-229.
3. Perreault, C., F. Decary, S. Brochu, M. Gyger, R. Belanger, and D. Roy. 1990. Minor histocompatibility antigens. Blood 76:1269-1280.
4. Perreault, C. 2010. The origin and role of MHC class I-associated self-peptides. Prog. Mol Biol. Transl. Sci. 92:41-60.
5. de Verteuil, D., D. P. Granados, P. Thibault, and C. Perreault. 2012. Origin and plasticity of MHC I-associated self peptides. Autoimmun. Rev. Epub November 2011.
6. Yewdell, J. W., E. Reits, and J. Neefjes. 2003. Making sense of mass destruction: quantitating MHC class I antigen presentation. Nature Rev. Immunol. 3:952-961.
7. Neefjes, J., M. L. M. Jongsma, P. Paul, and O. Bakke. 2011. Towards a systems understanding of MHC class I and MHC class II antigen presentation. Nat. Rev. Immunol. 11:823-836.
8. Yewdell, J. W. 2011. DRiPs solidify: progress in understanding endogenous MHC class I antigen processing. Trends Immunol. 32:548-558.
9. Roopenian, D., E. Y. Choi, and A. Brown. 2002. The immunogenomics of minor histocompatibility antigens. Immunol. Rev. 190:86-94.
10. Spierings, E., M. Hendriks, L. Absi, A. Canossi, S. Chhaya, J. Crowley, H. Dolstra, J. F. Eliaou, T. Ellis, J. Enczmann, M. E. Fasano, T. Gervais, C. Gorodezky, B. Kircher, D. Laurin, M. S. Leffell, P. Loiseau, M. Malkki, M. Markiewicz, M. Martinetti, E. Maruya, N. Mehra, F. Oguz, M. Oudshoorn, N. Pereira, R. Rani, R. Sergeant, J. Thomson, T. H. Tran, H. Turpeinen, K. L. Yang, R. Zunec, M. Carrington, P. de Knijff, and E. Goulmy. 2007. Phenotype frequencies of autosomal minor histocompatibility antigens display significant differences among populations. PLoS. Genet. 3:e103.
11. Perreault, C. and S. Brochu. 2002. Adoptive cancer immunotherapy: discovering the best targets. J. Mol. Med. 80:212-218.
12. Mullally, A. and J. Ritz. 2007. Beyond HLA: the significance of genomic variation for allogeneic hematopoietic stem cell transplantation. Blood 109:1355-1362.
13. Feng, X., K. M. Hui, H. M. Younes, and A. G. Brickner. 2008. Targeting minor histocompatibility antigens in graft versus tumor or graft versus leukemia responses. Trends Immunol. 29:624-632.
14. Brickner, A. G. 2006. Mechanisms of minor histocompatibility antigen immunogenicity: the role of infinitesimal versus structurally profound polymorphisms. Immunol. Res. 36:33-41.
15. Bleakley, M. and S. R. Riddell. 2011. Exploiting T cells specific for human minor histocompatibility antigens for therapy of leukemia. Immunol. Cell Biol. 89:396-407.
16. Kawase, T., Y. Akatsuka, H. Torikai, S. Morishima, A. Oka, A. Tsujimura, M. Miyazaki, K. Tsujimura, K. Miyamura, S. Ogawa, H. Inoko, Y. Morishima, Y. Kodera, K. Kuzushima, and T. Takahashi. 2007. Alternative splicing due to an intronic SNP in HMSD generates a novel minor histocompatibility antigen. Blood 110:1055-1063.
17. Rosenberg, S. A., J. C. Yang, and N. P. Restifo. 2004. Cancer immunotherapy: moving beyond current vaccines. Nat Med. 10:909-915.
18. Bleakley, M. and S. R. Riddell. 2004. Molecules and mechanisms of the graft-versus-leukaemia effect. Nat. Rev. Cancer 4:371-380.
19. Rosenberg, S. A., J. C. Yang, R. M. Sherry, U. S. Kammula, M. S. Hughes, G. Q. Phan, D. E. Citrin, N. P. Restifo, P. F. Robbins, J. R. Wunderlich, K. E. Morton, C. M. Laurencot, S. M. Steinberg, D. E. White, and M. E. Dudley. 2011. Durable complete responses in heavily pretreated patients with metastatic melanoma using T cell transfer immunotherapy. Clin. Cancer Res. 17:4550-4557.

20. Vincent, K., D. C. Roy, and C. Perreault. 2011. Next-generation leukemia immunotherapy. Blood 118:2951-2959.
21. Rezvani, K. and A. J. Barrett. 2008. Characterizing and optimizing immune responses to leukaemia antigens after allogeneic stem cell transplantation. Best. Pract. Res. Clin. Haematol. 21:437-453.
22. Barrett, A. J. 2008. Understanding and harnessing the graft-versus-leukaemia effect. Br. J. Haematol. 142:877-888.
23. Horowitz, M. M., R. P. Gale, P. M. Sondel, J. M. Goldman, J. Kersey, H. J. Kolb, A. A. Rimm, O. Ringden, C. Rozman, B. Speck, and. 1990. Graft-versus-leukemia reactions after bone marrow transplantation. Blood 75:555-562.
24. Thomas, E. D. 2005. Foreword. In Graft-vs.-host disease. J. L. M. Ferrara, K. R. Coke, and H. J. Deeg, editors. Marcel Dekker, New York. iii-iv.
25. Molldrem, J. J. and W. D. Shlomchik. 2005. Graft-vs.-leukemia effects. In Graft-vs.-host disease. J. L. M. Ferrara, K. R. Cooke, and H. J. Deeg, editors. Marcel Dekker, New York. 155-194.
26. O'Reilly, R. J., T. Dao, G. Koehne, D. Scheinberg, and E. Doubrovina. 2010. Adoptive transfer of unselected or leukemia-reactive T-cells in the treatment of relapse following allogeneic hematopoietic cell transplantation. Seminimmunol. 22:162-172.
27. Kolb, H. J., A. Schattenberg, J. M. Goldman, B. Hertenstein, N. Jacobsen, W. Arcese, P. Ljungman, A. Ferrant, L. Verdonck, and D. Niederwieser. 1995. Graft-versus-leukemia effect of donor lymphocyte transfusions in marrow grafted patients. European Group for Blood and Marrow Transplantation Working Party Chronic Leukemia. Cancer Cell 86:2041-2050.
28. Kolb, H.-J. 2008. Graft-versus-leukemia effects of transplantation and donor lymphocytes. Blood 112:4371-4383.
29. Childs, R. W. and J. Barrett. 2004. Nonmyeloablative allogeneic immunotherapy for solid tumors. Annu. Rev. Med. 55:459-475.
30. Tykodi, S. S., E. H. Warren, J. A. Thompson, S. R. Riddell, R. W. Childs, B. E. Otterud, M. F. Leppert, R. Storb, and B. M. Sandmaier. 2004. Allogeneic hematopoietic cell transplantation for metastatic renal cell carcinoma after nonmyeloablative conditioning: toxicity, clinical response, and immunological response to minor histocompatibility antigens. Clin. Cancer Res. 10:7799-7811.
31. Bishop, M. R., D. H. Fowler, D. Marchigiani, K. Castro, C. Kasten-Sportes, S. M. Steinberg, J. C. Gea-Banacloche, R. Dean, C. K. Chow, C. Carter, E. J. Read, S. Leitman, and R. Gress. 2004. Allogeneic lymphocytes induce tumor regression of advanced metastatic breast cancer. J. Clin. Oncol. 22:3886-3892.
32. Takahashi, Y., N. Harashima, S. Kajigaya, H. Yokoyama, E. Cherkasova, J. P. McCoy, K. I. Hanada, O. Mena, R. Kurlander, T. Abdul, R. Srinivasan, A. Lundqvist, E. Malinzak, N. Geller, M. I. Lerman, and R. W. Childs. 2008. Regression of human kidney cancer following allogeneic stem cell transplantation is associated with recognition of an HERV-E antigen by T cells. J. Clin. Invest. 118:1099-1109.
33. Meunier, M. C., J. S. Delisle, J. Bergeron, V. Rineau, C. Baron, and C. Perreault. 2005. T cells targeted against a single minor histocompatibility antigen can cure solid tumors. Nat. Med. 11:1222-1229.
34. Shlomchik, W. D. 2007. Graft-versus-host disease. Nat. Rev. Immunol. 7:340-352.
35. Ferrara, J. L., J. E. Levine, P. Reddy, and E. Holler. 2009. Graft-versus-host disease. Lancet 373:1550-1561.
36. Socie, G. and B. R. Blazar. 2009. Acute graft-versus-host disease; from the bench to the bedside. Blood 114:4327-4336.
37. Greinix, H. T., C. Loddenkemper, S. Z. Pavletic, E. Holler, G. Socie, A. Lawitschka, J. Halter, and D. Wolff. 2011. Diagnosis and staging of chronic graft-versus-host disease in the clinical practice. Biol. Blood Marrow Transplant. 17:167-175.
38. Vogelsang, G. B., L. Lee, and D. M. Bensen-Kennedy. 2003. Pathogenesis and treatment of graft-versus-host disease after bone marrow transplant. Annu. Rev. Med. 54:29-52.
39. Inaba, M., K. Kurasawa, M. Mamura, K. Kumano, Y. Saito, and I. Iwamoto. 1999. Primed T cells are more resistant to Fas-mediated activation-induced cell death than naive T cells. J Immunol 163:1315-1320.
40. Yang, J., M. O. Brook, M. Carvalho-Gaspar, J. Zhang, H. E. Ramon, M. H. Sayegh, K. J. Wood, L. A. Turka, and N. D. Jones. 2007. Allograft rejection mediated by memory T cells is resistant to regulation. Proc. Natl. Acad. Sci. U.S.A 104:19954-19959.
41. Massague, J. 2008. TGFb in Cancer. Cell 134:215-230.
42. Hanahan, D. and R. A. Weinberg. 2011. Hallmarks of cancer: the next generation. Cell 144:646-674.
43. Fontaine, P., G. Roy-Proulx, L. Knafo, C. Baron, D. C. Roy, and C. Perreault. 2001. Adoptive transfer of T lymphocytes targeted to a single immunodominant minor histocompatibility antigen eradicates leukemia cells without causing graft-versus-host disease. Nat. Med. 7:789-794.
44. Meunier, M. C., C. Baron, and C. Perreault. 2009. Two host factors regulate persistence of H7a-specific T cells injected in tumor bearing mice. PLoS One 4:e4116.
45. Fortier, M. H., E. Caron, M. P. Hardy, G. Voisin, S. Lemieux, C. Perreault, and P. Thibault. 2008. The MHC class I peptide repertoire is molded by the transcriptome. J. Exp. Med. 205:595-610.
46. de Verteuil, D., T. L. Muratore-Schroeder, D. P. Granados, M. H. Fortier, M. P. Hardy, A. Bramoullé, E. Caron, K. Vincent, S. Mader, S. Lemieux, P. Thibault, and C. Perreault. 2010. Deletion of immunoproteasome subunits imprints on the transcriptome and has a broad impact on peptides presented by major histocompatibility complex I molecules. Mol Cell Proteomics 9:2034-2047.
47. Caron, E., K. Vincent, M. H. Fortier, J. P. Laverdure, A. Bramoullé, M. P. Hardy, G. Voisin, P. Roux, S. Lemieux, P. Thibault, and C. Perreault. 2011. The MHC I immunopeptidome conveys to the cell surface an integrative view of cellular regulation. Mol. Syst. Biol. 7:533.
48. den Haan, J. M., N. E. Sherman, E. Blokland, E. Huczko, F. Koning, J. W. Drijfhout, J. Skipper, J. Shabanowitz, D. F. Hunt, V. H. Engelhard, and E. Goulmy. 1995. Identification of a graft versus host disease-associated human minor histocompatibility antigen. Science 268:1476-1480.
49. den Haan, J. M., L. M. Meadows, W. Wang, J. Pool, E. Blokland, T. L. Bishop, C. Reinhardus, J. Shabanowitz, R. Offringa, D. F. Hunt, V. H. Engelhard, and E. Goulmy. 1998. The minor histocompatibility antigen HA-1: a diallelic gene with a single amino acid polymorphism. Science 279:1054-1057.
50. Brickner, A. G., E. H. Warren, J. A. Caldwell, Y. Akatsuka, T. N. Golovina, A. L. Zarling, J. Shabanowitz, L. C. Eisenlohr, D. F. Hunt, V. H. Engelhard, and S. R. Riddell. 2001. The immunogenicity of a new human minor histocompatibility antigen results from differential antigen processing. J. Exp. Med. 193:195-205.
51. Spierings, E., A. G. Brickner, J. A. Caldwell, S. Zegveld, N. Tatsis, E. Blokland, J. Pool, R. A. Pierce, S. Mollah, J. Shabanowitz, L. C. Eisenlohr, V. P. van, F. Ossendorp, D. F. Hunt, E. Goulmy, and V. H. Engelhard. 2003. The minor histocompatibility antigen HA-3 arises from differential proteasome-mediated cleavage of the lymphoid blast crisis (Lbc) oncoprotein. Blood 102:621-629.
52. Brickner, A. G., A. M. Evans, J. K. Mito, S. M. Xuereb, X. Feng, T. Nishida, L. Fairfull, R. E. Ferrell, K. A. Foon, D. F. Hunt, J. Shabanowitz, V. H. Engelhard, S. R. Riddell, and E. H. Warren. 2006. The PANE1 gene encodes a novel human minor histocompatibility antigen that is selectively expressed in B-lymphoid cells and B-CLL. Blood 107:3779-3786.
53. van Bergen, C. A. M., M. G. D. Kester, I. Jedema, M. H. M. Heemskerk, S. A. P. van Luxemburg-Heijs, F. M. Kloosterboer, W. A. E. Marijt, A. H. de Ru, M. R. Schaafsma, R. Willemze, P. A. van Veelen, and J. H. F. Falkenburg. 2007. Multiple myeloma-reactive T cells recognize an activation-induced minor histocompatibility antigen encoded by the ATP-dependent interferon-responsive (ADIR) gene. Blood 109:4089-4096.
54. Slager, E. H., M. W. Honders, E. D. Van Der Meijden, S. A. Van Luxemburg-Heijs, F. M. Kloosterboer, M. G. Kester, I. Jedema, W. A. Marijt, M. R. Schaafsma, R. Willemze, and J. H. Falkenburg. 2006. Identification of the angiogenic endothelial-cell growth factor-1/thymidine phosphorylase as a potential target for immunotherapy of cancer. Blood 107:4954-4960.
55. Dolstra, H., H. Fredrix, F. Maas, P. G. Coulie, F. Brasseur, E. Mensink, G. J. Adema, T. M. de Witte, C. G. Figdor, and E. van de Wiel-van Kemenade. 1999. A human minor histocompatibility antigen specific for B cell acute lymphoblastic leukemia. J. Exp. Med. 189:301-308.
56. Murata, M., E. H. Warren, and S. R. Riddell. 2003. A human minor histocompatibility antigen resulting from differential expression due to a gene deletion. J. Exp. Med. 197:1279-1289.
57. Warren, E. H., N. J. Vigneron, M. A. Gavin, P. G. Coulie, V. Stroobant, A. Dalet, S. S. Tykodi, S. M. Xuereb, J. K. Mito, S. R. Riddell, and B. J. Van Den Eynde. 2006. An antigen produced by splicing of noncontiguous peptides in the reverse order. Science 313:1444-1447.
58. Griffioen, M., E. D. Van Der Meijden, E. H. Slager, M. W. Honders, C. E. Rutten, S. A. Van Luxemburg-Heijs, P. A. von dem Borne, J. J. van Rood, R. Willemze, and J. H. Falkenburg. 2008. Identification of phosphatidylinositol 4-kinase type II beta as HLA class II-restricted target in graft versus leukemia reactivity. Proc. Natl. Acad. Sci. U.S.A 105:3837-3842.
59. Stumpf, A. N., E. D. Van Der Meijden, C. A. Van Bergen, R. Willemze, J. H. Falkenburg, and M. Griffioen. 2009. Identification of 4 new HLA-DR-restricted minor histocompatibility antigens as hematopoietic targets in antitumor immunity. Blood 114:3684-3692.
60. Akatsuka, Y., T. Nishida, E. Kondo, M. Miyazaki, H. Taji, H. Iida, K. Tsujimura, M. Yazaki, T. Naoe, Y. Morishima, Y. Kodera, K. Kuzushima, and T. Takahashi. 2003. Identification of a polymorphic gene, BCL2A1, encoding two novel hematopoietic lineage-specific minor histocompatibility antigens. J. Exp. Med. 197:1489-1500.
61. Rijke, B. D., A. Horssen-Zoetbrood, J. M. Beekman, B. Otterud, F. Maas, R. Woestenenk, M. Kester, M. Leppert, A. V. Schattenberg, T. de Witte, van de Wiel-van Kemenade, and H. Dolstra. 2005. A frameshift polymorphism in P2X5 elicits an allogeneic cytotoxic T lymphocyte response associated with remission of chronic myeloid leukemia. J. Clin. Invest 115:3506-3516.
62. Kawase, T., Y. Nannya, H. Torikai, G. Yamamoto, M. Onizuka, S. Morishima, K. Tsujimura, K. Miyamura, Y. Kodera, Y. Morishima, T. Takahashi, K. Kuzushima, S. Ogawa, and Y. Akatsuka. 2008. Identification of human minor histocompatibility antigens based on genetic association with highly parallel genotyping of pooled DNA. Blood 111:3286-3294.
63. Kamei, M., Y. Nannya, H. Torikai, T. Kawase, K. Taura, Y. Inamoto, T. Takahashi, M. Yazaki, S. Morishima, K. Tsujimura, K. Miyamura, T. Ito, H. Togari, S. R. Riddell, Y. Kodera, Y. Morisima, T. Takahashi, K. Kuzushima, S. Ogawa, and Y. Akatsuka. 2009. HapMap scanning of novel human minor histocompatibility antigens. Blood 113:5041-5048.
64. Van Bergen, C. A., C. E. Rutten, E. D. Van Der Meijden, S. A. Van Luxemburg-Heijs, E. G. Lurvink, J. J. Houwing-Duistermaat, M. G. Kester, A. Mulder, R. Willemze, J. H. Falkenburg, and M. Griffioen. 2010. High-throughput characterization of 10 new minor histocompatibility antigens by whole genome association scanning. Cancer Res. 70:9073-9083.
65. Spaapen, R. M., H. M. Lokhorst, K. van den Oudenalder, B. E. Otterud, H. Dolstra, M. F. Leppert, M. C. Minnema, A. C. Bloem, and T. Mutis. 2008. Toward targeting B cell cancers with CD4+ CTLs: identification of a CD19-encoded minor histocompatibility antigen using a novel genome-wide analysis. J Exp. Med 205:2863-2872.
66. Spaapen, R. M., R. A. de Kort, K. van den Oudenalder, E. M. van, A. C. Bloem, H. M. Lokhorst, and T. Mutis. 2009. Rapid identification of clinical relevant minor histocompatibility antigens via genome-wide zygosity-genotype correlation analysis. Clin. Cancer Res. 15:7137-7143.
67. Warren, E. H., N. Fujii, Y. Akatsuka, C. N. Chaney, J. K. Mito, K. R. Loeb, T. A. Gooley, M. L. Brown, K. K. Koo, K. V. Rosinski, S. Ogawa, A. Matsubara, F. R. Appelbaum, and S. R. Riddell. 2010. Therapy of relapsed leukemia after allogeneic hematopoietic cell transplant with T cells specific for minor histocompatibility antigens. Blood 115:3869-3878.
68. Mason, D. 1998. A very high level of crossreactivity is an essential feature of the T-cell receptor. Immunol. Today 19:395-404.
69. Kessler, J. H. and C. J. Melief. 2007. Identification of T-cell epitopes for cancer immunotherapy. Leukemia 21:1859-1874.
70. Popovic, J., L. P. Li, P. M. Kloetzel, M. Leisegang, W. Uckert, and T. Blankenstein. 2011. The only proposed T-cell epitope derived from the TEL-AML1 translocation is not naturally processed. Blood 118:946-954.
71. Schreiber, H., J. D. Rowley, and D. A. Rowley. 2011. Targeting mutations predictably. Blood 118:830-831.
72. Granados, D. P., W. Yahyaoui, C. M. Laumont, T. Daouda, T. L. Muratore-Schroeder, C. Cote, J. P. Laverdure, S. Lemieux, P. Thibault, and C. Perreault. 2012. MHC I-associated peptides preferentially derive from transcripts bearing miRNA recognition elements. Blood Epub Mar. 21, 2012.
73. Karosiene, E., Lundegaard, C., Lund, O., and Nielsen, M. (2011). NetMHCcons: a consensus method for the major histocompatibility complex class I predictions. Immunogenetics.
74. Tosato, G. and Cohen, J. I. (2007). Generation of Epstein-Barr Virus (EBV)-immortalized B cell lines. Curr. Protoc. Immunol. Chapter 7, Unit.

75. Bencimon, C., Salles, G., Moreira, A., Guyomard, S., Coiffier, B., Bienvenu, J., and Fabien, N. (2005). Prevalence of anticentromere F protein autoantibodies in 347 patients with non-Hodgkin's lymphoma. Ann. N. Y. Acad. Sci. 1050, 319-326.

76. Chen, W. B., Cheng, X. B., Ding, W., Wang, Y. J., Chen, D., Wang, J. H., and Fei, R. S. (2011). Centromere protein F and survivin are associated with high risk and a poor prognosis in colorectal gastrointestinal stromal tumours. J Clin. Pathol. 64, 751-755.

77. de la Guardia, C., Casiano, C. A., Trinidad-Pinedo, J., and Baez, A. (2001). CENP-F gene amplification and overexpression in head and neck squamous cell carcinomas. Head Neck 23, 104-112.

78. O'Brien, S. L., Fagan, A., Fox, E. J., Millikan, R. C., Culhane, A. C., Brennan, D. J., McCann, A. H., Hegarty, S., Moyna, S., Duffy, M. J., Higgins, D. G., Jirstrom, K., Landberg, G., and Gallagher, W. M. (2007). CENP-F expression is associated with poor prognosis and chromosomal instability in patients with primary breast cancer. Int. J Cancer 120, 1434-1443.

79. Sherry, S. T., Ward, M. H., Kholodov, M., Baker, J., Phan, L., Smigielski, E. M., and Sirotkin, K. (2001). dbSNP: the NCBI database of genetic variation. Nucleic Acids Res. 29, 308-311.

80. Vita, R., Zarebski, L., Greenbaum, J. A., Emami, H., Hoof, I., Salimi, N., Damle, R., Sette, A., and Peters, B. (2010). The immune epitope database 2.0. Nucleic Acids Res. 38, D854-D862.

81. Endo, H., Ikeda, K., Urano, T., Horie-Inoue, K., and Inoue, S. (2012). Terf/TRIM17 stimulates degradation of kinetochore protein ZWINT and regulates cell proliferation. J. Biochem. 151, 139-144.

82. Ho, J. R., Chapeaublanc, E., Kirkwood, L., Nicolle, R., Benhamou, S., Lebret, T., Allory, Y., Southgate, J., Radvanyi, F., and Goud, B. (2012). Deregulation of rab and rab effector genes in bladder cancer. PLoS. ONE. 7, e39469.

83. Urbanucci, A., Sahu, B., Seppala, J., Larjo, A., Latonen, L. M., Waltering, K. K., Tammela, T. L., Vessella, R. L., Landesmaki, H., Janne, O. A., and Visakorpi, T. (2012). Overexpression of androgen receptor enhances the binding of the receptor to the chromatin in prostate cancer. Oncogene 31, 2153-2163.

84. Grinberg, M., Schwarz, M., Zaltsman, Y., Eini, T., Niv, H., Pietrokovski, S., and Gross, A. (2005). Mitochondrial carrier homolog 2 is a target of tBID in cells signaled to die by tumor necrosis factor alpha. Mol. Cell Biol. 25, 4579-4590.

85. Katz, C., Zaltsman-Amir, Y., Mostizky, Y., Kollet, N., Gross, A., and Friedler, A. (2012). Molecular basis of the interaction between proapoptotic truncated BID (tBID) protein and mitochondrial carrier homologue 2 (MTCH2) protein: key players in mitochondrial death pathway. J. Biol. Chem. 287, 15016-15023.

86. Yu, K., Ganesan, K., Tan, L. K., Laban, M., Wu, J., Zhao, X. D., Li, H., Leung, C. H., Zhu, Y., Wei, C. L., Hooi, S. C., Miller, L., and Tan, P. (2008). A precisely regulated gene expression cassette potently modulates metastasis and survival in multiple solid cancers. PLoS. Genet. 4, e1000129.

87. Andrews, P. G., Kennedy, M. W., Popadiuk, C. M., and Kao, K. R. (2008). Oncogenic activation of the human Pygopus2 promoter by E74-like factor-1. Mol. Cancer Res. 6, 259-266.

88. Xiang, P., Lo, C., Argiropoulos, B., Lai, C. B., Rouhi, A., Imren, S., Jiang, X., Mager, D., and Humphries, R. K. (2010). Identification of E74-like factor 1 (ELF1) as a transcriptional regulator of the Hox cofactor MEIS1. Exp. Hematol. 38, 798-8, 808.

89. Yang, D. X., Li, N. E., Ma, Y., Han, Y. C., and Shi, Y. (2010). Expression of Elf-1 and survivin in non-small cell lung cancer and their relationship to intratumoral microvessel density. Chin J. Cancer 29, 396-402.

90. Ding, R., Lin, S., and Chen, D. (2012). Association of NQO1 r51800566 polymorphism and the risk of colorectal cancer: a meta-analysis. Int. J Colorectal Dis. 27, 885-892.

91. Jamieson, D., Cresti, N., Bray, J., Sludden, J., Griffin, M. J., Hawsawi, N. M., Famie, E., Mould, E. V., Verrill, M. W., May, F. E., and Boddy, A. V. (2011). Two minor NQO1 and NQO2 alleles predict poor response of breast cancer patients to adjuvant doxorubicin and cyclophosphamide therapy. Pharmacogenet. Genomics 21, 808-819.

92. Kolesar, J. M., Dahlberg, S. E., Marsh, S., McLeod, H. L., Johnson, D. H., Keller, S. M., and Schiller, J. H. (2011). The NQO1*2/*2 polymorphism is associated with poor overall survival in patients following resection of stages II and IIIa non-small cell lung cancer. Oncol. Rep. 25, 1765-1772.

93. Patrick, B. A. and Jaiswal, A. K. (2012). Stress-induced NQO1 controls stability of C/EBPalpha against 20S proteasomal degradation to regulate p63 expression with implications in protection against chemical-induced skin cancer. Oncogene. 2012 Jan. 16. doi: 10.1038/onc.2011.600. [Epub ahead of print].

94. Wakai, T., Shirai, Y., Sakata, J., Matsuda, Y., Korita, P. V., Takamura, M., Ajioka, Y., and Hatakeyama, K. (2011). Prognostic significance of NQO1 expression in intrahepatic cholangiocarcinoma. Int. J Clin. Exp Pathol. 4, 363-370.

95. Yang, F. Y., Guan, Q. K., Cui, Y. H., Zhao, Z. Q., Rao, W., and Xi, Z. (2012). NAD(P)H quinone oxidoreductase 1 (NQO1) genetic C6091 polymorphism is associated with the risk of digestive tract cancer: a meta-analysis based on 21 case-control studies. Eur. J Cancer Prev. 2012 September; 21(5):432-41.

96. Huang X, Dong Y, Bey E A, Kilgore J A, Bair J S, Li L S, Patel M, Parkinson E I, Wang Y, Williams N S, Gao J, Hergenrother P J, Boothman D A. Cancer Res. 2012 Jun. 15; 72(12):3038-47. Epub 2012 Apr. 24.

97. Oishi, K., Okano, H., and Sawa, H. (2007). RMD-1, a novel microtubule-associated protein, functions in chromosome segregation in *Caenorhabditis elegans*. J Cell Biol. 179, 1149-1162.

What is claimed is:

1. A method of treating cancer, said method comprising administering to a subject in need thereof an effective amount of CD8 T lymphocytes recognizing:
   (a) a MHC class I molecule of the HLA-B*0801 allele loaded with a peptide of 8 to 12 amino acids comprising (i) one of the following sequences: ELQEKFLSL (SEQ ID NO:15) or ELQEKFSSL (SEQ ID NO:16); and/or (ii) one of the following sequences: SLFFRKVPF (SEQ ID NO:19) or SLFFRKVAF (SEQ ID NO:20), if said subject expresses said MHC class I molecule of the HLA-B*0801 allele;
   (b) a MHC class I molecule of the HLA-B*4403 allele loaded with a peptide of 10 to 12 amino acids comprising one the following sequences: QELDGVFQKL (SEQ ID NO:17) or QELDRVFQKL (SEQ ID NO:18), if said subject expresses said MHC class I molecule of the HLA-B*4403 allele; and/or
   (c) a MHC class I molecule of the HLA-A*0301 allele loaded with a peptide of 9 to 12 amino acids comprising (i) one of the following sequences: RVSLPTSPG (SEQ ID NO:25) or RVSLPTSPR (SEQ ID NO:26); (ii) one of the following sequences: SVLKPGNSK (SEQ ID NO:21) or TVLKPGNSK (SEQ ID NO:22); (iii) one of the following sequences: AMYDKGPFRSK (SEQ ID NO:23) or AMYDKGPFWSK (SEQ ID NO:24); and/or (iv) one of the following sequences: VMGNPGTFK (SEQ ID NO:27) or VMGNPGTFN (SEQ ID NO:28), if said subject expresses said MHC class I molecule of the HLA-A*0301 allele.

2. The method of claim 1, wherein said CD8 T lymphocytes are in vitro expanded primary CD8 T lymphocytes or CD8 T lymphocyte clones expressing a recombinant T cell receptor (TCR).

3. The method of claim 1, wherein said subject is an allogeneic stem cell transplantation (ASCT) recipient.

4. The method of claim 1, wherein said cancer is a hematologic cancer.

5. The method of claim 1, wherein said method further comprises administering an effective amount of one or more of the peptides defined in claim 1, or of a pharmaceutical composition comprising said one or more peptides.

6. The method of claim 1, wherein said method further comprises culturing and expanding said CD8 T lymphocytes in the presence of cells expressing said MHC class I molecule loaded with said peptide in vitro prior to administration to the subject.

7. The method of claim 6, wherein said CD8 T lymphocytes are in vitro expanded primary CD8 T lymphocytes or CD8 T lymphocyte clones expressing a recombinant T cell receptor (TCR).

8. The method of claim 6, wherein said subject is an allogeneic stem cell transplantation (ASCT) recipient.

9. The method of claim 6, wherein said cancer is a hematologic cancer.

10. The method of claim 6, wherein said method further comprises administering an effective amount of one or more of the peptides defined in claim 1, or of a pharmaceutical composition comprising said one or more peptides.

* * * * *

SEQUENCE LISTING

<160> NUMBER OF SEQ ID NOS: 28

<210> SEQ ID NO 1
<211> LENGTH: 10316
<212> TYPE: DNA

```
<213> ORGANISM: Homo sapiens
<220> FEATURE:
<221> NAME/KEY: CDS
<222> LOCATION: (175)..(9519)

<400> SEQUENCE: 1
gagaccagaa gcgggcgaat tgggcaccgg tggcggctgc gggcagtttg aattagactc      60
tgggctccag cccgccgaag ccgcgccaga actgtactct ccgagaggtc gttttcccgt     120
ccccgagagc aagtttattt acaaatgttg gagtaataaa gaaggcagaa caaa atg      177
                                                            Met
                                                             1 agc tgg gct ttg gaa gaa tgg aaa gaa ggg ctg cct aca aga gct ctt      225
Ser Trp Ala Leu Glu Glu Trp Lys Glu Gly Leu Pro Thr Arg Ala Leu
         5                  10                  15 cag aaa att caa gag ctt gaa gga cag ctt gac aaa ctg aag aag gaa      273
Gln Lys Ile Gln Glu Leu Glu Gly Gln Leu Asp Lys Leu Lys Lys Glu
     20                  25                  30 aag cag caa agg cag ttt cag ctt gac agt ctc gag gct gcg ctg cag      321
Lys Gln Gln Arg Gln Phe Gln Leu Asp Ser Leu Glu Ala Ala Leu Gln
 35                  40                  45 aag caa aaa cag aag gtt gaa aat gaa aaa acc gag ggt aca aac ctg      369
Lys Gln Lys Gln Lys Val Glu Asn Glu Lys Thr Glu Gly Thr Asn Leu
 50                  55                  60                  65 aaa agg gag aat caa aga ttg atg gaa ata tgt gaa agt ctg gag aaa      417
Lys Arg Glu Asn Gln Arg Leu Met Glu Ile Cys Glu Ser Leu Glu Lys
                 70                  75                  80 act aag cag aag att tct cat gaa ctt caa gtc aag gag tca caa gtg      465
Thr Lys Gln Lys Ile Ser His Glu Leu Gln Val Lys Glu Ser Gln Val
             85                  90                  95 aat ttc cag gaa gga caa ctg aat tca ggc aaa aaa caa ata gaa aaa      513
Asn Phe Gln Glu Gly Gln Leu Asn Ser Gly Lys Lys Gln Ile Glu Lys
        100                 105                 110 ctg gaa cag gaa ctt aaa agg tgt aaa tct gag ctt gaa aga agc caa      561
Leu Glu Gln Glu Leu Lys Arg Cys Lys Ser Glu Leu Glu Arg Ser Gln
    115                 120                 125 caa gct gcg cag tct gca gat gtc tct ctg aat cca tgc aat aca cca      609
Gln Ala Ala Gln Ser Ala Asp Val Ser Leu Asn Pro Cys Asn Thr Pro
130                 135                 140                 145 caa aaa att ttt aca act cca cta aca cca agt caa tat tat agt ggt      657
Gln Lys Ile Phe Thr Thr Pro Leu Thr Pro Ser Gln Tyr Tyr Ser Gly
                150                 155                 160 tcc aag tat gaa gat cta aaa gaa aaa tat aat aaa gag gtt gaa gaa      705
Ser Lys Tyr Glu Asp Leu Lys Glu Lys Tyr Asn Lys Glu Val Glu Glu
            165                 170                 175 cga aaa aga tta gag gca gag gtt aaa gcc ttg cag gct aaa aaa gca      753
Arg Lys Arg Leu Glu Ala Glu Val Lys Ala Leu Gln Ala Lys Lys Ala
        180                 185                 190 agc cag act ctt cca caa gcc acc atg aat cac cgc gac att gcc cgg      801
Ser Gln Thr Leu Pro Gln Ala Thr Met Asn His Arg Asp Ile Ala Arg
    195                 200                 205 cat cag gct tca tca tct gtg ttc tca tgg cag caa gag aag acc cca      849
His Gln Ala Ser Ser Ser Val Phe Ser Trp Gln Gln Glu Lys Thr Pro
210                 215                 220                 225 agt cat ctt tca tct aat tct caa aga act cca att agg aga gat ttc      897
Ser His Leu Ser Ser Asn Ser Gln Arg Thr Pro Ile Arg Arg Asp Phe
                230                 235                 240 tct gca tct tac ttt tct ggg gaa caa gag gtg act cca agt cga tca      945
Ser Ala Ser Tyr Phe Ser Gly Glu Gln Glu Val Thr Pro Ser Arg Ser
            245                 250                 255
```

-continued

| | |
|---|---|
| act ttg caa ata ggg aaa aga gat gct aat agc agt ttc ttt gac aat<br>Thr Leu Gln Ile Gly Lys Arg Asp Ala Asn Ser Ser Phe Phe Asp Asn<br>260                265                270 | 993 |
| tct agc agt cct cat ctt ttg gat caa tta aaa gcg cag aat caa gag<br>Ser Ser Ser Pro His Leu Leu Asp Gln Leu Lys Ala Gln Asn Gln Glu<br>275                280                285 | 1041 |
| cta aga aac aag att aat gag ttg gaa cta cgc ctg caa gga cat gaa<br>Leu Arg Asn Lys Ile Asn Glu Leu Glu Leu Arg Leu Gln Gly His Glu<br>290                295                300                305 | 1089 |
| aaa gaa atg aaa ggc caa gtg aat aag ttt caa gaa ctc caa ctc caa<br>Lys Glu Met Lys Gly Gln Val Asn Lys Phe Gln Glu Leu Gln Leu Gln<br>310                315                320 | 1137 |
| ctg gag aaa gca aaa gtg gaa tta att gaa aaa gag aaa gtt ttg aac<br>Leu Glu Lys Ala Lys Val Glu Leu Ile Glu Lys Glu Lys Val Leu Asn<br>325                330                335 | 1185 |
| aaa tgt agg gat gaa cta gtg aga aca aca gca caa tac gac cag gcg<br>Lys Cys Arg Asp Glu Leu Val Arg Thr Thr Ala Gln Tyr Asp Gln Ala<br>340                345                350 | 1233 |
| tca acc aag tat act gca ttg gaa caa aaa ctg aaa aaa ttg acg gaa<br>Ser Thr Lys Tyr Thr Ala Leu Glu Gln Lys Leu Lys Lys Leu Thr Glu<br>355                360                365 | 1281 |
| gat ttg agt tgt cag cga caa aat gca gaa agt gcc aga tgt tct ctg<br>Asp Leu Ser Cys Gln Arg Gln Asn Ala Glu Ser Ala Arg Cys Ser Leu<br>370                375                380                385 | 1329 |
| gaa cag aaa att aag gaa aaa gaa aag gag ttt caa gag gag ctc tcc<br>Glu Gln Lys Ile Lys Glu Lys Glu Lys Glu Phe Gln Glu Glu Leu Ser<br>390                395                400 | 1377 |
| cgt caa cag cgt tct ttc caa aca ctg gac cag gag tgc atc cag atg<br>Arg Gln Gln Arg Ser Phe Gln Thr Leu Asp Gln Glu Cys Ile Gln Met<br>405                410                415 | 1425 |
| aag gcc aga ctc acc cag gag tta cag caa gcc aag aat atg cac aac<br>Lys Ala Arg Leu Thr Gln Glu Leu Gln Gln Ala Lys Asn Met His Asn<br>420                425                430 | 1473 |
| gtc ctg cag gct gaa ctg gat aaa ctc aca tca gta aag caa cag cta<br>Val Leu Gln Ala Glu Leu Asp Lys Leu Thr Ser Val Lys Gln Gln Leu<br>435                440                445 | 1521 |
| gaa aac aat ttg gaa gag ttt aag caa aag ttg tgc aga gct gaa cag<br>Glu Asn Asn Leu Glu Glu Phe Lys Gln Lys Leu Cys Arg Ala Glu Gln<br>450                455                460                465 | 1569 |
| gcg ttc cag gcg agt cag atc aag gag aat gag ctg agg aga agc atg<br>Ala Phe Gln Ala Ser Gln Ile Lys Glu Asn Glu Leu Arg Arg Ser Met<br>470                475                480 | 1617 |
| gag gaa atg aag aag gaa aac aac ctc ctt aag agt cac tct gag caa<br>Glu Glu Met Lys Lys Glu Asn Asn Leu Leu Lys Ser His Ser Glu Gln<br>485                490                495 | 1665 |
| aag gcc aga gaa gtc tgc cac ctg gag gca gaa ctc aag aac atc aaa<br>Lys Ala Arg Glu Val Cys His Leu Glu Ala Glu Leu Lys Asn Ile Lys<br>500                505                510 | 1713 |
| cag tgt tta aat cag agc cag aat ttt gca gaa gaa atg aaa gcg aag<br>Gln Cys Leu Asn Gln Ser Gln Asn Phe Ala Glu Glu Met Lys Ala Lys<br>515                520                525 | 1761 |
| aat acc tct cag gaa acc atg tta aga gat ctt caa gaa aaa ata aat<br>Asn Thr Ser Gln Glu Thr Met Leu Arg Asp Leu Gln Glu Lys Ile Asn<br>530                535                540                545 | 1809 |
| cag caa gaa aac tcc ttg act tta gaa aaa ctg aag ctt gct gtg gct<br>Gln Gln Glu Asn Ser Leu Thr Leu Glu Lys Leu Lys Leu Ala Val Ala<br>550                555                560 | 1857 |
| gat ctg gaa aag cag cga gat tgt tct caa gac ctt ttg aag aaa aga<br>Asp Leu Glu Lys Gln Arg Asp Cys Ser Gln Asp Leu Leu Lys Lys Arg<br>565                570                575 | 1905 |

```
gaa cat cac att gaa caa ctt aat gat aag tta agc aag aca gag aaa      1953
Glu His His Ile Glu Gln Leu Asn Asp Lys Leu Ser Lys Thr Glu Lys
        580                 585                 590 gag tcc aaa gcc ttg ctg agt gct tta gag tta aaa aag aaa gaa tat      2001
Glu Ser Lys Ala Leu Leu Ser Ala Leu Glu Leu Lys Lys Lys Glu Tyr
    595                 600                 605 gaa gaa ttg aaa gaa gag aaa act ctg ttt tct tgt tgg aaa agt gaa      2049
Glu Glu Leu Lys Glu Glu Lys Thr Leu Phe Ser Cys Trp Lys Ser Glu
610                 615                 620                 625 aac gaa aaa ctt tta act cag atg gaa tca gaa aag gaa aac ttg cag      2097
Asn Glu Lys Leu Leu Thr Gln Met Glu Ser Glu Lys Glu Asn Leu Gln
                630                 635                 640 agt aaa att aat cac ttg gaa act tgt ctg aag aca cag caa ata aaa      2145
Ser Lys Ile Asn His Leu Glu Thr Cys Leu Lys Thr Gln Gln Ile Lys
            645                 650                 655 agt cat gaa tac aac gag aga gta aga acg ctg gag atg gac aga gaa      2193
Ser His Glu Tyr Asn Glu Arg Val Arg Thr Leu Glu Met Asp Arg Glu
        660                 665                 670 aac cta agt gtc gag atc aga aac ctt cac aac gtg tta gac agt aag      2241
Asn Leu Ser Val Glu Ile Arg Asn Leu His Asn Val Leu Asp Ser Lys
    675                 680                 685 tca gtg gag gta gag acc cag aaa cta gct tat atg gag cta cag cag      2289
Ser Val Glu Val Glu Thr Gln Lys Leu Ala Tyr Met Glu Leu Gln Gln
690                 695                 700                 705 aaa gct gag ttc tca gat cag aaa cat cag aag gaa ata gaa aat atg      2337
Lys Ala Glu Phe Ser Asp Gln Lys His Gln Lys Glu Ile Glu Asn Met
                710                 715                 720 tgt ttg aag act tct cag ctt act ggg caa gtt gaa gat cta gaa cac      2385
Cys Leu Lys Thr Ser Gln Leu Thr Gly Gln Val Glu Asp Leu Glu His
            725                 730                 735 aag ctt cag tta ctg tca aat gaa ata atg gac aaa gac cgg tgt tac      2433
Lys Leu Gln Leu Leu Ser Asn Glu Ile Met Asp Lys Asp Arg Cys Tyr
        740                 745                 750 caa gac ttg cat gcc gaa tat gag agc ctc agg gat ctg cta aaa tcc      2481
Gln Asp Leu His Ala Glu Tyr Glu Ser Leu Arg Asp Leu Leu Lys Ser
    755                 760                 765 aaa gat gct tct ctg gtg aca aat gaa gat cat cag aga agt ctt ttg      2529
Lys Asp Ala Ser Leu Val Thr Asn Glu Asp His Gln Arg Ser Leu Leu
770                 775                 780                 785 gct ttt gat cag cag cct gcc atg cat cat tcc ttt gca aat ata att      2577
Ala Phe Asp Gln Gln Pro Ala Met His His Ser Phe Ala Asn Ile Ile
                790                 795                 800 gga gaa caa gga agc atg cct tca gag agg agt gaa tgt cgt tta gaa      2625
Gly Glu Gln Gly Ser Met Pro Ser Glu Arg Ser Glu Cys Arg Leu Glu
            805                 810                 815 gca gac caa agt ccg aaa aat tct gcc atc cta caa aat aga gtt gat      2673
Ala Asp Gln Ser Pro Lys Asn Ser Ala Ile Leu Gln Asn Arg Val Asp
        820                 825                 830 tca ctt gaa ttt tca tta gag tct caa aaa cag atg aac tca gac ctg      2721
Ser Leu Glu Phe Ser Leu Glu Ser Gln Lys Gln Met Asn Ser Asp Leu
    835                 840                 845 caa aag cag tgt gaa gag ttg gtg caa atc aaa gga gaa ata gaa gaa      2769
Gln Lys Gln Cys Glu Glu Leu Val Gln Ile Lys Gly Glu Ile Glu Glu
850                 855                 860                 865 aat ctc atg aaa gca gaa cag atg cat caa agt ttt gtg gct gaa aca      2817
Asn Leu Met Lys Ala Glu Gln Met His Gln Ser Phe Val Ala Glu Thr
                870                 875                 880 agt cag cgc att agt aag tta cag gaa gac act tct gct cac cag aat      2865
Ser Gln Arg Ile Ser Lys Leu Gln Glu Asp Thr Ser Ala His Gln Asn
```

```
                    885                 890                 895
gtt gtt gct gaa acc tta agt gcc ctt gag aac aag gaa aaa gag ctg       2913
Val Val Ala Glu Thr Leu Ser Ala Leu Glu Asn Lys Glu Lys Glu Leu
            900                 905                 910 caa ctt tta aat gat aag gta gaa act gag cag gca gag att caa gaa       2961
Gln Leu Leu Asn Asp Lys Val Glu Thr Glu Gln Ala Glu Ile Gln Glu
    915                 920                 925 tta aaa aag agc aac cat cta ctt gaa gac tct cta aag gag cta caa       3009
Leu Lys Lys Ser Asn His Leu Leu Glu Asp Ser Leu Lys Glu Leu Gln
930                 935                 940                 945 ctt tta tcc gaa acc cta agc ttg gag aag aaa gaa atg agt tcc atc       3057
Leu Leu Ser Glu Thr Leu Ser Leu Glu Lys Lys Glu Met Ser Ser Ile
            950                 955                 960 att tct cta aat aaa agg gaa att gaa gag ctg acc caa gag aat ggg       3105
Ile Ser Leu Asn Lys Arg Glu Ile Glu Glu Leu Thr Gln Glu Asn Gly
            965                 970                 975 act ctt aag gaa att aat gca tcc tta aat caa gag aag atg aac tta       3153
Thr Leu Lys Glu Ile Asn Ala Ser Leu Asn Gln Glu Lys Met Asn Leu
            980                 985                 990 atc cag aaa agt gag agt ttt gca aac tat ata gat gaa agg gag aaa       3201
Ile Gln Lys Ser Glu Ser Phe Ala Asn Tyr Ile Asp Glu Arg Glu Lys
            995                 1000                1005 agc att tca gag tta tct gat cag tac aag caa gaa aaa ctt att           3246
Ser Ile Ser Glu Leu Ser Asp Gln Tyr Lys Gln Glu Lys Leu Ile
1010                1015                1020 tta cta caa aga tgt gaa gaa acc gga aat gca tat gag gat ctt           3291
Leu Leu Gln Arg Cys Glu Glu Thr Gly Asn Ala Tyr Glu Asp Leu
1025                1030                1035 agt caa aaa tac aaa gca gca cag gaa aag aat tct aaa tta gaa           3336
Ser Gln Lys Tyr Lys Ala Ala Gln Glu Lys Asn Ser Lys Leu Glu
1040                1045                1050 tgc ttg cta aat gaa tgc act agt ctt tgt gaa aat agg aaa aat           3381
Cys Leu Leu Asn Glu Cys Thr Ser Leu Cys Glu Asn Arg Lys Asn
1055                1060                1065 gag ttg gaa cag cta aag gaa gca ttt gca aag gaa cac caa gaa           3426
Glu Leu Glu Gln Leu Lys Glu Ala Phe Ala Lys Glu His Gln Glu
1070                1075                1080 ttc tta aca aaa tta gca ttt gct gaa gaa aga aat cag aat ctg           3471
Phe Leu Thr Lys Leu Ala Phe Ala Glu Glu Arg Asn Gln Asn Leu
1085                1090                1095 atg cta gag ttg gag aca gtg cag caa gct ctg aga tct gag atg           3516
Met Leu Glu Leu Glu Thr Val Gln Gln Ala Leu Arg Ser Glu Met
1100                1105                1110 aca gat aac caa aac aat tct aag agc gag gct ggt ggt tta aag           3561
Thr Asp Asn Gln Asn Asn Ser Lys Ser Glu Ala Gly Gly Leu Lys
1115                1120                1125 caa gaa atc atg act tta aag gaa gaa caa aac aaa atg caa aag           3606
Gln Glu Ile Met Thr Leu Lys Glu Glu Gln Asn Lys Met Gln Lys
1130                1135                1140 gaa gtt aat gac tta tta caa gag aat gaa cag ctg atg aag gta           3651
Glu Val Asn Asp Leu Leu Gln Glu Asn Glu Gln Leu Met Lys Val
1145                1150                1155 atg aag act aaa cat gaa tgt caa aat cta gaa tca gaa cca att           3696
Met Lys Thr Lys His Glu Cys Gln Asn Leu Glu Ser Glu Pro Ile
1160                1165                1170 agg aac tct gtg aaa gaa aga gag agt gag aga aat caa tgt aat           3741
Arg Asn Ser Val Lys Glu Arg Glu Ser Glu Arg Asn Gln Cys Asn
1175                1180                1185 ttt aaa cct cag atg gat ctt gaa gtt aaa gaa att tct cta gat           3786
Phe Lys Pro Gln Met Asp Leu Glu Val Lys Glu Ile Ser Leu Asp
```

|     |     |     |     |     |     |     |     |     |     |     |     |     |     |     |      |
| --- | --- | --- | --- | --- | --- | --- | --- | --- | --- | --- | --- | --- | --- | --- | ---- |
| Phe | Lys | Pro | Gln | Met | Asp | Leu | Glu | Val | Lys | Glu | Ile | Ser | Leu | Asp |      |
| 1190 |    |    |    | 1195 |  |    |    |    | 1200 |  |    |    |    |    |      |
| agt | tat | aat | gcg | cag | ttg | gtg | caa | tta | gaa | gct | atg | cta | aga | aat | 3831 |
| Ser | Tyr | Asn | Ala | Gln | Leu | Val | Gln | Leu | Glu | Ala | Met | Leu | Arg | Asn |      |
| 1205 |    |    |    | 1210 |  |    |    |    | 1215 |  |    |    |    |    |      |
| aag | gaa | tta | aaa | ctt | cag | gaa | agt | gag | aag | gag | aag | gag | tgc | ctg | 3876 |
| Lys | Glu | Leu | Lys | Leu | Gln | Glu | Ser | Glu | Lys | Glu | Lys | Glu | Cys | Leu |      |
| 1220 |    |    |    | 1225 |  |    |    |    | 1230 |  |    |    |    |    |      |
| cag | cat | gaa | tta | cag | aca | att | aga | gga | gat | ctt | gaa | acc | agc | aat | 3921 |
| Gln | His | Glu | Leu | Gln | Thr | Ile | Arg | Gly | Asp | Leu | Glu | Thr | Ser | Asn |      |
| 1235 |    |    |    | 1240 |  |    |    |    | 1245 |  |    |    |    |    |      |
| ttg | caa | gac | atg | cag | tca | caa | gaa | att | agt | ggc | ctt | aaa | gac | tgt | 3966 |
| Leu | Gln | Asp | Met | Gln | Ser | Gln | Glu | Ile | Ser | Gly | Leu | Lys | Asp | Cys |      |
| 1250 |    |    |    | 1255 |  |    |    |    | 1260 |  |    |    |    |    |      |
| gaa | ata | gat | gcg | gaa | gaa | aag | tat | att | tca | ggg | cct | cat | gag | ttg | 4011 |
| Glu | Ile | Asp | Ala | Glu | Glu | Lys | Tyr | Ile | Ser | Gly | Pro | His | Glu | Leu |      |
| 1265 |    |    |    | 1270 |  |    |    |    | 1275 |  |    |    |    |    |      |
| tca | aca | agt | caa | aac | gac | aat | gca | cac | ctt | cag | tgc | tct | ctg | caa | 4056 |
| Ser | Thr | Ser | Gln | Asn | Asp | Asn | Ala | His | Leu | Gln | Cys | Ser | Leu | Gln |      |
| 1280 |    |    |    | 1285 |  |    |    |    | 1290 |  |    |    |    |    |      |
| aca | aca | atg | aac | aag | ctg | aat | gag | cta | gag | aaa | ata | tgt | gaa | ata | 4101 |
| Thr | Thr | Met | Asn | Lys | Leu | Asn | Glu | Leu | Glu | Lys | Ile | Cys | Glu | Ile |      |
| 1295 |    |    |    | 1300 |  |    |    |    | 1305 |  |    |    |    |    |      |
| ctg | cag | gct | gaa | aag | tat | gaa | ctc | gta | act | gag | ctg | aat | gat | tca | 4146 |
| Leu | Gln | Ala | Glu | Lys | Tyr | Glu | Leu | Val | Thr | Glu | Leu | Asn | Asp | Ser |      |
| 1310 |    |    |    | 1315 |  |    |    |    | 1320 |  |    |    |    |    |      |
| agg | tca | gaa | tgt | atc | aca | gca | act | agg | aaa | atg | gca | gaa | gag | gta | 4191 |
| Arg | Ser | Glu | Cys | Ile | Thr | Ala | Thr | Arg | Lys | Met | Ala | Glu | Glu | Val |      |
| 1325 |    |    |    | 1330 |  |    |    |    | 1335 |  |    |    |    |    |      |
| ggg | aaa | cta | cta | aat | gaa | gtt | aaa | ata | tta | aat | gat | gac | agt | ggt | 4236 |
| Gly | Lys | Leu | Leu | Asn | Glu | Val | Lys | Ile | Leu | Asn | Asp | Asp | Ser | Gly |      |
| 1340 |    |    |    | 1345 |  |    |    |    | 1350 |  |    |    |    |    |      |
| ctt | ctc | cat | ggt | gag | tta | gtg | gaa | gac | ata | cca | gga | ggt | gaa | ttt | 4281 |
| Leu | Leu | His | Gly | Glu | Leu | Val | Glu | Asp | Ile | Pro | Gly | Gly | Glu | Phe |      |
| 1355 |    |    |    | 1360 |  |    |    |    | 1365 |  |    |    |    |    |      |
| ggt | gaa | caa | cca | aat | gaa | cag | cac | cct | gtg | tct | ttg | gct | cca | ttg | 4326 |
| Gly | Glu | Gln | Pro | Asn | Glu | Gln | His | Pro | Val | Ser | Leu | Ala | Pro | Leu |      |
| 1370 |    |    |    | 1375 |  |    |    |    | 1380 |  |    |    |    |    |      |
| gac | gag | agt | aat | tcc | tac | gag | cac | ttg | aca | ttg | tca | gac | aaa | gaa | 4371 |
| Asp | Glu | Ser | Asn | Ser | Tyr | Glu | His | Leu | Thr | Leu | Ser | Asp | Lys | Glu |      |
| 1385 |    |    |    | 1390 |  |    |    |    | 1395 |  |    |    |    |    |      |
| gtt | caa | atg | cac | ttt | gcc | gaa | ttg | caa | gag | aaa | ttc | tta | tct | tta | 4416 |
| Val | Gln | Met | His | Phe | Ala | Glu | Leu | Gln | Glu | Lys | Phe | Leu | Ser | Leu |      |
| 1400 |    |    |    | 1405 |  |    |    |    | 1410 |  |    |    |    |    |      |
| caa | agt | gaa | cac | aaa | att | tta | cat | gat | cag | cac | tgt | cag | atg | agc | 4461 |
| Gln | Ser | Glu | His | Lys | Ile | Leu | His | Asp | Gln | His | Cys | Gln | Met | Ser |      |
| 1415 |    |    |    | 1420 |  |    |    |    | 1425 |  |    |    |    |    |      |
| tct | aaa | atg | tca | gag | ctg | cag | acc | tat | gtt | gac | tca | tta | aag | gcc | 4506 |
| Ser | Lys | Met | Ser | Glu | Leu | Gln | Thr | Tyr | Val | Asp | Ser | Leu | Lys | Ala |      |
| 1430 |    |    |    | 1435 |  |    |    |    | 1440 |  |    |    |    |    |      |
| gaa | aat | ttg | gtc | ttg | tca | acg | aat | ctg | aga | aac | ttt | caa | ggt | gac | 4551 |
| Glu | Asn | Leu | Val | Leu | Ser | Thr | Asn | Leu | Arg | Asn | Phe | Gln | Gly | Asp |      |
| 1445 |    |    |    | 1450 |  |    |    |    | 1455 |  |    |    |    |    |      |
| ttg | gtg | aag | gag | atg | cag | ctg | ggc | ttg | gag | gag | ggg | ctc | gtt | cca | 4596 |
| Leu | Val | Lys | Glu | Met | Gln | Leu | Gly | Leu | Glu | Glu | Gly | Leu | Val | Pro |      |
| 1460 |    |    |    | 1465 |  |    |    |    | 1470 |  |    |    |    |    |      |
| tcc | ctg | tca | tcc | tct | tgt | gtg | cct | gac | agc | tct | agt | ctt | agc | agt | 4641 |
| Ser | Leu | Ser | Ser | Ser | Cys | Val | Pro | Asp | Ser | Ser | Ser | Leu | Ser | Ser |      |
| 1475 |    |    |    | 1480 |  |    |    |    | 1485 |  |    |    |    |    |      |

| | |
|---|---|
| ttg gga gac tcc tcc ttt tac aga gct ctt tta gaa cag aca gga<br>Leu Gly Asp Ser Ser Phe Tyr Arg Ala Leu Leu Glu Gln Thr Gly<br>1490                                1495                          1500 | 4686 |
| gat atg tct ctt ttg agt aat tta gaa ggg gct gtt tca gca aac<br>Asp Met Ser Leu Leu Ser Asn Leu Glu Gly Ala Val Ser Ala Asn<br>1505                                1510                          1515 | 4731 |
| cag tgc agt gta gat gaa gta ttt tgc agc agt ctg cag gag gag<br>Gln Cys Ser Val Asp Glu Val Phe Cys Ser Ser Leu Gln Glu Glu<br>1520                              1525                          1530 | 4776 |
| aat ctg acc agg aaa gaa acc cct tcg gcc cca gcg aag ggt gtt<br>Asn Leu Thr Arg Lys Glu Thr Pro Ser Ala Pro Ala Lys Gly Val<br>1535                              1540                          1545 | 4821 |
| gaa gag ctt gag tcc ctc tgt gag gtg tac cgg cag tcc ctc gag<br>Glu Glu Leu Glu Ser Leu Cys Glu Val Tyr Arg Gln Ser Leu Glu<br>1550                              1555                          1560 | 4866 |
| aag cta gaa gag aaa atg gaa agt caa ggg att atg aaa aat aag<br>Lys Leu Glu Glu Lys Met Glu Ser Gln Gly Ile Met Lys Asn Lys<br>1565                              1570                          1575 | 4911 |
| gaa att caa gag ctc gag cag tta tta agt tct gaa agg caa gag<br>Glu Ile Gln Glu Leu Glu Gln Leu Leu Ser Ser Glu Arg Gln Glu<br>1580                              1585                          1590 | 4956 |
| ctt gac tgc ctt agg aag cag tat ttg tca gaa aat gaa cag tgg<br>Leu Asp Cys Leu Arg Lys Gln Tyr Leu Ser Glu Asn Glu Gln Trp<br>1595                              1600                          1605 | 5001 |
| caa cag aag ctg aca agc gtg act ctg gag atg gag tcc aag ttg<br>Gln Gln Lys Leu Thr Ser Val Thr Leu Glu Met Glu Ser Lys Leu<br>1610                              1615                          1620 | 5046 |
| gcg gca gaa aag aaa cag acg gaa caa ctg tca ctt gag ctg gaa<br>Ala Ala Glu Lys Lys Gln Thr Glu Gln Leu Ser Leu Glu Leu Glu<br>1625                              1630                          1635 | 5091 |
| gta gca cga ctc cag cta caa ggt ctg gac tta agt tct cgg tct<br>Val Ala Arg Leu Gln Leu Gln Gly Leu Asp Leu Ser Ser Arg Ser<br>1640                              1645                          1650 | 5136 |
| ttg ctt ggc atc gac aca gaa gat gct att caa ggc cga aat gag<br>Leu Leu Gly Ile Asp Thr Glu Asp Ala Ile Gln Gly Arg Asn Glu<br>1655                              1660                          1665 | 5181 |
| agc tgt gac ata tca aaa gaa cat act tca gaa act aca gaa aga<br>Ser Cys Asp Ile Ser Lys Glu His Thr Ser Glu Thr Thr Glu Arg<br>1670                              1675                          1680 | 5226 |
| aca cca aag cat gat gtt cat cag att tgt gat aaa gat gct cag<br>Thr Pro Lys His Asp Val His Gln Ile Cys Asp Lys Asp Ala Gln<br>1685                              1690                          1695 | 5271 |
| cag gac ctc aat cta gac att gag aaa ata act gag act ggt gca<br>Gln Asp Leu Asn Leu Asp Ile Glu Lys Ile Thr Glu Thr Gly Ala<br>1700                              1705                          1710 | 5316 |
| gtg aaa ccc aca gga gag tgc tct ggg gaa cag tcc cca gat acc<br>Val Lys Pro Thr Gly Glu Cys Ser Gly Glu Gln Ser Pro Asp Thr<br>1715                              1720                          1725 | 5361 |
| aat tat gag cct cca ggg gaa gat aaa acc cag ggc tct tca gaa<br>Asn Tyr Glu Pro Pro Gly Glu Asp Lys Thr Gln Gly Ser Ser Glu<br>1730                              1735                          1740 | 5406 |
| tgc att tct gaa ttg tca ttt tct ggt cct aat gct ttg gta cct<br>Cys Ile Ser Glu Leu Ser Phe Ser Gly Pro Asn Ala Leu Val Pro<br>1745                              1750                          1755 | 5451 |
| atg gat ttc ctg ggg aat cag gaa gat atc cat aat ctt caa ctg<br>Met Asp Phe Leu Gly Asn Gln Glu Asp Ile His Asn Leu Gln Leu<br>1760                              1765                          1770 | 5496 |
| cgg gta aaa gag aca tca aat gag aat ttg aga tta ctt cat gtg<br>Arg Val Lys Glu Thr Ser Asn Glu Asn Leu Arg Leu Leu His Val<br>1775                              1780                          1785 | 5541 |

```
ata  gag gac cgt gac aga  aaa gtt gaa agt ttg  cta aat gaa atg      5586
Ile  Glu Asp Arg Asp Arg  Lys Val Glu Ser Leu  Leu Asn Glu Met
1790                 1795                 1800 aaa  gaa tta gac tca aaa  ctc cat tta cag gag  gta caa cta atg      5631
Lys  Glu Leu Asp Ser Lys  Leu His Leu Gln Glu  Val Gln Leu Met
1805                 1810                 1815 acc  aaa att gaa gca tgc  ata gaa ttg gaa aaa  ata gtt ggg gaa      5676
Thr  Lys Ile Glu Ala Cys  Ile Glu Leu Glu Lys  Ile Val Gly Glu
1820                 1825                 1830 ctt  aag aaa gaa aac tca  gat tta agt gaa aaa  ttg gaa tat ttt      5721
Leu  Lys Lys Glu Asn Ser  Asp Leu Ser Glu Lys  Leu Glu Tyr Phe
1835                 1840                 1845 tct  tgt gat cac cag gag  tta ctc cag aga gta  gaa act tct gaa      5766
Ser  Cys Asp His Gln Glu  Leu Leu Gln Arg Val  Glu Thr Ser Glu
1850                 1855                 1860 ggc  ctc aat tct gat tta  gaa atg cat gca gat  aaa tca tca cgt      5811
Gly  Leu Asn Ser Asp Leu  Glu Met His Ala Asp  Lys Ser Ser Arg
1865                 1870                 1875 gaa  gat att gga gat aat  gtg gcc aag gtg aat  gac agc tgg aag      5856
Glu  Asp Ile Gly Asp Asn  Val Ala Lys Val Asn  Asp Ser Trp Lys
1880                 1885                 1890 gag  aga ttt ctt gat gtg  gaa aat gag ctg agt  agg atc aga tcg      5901
Glu  Arg Phe Leu Asp Val  Glu Asn Glu Leu Ser  Arg Ile Arg Ser
1895                 1900                 1905 gag  aaa gct agc att gag  cat gaa gcc ctc tac  ctg gag gct gac      5946
Glu  Lys Ala Ser Ile Glu  His Glu Ala Leu Tyr  Leu Glu Ala Asp
1910                 1915                 1920 tta  gag gta gtt caa aca  gag aag cta tgt tta  gaa aaa gac aat      5991
Leu  Glu Val Val Gln Thr  Glu Lys Leu Cys Leu  Glu Lys Asp Asn
1925                 1930                 1935 gaa  aat aag cag aag gtt  att gtc tgc ctt gaa  gaa gaa ctc tca      6036
Glu  Asn Lys Gln Lys Val  Ile Val Cys Leu Glu  Glu Glu Leu Ser
1940                 1945                 1950 gtg  gtc aca agt gag aga  aac cag ctt cgt gga  gaa tta gat act      6081
Val  Val Thr Ser Glu Arg  Asn Gln Leu Arg Gly  Glu Leu Asp Thr
1955                 1960                 1965 atg  tca aaa aaa acc acg  gca ctg gat cag ttg  tct gaa aaa atg      6126
Met  Ser Lys Lys Thr Thr  Ala Leu Asp Gln Leu  Ser Glu Lys Met
1970                 1975                 1980 aag  gag aaa aca caa gag  ctt gag tct cat caa  agt gag tgt ctc      6171
Lys  Glu Lys Thr Gln Glu  Leu Glu Ser His Gln  Ser Glu Cys Leu
1985                 1990                 1995 cat  tgc att cag gtg gca  gag gca gag gtg aag  gaa aag acg gaa      6216
His  Cys Ile Gln Val Ala  Glu Ala Glu Val Lys  Glu Lys Thr Glu
2000                 2005                 2010 ctc  ctt cag act ttg tcc  tct gat gtg agt gag  ctg tta aaa gac      6261
Leu  Leu Gln Thr Leu Ser  Ser Asp Val Ser Glu  Leu Leu Lys Asp
2015                 2020                 2025 aaa  act cat ctc cag gaa  aag ctg cag agt ttg  gaa aag gac tca      6306
Lys  Thr His Leu Gln Glu  Lys Leu Gln Ser Leu  Glu Lys Asp Ser
2030                 2035                 2040 cag  gca ctg tct ttg aca  aaa tgt gag ctg gaa  aac caa att gca      6351
Gln  Ala Leu Ser Leu Thr  Lys Cys Glu Leu Glu  Asn Gln Ile Ala
2045                 2050                 2055 caa  ctg aat aaa gag aaa  gaa ttg ctt gtc aag  gaa tct gaa agc      6396
Gln  Leu Asn Lys Glu Lys  Glu Leu Leu Val Lys  Glu Ser Glu Ser
2060                 2065                 2070 ctg  cag gcc aga ctg agt  gaa tca gat tat gaa  aag ctg aat gtc      6441
Leu  Gln Ala Arg Leu Ser  Glu Ser Asp Tyr Glu  Lys Leu Asn Val
```

| | | | | | | | | | | | | | | |
|---|---|---|---|---|---|---|---|---|---|---|---|---|---|---|
| tcc | aag | gcc | ttg | gag | gcc | gca | ctg | gtg | gag | aaa | ggt | gag | ttc | gca | 6486 |
| Ser | Lys | Ala | Leu | Glu | Ala | Ala | Leu | Val | Glu | Lys | Gly | Glu | Phe | Ala | |
| 2090 | | | | 2095 | | | | | 2100 | | | | | | |
| ttg | agg | ctg | agc | tca | aca | cag | gag | gaa | gtg | cat | cag | ctg | aga | aga | 6531 |
| Leu | Arg | Leu | Ser | Ser | Thr | Gln | Glu | Glu | Val | His | Gln | Leu | Arg | Arg | |
| 2105 | | | | 2110 | | | | | 2115 | | | | | | |
| ggc | atc | gag | aaa | ctg | aga | gtt | cgc | att | gag | gcc | gat | gaa | aag | aag | 6576 |
| Gly | Ile | Glu | Lys | Leu | Arg | Val | Arg | Ile | Glu | Ala | Asp | Glu | Lys | Lys | |
| 2120 | | | | 2125 | | | | | 2130 | | | | | | |
| cag | ctg | cac | atc | gca | gag | aaa | ctg | aaa | gaa | cgc | gag | cgg | gag | aat | 6621 |
| Gln | Leu | His | Ile | Ala | Glu | Lys | Leu | Lys | Glu | Arg | Glu | Arg | Glu | Asn | |
| 2135 | | | | 2140 | | | | | 2145 | | | | | | |
| gat | tca | ctt | aag | gat | aaa | gtt | gag | aac | ctt | gaa | agg | gaa | ttg | cag | 6666 |
| Asp | Ser | Leu | Lys | Asp | Lys | Val | Glu | Asn | Leu | Glu | Arg | Glu | Leu | Gln | |
| 2150 | | | | 2155 | | | | | 2160 | | | | | | |
| atg | tca | gaa | gaa | aac | cag | gag | cta | gtg | att | ctt | gat | gcc | gag | aat | 6711 |
| Met | Ser | Glu | Glu | Asn | Gln | Glu | Leu | Val | Ile | Leu | Asp | Ala | Glu | Asn | |
| 2165 | | | | 2170 | | | | | 2175 | | | | | | |
| tcc | aaa | gca | gaa | gta | gag | act | cta | aaa | aca | caa | ata | gaa | gag | atg | 6756 |
| Ser | Lys | Ala | Glu | Val | Glu | Thr | Leu | Lys | Thr | Gln | Ile | Glu | Glu | Met | |
| 2180 | | | | 2185 | | | | | 2190 | | | | | | |
| gcc | aga | agc | ctg | aaa | gtt | ttt | gaa | tta | gac | ctt | gtc | acg | tta | agg | 6801 |
| Ala | Arg | Ser | Leu | Lys | Val | Phe | Glu | Leu | Asp | Leu | Val | Thr | Leu | Arg | |
| 2195 | | | | 2200 | | | | | 2205 | | | | | | |
| tct | gaa | aaa | gaa | aat | ctg | aca | aaa | caa | ata | caa | gaa | aaa | caa | ggt | 6846 |
| Ser | Glu | Lys | Glu | Asn | Leu | Thr | Lys | Gln | Ile | Gln | Glu | Lys | Gln | Gly | |
| 2210 | | | | 2215 | | | | | 2220 | | | | | | |
| cag | ttg | tca | gaa | cta | gac | aag | tta | ctc | tct | tca | ttt | aaa | agt | ctg | 6891 |
| Gln | Leu | Ser | Glu | Leu | Asp | Lys | Leu | Leu | Ser | Ser | Phe | Lys | Ser | Leu | |
| 2225 | | | | 2230 | | | | | 2235 | | | | | | |
| tta | gaa | gaa | aag | gag | caa | gca | gag | ata | cag | atc | aaa | gaa | gaa | tct | 6936 |
| Leu | Glu | Glu | Lys | Glu | Gln | Ala | Glu | Ile | Gln | Ile | Lys | Glu | Glu | Ser | |
| 2240 | | | | 2245 | | | | | 2250 | | | | | | |
| aaa | act | gca | gtg | gag | atg | ctt | cag | aat | cag | tta | aag | gag | cta | aat | 6981 |
| Lys | Thr | Ala | Val | Glu | Met | Leu | Gln | Asn | Gln | Leu | Lys | Glu | Leu | Asn | |
| 2255 | | | | 2260 | | | | | 2265 | | | | | | |
| gag | gca | gta | gca | gcc | ttg | tgt | ggt | gac | caa | gaa | att | atg | aag | gcc | 7026 |
| Glu | Ala | Val | Ala | Ala | Leu | Cys | Gly | Asp | Gln | Glu | Ile | Met | Lys | Ala | |
| 2270 | | | | 2275 | | | | | 2280 | | | | | | |
| aca | gaa | cag | agt | cta | gac | cca | cca | ata | gag | gaa | gag | cat | cag | ctg | 7071 |
| Thr | Glu | Gln | Ser | Leu | Asp | Pro | Pro | Ile | Glu | Glu | Glu | His | Gln | Leu | |
| 2285 | | | | 2290 | | | | | 2295 | | | | | | |
| aga | aat | agc | att | gaa | aag | ctg | aga | gcc | cgc | cta | gaa | gct | gat | gaa | 7116 |
| Arg | Asn | Ser | Ile | Glu | Lys | Leu | Arg | Ala | Arg | Leu | Glu | Ala | Asp | Glu | |
| 2300 | | | | 2305 | | | | | 2310 | | | | | | |
| aag | aag | cag | ctc | tgt | gtc | tta | caa | caa | ctg | aag | gaa | agt | gag | cat | 7161 |
| Lys | Lys | Gln | Leu | Cys | Val | Leu | Gln | Gln | Leu | Lys | Glu | Ser | Glu | His | |
| 2315 | | | | 2320 | | | | | 2325 | | | | | | |
| cat | gca | gat | tta | ctt | aag | ggt | aga | gtg | gag | aac | ctt | gaa | aga | gag | 7206 |
| His | Ala | Asp | Leu | Leu | Lys | Gly | Arg | Val | Glu | Asn | Leu | Glu | Arg | Glu | |
| 2330 | | | | 2335 | | | | | 2340 | | | | | | |
| cta | gag | ata | gcc | agg | aca | aac | caa | gag | cat | gca | gct | ctt | gag | gca | 7251 |
| Leu | Glu | Ile | Ala | Arg | Thr | Asn | Gln | Glu | His | Ala | Ala | Leu | Glu | Ala | |
| 2345 | | | | 2350 | | | | | 2355 | | | | | | |
| gag | aat | tcc | aaa | gga | gag | gta | gag | acc | cta | aaa | gca | aaa | ata | gaa | 7296 |
| Glu | Asn | Ser | Lys | Gly | Glu | Val | Glu | Thr | Leu | Lys | Ala | Lys | Ile | Glu | |
| 2360 | | | | 2365 | | | | | 2370 | | | | | | |
| ggg | atg | acc | caa | agt | ctg | aga | ggt | ctg | gaa | tta | gat | gtt | gtt | act | 7341 |

```
Gly Met Thr Gln Ser Leu Arg Gly Leu Glu Leu Asp Val Val Thr
2375                2380                2385 ata agg tca gaa aaa gaa aat ctg aca aat gaa tta caa aaa gag      7386
Ile Arg Ser Glu Lys Glu Asn Leu Thr Asn Glu Leu Gln Lys Glu
2390                2395                2400 caa gag cga ata tct gaa tta gaa ata ata aat tca tca ttt gaa      7431
Gln Glu Arg Ile Ser Glu Leu Glu Ile Ile Asn Ser Ser Phe Glu
2405                2410                2415 aat att ttg caa gaa aaa gag caa gag aaa gta cag atg aaa gaa      7476
Asn Ile Leu Gln Glu Lys Glu Gln Glu Lys Val Gln Met Lys Glu
2420                2425                2430 aaa tca agc act gcc atg gag atg ctt caa aca caa tta aaa gag      7521
Lys Ser Ser Thr Ala Met Glu Met Leu Gln Thr Gln Leu Lys Glu
2435                2440                2445 ctc aat gag aga gtg gca gcc ctg cat aat gac caa gaa gcc tgt      7566
Leu Asn Glu Arg Val Ala Ala Leu His Asn Asp Gln Glu Ala Cys
2450                2455                2460 aag gcc aaa gag cag aat ctt agt agt caa gta gag tgt ctt gaa      7611
Lys Ala Lys Glu Gln Asn Leu Ser Ser Gln Val Glu Cys Leu Glu
2465                2470                2475 ctt gag aag gct cag ttg cta caa ggc ctt gat gag gcc aaa aat      7656
Leu Glu Lys Ala Gln Leu Leu Gln Gly Leu Asp Glu Ala Lys Asn
2480                2485                2490 aat tat att gtt ttg caa tct tca gtg aat ggc ctc att caa gaa      7701
Asn Tyr Ile Val Leu Gln Ser Ser Val Asn Gly Leu Ile Gln Glu
2495                2500                2505 gta gaa gat ggc aag cag aaa ctg gag aag aag gat gaa gaa atc      7746
Val Glu Asp Gly Lys Gln Lys Leu Glu Lys Lys Asp Glu Glu Ile
2510                2515                2520 agt aga ctg aaa aat caa att caa gac caa gag cag ctt gtc tct      7791
Ser Arg Leu Lys Asn Gln Ile Gln Asp Gln Glu Gln Leu Val Ser
2525                2530                2535 aaa ctg tcc cag gtg gaa gga gag cac caa ctt tgg aag gag caa      7836
Lys Leu Ser Gln Val Glu Gly Glu His Gln Leu Trp Lys Glu Gln
2540                2545                2550 aac tta gaa ctg aga aat ctg aca gtg gaa ttg gag cag aag atc      7881
Asn Leu Glu Leu Arg Asn Leu Thr Val Glu Leu Glu Gln Lys Ile
2555                2560                2565 caa gtg cta caa tcc aaa aat gcc tct ttg cag gac aca tta gaa      7926
Gln Val Leu Gln Ser Lys Asn Ala Ser Leu Gln Asp Thr Leu Glu
2570                2575                2580 gtg ctg cag agt tct tac aag aat cta gag aat gag ctt gaa ttg      7971
Val Leu Gln Ser Ser Tyr Lys Asn Leu Glu Asn Glu Leu Glu Leu
2585                2590                2595 aca aaa atg gac aaa atg tcc ttt gtt gaa aaa gta aac aaa atg      8016
Thr Lys Met Asp Lys Met Ser Phe Val Glu Lys Val Asn Lys Met
2600                2605                2610 act gca aag gaa act gag ctg cag agg gaa atg cat gag atg gca      8061
Thr Ala Lys Glu Thr Glu Leu Gln Arg Glu Met His Glu Met Ala
2615                2620                2625 cag aaa aca gca gag ctg caa gaa gaa ctc agt gga gag aaa aat      8106
Gln Lys Thr Ala Glu Leu Gln Glu Glu Leu Ser Gly Glu Lys Asn
2630                2635                2640 agg cta gct gga gag ttg cag tta ctg ttg gaa gaa ata aag agc      8151
Arg Leu Ala Gly Glu Leu Gln Leu Leu Leu Glu Glu Ile Lys Ser
2645                2650                2655 agc aaa gat caa ttg aag gag ctc aca cta gaa aat agt gaa ttg      8196
Ser Lys Asp Gln Leu Lys Glu Leu Thr Leu Glu Asn Ser Glu Leu
2660                2665                2670
```

-continued

| | |
|---|---|
| aag aag agc cta gat tgc atg cac aaa gac cag gtg gaa aag gaa<br>Lys Lys Ser Leu Asp Cys Met His Lys Asp Gln Val Glu Lys Glu<br>2675     2680     2685 | 8241 |
| ggg aaa gtg aga gag gaa ata gct gaa tat cag cta cgg ctt cat<br>Gly Lys Val Arg Glu Glu Ile Ala Glu Tyr Gln Leu Arg Leu His<br>2690     2695     2700 | 8286 |
| gaa gct gaa aag aaa cac cag gct ttg ctt ttg gac aca aac aaa<br>Glu Ala Glu Lys Lys His Gln Ala Leu Leu Leu Asp Thr Asn Lys<br>2705     2710     2715 | 8331 |
| cag tat gaa gta gaa atc cag aca tac cga gag aaa ttg act tct<br>Gln Tyr Glu Val Glu Ile Gln Thr Tyr Arg Glu Lys Leu Thr Ser<br>2720     2725     2730 | 8376 |
| aaa gaa gaa tgt ctc agt tca cag aag ctg gag ata gac ctt tta<br>Lys Glu Glu Cys Leu Ser Ser Gln Lys Leu Glu Ile Asp Leu Leu<br>2735     2740     2745 | 8421 |
| aag tct agt aaa gaa gag ctc aat aat tca ttg aaa gct act act<br>Lys Ser Ser Lys Glu Glu Leu Asn Asn Ser Leu Lys Ala Thr Thr<br>2750     2755     2760 | 8466 |
| cag att ttg gaa gaa ttg aag aaa acc aag atg gac aat cta aaa<br>Gln Ile Leu Glu Glu Leu Lys Lys Thr Lys Met Asp Asn Leu Lys<br>2765     2770     2775 | 8511 |
| tat gta aat cag ttg aag aag gaa aat gaa cgt gcc cag ggg aaa<br>Tyr Val Asn Gln Leu Lys Lys Glu Asn Glu Arg Ala Gln Gly Lys<br>2780     2785     2790 | 8556 |
| atg aag ttg ttg atc aaa tcc tgt aaa cag ctg gaa gag gaa aag<br>Met Lys Leu Leu Ile Lys Ser Cys Lys Gln Leu Glu Glu Glu Lys<br>2795     2800     2805 | 8601 |
| gag ata ctg cag aaa gaa ctc tct caa ctt caa gct gca cag gag<br>Glu Ile Leu Gln Lys Glu Leu Ser Gln Leu Gln Ala Ala Gln Glu<br>2810     2815     2820 | 8646 |
| aag cag aaa aca ggt act gtt atg gat acc aag gtc gat gaa tta<br>Lys Gln Lys Thr Gly Thr Val Met Asp Thr Lys Val Asp Glu Leu<br>2825     2830     2835 | 8691 |
| aca act gag atc aaa gaa ctg aaa gaa act ctt gaa gaa aaa acc<br>Thr Thr Glu Ile Lys Glu Leu Lys Glu Thr Leu Glu Glu Lys Thr<br>2840     2845     2850 | 8736 |
| aag gag gca gat gaa tac ttg gat aag tac tgt tcc ttg ctt ata<br>Lys Glu Ala Asp Glu Tyr Leu Asp Lys Tyr Cys Ser Leu Leu Ile<br>2855     2860     2865 | 8781 |
| agc cat gaa aag tta gag aaa gct aaa gag atg tta gag aca caa<br>Ser His Glu Lys Leu Glu Lys Ala Lys Glu Met Leu Glu Thr Gln<br>2870     2875     2880 | 8826 |
| gtg gcc cat ctg tgt tca cag caa tct aaa caa gat tcc cga ggg<br>Val Ala His Leu Cys Ser Gln Gln Ser Lys Gln Asp Ser Arg Gly<br>2885     2890     2895 | 8871 |
| tct cct ttg cta ggt cca gtt gtt cca gga cca tct cca atc cct<br>Ser Pro Leu Leu Gly Pro Val Val Pro Gly Pro Ser Pro Ile Pro<br>2900     2905     2910 | 8916 |
| tct gtt act gaa aag agg tta tca tct ggc caa aat aaa gct tca<br>Ser Val Thr Glu Lys Arg Leu Ser Ser Gly Gln Asn Lys Ala Ser<br>2915     2920     2925 | 8961 |
| ggc aag agg caa aga tcc agt gga ata tgg gag aat ggt aga gga<br>Gly Lys Arg Gln Arg Ser Ser Gly Ile Trp Glu Asn Gly Arg Gly<br>2930     2935     2940 | 9006 |
| cca aca cct gct acc cca gag agc ttt tct aaa aaa agc aag aaa<br>Pro Thr Pro Ala Thr Pro Glu Ser Phe Ser Lys Lys Ser Lys Lys<br>2945     2950     2955 | 9051 |
| gca gtc atg agt ggt att cac cct gca gaa gac acg gaa ggt act<br>Ala Val Met Ser Gly Ile His Pro Ala Glu Asp Thr Glu Gly Thr<br>2960     2965     2970 | 9096 |

| | | | | | | | | | | |
|---|---|---|---|---|---|---|---|---|---|---|
| gag | ttt | gag | cca | gag | gga | ctt | cca | gaa | gtt | gta | aag | aaa | ggg | ttt | 9141 |
| Glu | Phe | Glu | Pro | Glu | Gly | Leu | Pro | Glu | Val | Val | Lys | Lys | Gly | Phe | |
| 2975 | | | | 2980 | | | | | 2985 | | | | | | |

```
gag ttt gag cca gag gga ctt cca gaa gtt gta aag aaa ggg ttt      9141
Glu Phe Glu Pro Glu Gly Leu Pro Glu Val Val Lys Lys Gly Phe
2975                2980                2985 gct gac atc ccg aca gga aag act agc cca tat atc ctg cga aga      9186
Ala Asp Ile Pro Thr Gly Lys Thr Ser Pro Tyr Ile Leu Arg Arg
2990                2995                3000 aca acc atg gca act cgg acc agc ccc cgc ctg gct gca cag aag      9231
Thr Thr Met Ala Thr Arg Thr Ser Pro Arg Leu Ala Ala Gln Lys
3005                3010                3015 tta gcg cta tcc cca ctg agt ctc ggc aaa gaa aat ctt gca gag      9276
Leu Ala Leu Ser Pro Leu Ser Leu Gly Lys Glu Asn Leu Ala Glu
3020                3025                3030 tcc tcc aaa cca aca gct ggt ggc agc aga tca caa aag gtc aaa      9321
Ser Ser Lys Pro Thr Ala Gly Gly Ser Arg Ser Gln Lys Val Lys
3035                3040                3045 gtt gct cag cgg agc cca gta gat tca ggc acc atc ctc cga gaa      9366
Val Ala Gln Arg Ser Pro Val Asp Ser Gly Thr Ile Leu Arg Glu
3050                3055                3060 ccc acc acg aaa tcc gtc cca gtc aat aat ctt cct gag aga agt      9411
Pro Thr Thr Lys Ser Val Pro Val Asn Asn Leu Pro Glu Arg Ser
3065                3070                3075 ccg act gac agc ccc aga gag ggc ctg agg gtc aag cga ggc cga      9456
Pro Thr Asp Ser Pro Arg Glu Gly Leu Arg Val Lys Arg Gly Arg
3080                3085                3090 ctt gtc ccc agc ccc aaa gct gga ctg gag tcc aac ggc agt gag      9501
Leu Val Pro Ser Pro Lys Ala Gly Leu Glu Ser Asn Gly Ser Glu
3095                3100                3105 aac tgt aag gtc cag tga aggcactttg tgtgtcagta ccctgggag          9549
Asn Cys Lys Val Gln
3110 gtgccagtca ttgaatagat aaggctgtgc ctacaggact tctctttagt cagggcatgc  9609 tttattagtg aggagaaaac aattcctag aagtcttaaa tatattgtac tctttagatc   9669 tcccatgtgt aggtattgaa aaagtttgga agcactgatc acctgttagc attgccattc  9729 ctctactgca atgtaaatag tataaagcta tgtatataaa gcttttggt aatatgttac   9789 aattaaaatg acaagcacta tatcacaatc tctgtttgta tgtgggtttt acactaaaaa  9849 aatgcaaaac acatttattt cttctaatta acagctccta ggaaaatgta gacttttgct  9909 ttatgatatt ctatctgtag tatgaggcat ggaatagttt tgtatcggga atttctcaga  9969 gctgagtaaa atgaaggaaa agcatgttat gtgttttaa ggaaaatgtg cacacatata  10029 catgtaggag tgtttatctt tctcttacaa tctgtttag acatctttgc ttatgaaacc  10089 tgtacatatg tgtgtgtggg tatgtgttta tttccagtga gggctgcagg cttcctagag  10149 gtgtgctata ccatgcgtct gtcgttgtgc ttttttctgt ttttagacca atttttaca   10209 gttctttggt aagcattgtc gtatctggtg atggattaac atatagcctt tgttttctaa  10269 taaaatagtc gccttcgttt tctgtaaaaa aaaaaaaaaa aaaaaaa              10316

<210> SEQ ID NO 2
<211> LENGTH: 3114
<212> TYPE: PRT
<213> ORGANISM: Homo sapiens

<400> SEQUENCE: 2

Met Ser Trp Ala Leu Glu Glu Trp Lys Glu Gly Leu Pro Thr Arg Ala
1               5                   10                  15

Leu Gln Lys Ile Gln Glu Leu Glu Gly Gln Leu Asp Lys Leu Lys Lys
```

-continued

```
               20                  25                  30
Glu Lys Gln Gln Arg Gln Phe Gln Leu Asp Ser Leu Glu Ala Ala Leu
           35                  40                  45
Gln Lys Gln Lys Gln Lys Val Glu Asn Glu Lys Thr Glu Gly Thr Asn
 50                  55                  60
Leu Lys Arg Glu Asn Gln Arg Leu Met Glu Ile Cys Glu Ser Leu Glu
 65                  70                  75                  80
Lys Thr Lys Gln Lys Ile Ser His Glu Leu Gln Val Lys Glu Ser Gln
                 85                  90                  95
Val Asn Phe Gln Glu Gly Gln Leu Asn Ser Gly Lys Lys Gln Ile Glu
                100                 105                 110
Lys Leu Glu Gln Glu Leu Lys Arg Cys Lys Ser Glu Leu Glu Arg Ser
            115                 120                 125
Gln Gln Ala Ala Gln Ser Ala Asp Val Ser Leu Asn Pro Cys Asn Thr
        130                 135                 140
Pro Gln Lys Ile Phe Thr Thr Pro Leu Thr Pro Ser Gln Tyr Tyr Ser
145                 150                 155                 160
Gly Ser Lys Tyr Glu Asp Leu Lys Glu Lys Tyr Asn Lys Glu Val Glu
                165                 170                 175
Glu Arg Lys Arg Leu Glu Ala Glu Val Lys Ala Leu Gln Ala Lys Lys
                180                 185                 190
Ala Ser Gln Thr Leu Pro Gln Ala Thr Met Asn His Arg Asp Ile Ala
            195                 200                 205
Arg His Gln Ala Ser Ser Val Phe Ser Trp Gln Gln Glu Lys Thr
        210                 215                 220
Pro Ser His Leu Ser Ser Asn Ser Gln Arg Thr Pro Ile Arg Arg Asp
225                 230                 235                 240
Phe Ser Ala Ser Tyr Phe Ser Gly Glu Gln Glu Val Thr Pro Ser Arg
                245                 250                 255
Ser Thr Leu Gln Ile Gly Lys Arg Asp Ala Asn Ser Ser Phe Phe Asp
            260                 265                 270
Asn Ser Ser Pro His Leu Leu Asp Gln Leu Lys Ala Gln Asn Gln
        275                 280                 285
Glu Leu Arg Asn Lys Ile Asn Glu Leu Glu Leu Arg Leu Gln Gly His
    290                 295                 300
Glu Lys Glu Met Lys Gly Gln Val Asn Lys Phe Gln Glu Leu Gln Leu
305                 310                 315                 320
Gln Leu Glu Lys Ala Lys Val Glu Leu Ile Glu Lys Glu Lys Val Leu
                325                 330                 335
Asn Lys Cys Arg Asp Glu Leu Val Arg Thr Thr Ala Gln Tyr Asp Gln
            340                 345                 350
Ala Ser Thr Lys Tyr Thr Ala Leu Glu Gln Lys Leu Lys Lys Leu Thr
        355                 360                 365
Glu Asp Leu Ser Cys Gln Arg Gln Asn Ala Glu Ser Ala Arg Cys Ser
    370                 375                 380
Leu Glu Gln Lys Ile Lys Glu Lys Glu Phe Gln Glu Glu Leu
385                 390                 395                 400
Ser Arg Gln Gln Arg Ser Phe Gln Thr Leu Asp Gln Glu Cys Ile Gln
                405                 410                 415
Met Lys Ala Arg Leu Thr Gln Glu Leu Gln Gln Ala Lys Asn Met His
            420                 425                 430
Asn Val Leu Gln Ala Glu Leu Asp Lys Leu Thr Ser Val Lys Gln Gln
        435                 440                 445
```

-continued

Leu Glu Asn Asn Leu Glu Glu Phe Lys Gln Lys Leu Cys Arg Ala Glu
        450                 455                 460

Gln Ala Phe Gln Ala Ser Gln Ile Lys Glu Asn Glu Leu Arg Arg Ser
465                 470                 475                 480

Met Glu Glu Met Lys Lys Glu Asn Asn Leu Leu Lys Ser His Ser Glu
                485                 490                 495

Gln Lys Ala Arg Glu Val Cys His Leu Glu Ala Glu Leu Lys Asn Ile
                500                 505                 510

Lys Gln Cys Leu Asn Gln Ser Gln Asn Phe Ala Glu Glu Met Lys Ala
        515                 520                 525

Lys Asn Thr Ser Gln Glu Thr Met Leu Arg Asp Leu Gln Glu Lys Ile
        530                 535                 540

Asn Gln Gln Glu Asn Ser Leu Thr Leu Glu Lys Leu Lys Leu Ala Val
545                 550                 555                 560

Ala Asp Leu Glu Lys Gln Arg Asp Cys Ser Gln Asp Leu Leu Lys Lys
                565                 570                 575

Arg Glu His His Ile Glu Gln Leu Asn Asp Lys Leu Ser Lys Thr Glu
                580                 585                 590

Lys Glu Ser Lys Ala Leu Leu Ser Ala Leu Glu Leu Lys Lys Lys Glu
        595                 600                 605

Tyr Glu Glu Leu Lys Glu Lys Thr Leu Phe Ser Cys Trp Lys Ser
        610                 615                 620

Glu Asn Glu Lys Leu Leu Thr Gln Met Glu Ser Gly Lys Glu Asn Leu
625                 630                 635                 640

Gln Ser Lys Ile Asn His Leu Glu Thr Cys Leu Lys Thr Gln Gln Ile
                645                 650                 655

Lys Ser His Glu Tyr Asn Glu Arg Val Arg Thr Leu Glu Met Asp Arg
                660                 665                 670

Glu Asn Leu Ser Val Glu Ile Arg Asn Leu His Asn Val Leu Asp Ser
        675                 680                 685

Lys Ser Val Glu Val Glu Thr Gln Lys Leu Ala Tyr Met Glu Leu Gln
        690                 695                 700

Gln Lys Ala Glu Phe Ser Asp Gln Lys His Gln Lys Glu Ile Glu Asn
705                 710                 715                 720

Met Cys Leu Lys Thr Ser Gln Leu Thr Gly Gln Val Glu Asp Leu Glu
                725                 730                 735

His Lys Leu Gln Leu Leu Ser Asn Glu Ile Met Asp Lys Asp Arg Cys
        740                 745                 750

Tyr Gln Asp Leu His Ala Glu Tyr Glu Ser Leu Arg Asp Leu Leu Lys
        755                 760                 765

Ser Lys Asp Ala Ser Leu Val Thr Asn Glu Asp His Gln Arg Ser Leu
770                 775                 780

Leu Ala Phe Asp Gln Gln Pro Ala Met His His Ser Phe Ala Asn Ile
785                 790                 795                 800

Ile Gly Glu Gln Gly Ser Met Pro Ser Glu Arg Ser Glu Cys Arg Leu
                805                 810                 815

Glu Ala Asp Gln Ser Pro Lys Asn Ser Ala Ile Leu Gln Asn Arg Val
        820                 825                 830

Asp Ser Leu Glu Phe Ser Leu Glu Ser Gln Lys Gln Met Asn Ser Asp
        835                 840                 845

Leu Gln Lys Gln Cys Glu Glu Leu Val Gln Ile Lys Gly Glu Ile Glu
        850                 855                 860

```
Glu Asn Leu Met Lys Ala Glu Gln Met His Gln Ser Phe Val Ala Glu
865                 870                 875                 880

Thr Ser Gln Arg Ile Ser Lys Leu Gln Glu Asp Thr Ser Ala His Gln
                885                 890                 895

Asn Val Val Ala Glu Thr Leu Ser Ala Leu Glu Asn Lys Glu Lys Glu
            900                 905                 910

Leu Gln Leu Leu Asn Asp Lys Val Glu Thr Glu Gln Ala Glu Ile Gln
        915                 920                 925

Glu Leu Lys Lys Ser Asn His Leu Leu Glu Asp Ser Leu Lys Glu Leu
    930                 935                 940

Gln Leu Leu Ser Glu Thr Leu Ser Leu Glu Lys Lys Glu Met Ser Ser
945                 950                 955                 960

Ile Ile Ser Leu Asn Lys Arg Glu Ile Glu Glu Leu Thr Gln Glu Asn
                965                 970                 975

Gly Thr Leu Lys Glu Ile Asn Ala Ser Leu Asn Gln Glu Lys Met Asn
            980                 985                 990

Leu Ile Gln Lys Ser Glu Ser Phe Ala Asn Tyr Ile Asp Glu Arg Glu
        995                 1000                1005

Lys Ser Ile Ser Glu Leu Ser Asp Gln Tyr Lys Gln Glu Lys Leu
    1010                1015                1020

Ile Leu Leu Gln Arg Cys Glu Glu Thr Gly Asn Ala Tyr Glu Asp
    1025                1030                1035

Leu Ser Gln Lys Tyr Lys Ala Ala Gln Glu Lys Asn Ser Lys Leu
    1040                1045                1050

Glu Cys Leu Leu Asn Glu Cys Thr Ser Leu Cys Glu Asn Arg Lys
    1055                1060                1065

Asn Glu Leu Glu Gln Leu Lys Glu Ala Phe Ala Lys Glu His Gln
    1070                1075                1080

Glu Phe Leu Thr Lys Leu Ala Phe Ala Glu Glu Arg Asn Gln Asn
    1085                1090                1095

Leu Met Leu Glu Leu Glu Thr Val Gln Gln Ala Leu Arg Ser Glu
    1100                1105                1110

Met Thr Asp Asn Gln Asn Asn Ser Lys Ser Glu Ala Gly Gly Leu
    1115                1120                1125

Lys Gln Glu Ile Met Thr Leu Lys Glu Glu Gln Asn Lys Met Gln
    1130                1135                1140

Lys Glu Val Asn Asp Leu Leu Gln Glu Asn Glu Gln Leu Met Lys
    1145                1150                1155

Val Met Lys Thr Lys His Glu Cys Gln Asn Leu Glu Ser Glu Pro
    1160                1165                1170

Ile Arg Asn Ser Val Lys Glu Arg Glu Ser Glu Arg Asn Gln Cys
    1175                1180                1185

Asn Phe Lys Pro Gln Met Asp Leu Glu Val Lys Glu Ile Ser Leu
    1190                1195                1200

Asp Ser Tyr Asn Ala Gln Leu Val Gln Leu Glu Ala Met Leu Arg
    1205                1210                1215

Asn Lys Glu Leu Lys Leu Gln Glu Ser Glu Lys Glu Lys Glu Cys
    1220                1225                1230

Leu Gln His Glu Leu Gln Thr Ile Arg Gly Asp Leu Glu Thr Ser
    1235                1240                1245

Asn Leu Gln Asp Met Gln Ser Gln Glu Ile Ser Gly Leu Lys Asp
    1250                1255                1260

Cys Glu Ile Asp Ala Glu Glu Lys Tyr Ile Ser Gly Pro His Glu
```

-continued

```
            1265                1270                1275
Leu Ser Thr Ser Gln Asn Asp Asn Ala His Leu Gln Cys Ser Leu
        1280                1285                1290
Gln Thr Thr Met Asn Lys Leu Asn Glu Leu Glu Lys Ile Cys Glu
        1295                1300                1305
Ile Leu Gln Ala Glu Lys Tyr Glu Leu Val Thr Glu Leu Asn Asp
        1310                1315                1320
Ser Arg Ser Glu Cys Ile Thr Ala Thr Arg Lys Met Ala Glu Glu
        1325                1330                1335
Val Gly Lys Leu Leu Asn Glu Val Lys Ile Leu Asn Asp Asp Ser
        1340                1345                1350
Gly Leu Leu His Gly Glu Leu Val Glu Asp Ile Pro Gly Gly Glu
        1355                1360                1365
Phe Gly Glu Gln Pro Asn Glu Gln His Pro Val Ser Leu Ala Pro
        1370                1375                1380
Leu Asp Glu Ser Asn Ser Tyr Glu His Leu Thr Leu Ser Asp Lys
        1385                1390                1395
Glu Val Gln Met His Phe Ala Glu Leu Gln Glu Lys Phe Leu Ser
        1400                1405                1410
Leu Gln Ser Glu His Lys Ile Leu His Asp Gln His Cys Gln Met
        1415                1420                1425
Ser Ser Lys Met Ser Glu Leu Gln Thr Tyr Val Asp Ser Leu Lys
        1430                1435                1440
Ala Glu Asn Leu Val Leu Ser Thr Asn Leu Arg Asn Phe Gln Gly
        1445                1450                1455
Asp Leu Val Lys Glu Met Gln Leu Gly Leu Glu Glu Gly Leu Val
        1460                1465                1470
Pro Ser Leu Ser Ser Ser Cys Val Pro Asp Ser Ser Ser Leu Ser
        1475                1480                1485
Ser Leu Gly Asp Ser Ser Phe Tyr Arg Ala Leu Leu Glu Gln Thr
        1490                1495                1500
Gly Asp Met Ser Leu Leu Ser Asn Leu Glu Gly Ala Val Ser Ala
        1505                1510                1515
Asn Gln Cys Ser Val Asp Glu Val Phe Cys Ser Ser Leu Gln Glu
        1520                1525                1530
Glu Asn Leu Thr Arg Lys Glu Thr Pro Ser Ala Pro Ala Lys Gly
        1535                1540                1545
Val Glu Glu Leu Glu Ser Leu Cys Glu Val Tyr Arg Gln Ser Leu
        1550                1555                1560
Glu Lys Leu Glu Glu Lys Met Glu Ser Gln Gly Ile Met Lys Asn
        1565                1570                1575
Lys Glu Ile Gln Glu Leu Glu Gln Leu Leu Ser Ser Glu Arg Gln
        1580                1585                1590
Glu Leu Asp Cys Leu Arg Lys Gln Tyr Leu Ser Glu Asn Glu Gln
        1595                1600                1605
Trp Gln Gln Lys Leu Thr Ser Val Thr Leu Glu Met Glu Ser Lys
        1610                1615                1620
Leu Ala Ala Glu Lys Lys Gln Thr Glu Gln Leu Ser Leu Glu Leu
        1625                1630                1635
Glu Val Ala Arg Leu Gln Leu Gln Gly Leu Asp Leu Ser Ser Arg
        1640                1645                1650
Ser Leu Leu Gly Ile Asp Thr Glu Asp Ala Ile Gln Gly Arg Asn
        1655                1660                1665
```

```
Glu Ser Cys Asp Ile Ser Lys Glu His Thr Ser Glu Thr Thr Glu
    1670                1675                1680

Arg Thr Pro Lys His Asp Val His Gln Ile Cys Asp Lys Asp Ala
    1685                1690                1695

Gln Gln Asp Leu Asn Leu Asp Ile Glu Lys Ile Thr Glu Thr Gly
    1700                1705                1710

Ala Val Lys Pro Thr Gly Glu Cys Ser Gly Gln Ser Pro Asp
    1715                1720                1725

Thr Asn Tyr Glu Pro Pro Gly Glu Asp Lys Thr Gln Gly Ser Ser
    1730                1735                1740

Glu Cys Ile Ser Glu Leu Ser Phe Ser Gly Pro Asn Ala Leu Val
    1745                1750                1755

Pro Met Asp Phe Leu Gly Asn Gln Glu Asp Ile His Asn Leu Gln
    1760                1765                1770

Leu Arg Val Lys Glu Thr Ser Asn Glu Asn Leu Arg Leu Leu His
    1775                1780                1785

Val Ile Glu Asp Arg Asp Arg Lys Val Glu Ser Leu Leu Asn Glu
    1790                1795                1800

Met Lys Glu Leu Asp Ser Lys Leu His Leu Gln Glu Val Gln Leu
    1805                1810                1815

Met Thr Lys Ile Glu Ala Cys Ile Glu Leu Glu Lys Ile Val Gly
    1820                1825                1830

Glu Leu Lys Lys Glu Asn Ser Asp Leu Ser Glu Lys Leu Glu Tyr
    1835                1840                1845

Phe Ser Cys Asp His Gln Glu Leu Leu Gln Arg Val Glu Thr Ser
    1850                1855                1860

Glu Gly Leu Asn Ser Asp Leu Glu Met His Ala Asp Lys Ser Ser
    1865                1870                1875

Arg Glu Asp Ile Gly Asp Asn Val Ala Lys Val Asn Asp Ser Trp
    1880                1885                1890

Lys Glu Arg Phe Leu Asp Val Glu Asn Glu Leu Ser Arg Ile Arg
    1895                1900                1905

Ser Glu Lys Ala Ser Ile Glu His Glu Ala Leu Tyr Leu Glu Ala
    1910                1915                1920

Asp Leu Glu Val Val Gln Thr Glu Lys Leu Cys Leu Glu Lys Asp
    1925                1930                1935

Asn Glu Asn Lys Gln Lys Val Ile Val Cys Leu Glu Glu Glu Leu
    1940                1945                1950

Ser Val Val Thr Ser Glu Arg Asn Gln Leu Arg Gly Glu Leu Asp
    1955                1960                1965

Thr Met Ser Lys Lys Thr Thr Ala Leu Asp Gln Leu Ser Glu Lys
    1970                1975                1980

Met Lys Glu Lys Thr Gln Glu Leu Glu Ser His Gln Ser Glu Cys
    1985                1990                1995

Leu His Cys Ile Gln Val Ala Glu Ala Glu Val Lys Glu Lys Thr
    2000                2005                2010

Glu Leu Leu Gln Thr Leu Ser Ser Asp Val Ser Glu Leu Leu Lys
    2015                2020                2025

Asp Lys Thr His Leu Gln Glu Lys Leu Gln Ser Leu Glu Lys Asp
    2030                2035                2040

Ser Gln Ala Leu Ser Leu Thr Lys Cys Glu Leu Glu Asn Gln Ile
    2045                2050                2055
```

```
Ala Gln Leu Asn Lys Glu Lys Glu Leu Leu Val Lys Glu Ser Glu
    2060            2065                2070

Ser Leu Gln Ala Arg Leu Ser Glu Ser Asp Tyr Glu Lys Leu Asn
    2075            2080                2085

Val Ser Lys Ala Leu Glu Ala Ala Leu Val Glu Lys Gly Glu Phe
    2090            2095                2100

Ala Leu Arg Leu Ser Ser Thr Gln Glu Val His Gln Leu Arg
    2105            2110                2115

Arg Gly Ile Glu Lys Leu Arg Val Arg Ile Glu Ala Asp Glu Lys
    2120            2125                2130

Lys Gln Leu His Ile Ala Glu Lys Leu Lys Glu Arg Glu Arg Glu
    2135            2140                2145

Asn Asp Ser Leu Lys Asp Lys Val Glu Asn Leu Glu Arg Glu Leu
    2150            2155                2160

Gln Met Ser Glu Glu Asn Gln Glu Leu Val Ile Leu Asp Ala Glu
    2165            2170                2175

Asn Ser Lys Ala Glu Val Glu Thr Leu Lys Thr Gln Ile Glu Glu
    2180            2185                2190

Met Ala Arg Ser Leu Lys Val Phe Glu Leu Asp Leu Val Thr Leu
    2195            2200                2205

Arg Ser Glu Lys Glu Asn Leu Thr Lys Gln Ile Gln Glu Lys Gln
    2210            2215                2220

Gly Gln Leu Ser Glu Leu Asp Lys Leu Leu Ser Ser Phe Lys Ser
    2225            2230                2235

Leu Leu Glu Glu Lys Glu Gln Ala Glu Ile Gln Ile Lys Glu Glu
    2240            2245                2250

Ser Lys Thr Ala Val Glu Met Leu Gln Asn Gln Leu Lys Glu Leu
    2255            2260                2265

Asn Glu Ala Val Ala Ala Leu Cys Gly Asp Gln Glu Ile Met Lys
    2270            2275                2280

Ala Thr Glu Gln Ser Leu Asp Pro Pro Ile Glu Glu Glu His Gln
    2285            2290                2295

Leu Arg Asn Ser Ile Glu Lys Leu Arg Ala Arg Leu Glu Ala Asp
    2300            2305                2310

Glu Lys Lys Gln Leu Cys Val Leu Gln Gln Leu Lys Glu Ser Glu
    2315            2320                2325

His His Ala Asp Leu Leu Lys Gly Arg Val Glu Asn Leu Glu Arg
    2330            2335                2340

Glu Leu Glu Ile Ala Arg Thr Asn Gln Glu His Ala Ala Leu Glu
    2345            2350                2355

Ala Glu Asn Ser Lys Gly Glu Val Glu Thr Leu Lys Ala Lys Ile
    2360            2365                2370

Glu Gly Met Thr Gln Ser Leu Arg Gly Leu Glu Leu Asp Val Val
    2375            2380                2385

Thr Ile Arg Ser Glu Lys Glu Asn Leu Thr Asn Glu Leu Gln Lys
    2390            2395                2400

Glu Gln Glu Arg Ile Ser Glu Leu Glu Ile Ile Asn Ser Ser Phe
    2405            2410                2415

Glu Asn Ile Leu Gln Glu Lys Glu Gln Glu Lys Val Gln Met Lys
    2420            2425                2430

Glu Lys Ser Ser Thr Ala Met Glu Met Leu Gln Thr Gln Leu Lys
    2435            2440                2445

Glu Leu Asn Glu Arg Val Ala Ala Leu His Asn Asp Gln Glu Ala
```

```
              2450                2455                2460
Cys Lys Ala Lys Glu Gln Asn Leu Ser Ser Gln Val Glu Cys Leu
    2465                2470                2475

Glu Leu Glu Lys Ala Gln Leu Leu Gln Gly Leu Asp Glu Ala Lys
    2480                2485                2490

Asn Asn Tyr Ile Val Leu Gln Ser Ser Val Asn Gly Leu Ile Gln
    2495                2500                2505

Glu Val Glu Asp Gly Lys Gln Lys Leu Glu Lys Lys Asp Glu Glu
    2510                2515                2520

Ile Ser Arg Leu Lys Asn Gln Ile Gln Asp Gln Glu Gln Leu Val
    2525                2530                2535

Ser Lys Leu Ser Gln Val Glu Gly Glu His Gln Leu Trp Lys Glu
    2540                2545                2550

Gln Asn Leu Glu Leu Arg Asn Leu Thr Val Glu Leu Glu Gln Lys
    2555                2560                2565

Ile Gln Val Leu Gln Ser Lys Asn Ala Ser Leu Gln Asp Thr Leu
    2570                2575                2580

Glu Val Leu Gln Ser Ser Tyr Lys Asn Leu Glu Asn Glu Leu Glu
    2585                2590                2595

Leu Thr Lys Met Asp Lys Met Ser Phe Val Glu Lys Val Asn Lys
    2600                2605                2610

Met Thr Ala Lys Glu Thr Glu Leu Gln Arg Glu Met His Glu Met
    2615                2620                2625

Ala Gln Lys Thr Ala Glu Leu Gln Glu Glu Leu Ser Gly Glu Lys
    2630                2635                2640

Asn Arg Leu Ala Gly Glu Leu Gln Leu Leu Glu Glu Ile Lys
    2645                2650                2655

Ser Ser Lys Asp Gln Leu Lys Glu Leu Thr Leu Glu Asn Ser Glu
    2660                2665                2670

Leu Lys Lys Ser Leu Asp Cys Met His Lys Asp Gln Val Glu Lys
    2675                2680                2685

Glu Gly Lys Val Arg Glu Glu Ile Ala Glu Tyr Gln Leu Arg Leu
    2690                2695                2700

His Glu Ala Glu Lys Lys His Gln Ala Leu Leu Leu Asp Thr Asn
    2705                2710                2715

Lys Gln Tyr Glu Val Glu Ile Gln Thr Tyr Arg Glu Lys Leu Thr
    2720                2725                2730

Ser Lys Glu Glu Cys Leu Ser Ser Gln Lys Leu Glu Ile Asp Leu
    2735                2740                2745

Leu Lys Ser Ser Lys Glu Glu Leu Asn Asn Ser Leu Lys Ala Thr
    2750                2755                2760

Thr Gln Ile Leu Glu Glu Leu Lys Lys Thr Lys Met Asp Asn Leu
    2765                2770                2775

Lys Tyr Val Asn Gln Leu Lys Lys Glu Asn Glu Arg Ala Gln Gly
    2780                2785                2790

Lys Met Lys Leu Leu Ile Lys Ser Cys Lys Gln Leu Glu Glu Glu
    2795                2800                2805

Lys Glu Ile Leu Gln Lys Glu Leu Ser Gln Leu Gln Ala Ala Gln
    2810                2815                2820

Glu Lys Gln Lys Thr Gly Thr Val Met Asp Thr Lys Val Asp Glu
    2825                2830                2835

Leu Thr Thr Glu Ile Lys Glu Leu Lys Glu Thr Leu Glu Glu Lys
    2840                2845                2850
```

| | | | | | | | | | | |
|---|---|---|---|---|---|---|---|---|---|---|
|Thr|Lys|Glu|Ala|Asp|Glu|Tyr|Leu|Asp|Lys|Tyr|Cys|Ser|Leu|Leu|
| |2855| | | |2860| | | |2865| |

Ile Ser His Glu Lys Leu Glu Lys Ala Lys Glu Met Leu Glu Thr
    2870            2875            2880

Gln Val Ala His Leu Cys Ser Gln Gln Ser Lys Gln Asp Ser Arg
    2885            2890            2895

Gly Ser Pro Leu Leu Gly Pro Val Val Pro Gly Pro Ser Pro Ile
    2900            2905            2910

Pro Ser Val Thr Glu Lys Arg Leu Ser Ser Gly Gln Asn Lys Ala
    2915            2920            2925

Ser Gly Lys Arg Gln Arg Ser Ser Gly Ile Trp Glu Asn Gly Arg
    2930            2935            2940

Gly Pro Thr Pro Ala Thr Pro Glu Ser Phe Ser Lys Lys Ser Lys
    2945            2950            2955

Lys Ala Val Met Ser Gly Ile His Pro Ala Glu Asp Thr Glu Gly
    2960            2965            2970

Thr Glu Phe Glu Pro Glu Gly Leu Pro Glu Val Val Lys Lys Gly
    2975            2980            2985

Phe Ala Asp Ile Pro Thr Gly Lys Thr Ser Pro Tyr Ile Leu Arg
    2990            2995            3000

Arg Thr Thr Met Ala Thr Arg Thr Ser Pro Arg Leu Ala Ala Gln
    3005            3010            3015

Lys Leu Ala Leu Ser Pro Leu Ser Leu Gly Lys Glu Asn Leu Ala
    3020            3025            3030

Glu Ser Ser Lys Pro Thr Ala Gly Gly Ser Arg Ser Gln Lys Val
    3035            3040            3045

Lys Val Ala Gln Arg Ser Pro Val Asp Ser Gly Thr Ile Leu Arg
    3050            3055            3060

Glu Pro Thr Thr Lys Ser Val Pro Val Asn Asn Leu Pro Glu Arg
    3065            3070            3075

Ser Pro Thr Asp Ser Pro Arg Glu Gly Leu Arg Val Lys Arg Gly
    3080            3085            3090

Arg Leu Val Pro Ser Pro Lys Ala Gly Leu Glu Ser Asn Gly Ser
    3095            3100            3105

Glu Asn Cys Lys Val Gln
    3110

```
<210> SEQ ID NO 3
<211> LENGTH: 1687
<212> TYPE: DNA
<213> ORGANISM: Homo sapiens
<220> FEATURE:
<221> NAME/KEY: CDS
<222> LOCATION: (38)..(871)

<400> SEQUENCE: 3
gattgtggga aggcagctga actcggcgcc tggaaag atg gag gca gcg gag aca      55
                                         Met Glu Ala Ala Glu Thr
                                         1               5 gag gcg gaa gct gca gcc cta gag gtc ctg gct gag gtg gca ggc atc     103
Glu Ala Glu Ala Ala Ala Leu Glu Val Leu Ala Glu Val Ala Gly Ile
            10                  15                  20 ttg gaa cct gta ggc ctg cag gag gag gca gaa ctg cca gcc aag atc     151
Leu Glu Pro Val Gly Leu Gln Glu Glu Ala Glu Leu Pro Ala Lys Ile
        25                  30                  35 ctg gtt gag ttt gtg gtg gac tct cag aag aaa gac aag ctg ctc tgc     199
```

```
              Leu Val Glu Phe Val Val Asp Ser Gln Lys Lys Asp Lys Leu Leu Cys
                   40                  45                  50 agc cag ctt cag gta gcg gat ttc ctg cag aac atc ctg gct cag gag        247
Ser Gln Leu Gln Val Ala Asp Phe Leu Gln Asn Ile Leu Ala Gln Glu
 55                  60                  65                  70 gac act gct aag ggt ctc gac ccc ttg gct tct gaa gac acg agc cga        295
Asp Thr Ala Lys Gly Leu Asp Pro Leu Ala Ser Glu Asp Thr Ser Arg
                 75                  80                  85 cag aag gca att gca gct aag gaa caa tgg aaa gag ctg aag gcc acc        343
Gln Lys Ala Ile Ala Ala Lys Glu Gln Trp Lys Glu Leu Lys Ala Thr
                     90                  95                 100 tac agg gag cac gta gag gcc atc aaa att ggc ctc acc aag gcc ctg        391
Tyr Arg Glu His Val Glu Ala Ile Lys Ile Gly Leu Thr Lys Ala Leu
                105                 110                 115 act cag atg gag gaa gcc cag agg aaa cgg aca caa ctc cgg gaa gcc        439
Thr Gln Met Glu Glu Ala Gln Arg Lys Arg Thr Gln Leu Arg Glu Ala
        120                 125                 130 ttt gag cag ctc cag gcc aag aaa caa atg gcc atg gag aaa cgc aga        487
Phe Glu Gln Leu Gln Ala Lys Lys Gln Met Ala Met Glu Lys Arg Arg
135                 140                 145                 150 gca gtc cag aac cag tgg cag cta caa cag gag aag cat ctg cag cat        535
Ala Val Gln Asn Gln Trp Gln Leu Gln Gln Glu Lys His Leu Gln His
                        155                 160                 165 ctg gcg gag gtt tct gca gag gtg agg gag cgt aag aca ggg act cag        583
Leu Ala Glu Val Ser Ala Glu Val Arg Glu Arg Lys Thr Gly Thr Gln
                170                 175                 180 cag gag ctt gac agg gtg ttt cag aaa ctt gga aac ctg aag cag cag        631
Gln Glu Leu Asp Arg Val Phe Gln Lys Leu Gly Asn Leu Lys Gln Gln
            185                 190                 195 gca gaa cag gag cgg gac aag ctg cag agg tat cag acc ttc ctc cag        679
Ala Glu Gln Glu Arg Asp Lys Leu Gln Arg Tyr Gln Thr Phe Leu Gln
200                 205                 210 ctt ctg tat acc ctg cag ggt aag ctg ttg ttc cct gag gct gag gct        727
Leu Leu Tyr Thr Leu Gln Gly Lys Leu Leu Phe Pro Glu Ala Glu Ala
215                 220                 225                 230 gag gca gag aat ctt cca gat gat aaa ccc cag cag ccg act cga ccc        775
Glu Ala Glu Asn Leu Pro Asp Asp Lys Pro Gln Gln Pro Thr Arg Pro
                    235                 240                 245 cag gag cag agt aca gga gac acc atg ggg aga gac cct ggt gtg tcc        823
Gln Glu Gln Ser Thr Gly Asp Thr Met Gly Arg Asp Pro Gly Val Ser
                250                 255                 260 ttc aag gct gtt ggt cta caa cct gct gga gat gta aat ttg cca tga       871
Phe Lys Ala Val Gly Leu Gln Pro Ala Gly Asp Val Asn Leu Pro
            265                 270                 275 cttcctggag acagcagca tggagaaaga tcctagaaaa ggcctctgac ttccctcacc      931
tcccaaccat cattacagga aagactgtga actcctgagt tcagcttgat ttctgactac    991
atcccagcaa gctctggcat ctgtggatta aaatccctgg atctctctca gttgtgtatt   1051
tgttcatctt catatgctgg caggaacaac tattaataca gatactcaga agccaataac    1111
atgacaggag ctgggactgg tttgaacaca gggtgtgcag atggggaggg ggtactggcc    1171
ttgggcctcc tatgatgcag acatggtgaa tttaattcaa ggaggaggag aatgttttag    1231
gcaggtggtt atatgtggga agataatttt attcatggat ccaaatgttt gttgagtcct   1291
ttctttgtgc taaggttctt gcggtgaacc agaattataa cagtgagctc atctgactgt    1351
tttaggatgt acagcctagt gttaacattc tggtatctt tttgtgcctt atctaaaaca     1411
tttctcgatc actggtttca gatgttcatt tattatattc ttttcaaaga ttcagagatt    1471
```

```
ggcttttgtc atccactatt gtatgttttg tttcattgac ctctagtgat accttgatct    1531
ttcccacttt ctgttttcgg attggagaag atgtaccttt tttgtcaact cttactttta    1591
tcagatgatc aactcacgta tttggatctt tatttgtttt ctcaaataaa tatttaaggt    1651
tatacattta aaaaaaaaaa aaaaaaaaaa aaaaaa                              1687
```

<210> SEQ ID NO 4
<211> LENGTH: 277
<212> TYPE: PRT
<213> ORGANISM: Homo sapiens

<400> SEQUENCE: 4

```
Met Glu Ala Ala Glu Thr Glu Ala Glu Ala Ala Leu Glu Val Leu
 1               5                  10                  15

Ala Glu Val Ala Gly Ile Leu Glu Pro Val Gly Leu Gln Glu Ala
            20                  25                  30

Glu Leu Pro Ala Lys Ile Leu Glu Phe Val Val Asp Ser Gln Lys
        35                  40                  45

Lys Asp Lys Leu Leu Cys Ser Gln Leu Gln Val Ala Asp Phe Leu Gln
    50                  55                  60

Asn Ile Leu Ala Gln Glu Asp Thr Ala Lys Gly Leu Asp Pro Leu Ala
65                  70                  75                  80

Ser Glu Asp Thr Ser Arg Gln Lys Ala Ile Ala Ala Lys Glu Gln Trp
                85                  90                  95

Lys Glu Leu Lys Ala Thr Tyr Arg Glu His Val Glu Ala Ile Lys Ile
            100                 105                 110

Gly Leu Thr Lys Ala Leu Thr Gln Met Glu Gly Ala Gln Arg Lys Arg
        115                 120                 125

Thr Gln Leu Arg Glu Ala Phe Glu Gln Leu Gln Ala Lys Lys Gln Met
    130                 135                 140

Ala Met Glu Lys Arg Arg Ala Val Gln Asn Gln Trp Gln Leu Gln Gln
145                 150                 155                 160

Glu Lys His Leu Gln His Leu Ala Glu Val Ser Ala Glu Val Arg Glu
                165                 170                 175

Arg Lys Thr Gly Thr Gln Gln Glu Leu Asp Arg Val Phe Gln Lys Leu
            180                 185                 190

Gly Asn Leu Lys Gln Gln Ala Glu Gln Glu Arg Asp Lys Leu Gln Arg
        195                 200                 205

Tyr Gln Thr Phe Leu Gln Leu Leu Tyr Thr Leu Gln Gly Lys Leu Leu
    210                 215                 220

Phe Pro Glu Ala Glu Ala Glu Ala Glu Asn Leu Pro Asp Asp Lys Pro
225                 230                 235                 240

Gln Gln Pro Thr Arg Pro Gln Glu Gln Ser Thr Gly Asp Thr Met Gly
                245                 250                 255

Arg Asp Pro Gly Val Ser Phe Lys Ala Val Gly Leu Gln Pro Ala Gly
            260                 265                 270

Asp Val Asn Leu Pro
        275
```

<210> SEQ ID NO 5
<211> LENGTH: 2628
<212> TYPE: DNA
<213> ORGANISM: Homo sapiens
<220> FEATURE:
<221> NAME/KEY: CDS
<222> LOCATION: (190)..(1101)

```
<400> SEQUENCE: 5
gagcgcctgc cgtttctcgg ggcgggacgg gggggcgggg actgggcgga gaggcgcgtg      60
ctgctgcgtg cgtgcgcgcg cgccgcgggc gggccagtga aaccggcggc cctggcacgt     120
gacctaggac cggctcaccg gtcgcttgg tggctccgtc tgtctgtccg tccgcccgcg     180 ggtgccatc atg gcg gac gcg gcc agt cag gtg ctc ctg ggc tcc ggt ctc    231
          Met Ala Asp Ala Ala Ser Gln Val Leu Leu Gly Ser Gly Leu
            1               5                  10 acc atc ctg tcc cag ccg ctc atg tac gtg aaa gtg ctc atc cag gtg      279
Thr Ile Leu Ser Gln Pro Leu Met Tyr Val Lys Val Leu Ile Gln Val
 15              20                  25                  30 gga tat gag cct ctt cct cca aca ata gga cga aat att ttt ggg cgg      327
Gly Tyr Glu Pro Leu Pro Pro Thr Ile Gly Arg Asn Ile Phe Gly Arg
                 35                  40                  45 caa gtg tgt cag ctt cct ggt ctc ttt agt tat gct cag cac att gcc      375
Gln Val Cys Gln Leu Pro Gly Leu Phe Ser Tyr Ala Gln His Ile Ala
             50                  55                  60 agt atc gat ggg agg cgc ggg ttg ttc aca ggc tta act cca aga ctg      423
Ser Ile Asp Gly Arg Arg Gly Leu Phe Thr Gly Leu Thr Pro Arg Leu
         65                  70                  75 tgt tcg gga gtc ctt gga act gtg gtc cat ggt aaa gtt tta cag cat      471
Cys Ser Gly Val Leu Gly Thr Val Val His Gly Lys Val Leu Gln His
     80                  85                  90 tac cag gag agt gac aag ggt gag gag tta gga cct gga aat gta cag      519
Tyr Gln Glu Ser Asp Lys Gly Glu Glu Leu Gly Pro Gly Asn Val Gln
 95                 100                 105                 110 aaa gaa gtc tca tct tcc ttt gac cac gtt atc aag gag aca act cga      567
Lys Glu Val Ser Ser Ser Phe Asp His Val Ile Lys Glu Thr Thr Arg
                115                 120                 125 gag atg atc gct cgt tct gct gct acc ctc atc aca cat ccc ttc cat      615
Glu Met Ile Ala Arg Ser Ala Ala Thr Leu Ile Thr His Pro Phe His
            130                 135                 140 gtg atc act ctg aga tct atg gta cag ttc att ggc aga gaa tcc aag      663
Val Ile Thr Leu Arg Ser Met Val Gln Phe Ile Gly Arg Glu Ser Lys
        145                 150                 155 tac tgt gga ctt tgt gat tcc ata ata acc atc tat cgg gaa gag ggc      711
Tyr Cys Gly Leu Cys Asp Ser Ile Ile Thr Ile Tyr Arg Glu Glu Gly
    160                 165                 170 att cta gga ttt ttc gcg ggt ctt gtt cct cgc ctt cta ggt gac atc      759
Ile Leu Gly Phe Phe Ala Gly Leu Val Pro Arg Leu Leu Gly Asp Ile
175                 180                 185                 190 ctt tct ttg tgg ctg tgt aac tca ctg gcc tac ctc gtc aat acc tat      807
Leu Ser Leu Trp Leu Cys Asn Ser Leu Ala Tyr Leu Val Asn Thr Tyr
                195                 200                 205 gca ctg gac agt ggg gtt tct acc atg aat gaa atg aag agt tat tct      855
Ala Leu Asp Ser Gly Val Ser Thr Met Asn Glu Met Lys Ser Tyr Ser
            210                 215                 220 caa gct gtc aca gga ttt ttt gcg agt atg ttg acc tat ccc ttt gtg      903
Gln Ala Val Thr Gly Phe Phe Ala Ser Met Leu Thr Tyr Pro Phe Val
        225                 230                 235 ctt gtc tcc aat ctt atg gct gtc aac aac tgt ggt ctt gct ggt gga      951
Leu Val Ser Asn Leu Met Ala Val Asn Asn Cys Gly Leu Ala Gly Gly
    240                 245                 250 tgc cct cct tac tcc cca ata tat acg tct tgg ata gac tgt tgg tgc      999
Cys Pro Pro Tyr Ser Pro Ile Tyr Thr Ser Trp Ile Asp Cys Trp Cys
255                 260                 265                 270 atg cta caa aaa gag ggg aat atg agc cga gga aat agc tta ttt ttc     1047
Met Leu Gln Lys Glu Gly Asn Met Ser Arg Gly Asn Ser Leu Phe Phe
                275                 280                 285
```

```
cgg aag gtc ccc ttt ggg aag act tat tgt tgt gac ctg aaa atg tta    1095
Arg Lys Val Pro Phe Gly Lys Thr Tyr Cys Cys Asp Leu Lys Met Leu
            290                 295                 300 att tga agatgtgggg cagggacagt gacatttctg tagtcccaga tgcacagaat     1151
Ile tatgggagag aatgttgatt tctatacagt gtggcgcgct tttttaataa tcatttaatc  1211
ttgggaaaat tcaggtgttt ggtgtctgcc tttttgttc tttttccag cacaacataa    1271 cttaccactg atactccccc tttagttatt ctgaattagg atattttgc tccaaattct   1331 tattttactt aaccagaagg gaaaaaaagt tgtattttcc tgaagctaca ggcactttgt   1391
catgtgattt ttgagtctca atttaaggct ttgtaaaatg aagagtagaa ttccaagaaa  1451
aatgagaaat aattttgtaa aacttaacaa aatcactaaa ttaaactata tgggaggtta  1511
tgaattactt tttcttgggt agaccctaaa atgtcagtag catgcaccag aatctgactc  1571
ccattatgct tctaagcaca tttcattgac cttgtctctc atacttcaag aaaaggacag  1631
tacattgcta cattacccta gaaagtctgt gtgaggatct gccccttcag tctgttattg   1691
caaagtaata aaatgtcacc tacagggagc ctctgagcct actctagttc aagaggctac  1751
ctgaaaaaaa ataaataaga taaagggtca gcaacaacaa agaaaagac aattacagaa    1811 aataagcaag atttggaaag gaagtataat ggcactttt tcctcaaagg aagttcttgt   1871
tttcacataa aatatgaaaa gcagatcctg caggagtaac ccccttcttt aagagccaag  1931
tatttgccag tgcttaaatt acaccataca gttctaatta tatataatct tttgttcttc  1991
agttttttgt tttgtttcct ttttgttatt gttgccgaag gtgagtagtt ttgcatttct   2051
gatgacagcc ttggaaagta tatttgtaac tccatgtctg gtaatgccaa cccaagtcga  2111
catgggtctt aggacactga ccacctcaca tgccatacccc tcagttaagc atgttaacat  2171
ttataggagg aaaaaaatca ctttgggaga aaataaaatt caactcaagc ataaagcttc  2231
tgtttactca ggccttctaa aaagcaggtt aaaatgctct aaaatgagaa agcctgtggt  2291
ttcacttatt tatataactc actgggacat tgccaaatga gtaagcactt aattcgctgc  2351
ttctgagact tctctgtcaa aacagcccca ctgataatat tagacagaac gagaatgcag  2411
gggtctcttc cctcccctgg ggtttaggaa gctcatgagg agctcggctt aaaatgtctt   2471
tgatgtctct tcctttgtct caaaaagtaa tgtcaatttt atatactatt tcaatattac  2531
tatctgcatt tgttttaata taaaaatgtt tgctgcctac cttttctcc caaaaaatct    2591 ttaagtaaag atgatctggg aaaatgtgcc atgttta                           2628
```

<210> SEQ ID NO 6
<211> LENGTH: 303
<212> TYPE: PRT
<213> ORGANISM: Homo sapiens

<400> SEQUENCE: 6

```
Met Ala Asp Ala Ala Ser Gln Val Leu Leu Gly Ser Gly Leu Thr Ile
1               5                   10                  15

Leu Ser Gln Pro Leu Met Tyr Val Lys Val Leu Ile Gln Val Gly Tyr
            20                  25                  30

Glu Pro Leu Pro Pro Thr Ile Gly Arg Asn Ile Phe Gly Arg Gln Val
        35                  40                  45

Cys Gln Leu Pro Gly Leu Phe Ser Tyr Ala Gln His Ile Ala Ser Ile
    50                  55                  60

Asp Gly Arg Arg Gly Leu Phe Thr Gly Leu Thr Pro Arg Leu Cys Ser
```

```
                65                  70                  75                  80
Gly Val Leu Gly Thr Val Val His Gly Lys Val Leu Gln His Tyr Gln
                    85                  90                  95
Glu Ser Asp Lys Gly Glu Leu Gly Pro Gly Asn Val Gln Lys Glu
                100                 105                 110
Val Ser Ser Phe Asp His Val Ile Lys Glu Thr Thr Arg Glu Met
            115                 120                 125
Ile Ala Arg Ser Ala Ala Thr Leu Ile Thr His Pro Phe His Val Ile
130                 135                 140
Thr Leu Arg Ser Met Val Gln Phe Ile Gly Arg Glu Ser Lys Tyr Cys
145                 150                 155                 160
Gly Leu Cys Asp Ser Ile Ile Thr Ile Tyr Arg Glu Glu Gly Ile Leu
                165                 170                 175
Gly Phe Phe Ala Gly Leu Val Pro Arg Leu Leu Gly Asp Ile Leu Ser
                180                 185                 190
Leu Trp Leu Cys Asn Ser Leu Ala Tyr Leu Val Asn Thr Tyr Ala Leu
        195                 200                 205
Asp Ser Gly Val Ser Thr Met Asn Glu Met Lys Ser Tyr Ser Gln Ala
210                 215                 220
Val Thr Gly Phe Phe Ala Ser Met Leu Thr Tyr Pro Phe Val Leu Val
225                 230                 235                 240
Ser Asn Leu Met Ala Val Asn Asn Cys Gly Leu Ala Gly Gly Cys Pro
                245                 250                 255
Pro Tyr Ser Pro Ile Tyr Thr Ser Trp Ile Asp Cys Trp Cys Met Leu
                260                 265                 270
Gln Lys Glu Gly Asn Met Ser Arg Gly Asn Ser Leu Phe Phe Arg Lys
            275                 280                 285
Val Pro Phe Gly Lys Thr Tyr Cys Cys Asp Leu Lys Met Leu Ile
        290                 295                 300

<210> SEQ ID NO 7
<211> LENGTH: 3760
<212> TYPE: DNA
<213> ORGANISM: Homo sapiens
<220> FEATURE:
<221> NAME/KEY: CDS
<222> LOCATION: (374)..(2233)

<400> SEQUENCE: 7
agaaacactt ggtttcatgt atgactcata agctgaagca cagacaccac ttccccaatc      60
tacaggagcc attttaacag ctaaaacttg tcggattgct ttttattttc aagctcaaaa     120
gacgatagag aaagaatact tgaaggccaa gaagcttgag agaagaaaaa tttcagaaaa     180
attgtctcaa tttgactaga atatcaatga accaggaaaa ctgaagcacc ttccctaaag     240
aaaacttggg tatacaatta ctccacagac agagctgagg gttttttacc caaatcagtc     300
actggatttt gctgcctgat acgtgaatct tcttggaatt tttctcatgt ggatctaagg     360
ggaatgcttt att atg gct gct gtt gtc caa cag aac gac cta gta ttt        409
            Met Ala Ala Val Val Gln Gln Asn Asp Leu Val Phe
              1               5                  10 gaa ttt gct agt aac gtc atg gag gat gaa cga cag ctt ggt gat cca       457
Glu Phe Ala Ser Asn Val Met Glu Asp Glu Arg Gln Leu Gly Asp Pro
        15                  20                  25 gct att ttt cct gcc gta att gtg gaa cat gtt cct ggt gct gat att       505
Ala Ile Phe Pro Ala Val Ile Val Glu His Val Pro Gly Ala Asp Ile
    30                  35                  40
```

| | | |
|---|---|---|
| ctc aat agt tat gcc ggt cta gcc tgt gtg gaa gag ccc aat gac atg<br>Leu Asn Ser Tyr Ala Gly Leu Ala Cys Val Glu Glu Pro Asn Asp Met<br>45                      50                      55                  60 | | 553 |
| att act gag agt tca ctg gat gtt gct gaa gaa gaa atc ata gac gat<br>Ile Thr Glu Ser Ser Leu Asp Val Ala Glu Glu Glu Ile Ile Asp Asp<br>                   65                      70                      75 | | 601 |
| gat gat gat gat gac atc acc ctt aca gtt gaa gct tct tgt cat gac ggg<br>Asp Asp Asp Asp Ile Thr Leu Thr Val Glu Ala Ser Cys His Asp Gly<br>                80                      85                      90 | | 649 |
| gat gaa aca att gaa act att gag gct gct gag gca ctc ctc aat atg<br>Asp Glu Thr Ile Glu Thr Ile Glu Ala Ala Glu Ala Leu Leu Asn Met<br>      95                      100                      105 | | 697 |
| gat tcc cct ggc cct atg ctg gat gaa aaa cga ata aat aat aat ata<br>Asp Ser Pro Gly Pro Met Leu Asp Glu Lys Arg Ile Asn Asn Asn Ile<br>110                      115                      120 | | 745 |
| ttt agt tca cct gaa gat gac atg gtt gtt gcc cca gtc acc cat gtg<br>Phe Ser Ser Pro Glu Asp Asp Met Val Val Ala Pro Val Thr His Val<br>125                      130                      135                  140 | | 793 |
| tcc gtc aca tta gat ggg att cct gaa gtg atg gaa aca cag cag gtg<br>Ser Val Thr Leu Asp Gly Ile Pro Glu Val Met Glu Thr Gln Gln Val<br>                  145                      150                      155 | | 841 |
| caa gaa aaa tat gca gac tca ccg gga gcc tca tca cca gaa cag cct<br>Gln Glu Lys Tyr Ala Asp Ser Pro Gly Ala Ser Ser Pro Glu Gln Pro<br>            160                      165                      170 | | 889 |
| aag agg aaa aaa gga aga aaa act aaa cca cca cga cca gat tcc cca<br>Lys Arg Lys Lys Gly Arg Lys Thr Lys Pro Pro Arg Pro Asp Ser Pro<br>      175                      180                      185 | | 937 |
| gcc act acg cca aat ata tct gtg aag aag aaa aac aaa gat gga aag<br>Ala Thr Thr Pro Asn Ile Ser Val Lys Lys Lys Asn Lys Asp Gly Lys<br>190                      195                      200 | | 985 |
| gga aac aca att tat ctt tgg gag ttt tta ctg gca ctg ctc cag gac<br>Gly Asn Thr Ile Tyr Leu Trp Glu Phe Leu Leu Ala Leu Leu Gln Asp<br>205                      210                      215                  220 | | 1033 |
| aag gct act tgt cct aaa tac atc aag tgg acc cag cga gag aaa ggc<br>Lys Ala Thr Cys Pro Lys Tyr Ile Lys Trp Thr Gln Arg Glu Lys Gly<br>                225                      230                      235 | | 1081 |
| att ttt aaa ttg gtg gat tct aaa gca gtg tcc agg ttg tgg ggg aag<br>Ile Phe Lys Leu Val Asp Ser Lys Ala Val Ser Arg Leu Trp Gly Lys<br>            240                      245                      250 | | 1129 |
| cac aaa aac aaa cct gat atg aat tat gag acc atg gga aga gca ctc<br>His Lys Asn Lys Pro Asp Met Asn Tyr Glu Thr Met Gly Arg Ala Leu<br>         255                      260                      265 | | 1177 |
| agg tac tat tac caa agg ggt att ctg gca aaa gtg gaa ggt cag cgc<br>Arg Tyr Tyr Tyr Gln Arg Gly Ile Leu Ala Lys Val Glu Gly Gln Arg<br>270                      275                      280 | | 1225 |
| ttg gtg tat cag ttt aaa gaa atg cca aaa gat ctt ata tat ata aat<br>Leu Val Tyr Gln Phe Lys Glu Met Pro Lys Asp Leu Ile Tyr Ile Asn<br>285                      290                      295                  300 | | 1273 |
| gat gag gat cca agt tcc agc ata gag tct tca gat cca tcg cta tct<br>Asp Glu Asp Pro Ser Ser Ser Ile Glu Ser Ser Asp Pro Ser Leu Ser<br>                305                      310                      315 | | 1321 |
| tca tca gcc act tca aat agg aat caa acc agc cgg tcg aga gta tct<br>Ser Ser Ala Thr Ser Asn Arg Asn Gln Thr Ser Arg Ser Arg Val Ser<br>            320                      325                      330 | | 1369 |
| tca agt cca ggg gta aaa gga gga gcc act aca gtt cta aaa cca ggg<br>Ser Ser Pro Gly Val Lys Gly Gly Ala Thr Thr Val Leu Lys Pro Gly<br>         335                      340                      345 | | 1417 |
| aat tct aaa gct gca aaa ccc aaa gat cct gtg gaa gtt gca caa cca<br>Asn Ser Lys Ala Ala Lys Pro Lys Asp Pro Val Glu Val Ala Gln Pro<br>350                      355                      360 | | 1465 |

-continued

```
tca gaa gtt ttg agg aca gtg cag ccc acg cag tct cca tat cct acc    1513
Ser Glu Val Leu Arg Thr Val Gln Pro Thr Gln Ser Pro Tyr Pro Thr
365                 370                 375                 380 cag ctc ttc cgg act gtt cat gta gta cag cca gta cag gct gtc cca    1561
Gln Leu Phe Arg Thr Val His Val Val Gln Pro Val Gln Ala Val Pro
                385                 390                 395 gag gga gaa gca gct aga acc agt acc atg cag gat gaa aca tta aat    1609
Glu Gly Glu Ala Ala Arg Thr Ser Thr Met Gln Asp Glu Thr Leu Asn
            400                 405                 410 tct tcc gtt cag agt att agg act ata cag gct cca acc caa gtt cca    1657
Ser Ser Val Gln Ser Ile Arg Thr Ile Gln Ala Pro Thr Gln Val Pro
        415                 420                 425 gtg gtt gtg tct cct agg aat cag cag ttg cat aca gta aca ctc caa    1705
Val Val Val Ser Pro Arg Asn Gln Gln Leu His Thr Val Thr Leu Gln
    430                 435                 440 aca gtg cca ctc aca aca gtt ata gcc agc aca gat cca tca gca ggt    1753
Thr Val Pro Leu Thr Thr Val Ile Ala Ser Thr Asp Pro Ser Ala Gly
445                 450                 455                 460 act gga tct cag aag ttt att tta caa gcc att cca tca tca cag ccc    1801
Thr Gly Ser Gln Lys Phe Ile Leu Gln Ala Ile Pro Ser Ser Gln Pro
                465                 470                 475 atg aca gta ctg aaa gaa aat gtc atg ctg cag tca caa aag gcg ggc    1849
Met Thr Val Leu Lys Glu Asn Val Met Leu Gln Ser Gln Lys Ala Gly
            480                 485                 490 tct cct cct tca att gtc ttg ggc cct gcc cag gtt cag cag gtc ctt    1897
Ser Pro Pro Ser Ile Val Leu Gly Pro Ala Gln Val Gln Gln Val Leu
        495                 500                 505 act agc aat gtt cag acc att tgc aat gga acc gtc agt gtg gct tcc    1945
Thr Ser Asn Val Gln Thr Ile Cys Asn Gly Thr Val Ser Val Ala Ser
    510                 515                 520 tct cca tcc ttc agt gct act gca cct gtg gtg acc ttt tct cct cgc    1993
Ser Pro Ser Phe Ser Ala Thr Ala Pro Val Val Thr Phe Ser Pro Arg
525                 530                 535                 540 agt tca cag ctg gtt gct cac cca cct ggc act gta atc act tca gtt    2041
Ser Ser Gln Leu Val Ala His Pro Pro Gly Thr Val Ile Thr Ser Val
                545                 550                 555 atc aaa act caa gaa aca aaa act ctt aca cag gaa gta gag aaa aag    2089
Ile Lys Thr Gln Glu Thr Lys Thr Leu Thr Gln Glu Val Glu Lys Lys
            560                 565                 570 gaa tct gaa gat cat ttg aaa gag aac act gag aaa acg gag cag cag    2137
Glu Ser Glu Asp His Leu Lys Glu Asn Thr Glu Lys Thr Glu Gln Gln
        575                 580                 585 cca cag cct tat gtg atg gta gtg tcc agt tcc aat gga ttt act tct    2185
Pro Gln Pro Tyr Val Met Val Val Ser Ser Ser Asn Gly Phe Thr Ser
    590                 595                 600 cag gta gct atg aaa caa aac gaa ctg ctg gaa ccc aac tct ttt tag    2233
Gln Val Ala Met Lys Gln Asn Glu Leu Leu Glu Pro Asn Ser Phe
605                 610                 615 ttaatatacc aaagcttatg aataattgtt tgttaattga acattttcaa ttatatgcag   2293
actgactgat tctaagataa attctaagga gggtttctaat tttgtaattg ttaaaaatag   2353
agttaatttt gactttgtta gatgagggag gaaaactcaa ctgtttctct ttgttatcta   2413
aatgtttcag aattcaatcg tgaaggaaca ggcattttac actatgaaga cattcttttg   2473
agatttttat ttcagttgct atatcataag cattttaaa gtttcttttc taattttaca    2533
ttgtattaga ttttctgatt cttttgtaaa tacagaactt aaatagaagg caacaggaaa   2593
tttatatagg aactatttc attccacttg tgtaagttaa gtcttgactc tttcaaatgc    2653
```

```
aaaaaaccta ttttatgctt tgttaaaatt atggtgtcac ttagattgac tttagttgac    2713
tgcactatat aatatagaac tatgaatatg tagaataaca tgaaaaattg gaggtgctgg    2773
tggtatggct gaccctgttt cagaagcagg atagtataaa agcatcagcc taagaatggc    2833
actcccacta actagctatg taatcttgac ctctttgggc tttagttcct ctcataaaag    2893
gaagagatgt attggattag actagatgat caccactttc tcttctagtt ctaattttt     2953 taattctaat acctatattt tcaagttatg tcaattaaat cattatcagg ttatttccta    3013
atgtaagaat agctaaaatg ttgcagagaa ataagtgacc caacaaaatt tattcatctg    3073
ttatgggtaa gatctgccat aaattcttcc taaataattt gtttactaac tctttaggcc    3133
actgtgcttt gcggtccatt agtaaacttg tgttgctaag tgctaaacag aatactgcta    3193
ttttgagaga gtcaagactc tttcttaagg gccaagaaag caacttgagc cttgggctaa    3253
tctggctgag tagtcagtta taaaagcata attgctttat attttggatc atttttact      3313 gggggcggac ttggggggg ttgcatacaa agataacata tatatccaac tttctgaaat      3373
gaaatgtttt tagattactt tttcaactgt aaataatgta catttaatgt cacaagaaaa     3433
aaatgtcttc tgcaaatttt ctagtataac agaaattttt gtagatgaaa aaaatcatta    3493
tgtttagagg tctaatgcta tgttttcata ttacagagtg aatttgtatt taaacaaaaa    3553 tttaaattt ggaatcctct aaacattttt gtatctttaa ttggtttatt attaaataaa     3613
tcatataaaa attctcagtg tctgttttca ggcaaaagtt tcttaaagaa taagtgtgca    3673
gagaatatta ctagaacatc agcattactt aatgtttata aataaatttc attagtcaga    3733
attgcaaaaa aaaaaaaaaa aaaaaaa                                         3760
```

<210> SEQ ID NO 8
<211> LENGTH: 619
<212> TYPE: PRT
<213> ORGANISM: Homo sapiens

<400> SEQUENCE: 8

Met Ala Ala Val Val Gln Gln Asn Asp Leu Val Phe Glu Phe Ala Ser
1               5                   10                  15

Asn Val Met Glu Asp Glu Arg Gln Leu Gly Asp Pro Ala Ile Phe Pro
                20                  25                  30

Ala Val Ile Val Glu His Val Pro Gly Ala Asp Ile Leu Asn Ser Tyr
            35                  40                  45

Ala Gly Leu Ala Cys Val Glu Pro Asn Asp Met Ile Thr Glu Ser
        50                  55                  60

Ser Leu Asp Val Ala Glu Glu Ile Ile Asp Asp Asp Asp
65                  70                  75                  80

Ile Thr Leu Thr Val Glu Ala Ser Cys His Asp Gly Asp Glu Thr Ile
                85                  90                  95

Glu Thr Ile Glu Ala Ala Glu Ala Leu Leu Asn Met Asp Ser Pro Gly
            100                 105                 110

Pro Met Leu Asp Glu Lys Arg Ile Asn Asn Asn Ile Phe Ser Ser Pro
        115                 120                 125

Glu Asp Asp Met Val Val Ala Pro Val Thr His Val Ser Val Thr Leu
    130                 135                 140

Asp Gly Ile Pro Glu Val Met Glu Thr Gln Gln Val Gln Glu Lys Tyr
145                 150                 155                 160

Ala Asp Ser Pro Gly Ala Ser Ser Pro Glu Gln Pro Lys Arg Lys Lys
                165                 170                 175

```
Gly Arg Lys Thr Lys Pro Pro Arg Pro Asp Ser Pro Ala Thr Thr Pro
                180                 185                 190

Asn Ile Ser Val Lys Lys Asn Lys Asp Gly Lys Gly Asn Thr Ile
    195                 200                 205

Tyr Leu Trp Glu Phe Leu Leu Ala Leu Leu Gln Asp Lys Ala Thr Cys
    210                 215                 220

Pro Lys Tyr Ile Lys Trp Thr Gln Arg Glu Lys Gly Ile Phe Lys Leu
225                 230                 235                 240

Val Asp Ser Lys Ala Val Ser Arg Leu Trp Gly Lys His Lys Asn Lys
                245                 250                 255

Pro Asp Met Asn Tyr Glu Thr Met Gly Arg Ala Leu Arg Tyr Tyr Tyr
        260                 265                 270

Gln Arg Gly Ile Leu Ala Lys Val Glu Gly Gln Arg Leu Val Tyr Gln
        275                 280                 285

Phe Lys Glu Met Pro Lys Asp Leu Ile Tyr Ile Asn Asp Glu Asp Pro
    290                 295                 300

Ser Ser Ser Ile Glu Ser Ser Asp Pro Ser Leu Ser Ser Ala Thr
305                 310                 315                 320

Ser Asn Arg Asn Gln Thr Ser Arg Ser Arg Val Ser Ser Pro Gly
                325                 330                 335

Val Lys Gly Gly Ala Thr Thr Val Leu Lys Pro Gly Asn Ser Lys Ala
                340                 345                 350

Ala Lys Pro Lys Asp Pro Val Glu Val Ala Gln Pro Ser Glu Val Leu
        355                 360                 365

Arg Thr Val Gln Pro Thr Gln Ser Pro Tyr Pro Thr Gln Leu Phe Arg
370                 375                 380

Thr Val His Val Val Gln Pro Val Gln Ala Val Pro Glu Gly Glu Ala
385                 390                 395                 400

Ala Arg Thr Ser Thr Met Gln Asp Glu Thr Leu Asn Ser Ser Val Gln
                405                 410                 415

Ser Ile Arg Thr Ile Gln Ala Pro Thr Gln Val Pro Val Val Val Ser
                420                 425                 430

Pro Arg Asn Gln Gln Leu His Thr Val Thr Leu Gln Thr Val Pro Leu
        435                 440                 445

Thr Thr Val Ile Ala Ser Thr Asp Pro Ser Ala Gly Thr Gly Ser Gln
    450                 455                 460

Lys Phe Ile Leu Gln Ala Ile Pro Ser Ser Gln Pro Met Thr Val Leu
465                 470                 475                 480

Lys Glu Asn Val Met Leu Gln Ser Gln Lys Ala Gly Ser Pro Pro Ser
                485                 490                 495

Ile Val Leu Gly Pro Ala Gln Val Gln Gln Val Leu Thr Ser Asn Val
                500                 505                 510

Gln Thr Ile Cys Asn Gly Thr Val Ser Val Ala Ser Ser Pro Ser Phe
    515                 520                 525

Ser Ala Thr Ala Pro Val Val Thr Phe Ser Pro Arg Ser Ser Gln Leu
    530                 535                 540

Val Ala His Pro Pro Gly Thr Val Ile Thr Ser Val Ile Lys Thr Gln
545                 550                 555                 560

Glu Thr Lys Thr Leu Thr Gln Glu Val Glu Lys Lys Glu Ser Glu Asp
                565                 570                 575

His Leu Lys Glu Asn Thr Glu Lys Thr Glu Gln Gln Pro Gln Pro Tyr
        580                 585                 590

Val Met Val Val Ser Ser Ser Asn Gly Phe Thr Ser Gln Val Ala Met
```

```
                    595                 600                 605
Lys Gln Asn Glu Leu Leu Glu Pro Asn Ser Phe
    610                 615

<210> SEQ ID NO 9
<211> LENGTH: 2601
<212> TYPE: DNA
<213> ORGANISM: Homo sapiens
<220> FEATURE:
<221> NAME/KEY: CDS
<222> LOCATION: (192)..(1016)

<400> SEQUENCE: 9
ccgcccttgt aggctgtcca cctcaaacgg gccggacagg atatataaga gagaatgcac    60
cgtgcactac acacgcgact cccacaaggt tgcagccgga gccgcccagc tcaccgagag   120
cctagttccg gccagggtcg ccccggcaac cacgagccca gccaatcagc gccccggact   180
gcaccagagc c atg gtc ggc aga aga gca ctg atc gta ctg gct cac tca    230
             Met Val Gly Arg Arg Ala Leu Ile Val Leu Ala His Ser
               1               5                  10 gag agg acg tcc ttc aac tat gcc atg aag gag gct gct gca gcg gct    278
Glu Arg Thr Ser Phe Asn Tyr Ala Met Lys Glu Ala Ala Ala Ala Ala
         15                  20                  25 ttg aag aag aaa gga tgg gag gtg gtg gag tcg gac ctc tat gcc atg    326
Leu Lys Lys Lys Gly Trp Glu Val Val Glu Ser Asp Leu Tyr Ala Met
 30                  35                  40                  45 aac ttc aat ccc atc att tcc aga aag gac atc aca ggt aaa ctg aag    374
Asn Phe Asn Pro Ile Ile Ser Arg Lys Asp Ile Thr Gly Lys Leu Lys
                 50                  55                  60 gac cct gcg aac ttt cag tat cct gcc gag tct gtt ctg gct tat aaa    422
Asp Pro Ala Asn Phe Gln Tyr Pro Ala Glu Ser Val Leu Ala Tyr Lys
             65                  70                  75 gaa ggc cat ctg agc cca gat att gtg gct gaa caa aag aag ctg gaa    470
Glu Gly His Leu Ser Pro Asp Ile Val Ala Glu Gln Lys Lys Leu Glu
         80                  85                  90 gcc gca gac ctt gtg ata ttc cag ttc ccc ctg cag tgg ttt gga gtc    518
Ala Ala Asp Leu Val Ile Phe Gln Phe Pro Leu Gln Trp Phe Gly Val
     95                 100                 105 cct gcc att ctg aaa ggc tgg ttt gag cga gtg ttc ata gga gag ttt    566
Pro Ala Ile Leu Lys Gly Trp Phe Glu Arg Val Phe Ile Gly Glu Phe
110                 115                 120                 125 gct tac act tac gct gcc atg tat gac aaa gga ccc ttc cgg agt aag    614
Ala Tyr Thr Tyr Ala Ala Met Tyr Asp Lys Gly Pro Phe Arg Ser Lys
                130                 135                 140 aag gca gtg ctt tcc atc acc act ggt ggc agt ggc tcc atg tac tct    662
Lys Ala Val Leu Ser Ile Thr Thr Gly Gly Ser Gly Ser Met Tyr Ser
            145                 150                 155 ctg caa ggg atc cac ggg gac atg aat gtc att ctc tgg cca att cag    710
Leu Gln Gly Ile His Gly Asp Met Asn Val Ile Leu Trp Pro Ile Gln
        160                 165                 170 agt ggc att ctg cat ttc tgt ggc ttc caa gtc tta gaa cct caa ctg    758
Ser Gly Ile Leu His Phe Cys Gly Phe Gln Val Leu Glu Pro Gln Leu
    175                 180                 185 aca tat agc att ggg cac act cca gca gac gcc cga att caa atc ctg    806
Thr Tyr Ser Ile Gly His Thr Pro Ala Asp Ala Arg Ile Gln Ile Leu
190                 195                 200                 205 gaa gga tgg aag aaa cgc ctg gag aat att tgg gat gag aca cca ctg    854
Glu Gly Trp Lys Lys Arg Leu Glu Asn Ile Trp Asp Glu Thr Pro Leu
                210                 215                 220 tat ttt gct cca agc agc ctc ttt gac cta aac ttc cag gca gga ttc    902
```

|   |   |   |   |   |   |   |   |   |   |   |   |   |   |   |   |
|---|---|---|---|---|---|---|---|---|---|---|---|---|---|---|---|
| Tyr | Phe | Ala | Pro | Ser | Ser | Leu | Phe | Asp | Leu | Asn | Phe | Gln | Ala | Gly | Phe |
|     |     |     | 225 |     |     |     |     | 230 |     |     |     |     | 235 |     |     |

```
tta atg aaa aaa gag gta cag gat gag gag aaa aac aag aaa ttt ggc      950
Leu Met Lys Lys Glu Val Gln Asp Glu Glu Lys Asn Lys Lys Phe Gly
        240                 245                 250 ctt tct gtg ggc cat cac ttg ggc aag tcc atc cca act gac aac cag      998
Leu Ser Val Gly His His Leu Gly Lys Ser Ile Pro Thr Asp Asn Gln
    255                 260                 265 atc aaa gct aga aaa tga gattccttag cctggatttc cttctaacat            1046
Ile Lys Ala Arg Lys
270 gttatcaaat ctgggtatct ttccaggctt ccctgacttg ctttagtttt taagatttgt    1106
gtttttcttt ttccacaagg aataaatgag agggaatcga ctgtattcgt gcattttgg     1166
atcatttta actgattctt atgattacta tcatggcata taaccaaaat ccgactgggc     1226
tcaagaggcc acttagggaa agatgtagaa agatgctaga aaaatgttct ttaaaggcat    1286
ctacacaatt taattcctct ttttagggct aaagtttag ggtacagttt ggctaggtat    1346
cattcaactc tccaatgttc tattaatcac ctctctgtag tttatggcag aagggaattg    1406
ctcagagaag gaaagactg aatctacctg ccctaaggga cttaacttgt ttggtagtta    1466
gccatctaat gcttgtttat gatatttctt gctttcaatt acaaagcagt tactaatatg    1526
cctagcacaa gtaccactct tggtcagctt ttgttgttta tatacagtac acagatacct    1586
tgaaggaag agctaataaa tctcttcttt gctgcagtca tctactttt ttttaattaa     1646
aaaaaatttt tttttgaagc agtcttgctc tgttacccag gctggagtgc agtggtgtga    1706
tctcggctca ctgcaacctc tgcctcccag gttccagcaa ttctcctgcc tcagcctccc    1766
tagtagctgg gatgacaggc gcctgccatc atgcctgact aatttttgta ttttagtag    1826
agacggcgtt tcaccatgtt ggccaggctg gtctcaaact cctgacctca ggtgatccgc    1886
ctacctcagc ctcccaaagt gctgggatta caggcgtgat ccaccacacc tggcccttgc    1946
aatcttctac tttaaggttt gcagagataa accaataaat ccacaccgta catctgcaat    2006
atgaattcaa gaaaggaaat agtaccttca atacttaaaa atagtcttcc acaaaaaata    2066
ctttatttct gatctataca aattttcaga aggttatttt cttatcatt gctaaactga    2126
tgacttacta tgggatgggg tccagtccca tgaccttggg gtacaattgt aaacctagag    2186
ttttatcaac tttggtgaac agttttggca taatagtcaa tttctacttc tggaagtcat    2246
ctcattccac tgttggtatt atataattca aggagaatat gataaaacac tgccctcttg    2306
tggtgcattg aaagaagaga tgagaaatga tgaaaaggtt gcctgaaaaa tgggagacag    2366
cctcttactt gccaagaaaa tgaagggatt ggaccgagct ggaaaacctc ctttaccaga    2426
tgctgactgg cactggtggt ttttgctctc gacagtatcc acaatagctg acggctgggt    2486
gtttcagttt gaaatatttt tgttgccttc atcttcactg caattttgtg taaatttctc    2546
aaagatctga attaaataaa taaaattcat ttctacagac ccacaaaaaa aaaaa         2601
```

<210> SEQ ID NO 10
<211> LENGTH: 274
<212> TYPE: PRT
<213> ORGANISM: Homo sapiens

<400> SEQUENCE: 10

|   |   |   |   |   |   |   |   |   |   |   |   |   |   |   |
|---|---|---|---|---|---|---|---|---|---|---|---|---|---|---|
| Met | Val | Gly | Arg | Arg | Ala | Leu | Ile | Val | Leu | Ala | His | Ser | Glu | Arg | Thr |
| 1 |   |   |   | 5 |   |   |   |   | 10 |   |   |   |   | 15 |   |

| Ser | Phe | Asn | Tyr | Ala | Met | Lys | Glu | Ala | Ala | Ala | Ala | Leu | Lys | Lys |

```
            20                  25                  30
Lys Gly Trp Glu Val Val Glu Ser Asp Leu Tyr Ala Met Asn Phe Asn
         35                  40                  45

Pro Ile Ile Ser Arg Lys Asp Ile Thr Gly Lys Leu Lys Asp Pro Ala
 50                  55                  60

Asn Phe Gln Tyr Pro Ala Glu Ser Val Leu Ala Tyr Lys Glu Gly His
 65                  70                  75                  80

Leu Ser Pro Asp Ile Val Ala Glu Gln Lys Lys Leu Glu Ala Ala Asp
                 85                  90                  95

Leu Val Ile Phe Gln Phe Pro Leu Gln Trp Phe Gly Val Pro Ala Ile
                100                 105                 110

Leu Lys Gly Trp Phe Glu Arg Val Phe Ile Gly Glu Phe Ala Tyr Thr
            115                 120                 125

Tyr Ala Ala Met Tyr Asp Lys Gly Pro Phe Arg Ser Lys Lys Ala Val
        130                 135                 140

Leu Ser Ile Thr Thr Gly Gly Ser Gly Ser Met Tyr Ser Leu Gln Gly
145                 150                 155                 160

Ile His Gly Asp Met Asn Val Ile Leu Trp Pro Ile Gln Ser Gly Ile
                165                 170                 175

Leu His Phe Cys Gly Phe Gln Val Leu Glu Pro Gln Leu Thr Tyr Ser
            180                 185                 190

Ile Gly His Thr Pro Ala Asp Ala Arg Ile Gln Ile Leu Glu Gly Trp
        195                 200                 205

Lys Lys Arg Leu Glu Asn Ile Trp Asp Glu Thr Pro Leu Tyr Phe Ala
    210                 215                 220

Pro Ser Ser Leu Phe Asp Leu Asn Phe Gln Ala Gly Phe Leu Met Lys
225                 230                 235                 240

Lys Glu Val Gln Asp Glu Glu Lys Asn Lys Phe Gly Leu Ser Val
                245                 250                 255

Gly His His Leu Gly Lys Ser Ile Pro Thr Asp Asn Gln Ile Lys Ala
            260                 265                 270

Arg Lys

<210> SEQ ID NO 11
<211> LENGTH: 3993
<212> TYPE: DNA
<213> ORGANISM: Homo sapiens
<220> FEATURE:
<221> NAME/KEY: CDS
<222> LOCATION: (606)..(2594)

<400> SEQUENCE: 11
ggatttctag gaggaccggc agaggcgcgc ataggtgcgt ggtgctgggc ccgggcgccg      60
cggcaccggt gtaggagcgc gcatctccag agtttcttcc atctgggcga cgtctcggtg     120
cctgcggcgg gaacggcgct ttgcttccct gaggagcttc tagagagcta cggtggcccc     180
cgtgtgggag gcggggggcg tggcggcgtc ggggcgtcgc tgtcccctcc tcggtagctc     240
tcctccctcc cctttctgct gttaccggga gcgcggtggc cacggaacgc tgcccggagc     300
cgcgcgaggg aggacccgac gcgcggcgtt tacccagcgc agcgttccac cgctcgggtt     360
tggctggata aaataaaaaa tggggatatt gacctcctgt cactactgca tggactttga     420
tggtttccaa tcattacttt ctcctctgtg tcaatctgcc tcttcgagaa attcatactc     480
ctgaatagct ctccagaccc ccagctggcc atgtggtgag ttcagggccc aaatcaagta     540
gtaccagcaa tcaggggaact cctatctgtt ttgaatggat tcacaccagc cacaagcctg     600
```

```
gaaag atg gtg tca caa tct aca gtc agg cag gat tct cct gtg gag ccc         650
      Met Val Ser Gln Ser Thr Val Arg Gln Asp Ser Pro Val Glu Pro
      1               5                   10                  15 tgg gaa ggg atc agc gat cac tct ggc att att gat ggt tcg ccc aga           698
Trp Glu Gly Ile Ser Asp His Ser Gly Ile Ile Asp Gly Ser Pro Arg
                20                  25                  30 ctc ctg aac act gac cat cct cct tgc caa tta gac atc agg ctc atg           746
Leu Leu Asn Thr Asp His Pro Pro Cys Gln Leu Asp Ile Arg Leu Met
            35                  40                  45 agg cac aaa gct gtc tgg att aac ccc cag gat gtg cag caa cag ccg           794
Arg His Lys Ala Val Trp Ile Asn Pro Gln Asp Val Gln Gln Gln Pro
        50                  55                  60 cag gac ttg caa tct cag gtg cca gca gca ggg aac agt ggg acc cat           842
Gln Asp Leu Gln Ser Gln Val Pro Ala Ala Gly Asn Ser Gly Thr His
    65                  70                  75 ttt gtg aca gat gct gcc tct ccc tca ggc cct tca cct tcg tgc ctc           890
Phe Val Thr Asp Ala Ala Ser Pro Ser Gly Pro Ser Pro Ser Cys Leu
80                  85                  90                  95 ggg gac tcc ctg gca gag aca acg ttg tct gag gat acc aca gac tcc           938
Gly Asp Ser Leu Ala Glu Thr Thr Leu Ser Glu Asp Thr Thr Asp Ser
                100                 105                 110 gtt ggc agc gct tct ccc cat ggc tcg agt gaa aag agt agc agc ttc           986
Val Gly Ser Ala Ser Pro His Gly Ser Ser Glu Lys Ser Ser Ser Phe
            115                 120                 125 tct ctg tcc tca aca gag gta cac atg gtc cgc cca gga tac tct cat          1034
Ser Leu Ser Ser Thr Glu Val His Met Val Arg Pro Gly Tyr Ser His
        130                 135                 140 cgg gtg tct ctg ccc aca agc cct ggg att ttg gcc acc tcc cca tat          1082
Arg Val Ser Leu Pro Thr Ser Pro Gly Ile Leu Ala Thr Ser Pro Tyr
    145                 150                 155 cct gag act gac agt gct ttt ttt gag cct tcc cat ctg aca tct gct          1130
Pro Glu Thr Asp Ser Ala Phe Phe Glu Pro Ser His Leu Thr Ser Ala
160                 165                 170                 175 gct gat gaa ggt gct gtt caa gtc agt aga aga acc att tct tcg aat          1178
Ala Asp Glu Gly Ala Val Gln Val Ser Arg Arg Thr Ile Ser Ser Asn
                180                 185                 190 tcc ttc tca cca gag gta ttt gtg ctg cct gtt gat gta gaa aag gaa          1226
Ser Phe Ser Pro Glu Val Phe Val Leu Pro Val Asp Val Glu Lys Glu
            195                 200                 205 aat gcc cac ttt tat gtt gca gat atg att ata tca gca atg gag aaa          1274
Asn Ala His Phe Tyr Val Ala Asp Met Ile Ile Ser Ala Met Glu Lys
        210                 215                 220 atg aag tgt aac att ctg agt caa cag cag aca gag agc tgg agt aaa          1322
Met Lys Cys Asn Ile Leu Ser Gln Gln Gln Thr Glu Ser Trp Ser Lys
    225                 230                 235 gaa gtc agt ggg tta ctt ggg agt gat cag cct gac tct gaa atg act          1370
Glu Val Ser Gly Leu Leu Gly Ser Asp Gln Pro Asp Ser Glu Met Thr
240                 245                 250                 255 ttt gat acc aac ata aag caa gag tct ggg tct tct act tct tca tac          1418
Phe Asp Thr Asn Ile Lys Gln Glu Ser Gly Ser Ser Thr Ser Ser Tyr
                260                 265                 270 agt ggc tat gaa ggt tgt gct gtg tta cag gtc agc cca gtg act gaa          1466
Ser Gly Tyr Glu Gly Cys Ala Val Leu Gln Val Ser Pro Val Thr Glu
            275                 280                 285 aca cgt act tac cat gat gtg aaa gag att tgc aaa tgc gat gtt gat          1514
Thr Arg Thr Tyr His Asp Val Lys Glu Ile Cys Lys Cys Asp Val Asp
        290                 295                 300 gaa ttt gtt att tta gag ctt gga gat ttt aat gat atc aca gaa acc          1562
Glu Phe Val Ile Leu Glu Leu Gly Asp Phe Asn Asp Ile Thr Glu Thr
```

-continued

| | | | |
|---|---|---|---|
| | 305 | 310 | 315 |
| tgt agc tgt tcc tgc agc tcc tct aag agt gtc act tat gag cca gac<br>Cys Ser Cys Ser Cys Ser Ser Ser Lys Ser Val Thr Tyr Glu Pro Asp<br>320                                 325                            330                           335 | | | 1610 |

```
                    305                 310                 315
tgt agc tgt tcc tgc agc tcc tct aag agt gtc act tat gag cca gac    1610
Cys Ser Cys Ser Cys Ser Ser Ser Lys Ser Val Thr Tyr Glu Pro Asp
320                 325                 330                 335 ttc aat tct gca gaa cta tta gcc aaa gag ctg tac cgc gtg ttc cag    1658
Phe Asn Ser Ala Glu Leu Leu Ala Lys Glu Leu Tyr Arg Val Phe Gln
                340                 345                 350 aag tgc tgg ata ctg tca gta gtt aat tct cag ctg gca ggt tcc ctg    1706
Lys Cys Trp Ile Leu Ser Val Val Asn Ser Gln Leu Ala Gly Ser Leu
            355                 360                 365 agt gca gct ggc tcg ata gtc gta aat gaa gag tgt gtc cga aaa gac    1754
Ser Ala Ala Gly Ser Ile Val Val Asn Glu Glu Cys Val Arg Lys Asp
        370                 375                 380 ttt gaa tcc agt atg aat gta gta cag gaa att aaa ttt aag tct agg    1802
Phe Glu Ser Ser Met Asn Val Val Gln Glu Ile Lys Phe Lys Ser Arg
385                 390                 395 atc aga ggg act gaa gac tgg gct cct cct aga ttt caa atc ata ttt    1850
Ile Arg Gly Thr Glu Asp Trp Ala Pro Pro Arg Phe Gln Ile Ile Phe
400                 405                 410                 415 aat att cat cca cca ctc aag agg gac ctt gtg gtg gca gcc cag aat    1898
Asn Ile His Pro Pro Leu Lys Arg Asp Leu Val Val Ala Ala Gln Asn
                420                 425                 430 ttt ttc tgt gcc ggc tgt gga act cca gta gag cct aag ttt gtg aag    1946
Phe Phe Cys Ala Gly Cys Gly Thr Pro Val Glu Pro Lys Phe Val Lys
            435                 440                 445 cgg ctc cgg tac tgc gaa tac cta ggg aag tat ttc tgt gac tgc tgc    1994
Arg Leu Arg Tyr Cys Glu Tyr Leu Gly Lys Tyr Phe Cys Asp Cys Cys
        450                 455                 460 cac tca tat gca gag tcg tgc atc cct gcc cga atc ctg atg atg tgg    2042
His Ser Tyr Ala Glu Ser Cys Ile Pro Ala Arg Ile Leu Met Met Trp
465                 470                 475 gac ttc aag aag tac tac gtc agc aat ttc tcc aaa cag ctg ctc gac    2090
Asp Phe Lys Lys Tyr Tyr Val Ser Asn Phe Ser Lys Gln Leu Leu Asp
480                 485                 490                 495 agc ata tgg cac cag ccc att ttc aat ttg ctg agc atc ggc caa agc    2138
Ser Ile Trp His Gln Pro Ile Phe Asn Leu Leu Ser Ile Gly Gln Ser
                500                 505                 510 ctg tat gcg aaa gcc aag gag ctg gac aga gtg aag gaa att cag gag    2186
Leu Tyr Ala Lys Ala Lys Glu Leu Asp Arg Val Lys Glu Ile Gln Glu
            515                 520                 525 cag ctc ttc cat atc aag aag ctg ttg aag acc tgt agg ttt gct aac    2234
Gln Leu Phe His Ile Lys Lys Leu Leu Lys Thr Cys Arg Phe Ala Asn
        530                 535                 540 agt gca tta aag gag ttc gag cag gtg ccg gga cac ttg act gat gag    2282
Ser Ala Leu Lys Glu Phe Glu Gln Val Pro Gly His Leu Thr Asp Glu
545                 550                 555 ctc cac ctg ttc tcc ctt gag gac ctg gtc agg atc aag aaa ggg ctg    2330
Leu His Leu Phe Ser Leu Glu Asp Leu Val Arg Ile Lys Lys Gly Leu
560                 565                 570                 575 ctg gca ccc tta ctc aag gac att ctg aaa gct tcc ctt gca cat gtg    2378
Leu Ala Pro Leu Leu Lys Asp Ile Leu Lys Ala Ser Leu Ala His Val
                580                 585                 590 gct ggc tgt gag ctg tgt caa gga aag ggc ttt att tgt gaa ttt tgc    2426
Ala Gly Cys Glu Leu Cys Gln Gly Lys Gly Phe Ile Cys Glu Phe Cys
            595                 600                 605 cag aat acg act gtc atc ttc cca ttt cag aca gca aca tgt aga aga    2474
Gln Asn Thr Thr Val Ile Phe Pro Phe Gln Thr Ala Thr Cys Arg Arg
        610                 615                 620 tgt tca gcg tgc agg gct tgc ttt cac aaa cag tgc ttc agt cc tcc     2522
```

```
Cys Ser Ala Cys Arg Ala Cys Phe His Lys Gln Cys Phe Gln Ser Ser
            625                 630                 635 gag tgc ccc cgg tgt gcg agg atc aca gcg agg aga aaa ctt ctg gaa      2570
Glu Cys Pro Arg Cys Ala Arg Ile Thr Ala Arg Arg Lys Leu Leu Glu
640                 645                 650                 655 agt gtg gcc tct gca gca aca tga tgccctgag tactgtgaaa aagactgttc      2624
Ser Val Ala Ser Ala Ala Thr
                660 aacatgcctt atgataacac cgatttgtgt ctattattgg tgacattgtt ttagatattg    2684
ggtattgtat attaaggaaa agatggtct  atattctctt tattgcatat acttaatgtt   2744
tcaaagaat  gcagattctg tgtttaagca cagggctgat agttgtggtt ttgtttacaa   2804
atgttctgtt ttggctgcta ttggttttt  aaagaggttt tttatacttt tgtatttgaa   2864
tagttatgtt tcactgatgc tgagccagtt tgtatgtgtg tgcatatatg tgaactgtaa   2924
ctgacaagat gaattactca gtttctcttt ctctaaagct tgtttgatga aactggttgg   2984
tcctttcagt gaacaaaaat atgaccccaa atctgtttgc tctggctttt atttcttcag   3044
gaagcagact tccacttaaa tgccattttg tgattgtgtc aatcatacac attttattta   3104
cttcagagtt tgaatagaga gtacacattt cttctgcaga tttatttcat gatgagtttg   3164
agttgcttag cagggcgtgt gggtcccgtt gaagtgcagt ttgaagcaac tgcttctaga   3224
tggcactctt tcaggtggca caaattgaac ctgtatttgt catctctgtt ccacacactg   3284
caatgtcaag ggatgcagaa gtgagtagaa ttccatccct gcccttgagg atcttgcttt   3344
aacagatgta aaactgaaca taaggtattt gcagatttaa acgaactggg ggaaataatg   3404
aacagtgtga ttctagtaat aacattaaaa tcatagacat tgactaataa ggttaaatga   3464
atcacaaaac ctttatgaat ttctttttc  taatagttct tatatgtttt cctgaaacat    3524
gtgagcctat tctttttct  tctactttct atatactttc tcccacttga gaaggggcc    3584
ttgaggctgg gtcccttcat ggtataccct tagactgaac ggtttgcaac ctagggcttg   3644
ggcattacat tccctgggat tcacatgccc taactaaacc taccttgatt ttctcagaca   3704
gcacaggcag gcaataaagc gtcacagatt gtccctaac  cccatccagc catgtgtatg   3764
agtgtgtttt attcaatggg atagtactga gcacatgaaa gaaatgaatg acttctgtca   3824
atctctttc  attcagtctt ctcattctgt caattgtttt ctcatccgca gtgcctctgc   3884
cagaactgtg ctcacatcca ttatttaagc cagatctttt ctaagtatta tagaagtgta   3944
gaggcacata gaataaataa aaccagactt caaaaaaaaa aaaaaaaa               3993
```

<210> SEQ ID NO 12
<211> LENGTH: 662
<212> TYPE: PRT
<213> ORGANISM: Homo sapiens

<400> SEQUENCE: 12

```
Met Val Ser Gln Ser Thr Val Arg Gln Asp Ser Pro Val Glu Pro Trp
1               5                  10                  15

Glu Gly Ile Ser Asp His Ser Gly Ile Ile Asp Gly Ser Pro Arg Leu
            20                  25                  30

Leu Asn Thr Asp His Pro Pro Cys Gln Leu Asp Ile Arg Leu Met Arg
        35                  40                  45

His Lys Ala Val Trp Ile Asn Pro Gln Asp Val Gln Gln Pro Gln
    50                  55                  60

Asp Leu Gln Ser Gln Val Pro Ala Ala Gly Asn Ser Gly Thr His Phe
65                  70                  75                  80
```

-continued

```
Val Thr Asp Ala Ala Ser Pro Ser Gly Pro Ser Pro Ser Cys Leu Gly
                 85                  90                  95

Asp Ser Leu Ala Glu Thr Thr Leu Ser Glu Asp Thr Asp Ser Val
                100                 105                 110

Gly Ser Ala Ser Pro His Gly Ser Ser Glu Lys Ser Ser Phe Ser
                115                 120                 125

Leu Ser Ser Thr Glu Val His Met Val Arg Pro Gly Tyr Ser His Arg
130                 135                 140

Val Ser Leu Pro Thr Ser Pro Gly Ile Leu Ala Thr Ser Pro Tyr Pro
145                 150                 155                 160

Glu Thr Asp Ser Ala Phe Phe Glu Pro Ser His Leu Thr Ser Ala Ala
                165                 170                 175

Asp Glu Gly Ala Val Gln Val Ser Arg Arg Thr Ile Ser Ser Asn Ser
                180                 185                 190

Phe Ser Pro Glu Val Phe Val Leu Pro Val Asp Val Glu Lys Glu Asn
                195                 200                 205

Ala His Phe Tyr Val Ala Asp Met Ile Ile Ser Ala Met Glu Lys Met
                210                 215                 220

Lys Cys Asn Ile Leu Ser Gln Gln Gln Thr Glu Ser Trp Ser Lys Glu
225                 230                 235                 240

Val Ser Gly Leu Leu Gly Ser Asp Gln Pro Asp Ser Glu Met Thr Phe
                245                 250                 255

Asp Thr Asn Ile Lys Gln Glu Ser Gly Ser Ser Thr Ser Ser Tyr Ser
                260                 265                 270

Gly Tyr Glu Gly Cys Ala Val Leu Gln Val Ser Pro Val Thr Glu Thr
                275                 280                 285

Arg Thr Tyr His Asp Val Lys Glu Ile Cys Lys Cys Asp Val Asp Glu
                290                 295                 300

Phe Val Ile Leu Glu Leu Gly Asp Phe Asn Asp Ile Thr Glu Thr Cys
305                 310                 315                 320

Ser Cys Ser Cys Ser Ser Lys Ser Val Thr Tyr Glu Pro Asp Phe
                325                 330                 335

Asn Ser Ala Glu Leu Leu Ala Lys Glu Leu Tyr Arg Val Phe Gln Lys
                340                 345                 350

Cys Trp Ile Leu Ser Val Val Asn Ser Gln Leu Ala Gly Ser Leu Ser
                355                 360                 365

Ala Ala Gly Ser Ile Val Val Asn Glu Glu Cys Val Arg Lys Asp Phe
                370                 375                 380

Glu Ser Ser Met Asn Val Val Gln Glu Ile Lys Phe Lys Ser Arg Ile
385                 390                 395                 400

Arg Gly Thr Glu Asp Trp Ala Pro Pro Arg Phe Gln Ile Ile Phe Asn
                405                 410                 415

Ile His Pro Pro Leu Lys Arg Asp Leu Val Val Ala Ala Gln Asn Phe
                420                 425                 430

Phe Cys Ala Gly Cys Gly Thr Pro Val Glu Pro Lys Phe Val Lys Arg
                435                 440                 445

Leu Arg Tyr Cys Glu Tyr Leu Gly Lys Tyr Phe Cys Asp Cys Cys His
                450                 455                 460

Ser Tyr Ala Glu Ser Cys Ile Pro Ala Arg Ile Leu Met Met Trp Asp
465                 470                 475                 480

Phe Lys Lys Tyr Tyr Val Ser Asn Phe Ser Lys Gln Leu Leu Asp Ser
                485                 490                 495
```

```
Ile Trp His Gln Pro Ile Phe Asn Leu Leu Ser Ile Gly Gln Ser Leu
            500                 505                 510
Tyr Ala Lys Ala Lys Glu Leu Asp Arg Val Lys Glu Ile Gln Glu Gln
        515                 520                 525
Leu Phe His Ile Lys Lys Leu Leu Lys Thr Cys Arg Phe Ala Asn Ser
    530                 535                 540
Ala Leu Lys Glu Phe Glu Gln Val Pro Gly His Leu Thr Asp Glu Leu
545                 550                 555                 560
His Leu Phe Ser Leu Glu Asp Leu Val Arg Ile Lys Lys Gly Leu Leu
            565                 570                 575
Ala Pro Leu Leu Lys Asp Ile Leu Lys Ala Ser Leu Ala His Val Ala
        580                 585                 590
Gly Cys Glu Leu Cys Gln Gly Lys Gly Phe Ile Cys Glu Phe Cys Gln
    595                 600                 605
Asn Thr Thr Val Ile Phe Pro Phe Gln Thr Ala Thr Cys Arg Arg Cys
610                 615                 620
Ser Ala Cys Arg Ala Cys Phe His Lys Gln Cys Phe Gln Ser Ser Glu
625                 630                 635                 640
Cys Pro Arg Cys Ala Arg Ile Thr Ala Arg Arg Lys Leu Leu Glu Ser
            645                 650                 655
Val Ala Ser Ala Ala Thr
            660

<210> SEQ ID NO 13
<211> LENGTH: 3064
<212> TYPE: DNA
<213> ORGANISM: Homo sapiens
<220> FEATURE:
<221> NAME/KEY: CDS
<222> LOCATION: (161)..(1105)

<400> SEQUENCE: 13
aaaccatggg ggcggaagag gtgctgggca ggaggcggaa gaggtgctgt gcaggaggcg      60
ggcgggcgcg gttctttccg gaaggattga atctccttta gccccgcccg cctccgtagc    120
tgcctgaagt agtgcagggt cagcccgcaa gttgcaggtc atg gcg ctg gct gct    175
                                            Met Ala Leu Ala Ala
                                              1               5 cga ctg tgg cgc ctt ctg cct ttc cga cgt gga gcc gcc ccg ggg tct    223
Arg Leu Trp Arg Leu Leu Pro Phe Arg Arg Gly Ala Ala Pro Gly Ser
            10                  15                  20 cgt ctc cct gcg ggg act tcg ggc agc cgc ggg cat tgc ggc ccc tgt    271
Arg Leu Pro Ala Gly Thr Ser Gly Ser Arg Gly His Cys Gly Pro Cys
        25                  30                  35 cga ttc cgc ggc ttc gag gta atg gga aac cca gga act ttc aaa aga    319
Arg Phe Arg Gly Phe Glu Val Met Gly Asn Pro Gly Thr Phe Lys Arg
    40                  45                  50 ggc ctt tta ctc tca gct ttg tcg tat ttg ggt ttt gaa act tac cag    367
Gly Leu Leu Leu Ser Ala Leu Ser Tyr Leu Gly Phe Glu Thr Tyr Gln
55                  60                  65 gtt atc tct cag gct gct gtg gtt cat gcc aca gcc aaa gtt gaa gaa    415
Val Ile Ser Gln Ala Ala Val Val His Ala Thr Ala Lys Val Glu Glu
70                  75                  80                  85 ata ctt gaa caa gca gac tac ctg tat gaa agc gga gaa aca gaa aaa    463
Ile Leu Glu Gln Ala Asp Tyr Leu Tyr Glu Ser Gly Glu Thr Glu Lys
            90                  95                 100 ctt tat cag ttg cta acc caa tac aag gaa agt gaa gat gca gag tta    511
Leu Tyr Gln Leu Leu Thr Gln Tyr Lys Glu Ser Glu Asp Ala Glu Leu
        105                 110                 115
```

```
ctg tgg cgt ttg gca cgg gca tca cgt gat gta gct cag ctt agc aga        559
Leu Trp Arg Leu Ala Arg Ala Ser Arg Asp Val Ala Gln Leu Ser Arg
        120                 125                 130 acc tca gaa gag gag aaa aag cta ttg gtg tat gaa gcc cta gag tat        607
Thr Ser Glu Glu Glu Lys Lys Leu Leu Val Tyr Glu Ala Leu Glu Tyr
135                 140                 145 gca aaa aga gca cta gaa aaa aat gaa tca agt ttt gca tct cat aag        655
Ala Lys Arg Ala Leu Glu Lys Asn Glu Ser Ser Phe Ala Ser His Lys
150                 155                 160                 165 tgg tat gca atc tgc ctt agt gat gtt gga gat tat gaa ggc atc aag        703
Trp Tyr Ala Ile Cys Leu Ser Asp Val Gly Asp Tyr Glu Gly Ile Lys
                170                 175                 180 gct aaa att gca aat gca tat atc atc aag gag cat ttt gag aaa gca        751
Ala Lys Ile Ala Asn Ala Tyr Ile Ile Lys Glu His Phe Glu Lys Ala
                185                 190                 195 att gaa ctg aac cct aaa gat gct act tca att cac ctt atg ggt att        799
Ile Glu Leu Asn Pro Lys Asp Ala Thr Ser Ile His Leu Met Gly Ile
                200                 205                 210 tgg tgc tat aca ttt gcc gaa atg cct tgg tat caa aga aga att gct        847
Trp Cys Tyr Thr Phe Ala Glu Met Pro Trp Tyr Gln Arg Arg Ile Ala
        215                 220                 225 aaa atg ctg ttt gca act cct cct agt tcc acc tat gag aag gcc tta        895
Lys Met Leu Phe Ala Thr Pro Pro Ser Ser Thr Tyr Glu Lys Ala Leu
230                 235                 240                 245 ggc tac ttt cac agg gca gaa caa gtg gat cca aac ttc tac agc aaa        943
Gly Tyr Phe His Arg Ala Glu Gln Val Asp Pro Asn Phe Tyr Ser Lys
                250                 255                 260 aac tta ctt ctt tta gga aag aca tac ttg aaa cta cac aac aaa aag        991
Asn Leu Leu Leu Leu Gly Lys Thr Tyr Leu Lys Leu His Asn Lys Lys
                265                 270                 275 ctt gct gct ttc tgg cta atg aaa gcc aag gac tat cca gca cac aca       1039
Leu Ala Ala Phe Trp Leu Met Lys Ala Lys Asp Tyr Pro Ala His Thr
                280                 285                 290 gag gag gat aaa cag ata cag aca gaa gct gct cag ttg ctt aca agt       1087
Glu Glu Asp Lys Gln Ile Gln Thr Glu Ala Ala Gln Leu Leu Thr Ser
        295                 300                 305 ttc agt gag aag aat tga gaactttcta gagaagattt atgaaatagc              1135
Phe Ser Glu Lys Asn
310 taataaacat tgcctttct tttaattcta aacttaatat atgaactata actgttctac      1195 ggcttttaa atgttgtgac catttaaccg tgtaaatata aatattcta ggcttcttca       1255 caaataatag ggtaaaataa ataatcgcca taagagtggg agaaataaat ctccatggct     1315 caggcaaaga gattattttg catcctggat accagcaatg caaaatggta tgagatttct    1375 aaggattgat cacattggga tgggagatca agcaaagaaa tatttgtaga ggaggggaaa    1435 tggatctata ggggatatac aggggatgg atttcaaat tggattgatt ctaagttgaa      1495 atcttgaaga gaaggtgtgg tgacagtggt taggatgttg tgggttcctg acataaagta    1555 gttaaatgat atatcttgga gctaacctgt gtaagtaaag aactaagtaa ggagatgact    1615 aaaaatggag tagtttcctt ttttatttt ttgagacaga gtctcacttt gtttcccagg     1675 ctggtgtgca gtggcacaat ctcggcccac tgcagcctcc gcctcccggg ttcaagtgat    1735 tctcctgcct tagcctcctg agtggctggg attacagggt tgtaccacca cactcggcta    1795 acttttgtat ttttggtaga gatggggttt gccatgttg gctaggctgg tctcaaactc     1855 ctggcctcaa gtgatctgcc cgccttggcc tcccaaattg ctgggattac aggcgtgagc    1915
```

```
caccgcacct ggccagttta ctttaaatgt ggtgtagtct catggtaaac tgaatttgtc    1975
atcagatgca aagttctatt ccctaatgga atggaaggaa cacaaaactt aagagtgaaa    2035
tggaatacta agatgttttt aaataggcag gactatgcta ctcacttgag gctggagtgc    2095
caccactgca aaatcttttt aagttttgta aaaaggagca tcttgaatcc acttagataa    2155
agacagactg tgtgtgtagg tggattttttc ccaaaggatt tgggaattgt aatgttacaa    2215
tgaactgtat ggatatgttt gtcatgtaca ttttcaaaca aaaggaaaaa ctgaaagtag    2275
tgatctttgt atacccatct cttagattca gtgattttgc tatataggtt gtgtatccct    2335
tatctgaaat acttgggact agtagaagca tcttggattt gggatgtttt tccaaatttt    2395
ggaatacctg catacacaca ataagatatc ttggagatgg gacccaagtt taaacacaaa    2455
ttcacttgtt tcatatatac cttatgcaca tagcttgaag gtaactttat ataacattat    2515
ttttaataat tttgtgcatt gagaccaagt ttgcatacct tgaaccatca gaaagcaaag    2575
gtgtcattat ctcagccact catgtgggta atttgtggtt ggttgatgtc accatcattc    2635
ctgactgaat gtatatgcta ccaataagca gttattttct tatacttatt catgcataag    2695
tacttaacag taaaaaatat gacataactc gcacaggaac aaggatggca aaaaaaaaaa    2755
tatgacacac cactgataca gtgaaaaaat aatgtggtca gggtagctag caacagtag    2815 catcaccaga aacctgtatc agctgttaaa cggcaacaac aatggcaggc tttcagtttc    2875
ccacttaatg atgctgtatt ttaaaaggtt attgtatact gtaattttat ttttgtaggt    2935
gaagagaaac agaagcagct gaagggccag gaagtgggtc tttctaggga tgtggcattc    2995
tgctggatgg cttttttaaaa tgggtttttt cctttaggga gaccgaataa actgtgttgt    3055
gcacctgca                                                             3064
```

<210> SEQ ID NO 14  
<211> LENGTH: 314  
<212> TYPE: PRT  
<213> ORGANISM: Homo sapiens

<400> SEQUENCE: 14

```
Met Ala Leu Ala Ala Arg Leu Trp Arg Leu Leu Pro Phe Arg Arg Gly
1               5                  10                  15

Ala Ala Pro Gly Ser Arg Leu Pro Ala Gly Thr Ser Gly Ser Arg Gly
                20                  25                  30

His Cys Gly Pro Cys Arg Phe Arg Gly Phe Glu Val Met Gly Asn Pro
            35                  40                  45

Gly Thr Phe Lys Arg Gly Leu Leu Ser Ala Leu Ser Tyr Leu Gly
        50                  55                  60

Phe Glu Thr Tyr Gln Val Ile Ser Gln Ala Ala Val Val His Ala Thr
65                  70                  75                  80

Ala Lys Val Glu Glu Ile Leu Glu Gln Ala Asp Tyr Leu Tyr Glu Ser
                85                  90                  95

Gly Glu Thr Glu Lys Leu Tyr Gln Leu Leu Thr Gln Tyr Lys Glu Ser
            100                 105                 110

Glu Asp Ala Glu Leu Leu Trp Arg Leu Ala Arg Ala Ser Arg Asp Val
        115                 120                 125

Ala Gln Leu Ser Arg Thr Ser Glu Glu Lys Lys Leu Leu Val Tyr
    130                 135                 140

Glu Ala Leu Glu Tyr Ala Lys Arg Ala Leu Glu Lys Asn Glu Ser Ser
145                 150                 155                 160

Phe Ala Ser His Lys Trp Tyr Ala Ile Cys Leu Ser Asp Val Gly Asp
```

```
                    165                 170                 175
Tyr Glu Gly Ile Lys Ala Lys Ile Ala Asn Ala Tyr Ile Ile Lys Glu
            180                 185                 190

His Phe Glu Lys Ala Ile Glu Leu Asn Pro Lys Asp Ala Thr Ser Ile
        195                 200                 205

His Leu Met Gly Ile Trp Cys Tyr Thr Phe Ala Glu Met Pro Trp Tyr
    210                 215                 220

Gln Arg Arg Ile Ala Lys Met Leu Phe Ala Thr Pro Pro Ser Ser Thr
225                 230                 235                 240

Tyr Glu Lys Ala Leu Gly Tyr Phe His Arg Ala Glu Gln Val Asp Pro
                245                 250                 255

Asn Phe Tyr Ser Lys Asn Leu Leu Leu Gly Lys Thr Tyr Leu Lys
            260                 265                 270

Leu His Asn Lys Lys Leu Ala Ala Phe Trp Leu Met Lys Ala Lys Asp
        275                 280                 285

Tyr Pro Ala His Thr Glu Glu Asp Lys Gln Ile Gln Thr Glu Ala Ala
    290                 295                 300

Gln Leu Leu Thr Ser Phe Ser Glu Lys Asn
305                 310

<210> SEQ ID NO 15
<211> LENGTH: 9
<212> TYPE: PRT
<213> ORGANISM: Homo sapiens

<400> SEQUENCE: 15

Glu Leu Gln Glu Lys Phe Leu Ser Leu
1               5

<210> SEQ ID NO 16
<211> LENGTH: 9
<212> TYPE: PRT
<213> ORGANISM: Homo sapiens

<400> SEQUENCE: 16

Glu Leu Gln Glu Lys Phe Ser Ser Leu
1               5

<210> SEQ ID NO 17
<211> LENGTH: 10
<212> TYPE: PRT
<213> ORGANISM: Homo sapiens

<400> SEQUENCE: 17

Gln Glu Leu Asp Gly Val Phe Gln Lys Leu
1               5                   10

<210> SEQ ID NO 18
<211> LENGTH: 10
<212> TYPE: PRT
<213> ORGANISM: Homo sapiens

<400> SEQUENCE: 18

Gln Glu Leu Asp Arg Val Phe Gln Lys Leu
1               5                   10

<210> SEQ ID NO 19
<211> LENGTH: 9
<212> TYPE: PRT
<213> ORGANISM: Homo sapiens
```

<400> SEQUENCE: 19

Ser Leu Phe Phe Arg Lys Val Pro Phe
1               5

<210> SEQ ID NO 20
<211> LENGTH: 9
<212> TYPE: PRT
<213> ORGANISM: Homo sapiens

<400> SEQUENCE: 20

Ser Leu Phe Phe Arg Lys Val Ala Phe
1               5

<210> SEQ ID NO 21
<211> LENGTH: 9
<212> TYPE: PRT
<213> ORGANISM: Homo sapiens

<400> SEQUENCE: 21

Ser Val Leu Lys Pro Gly Asn Ser Lys
1               5

<210> SEQ ID NO 22
<211> LENGTH: 9
<212> TYPE: PRT
<213> ORGANISM: Homo sapiens

<400> SEQUENCE: 22

Thr Val Leu Lys Pro Gly Asn Ser Lys
1               5

<210> SEQ ID NO 23
<211> LENGTH: 11
<212> TYPE: PRT
<213> ORGANISM: Homo sapiens

<400> SEQUENCE: 23

Ala Met Tyr Asp Lys Gly Pro Phe Arg Ser Lys
1               5                   10

<210> SEQ ID NO 24
<211> LENGTH: 11
<212> TYPE: PRT
<213> ORGANISM: Homo sapiens

<400> SEQUENCE: 24

Ala Met Tyr Asp Lys Gly Pro Phe Trp Ser Lys
1               5                   10

<210> SEQ ID NO 25
<211> LENGTH: 9
<212> TYPE: PRT
<213> ORGANISM: Homo sapiens

<400> SEQUENCE: 25

Arg Val Ser Leu Pro Thr Ser Pro Gly
1               5

<210> SEQ ID NO 26
<211> LENGTH: 9
<212> TYPE: PRT
<213> ORGANISM: Homo sapiens

<400> SEQUENCE: 26

```
Arg Val Ser Leu Pro Thr Ser Pro Arg
1               5

<210> SEQ ID NO 27
<211> LENGTH: 9
<212> TYPE: PRT
<213> ORGANISM: Homo sapiens

<400> SEQUENCE: 27

Val Met Gly Asn Pro Gly Thr Phe Lys
1               5

<210> SEQ ID NO 28
<211> LENGTH: 9
<212> TYPE: PRT
<213> ORGANISM: Homo sapiens

<400> SEQUENCE: 28

Val Met Gly Asn Pro Gly Thr Phe Asn
1               5
```